(12) United States Patent
Robaina et al.

(10) Patent No.: US 10,838,210 B2
(45) Date of Patent: Nov. 17, 2020

(54) IMAGING MODIFICATION, DISPLAY AND VISUALIZATION USING AUGMENTED AND VIRTUAL REALITY EYEWEAR

(71) Applicant: Magic Leap, Inc., Plantation, FL (US)

(72) Inventors: Nastasja U. Robaina, Coconut Grove, FL (US); Nicole Elizabeth Samec, Ft. Lauderdale, FL (US); Christopher M. Harrises, Nashua, NH (US); Rony Abovitz, Hollywood, FL (US); Mark Baerenrodt, Delray Beach, FL (US); Brian Lloyd Schmidt, Bellevue, WA (US)

(73) Assignee: Magic Leap, Inc., Plantation, FL (US)

( * ) Notice: Subject to any disclaimer, the term of this patent is extended or adjusted under 35 U.S.C. 154(b) by 0 days.

(21) Appl. No.: 15/657,589

(22) Filed: Jul. 24, 2017

(65) Prior Publication Data
US 2019/0011703 A1    Jan. 10, 2019

Related U.S. Application Data

(60) Provisional application No. 62/440,332, filed on Dec. 29, 2016, provisional application No. 62/396,071, (Continued)

(51) Int. Cl.
*G02B 27/01*    (2006.01)
*G06F 3/01*    (2006.01)
(Continued)

(52) U.S. Cl.
CPC .......... *G02B 27/0172* (2013.01); *A61B 34/25* (2016.02); *A61B 90/36* (2016.02);
(Continued)

(58) Field of Classification Search
CPC ...... G02B 27/0172; G02B 27/01; A61B 4/00; G06F 3/011; G06F 3/012; G06F 3/013;
(Continued)

(56) References Cited

U.S. PATENT DOCUMENTS

| 6,850,221 B1 | 2/2005 | Tickle |
| 8,223,088 B1 | 7/2012 | Gomez et al. |

(Continued)

FOREIGN PATENT DOCUMENTS

| WO | WO 2015/077766 | 5/2015 |
| WO | WO 2015/161307 | 10/2015 |
| WO | WO 2018/022523 | 2/2018 |

OTHER PUBLICATIONS

"About the Curawave (MRgFUS) Treatment", Curawave, 2016, as archived Aug. 16, 2017, in 4 pages. URL: https://web.archive.org/web/20170816232429/http://usa.uterine-fibroids.org/about-mrgfus/.

(Continued)

*Primary Examiner* — Mark Edwards
(74) *Attorney, Agent, or Firm* — Knobbe, Martens, Olson & Bear, LLP

(57) ABSTRACT

A display system can include a head-mounted display configured to project light to an eye of a user to display augmented reality image content to the user. The display system can include one or more user sensors configured to sense the user and can include one or more environmental sensors configured to sense surroundings of the user. The display system can also include processing electronics in communication with the display, the one or more user sensors, and the one or more environmental sensors. The processing electronics can be configured to sense a situation involving user focus, determine user intent for the situation, and alter user perception of a real or virtual object within the vision field of the user based at least in part on the user intent and/or sensed situation involving user focus. The processing (Continued)

electronics can be configured to at least one of enhance or de-emphasize the user perception of the real or virtual object within the vision field of the user.

31 Claims, 27 Drawing Sheets

Related U.S. Application Data filed on Sep. 16, 2016, provisional application No. 62/366,599, filed on Jul. 25, 2016.

(51) Int. Cl.
 *A61B 34/00*    (2016.01)
 *A61B 90/00*    (2016.01)
 *G06F 3/03*     (2006.01)
 *G06T 19/00*    (2011.01)
 *A61B 17/00*    (2006.01)
 *A61B 34/20*    (2016.01)
 *A61B 90/50*    (2016.01)

(52) U.S. Cl.
 CPC .............. *A61B 90/37* (2016.02); *G02B 27/01* (2013.01); *G06F 3/011* (2013.01); *G06F 3/012* (2013.01); *G06F 3/013* (2013.01); *G06F 3/017* (2013.01); *G06F 3/0304* (2013.01); *G06T 19/006* (2013.01); *A61B 2017/00203* (2013.01); *A61B 2017/00207* (2013.01); *A61B 2017/00216* (2013.01); *A61B 2034/2048* (2016.02); *A61B 2034/254* (2016.02); *A61B 2034/258* (2016.02); *A61B 2090/365* (2016.02); *A61B 2090/367* (2016.02); *A61B 2090/368* (2016.02); *A61B 2090/371* (2016.02); *A61B 2090/372* (2016.02); *A61B 2090/378* (2016.02); *A61B 2090/502* (2016.02)

(58) Field of Classification Search
 CPC ..... G06F 3/017; G06F 3/0304; G06T 19/006; G06T 19/20
 USPC ............................................................ 345/8
 See application file for complete search history.

(56) References Cited

U.S. PATENT DOCUMENTS

| | | | |
|---|---|---|---|
| 8,681,256 B2 | 3/2014 | Sako et al. | |
| 8,950,867 B2 | 2/2015 | Macnamara | |
| 8,988,474 B2 | 3/2015 | Travis | |
| 9,081,426 B2 | 7/2015 | Armstrong | |
| 9,213,405 B2 | 12/2015 | Perez et al. | |
| 9,215,293 B2 | 12/2015 | Miller | |
| 9,310,559 B2 | 4/2016 | Macnamara | |
| 9,323,325 B2 | 4/2016 | Perez et al. | |
| 9,348,143 B2 | 5/2016 | Gao et al. | |
| D758,367 S | 6/2016 | Natsume | |
| 9,417,452 B2 | 8/2016 | Schowengerdt et al. | |
| 9,470,906 B2 | 10/2016 | Kaji et al. | |
| 9,547,174 B2 | 1/2017 | Gao et al. | |
| 9,671,566 B2 | 6/2017 | Abovitz et al. | |
| 9,740,006 B2 | 8/2017 | Gao | |
| 9,791,700 B2 | 10/2017 | Schowengerdt et al. | |
| 9,851,563 B2 | 12/2017 | Gao et al. | |
| 9,857,591 B2 | 1/2018 | Welch et al. | |
| 9,874,749 B2 | 1/2018 | Bradski | |
| 2007/0132663 A1 | 6/2007 | Iba et al. | |
| 2011/0112756 A1 | 5/2011 | Winkler et al. | |
| 2012/0127062 A1 | 5/2012 | Bar-Zeev et al. | |
| 2012/0154557 A1* | 6/2012 | Perez .............. | H04N 21/25891 348/53 |
| 2012/0212399 A1 | 8/2012 | Border et al. | |
| 2013/0082922 A1 | 4/2013 | Miller | |
| 2013/0117377 A1 | 5/2013 | Miller | |
| 2013/0125027 A1 | 5/2013 | Abovitz | |
| 2013/0250135 A1 | 9/2013 | Blum et al. | |
| 2014/0071539 A1 | 3/2014 | Gao | |
| 2014/1255583 | 5/2014 | Miyajima et al. | |
| 2014/0177023 A1 | 6/2014 | Gao et al. | |
| 2014/0192084 A1 | 7/2014 | Latta et al. | |
| 2014/0198017 A1 | 7/2014 | Lamb et al. | |
| 2014/0218468 A1 | 8/2014 | Gao et al. | |
| 2014/0267410 A1* | 9/2014 | Fein ........................ | G06T 11/00 345/633 |
| 2014/0267420 A1 | 9/2014 | Schowengerdt | |
| 2014/0306866 A1 | 10/2014 | Miller et al. | |
| 2015/0016777 A1 | 1/2015 | Abovitz et al. | |
| 2015/0103306 A1 | 4/2015 | Kaji et al. | |
| 2015/0178939 A1 | 6/2015 | Bradski et al. | |
| 2015/0205126 A1 | 7/2015 | Schowengerdt | |
| 2015/0222883 A1 | 8/2015 | Welch | |
| 2015/0222884 A1 | 8/2015 | Cheng | |
| 2015/0241707 A1 | 8/2015 | Schowengerdt | |
| 2015/0268415 A1 | 9/2015 | Schowengerdt et al. | |
| 2015/0302652 A1 | 10/2015 | Miller et al. | |
| 2015/0309263 A2 | 10/2015 | Abovitz et al. | |
| 2015/0326570 A1 | 11/2015 | Publicover et al. | |
| 2015/0346490 A1 | 12/2015 | TeKolste et al. | |
| 2015/0346495 A1 | 12/2015 | Welch et al. | |
| 2016/0011419 A1 | 1/2016 | Gao | |
| 2016/0026253 A1 | 1/2016 | Bradski et al. | |
| 2016/0085302 A1* | 3/2016 | Publicover .............. | G06F 3/012 345/633 |
| 2016/0098861 A1* | 4/2016 | Sisbot ................... | G06T 19/006 345/633 |
| 2016/0131905 A1 | 5/2016 | Takahashi et al. | |
| 2016/0131912 A1* | 5/2016 | Border ............... | G02B 27/0075 345/8 |
| 2016/0161740 A1 | 6/2016 | Bar-Zeev et al. | |
| 2016/0203359 A1 | 7/2016 | Liechtenstein | |
| 2016/0270656 A1 | 9/2016 | Samec et al. | |
| 2017/0109936 A1 | 4/2017 | Powderly et al. | |
| 2017/0206691 A1 | 7/2017 | Harrises et al. | |
| 2017/0308262 A1* | 10/2017 | Murase .................. | B60K 35/00 |
| 2017/0323485 A1 | 11/2017 | Samec et al. | |
| 2017/0365101 A1 | 12/2017 | Samec et al. | |
| 2018/0136486 A1 | 5/2018 | Macnamara et al. | |

OTHER PUBLICATIONS

"Basic Psychological Process—B.Sc. in Counseling Psychology Core Course", University of Calicut, School of Distance Education (2011 Admission onwards) in 189 pages. URL: http://www.universityofcalicut.info/syl/CP1B01BasicPsychologicalProcesses.pdf.

"Fiducial Marker Placement", RadiologyInfo; reviewed Jan. 26, 2016, printed Oct. 23, 2017 in 5 pages; URL: http://www.radiologyinfo.org/en/info.cfm?pg=fiducial-marker.

Kodak In-vivo Multispectral System FX, published by CareStream Health, Inc. (Jan. 2008) Brochure in 8 pages; URL: http://clab.ajums.ac.ir/_clab/documents/Multrispectral_in-Vivo_Imaging.pdf.

"Scientists Literally Stretch Brain to Map Details", Medgadget, Aug. 1, 2016, as archived Aug. 4, 2017, in 5 pages. URL: https://web.archive.org/web/20170804161858/https://www.medgadget.com/2016/08/scientists-stretch-brain.html.

Anthony, S., "MIT releases open-source software that reveals invisible motion and detail in video", Extreme Tech, Feb. 28, 2013, as archived Aug. 4, 2017, in 5 pages.

Borghino, D., "Hi-tech glasses aim to assist the blind with directions and obstacle detection", New Atlas, May 22, 2014, in 4 pages. URL: http://newatlas.com/stereoscopic-ultrasound-gps-ai-glasses-blind-assistance/32166/.

Carter, T. et al., "UltraHaptics: Multi-Point Mid-Air Haptic Feedback for Touch Surfaces", UIST '13 Proceedings of the 26th Annual ACM Symposium on User Interface Software and Technology, Oct. 2013, in 10 pages. URL: http://big.cs.bris.ac.uk/wp-content/uploads/2013/10/Ultrahaptics.Carter.2013.pdf.

(56) References Cited

OTHER PUBLICATIONS

Gilliam, C., "Can VR Justify QHD and 4K Displays?", XDA Developers, Feb. 11, 2015, as archived Aug. 4, 2017, in 7 pages. URL:https://web.archive.org/web/20170804164547/https://www.xda-developers.com/can-vr-justify-qhd-and-4k-displays/.
Green, M., "Night Vision", Visual Expert, 2013, as archived Aug. 4, 2017, in 9 pages. URL: https://web.archive.org/web/20170804160954/http://www.visualexpert.com/Resources/nightvision.html.
Griffith, D., "'Digital neurotherapeutic' developed at UC Davis Mind Institute", Daily Democrat, Jun. 24, 2016, as archived Aug. 3, 2017, in 3 pages. URL: https://web.archive.org/web/20170803232850/http://www.dailydemocrat.com/general-news/20160624/digital-neurotherapeutic-developed-at-uc-davis-mind-institute.
Harrison, W., "Eye movement targets are released from visual crowding", Will J Harrison, Mar. 13, 2013, as archived Aug. 4, 2017, in 3 pages. URL: https://web.archive.org/web/20170804165524/http://willjharrison.com/2013/03/eye-movement-targets-are-released-from-visual-crowding/.
Mrovlje, J. et al., "Distance measuring based on stereoscopic pictures", 9th International PhD Workshop on Systems and Control: Young Generation Viewpoint, Oct. 2008, in 6 pages. URL: http://dsc.ijs.si/files/papers/S101%20Mrovlje.pdf.
The New York Times, "MIT Computer Program Reveals Invisible Motion in Video | The New York Times", YouTube, published Feb. 27, 2013, as archived Sep. 8, 2017, in 10 pages (with video transcription). URL: https://web.archive.org/web/20170906180629/https://www.youtube.com/watch?feature-youtu.be&t=1m5s&v=3rWycBEHn3s&app-desktop.
International Search Report and Written Opinion for PCT Application No. PCT/US2017/043555, dated Oct. 6, 2017 in 15 pages.
International Preliminary Report on Patentability for PCT Application No. PCT/US2017/043555, dated Jan. 29, 2019.
European Extended Search Report, re EP Application No. 17835070,8, dated Mar. 11, 2020.
"Big Tree Measuring Methods", Nature Nova Scotia, archived Jun. 6, 2016, in 4 pages, URL: https://web.archive.org/web/20160606110252/http://www.nature1st.net/naturens/files/tree_measure.html
"How do I calculate total acceleration from the x, y, and z g-force values given by an accelerometer?", Quora, answered Dec. 28, 2015, accessed Jul. 11, 2017, in 4 pages. URL: https://www.quora.com/How-do-l-calculate-total-acceleration-from-the--y-and-z-g-force-vaiues-given-by-an-accelerometer.
"MAKO—Robotic-Arm Assisted Surgery", Stryker, printed Oct. 23, 2017, in 2 pages; URL: https://www.stryker.com/us/en/portfolios/orthopaedics/joint-replacernent/mako-robotic-arm-assisted-surgery.html.
"Eye Intensity Response, Contrast Sensitivity", Telescope-Optics.net, archived Jul. 13, 2016, in 10 pages, URL: https://web.archive.org/web/20160713100211/https://www.telescope-optics.net/eye_intensity_response.htm.
"Eye Spectral Response", Telescope-Optics.net, retrieved Dec. 8, 2015, in 9 pages. URL: https://www.telescope-optics.net/eye_spectral_response.htm.
"Telescope images are degraded by the blurring effects of the atmosphere arid by light pollution" Chapter 6-3 https://web.archive.org/web/20160726162320/http://www.public.asu.edu/~atpcs/atpcs/Univl10e/chapter06-03.html as archived Jul. 26, 2016 in 2 pages.
"The Telescopic Eye", Telescope-Optics.rret, archived Jul. 21, 2016, in 5 pages, URL: https://web.archive.org/web/20160721003510/https://www.telescope-optics.net/eye.htm.
Binocular Visual Field, URL: https://www.med.kindai.ac.jp/optho/english/olaboratory.html Jun. 2016 in 1 page.
Brunelli, Roberto, Template Matching Techniques in Computer Vision, Theory and Practice, pp. 25- 28, published 2009.
Chadd, L., "Natural Health—Bio-Identical Hormons", downloaded Oct. 23, 2017 in 7 pages; URL: https://www.lynnchadd.com/services/#thermal-imaging-breast-health.

Cornish et ai., "Distribution of short-wavelength-sensitive cones in human fetal and postnatal retinal early development of spatial order and density profiles" Science Direct, Vision Research 44, 2004, in 8 pages.
EKO Devices "Duo electronic stethoscope + EKG—Telemedicine Solutions", retrieved Oct. 23, 2017 in 2 pages: URL: https://ekodevices.com/.
Evena Medical: "Eyes-On Glasses 3.0—Medical Smart Glasses", Evena Medical Products, archived Mar. 18, 2016 in 6 pages; URL: https://web.archive.org/web/20160318125251/http://evenarned.com/eyes-on-glasses/.
Gillam, C., "Can VR Justify QHD and 4K Displays?", XDA Developers, Feb. 11, 2015, https://web.archive.org/web/20150903005229/https://www.xda-developers.com/can-vr-justify-qhd-and-4k-displays/ as arvived Sep. 3, 2015 in 7 pages.
Huamn Vision, Physics Including Human Applications, Chapter 20, pp. 440-452, 1978. http://physics.doane.edu/hpp/Resources/Fuller3/pdf/F3Chapter_20A.
HyperPhysics, "The Color-Sensitive Cones", archived Jul. 10, 2016 in 2 pages. URL: https://web.archive.org/web/20160710054648/http:/thyperphysics.phy-astr.gsu.edu/hbase/visionlcolcon.html.
Kolb, H., "Part XIII: Facts and Figures concerning the human retina by Helga Kolb", Webvision, archived Jul. 2, 2016, in 6 pages. URL: https://web.archive.org/web/20160702134518/http://webvision.med.utah.edu/book/part-xiii-facts-and-figures-concerning-the-hurnan-retina/.
MIT, "MIT Media Lab Medical Mirror", YouTube, published Oct. 1, 2010, in 2 pages, URL: https://www.youtube.com/watch?v=LyWnvAWEbWE.
Murch, G. "Physiological Principles for the Effective Use of Color", IEEE CG&A, pp. 49-54, Nov. 1984, https://education.siggraph.org/static/HyperGraph/color/coloreff.htm.
Philips expands Benelux borne healthcare offering with innovative home medication dispensing service, Philips News center, Feb. 20, 2014. https://www,philips.corn/a-w/about/news/archive/standard/news/press/2014/20140220-Philips-expands-Benelux-home-healthcare-offering-with-innovative-home-medication-dispensing-service.html#.UwvusvidXax.
Sharma, N. et al., "Automated Medical image Segmentation Techniques", J. Med. Phys, 35(1), Jan-Mar. 2010, pp. 3-14, URL: http://www.ncbi.nlm.nih.gov/pmc/articles/PMC28250011.
Snowbrains.com, illustration Blind Spot, as archived May 18, 2015 in 1 page, https://web.archive.org/web.20150518201835/https://snowbrains.com/wp-content/uploads/2013/07/illustration-blind-spot.gif.
"Super-resolution 3D Microscopy of Whole Cells Opens New Window for Scientists" Jul. 14, 2016 in 8 pages, https://www.medgadget.com/2016/07/super-resolution-3d-microscopy-whole-cells-opens-new-window-scientists.html.
Ultrahaptics, "A Remarkable Connection with Technology", retrieved Oct. 31, 2017 in 8 pages. URL: http://ultrahaptics.com/.
Wandell, Brian A., "The Photoreceptor Mosaic," Foundations of Vision, Chapter 3. Stanford University, 1995, in 21 pages, https://foundationsofvision.stanford.edu/chapter-3-the-photoreceptor-mosaic.
Webvision, Graph of Rod and Cone Densities along the Horizontal Meridian, as archived Jul. 22, 2016 in 1 page, https://web.archive.org/web/20160722010221/https://webvision.med.utah.edu/imageswv/Osterg.jpeg.
Webvision, Isodensity Maps of Cone Densities (X1000) in the Human Retina, as archived Jul. 22, 2016 in 1 page, https://web.archive.org/web/20160722041212/http://webvision.med.utah.edu/imageswv/Curciopl.jpeg.
Wikipedia Blind spot (vision), archived Jun. 9, 2016, in 2 pages. URL: https://web.archive.org/web/20160609224858/https:en.wikipedia.org/wiki/Blind_spot(vision).
Wikipedia: "Angular resolution", Wikipedia, as archived Jul. 17, 2015, in 6 pages. URL: https://web.archive.org/web/20150717175037/https://en.wikipedia.org/wiki/Angular_resolution.
Wikipedia, "Crowding", as archived Oct. 17, 2015 in 2 pages. https://web.archive.org/web/20151017044343/https://en.wikipedia.org/wiki/Crowding.

(56) References Cited

OTHER PUBLICATIONS

Wikipedia: "Adaptation", as archived Nov. 17, 2015, in 6 pages. https://web.archive.org/web/20151117222707/https://en.m.wikipedia.org/wiki/Adaptation_(eye).

Wikipedia: "Peripheral vision", as archived Jul. 21, 2016, in 6 pages. https://web.archive.org/web/20160721034342/https://en.wikipedia.org/wiki/Peripheral_vision.

Wikipedia: "Photopic vision", Wikipedia, as archived May 6, 2015, in 2 pages. URL: https://web.archive.org/web/20150506191509/https://en.wikipedia.org/wiki/Photopic_vision.

"Positron emission tomography", as archived Jun. 17, 2016, in 14 pages. https://web.archive.org/web/20160617062029/http://en.wikipedia.org/wiki/Positron_emission_tomography.

"Eye Chromatism", Telescope-Optics.net, archived Mar. 10, 2016, in 5 pages. URL: http://web.archive.org/web/20160310131809/http://www.telescopeoptics.net/eye_chromatism.htm Sunnex, "The Role of Blue Light in the Pathogenesis of AMD", archived Jul. 8, 2016, in 19 pages. https://web.archive.org/web/20160708064257/https://www.sunnexbiotech.com/therapistibluelight and amd.html.

* cited by examiner

IMAGING MODIFICATION, DISPLAY AND VISUALIZATION USING AUGMENTED AND VIRTUAL REALITY EYEWEAR

PRIORITY CLAIM

This application claims the benefit of priority under 35 U.S.C. 119(e) of U.S. Provisional Application No. 62/366,599 filed on Jul. 25, 2016; U.S. Provisional Application No. 62/396,071 filed on Sep. 16, 2016; and U.S. Provisional Application No. 62/440,332 filed Dec. 29, 2016. The entire disclosure of each of these priority documents is incorporated herein by reference.

INCORPORATION BY REFERENCE

This application incorporates by reference the entirety of each of the following patent applications: U.S. Provisional Application No. 62/366,555 filed on Jul. 25, 2016; U.S. Provisional Application No. 62/352,539 filed on Jun. 20, 2016; and U.S. Provisional Application No. 62/333,734 filed on May 9, 2016; U.S. application Ser. No. 14/212,961 filed on Mar. 14, 2014; U.S. application Ser. No. 14/331,218 filed on Jul. 14, 2014; U.S. application Ser. No. 15/072,290 filed on Mar. 16, 2016; and U.S. Provisional Application No. 62/294,147 filed on Feb. 11, 2016.

BACKGROUND

Field

The present disclosure relates to display systems and, more particularly, to augmented reality display systems.

Description of the Related Art

Modern computing and display technologies have facilitated the development of systems for so called "virtual reality" or "augmented reality" experiences, wherein digitally reproduced images or portions thereof are presented to a user in a manner wherein they seem to be, or may be perceived as, real. A virtual reality, or "VR", scenario typically involves presentation of digital or virtual image information without transparency to other actual real-world visual input; an augmented reality, or "AR", scenario typically involves presentation of digital or virtual image information as an augmentation to visualization of the actual world around the user. A mixed reality, or "MR", scenario is a type of AR scenario and typically involves virtual objects that are integrated into, and responsive to, the natural world. For example, in an MR scenario, AR image content may be blocked by or otherwise be perceived as interacting with objects in the real world.

Referring to FIG. 1A, an augmented reality scene 1 is depicted wherein a user of an AR technology sees a real-world park-like setting 1100 featuring people, trees, buildings in the background, and a concrete platform 1120. In addition to these items, the user of the AR technology also perceives that he "sees" "virtual content" such as a robot statue 1110 standing upon the real-world platform 1120, and a cartoon-like avatar character 1130 flying by which seems to be a personification of a bumble bee, even though these elements 1130, 1110 do not exist in the real world. Because the human visual perception system is complex, it is challenging to produce an AR technology that facilitates a comfortable, natural-feeling, rich presentation of virtual image elements amongst other virtual or real-world imagery elements.

Systems and methods disclosed herein address various challenges related to AR and VR technology.

SUMMARY

This disclosure provides various examples of display systems. Such examples include but are not limited to the following examples.

1. A display system configured to project light to an eye of a user to display augmented reality image content in a vision field of said user, said head-mounted display system comprising:
   a frame configured to be supported on a head of the user;
   a head-mounted display disposed on the frame, said display configured to project light into said user's eye to display augmented reality image content to the user's vision field at different amounts of divergences as if projected from different distances from the user's eye, at least a portion of said display being transparent and disposed at a location in front of the user's eye when the user wears said head-mounted display such that said transparent portion transmits light from a portion of the environment in front of the user to the user's eye to provide a view of said portion of the environment in front of the user;
   one or more environmental sensors configured to sense surroundings of the user;
   processing electronics in communication with the display and the one or more environmental sensors, the processing electronics configured to:
   sense a situation involving increased user focus; and
   alter user perception of a real or virtual object within the vision field of the user based at least in part on sensing the increased focus.

2. The display system of Example 1, wherein the processing electronics are configured to alter the user perception of a virtual object within the vision field of the user by altering image content comprising the object.

3. The display system of Example 1 or 2, wherein the processing electronics are configured to alter the user perception of an object by moving the object from a first location to a second location.

4. The display system of Example 3, wherein the first location is the peripheral region and the second location is the central region or wherein the first location is the central region and the second location is the peripheral region.

5. The display system of any of Examples 2 to 4, wherein altering image content comprises altering at least one of contrast, opacity, color, color saturation, color balance, size, brightness, edges, or sharpness of image content comprising the object.

6. The display system of any of Examples 1 to 5, further configured to provide an alert to the user.

7. The display system of Example 6, wherein the alert is a visual alert or an audio alert.

8. The display system of any of Examples 1 to 7, wherein the one or more environmental sensors comprise a depth sensor, a pair of binocular world cameras, a geolocation sensor, a proximity sensor, or a GPS.

9. The display system of any of Examples 1-8, further comprising one or more user sensors configured to sense the user, said processing electronics in communication with said one or more user sensors.

10. The display system of Example 9, wherein the one or more user sensors comprise one or more cameras.

11. The display system of any of Examples 1-10, wherein the head-mounted display comprises a waveguide comprising diffractive optical elements configured to output the light by extracting the light out of the waveguide, wherein the waveguide is one of a stack of waveguides, wherein different waveguides of the stack of waveguides are configured to output light with different wavefront divergence.

12. The display system of any of Examples 1 to 11, wherein the processing electronics is further configured to determine the user intent for the situation and alter the user perception of the real or virtual object within the vision field of the user based at least in part on said determined intent.

13. The display system of any of Examples 1 to 12, wherein the processing electronics is further configured to determine the user intent for the situation and alter the user perception of the real or virtual object within the vision field of the user based at least in part on sensing the increased focus.

14. The display system of any of Examples 1-13, wherein said environmental sensor comprises a sensor configured to detect a radio signal.

15. The display system of any of Examples 1-14, wherein said environmental sensor comprises a sensor configured to detect a blue tooth signal from an automobile.

16. The display system of any of Examples 1-15, wherein said situation involving increased user focus comprises driving a motor vehicle.

17. The display system of Example 16, wherein said processing electronics are configured to alter user perception of said real or virtual object within the vision field of the user based at least in part on one or more data records regarding the user, said one or more data records comprising a driving record of said user.

18. The display system of any of Examples 1 to 17, wherein the processing electronics are configured to alter the user perception of the real or virtual object within the vision field of the user by altering background.

19. The display system of Example 18, wherein altering background comprises increasing homogenization of background thereby reducing visible features in the background.

20. The display system of Example 19, wherein increasing homogenization of background comprises washing out or painting over features in the background.

21. The display system of any of Examples 18 to 20, wherein the processing electronics are configured to alter the background by increasing the intensity of light in the background such that features in the environment in front of the user and the head-mounted display are less prominent to the user.

22. The display system of any of Examples 1 to 21, wherein the processing electronics are configured to increase the intensity of light such that features in the environment in front of the user and the head-mounted display are less prominent to the user.

23. The display system of any of Examples 1 to 22, wherein altering the user perception of an object within the vision field of the user comprises highlighting the object.

24. The display system of Example 23, wherein highlighting the object comprises superimposing a partially transparent color over the object.

25. The display system of any of Example 1-24, further comprising one or more light sources configured to direct light into the eye of said user to form images in the eye.

26. The display system of any of Example 1-25, wherein said at least a portion of said display that is transparent and disposed at a location in front of the user's eye comprises one or more waveguides configured to project the light to the user.

27. The display system of Example 25, wherein said one or more light sources are configured to direct light into said one or more waveguides.

28. The display system of any of Examples 25-27, wherein said light source comprises a fiber scanning projector.

29. The display system of any of Example 1-28, wherein said one or more environmental sensors comprise one or more outward-facing image capture systems configured to image said environment.

30. The display system of Example 1-29, wherein said environmental sensors comprise one or more outward-facing cameras.

31. The display system of any of Examples 1-30, wherein one or more environmental sensors comprise a distance measuring system.

32. The display system of Example 31, wherein said distance measuring system comprises a laser rangefinder.

33. The display system of any of Examples 1-32, further comprising an eye tracking system configured to track position and/or movement of said user's eye.

34. The display system of any of Examples 1-33, further comprising one or more inward-facing image capture systems configured to image said user's eye.

35. The display system of any of Examples 1-34, wherein the head-mounted display system is configured to process image content presented to at least a first portion of the user's vision field differently in comparison to image content presented to the a second portion of the user's vision field.

36. The display system of any of Examples 1-35, wherein the head-mounted display system is configured to process image content presented to at least a portion of said peripheral region of the user's vision field differently in comparison to image content presented to the central region of the user's vision field.

37. The display system of any of Examples 1-37, wherein altering said user perception comprise enhancing or de-emphasizing.

38. The display system of Example 37, wherein enhancing provided by said the processing electronics comprises magnifying image content.

39. The display system of any of Examples 37 to 38, wherein enhancing or de-emphasizing provided by said processing electronics comprises altering brightness.

40. The display system of any of Examples 37 to 39, wherein enhancing provided by said processing electronics comprises increasing brightness.

41. The display system of any of Examples 37 to 40, wherein de-emphasizing provided by said processing electronics comprises decreasing brightness.

42. The display system of any of Examples 37 to 41, wherein de-emphasizing provided by said processing electronics comprises increasing brightness.

43. The display system of any of Examples 37 to 42, wherein enhancing or de-emphasizing provided by said processing electronics comprises altering contrast.

44. The display system of any of Examples 37 to 43, wherein enhancing provided by said processing electronics comprises increasing contrast.

45. The display system of any of Examples 37 to 44, wherein de-emphasizing provided by said processing electronics comprises decreasing contrast.

46. The display system of any of Examples 37 to 45, wherein enhancing or de-emphasizing provided by said processing electronics comprises altering color saturation.

47. The display system of any of Examples 37 to 46, wherein enhancing provided by said processing electronics comprises increasing color saturation.

48. The display system of any of Examples 37 to 47, wherein de-emphasizing provided by said processing electronics comprises decreasing color saturation.

49. The display system of any of Examples 37 to 48, wherein enhancing or de-emphasizing provided by said processing electronics comprises altering sharpness.

50. The display system of any of Examples 37 to 49, wherein enhancing provided by said processing electronics comprises increasing sharpness.

51. The display system of any of Examples 37 to 50, wherein de-emphasizing provided by said processing electronics comprises decreasing sharpness.

52. The display system of any of Examples 37 to 51, wherein enhancing or de-emphasizing provided by said processing electronics comprises altering opacity.

53. The display system of any of Examples 37 to 52, wherein enhancing provided by said processing electronics comprises increasing opacity.

54. The display system of any of Examples 37 to 53, wherein de-emphasizing provided by said processing electronics comprises decreasing opacity.

55. The display system of any of Examples 37 to 54, wherein de-emphasizing provided by said processing electronics comprises increasing opacity.

56. The display system of any of Examples 37 to 55, wherein enhancing comprises edge enhancing features.

57. The display system of any of Examples 37 to 56, enhancing or de-emphasizing provided by said processing electronics comprises shifting the color balance.

1. A display system configured to project light to an eye of a user to display augmented reality image content in a vision field of said user, said head-mounted display system comprising:
   a frame configured to be supported on a head of the user;
   a head-mounted display disposed on the frame, said display configured to project light into said user's eye so as to present image content to said user's vision field, at least a portion of said display being transparent and disposed at a location in front of the user's eye when the user wears said head-mounted display system such that said transparent portion transmits light from a portion of the environment in front of the user and the head-mounted display to the user's eye to provide a view of said portion of the environment in front of the user and head-mounted display;
   one or more outwardly facing cameras configured to image objects in the user's environment;
   one or more eye tracking sensors configured to determine where the user's eye is viewing;
   processing electronics in communication with said display, said outwardly facing camera, and said eye tracking sensors to control presentation of image content on said display, the processing electronics configured to:
   display image content to said user's vision field;
   determine the object at which the eye is directed; and
   at least one of enhancing the rendering of the object at which the eye is directed or de-emphasizing one or more features surrounding the object at which the eye is directed.

2. The display system of Example 1, wherein the processing electronics are configured to display the object on the display and to enhance the rendering of the object.

3. The display system of Example 1 or 2, wherein the processing electronics are configured to display on the display said one or more features surrounding the object and to de-emphasize said one or more features surrounding the object at which the eye is directed as rendered on the display.

4. The display system of any of Examples 1 to 3, wherein said one or more features surrounding the object comprise real features in the environment in front of the user and the head mounted display system and the processing electronics are configured to de-emphasize said one or more real features surrounding the object at which the eye is directed.

5. The display system of Example 4, wherein the processing electronics are configured to de-emphasize said one or more real features surrounding the object at which the eye is directed by increasing the intensity of light directed into the eye such that said one or more real features in the environment in front of the user and the head-mounted display are less prominent to the user.

6. The display system of any of Examples 1 to 4, wherein the processing electronics are configured to increase the intensity of light projected into the eye such that features in the environment in front of the user and the head-mounted display are less prominent to the user.

7. The display system of any of Examples 1 to 6, wherein said de-emphasizing comprises one or more of decreasing brightness, visibility, sharpness, or contrast of the view of the environment through said transparent portion or altering the color of the environment through said transparent portion.

8. The display system of any of Examples 1 to 7, wherein the processing electronics are configured to increase the intensity of light projected into the eye such that features in the environment in front of the user and the head-mounted display are less prominent to the user, other than by displaying images on said display.

9. The display system of any of Examples 1 to 8 wherein said de-emphasizing comprises increasing opacity to attenuate the view of the environment through said transparent portion.

10. The display system of any of Examples 1 to 9, wherein said de-emphasizing comprises one or more of decreasing brightness, visibility, sharpness, or contrast of the view of the environment through said transparent portion or altering the color of the environment through said transparent portion, other than by displaying images on said display.

11. The display system of any of Examples 1 to 10, wherein said de-emphasizing comprises increasing opacity to attenuate the view of the environment through said transparent portion, other than by displaying images on said display.

12. The display system of any of Examples 1 to 11, wherein the processing electronics are configured to alter the user perception of the real or virtual object within the vision field of the user by altering background.

13. The display system of Example 12, wherein altering background comprises increasing homogenization of background thereby reducing visible features in the background.

14. The display system of Example 13, wherein increasing homogenization of background comprises washing out or painting over features in the background.

15. The display system of any of Examples 12 to 14, wherein the processing electronics are configured to alter the background by increasing the intensity of light in the background such that features in the environment in front of the user and the head-mounted display are less prominent to the user.

16. The display system of any of Examples 1 to 15, wherein the processing electronics are configured to enhance the rendering of the image content displayed by said display.

17. The display system of any of Examples 1 to 16, wherein the processing electronics are configured to de-emphasize the rendering of image content displayed by said display.

18. A display system configured to project light to an eye of a user to display augmented reality image content in a vision field of said user, said head-mounted display system comprising:
  a frame configured to be supported on a head of the user;
  a head-mounted display disposed on the frame, said display configured to project light into said user's eye so as to present image content to said user's vision field, at least a portion of said display being transparent and disposed at a location in front of the user's eye when the user wears said head-mounted display system such that said transparent portion transmits light from a portion of the environment in front of the user and said head-mounted display to the user's eye to provide a view of said portion of the environment in front of the user and said head-mounted display;
  processing electronics in communication with said display, the processing electronics configured to:
    display image content to said user's vision field;
    at least one of enhancing the rendering of the image content or de-emphasizing the rendering of the image content displayed by said display,
    wherein said enhancing comprises one or more of increasing contrast, color saturation, brightness, edges visibility, opacity, or sharpness, highlighting, or altering the color or color balance of the rendered image content relative to other image content displayed by the display, and
    wherein said de-emphasizing comprising one or more of decreasing contrast, color saturation, brightness, edges visibility, opacity, or sharpness, or altering the color or color balance of the rendered image content relative to other image content displayed by the display.

19. The display system of Example 18, wherein the processing electronics are configured to enhance the rendering of the image content displayed by said display.

20. The display system of Examples 18 or 19, wherein the processing electronics are configured to de-emphasize the rendering of image content displayed by said display.

21. The display system of any of Examples 18-20, wherein the processing electronics are configured to enhance the rendering of the image content displayed by said display relative to surrounding image content displayed by the display.

22. The display system of any of Examples 18-21, wherein the processing electronics is configured to de-emphasize the rendering of the image content displayed by said display relative to image content displayed by the display that is surrounded by said de-emphasized image content.

23. The display system of any of Examples 18-22, further comprising one or more outwardly facing cameras configured to image objects in the user's environment.

24. The display system of any of Examples 18-23, further comprising one or more eye tracking sensors configured to determine where the user's eye is viewing.

25. A head-mounted display system configured to project light to an eye of a user to display augmented reality image content in a vision field of said user, said head-mounted display system comprising:
  a frame configured to be supported on a head of the user;
  a head-mounted display disposed on the frame, said display configured to project light into said user's eye so as to present image content to said user's vision field, at least a portion of said display being transparent and disposed at a location in front of the user's eye when the user wears said head-mounted display system such that said transparent portion transmits light from a portion of the environment in front of the user and said head-mounted display to the user's eye to provide a view of said portion of the environment in front of the user and said head-mounted display;
  one or more outwardly facing cameras configured to image objects in the user's environment;
  processing electronics in communication with said display and said outwardly facing cameras, the processing electronics configured to:
    display image content to said user's vision field;
    recognize one or more objects in the user's environment by applying object recognition to images received from the one or more outwardly facing cameras; and
    based on said object recognition, at least one of enhancing the rendering of the image content or de-emphasizing the rendering of the image content displayed by said display,
    wherein said enhancing comprises one or more of increasing contrast, color saturation, brightness, edges visibility, opacity, sharpness, highlighting, or alter the color or color balance of the rendered image content, and
    wherein said de-emphasizing comprising one or more of decreasing contrast, color saturation, brightness, edges visibility, opacity, or sharpness, or alter the color or color balance of the rendered image content.

26. The display system of Example 25, wherein said one or more outwardly facing cameras is disposed on the frame.

27. The display system of Example 25 or 26, wherein the processing electronics are configured to enhance the rendering of the image content displayed by said display.

28. The display system of any of Examples 25 to 27, wherein the processing electronics are configured to de-emphasize the rendering of image content displayed by said display.

29. A head-mounted display system configured to project light to an eye of a user to display augmented reality image content in a vision field of said user, said head-mounted display system comprising:
  a frame configured to be supported on a head of the user;
  a head-mounted display disposed on the frame, said display configured to project light into said user's eye so as to present image content to said user's vision field, at least a portion of said display being transparent and disposed at a location in front of the user's eye when the user wears said head-mounted display system such that said transparent portion transmits light from a portion of the environment in front of the user and said head-mounted display to the user's eye to provide a view of said portion of the environment in front of the user and said head-mounted display;
  one or more outwardly facing cameras configured to image objects in the user's environment;

processing electronics in communication with said display and said outwardly facing cameras, the processing electronics configured to:
- display image content to said user's vision field;
- recognize one or more objects in the user's environment by applying object recognition to images received from the one or more outwardly facing cameras; and
- based on said object recognition, de-emphasize a least a portion of the view of said environment in front of the user to the user's eye through said transparent portion.

30. The display system of Examples 29, wherein said de-emphasizing comprises one or more of decreasing brightness, visibility, sharpness, or contrast of the view of the environment through said transparent portion or altering the color of the environment through said transparent portion.

31. The display system of Example 29 or 30, wherein said de-emphasizing comprises increasing opacity to attenuate the view of the environment through said transparent portion.

32. The display system of any of Examples 29 to 31, wherein said de-emphasizing comprises one or more of decreasing brightness, visibility, sharpness, or contrast of the view of the environment through said transparent portion or altering the color of the environment through said transparent portion, other than by displaying images on said display.

33. The display system of any of Examples 29 to 32, wherein said de-emphasizing comprises increasing opacity to attenuate the view of the environment through said transparent portion, other than by displaying images on said display.

34. The display system of any of Examples 29 to 33, wherein the processing electronics are configured to alter the user perception of the real or virtual object within the vision field of the user by altering background.

35. The display system of Example 34, wherein altering background comprises increasing homogenization of background thereby reducing visible features in the background.

36. The display system of Example 35, wherein increasing homogenization of background comprises washing out or painting over features in the background.

37. The display system of any of Examples 29 to 36, wherein the processing electronics are configured to alter the background by increasing the intensity of light in the background such that features in the environment in front of the user and the head-mounted display are less prominent to the user.

38. The display system of any of Examples 29 to 37, wherein the processing electronics are configured to increase the intensity of light such that features in the environment in front of the user and the head-mounted display are less prominent to the user.

39. A head-mounted display system configured to project light to an eye of a user to display augmented reality image content in a vision field of said user, said head-mounted display system comprising:
- a frame configured to be supported on a head of the user;
- one or more outwardly facing sensors to sense the environment of the user:
- a head-mounted display disposed on the frame, said display configured to project light into said user's eye so as to present image content to said user's vision field, at least a portion of said display being transparent and disposed at a location in front of the user's eye when the user wears said head-mounted display system such that said transparent portion transmits light from a portion of the environment in front of the user and said head-mounted display to the user's eye to provide a view of said portion of the environment in front of the user and said head-mounted display;
- processing electronics in communication with said display and one or more storage system including data records regarding the user, the processing electronics configured to:
  - display image content to said user's vision field; and
  - based on output from said one or more outwardly facing sensors and said one or more data records regarding the user, alter user perception of a real or virtual object within the vision field of the user.

40. The display system of Example 39, wherein said one or more outwardly facing sensors comprise one or more outwardly facing cameras is disposed on the frame.

41. The display system of Example 39 or 40, wherein said one or more outwardly facing cameras are configured to image objects in the user's environment and said processing electronics are configured to recognize one or more objects in the user's environment by applying object recognition to images received from the one or more outwardly facing cameras and to, based on said object recognition, alter user perception of the real or virtual object within the vision field of the user.

42. The display system of any of Examples 39 to 41, wherein said processing electronics is configured to sense a situation involving user focus, to determine user intent for the situation and to, based at least in part on said user intent, alter user perception of the real or virtual object within the vision field of the user.

43. The display system of any of Examples 39 to 42, wherein altering user perception of a real or virtual object within the vision field of the user comprises at least one of enhancing or de-emphasizing user perception of the real or virtual object within the vision field of the user.

44. The display system of any of Examples 39 to 43, wherein said one or more outwardly facing cameras are configured to image objects in the user's environment and said processing electronics are configured to recognize one or more objects in the user's environment by applying object recognition to images received from the one or more outwardly facing cameras and to, based on said object recognition, at least one of enhance or de-emphasize user perception of the real or virtual object within the vision field of the user.

45. The display system of any of Examples 39 to 44, wherein said data record comprises the user's driving record.

46. The display system of any of Examples 45, wherein said data record comprises whether the user has had driving violations.

47. The display system of any of Examples 45 or 46, wherein said data record comprises at least one of the user's age and whether the user is a teenage driver.

48. A head-mounted display system configured to project light to an eye of a user to display augmented reality image content in a vision field of said user, said head-mounted display system comprising:
- a frame configured to be supported on a head of the user;
- a head-mounted display disposed on the frame, said display configured to project light into said user's eye so as to present image content to said user's vision field, at least a portion of said display being transparent and disposed at a location in front of the user's eye when the user wears said head-mounted display system such that said transparent portion transmits light from a portion of the environment in front of the user and said head-mounted display to the user's eye to provide a view of said portion of the environment in front of the user and said head-mounted display;

one or more outwardly facing cameras configured to image objects in the user's environment;

processing electronics in communication with said display and said outwardly facing cameras, the processing electronics configured to:

display image content to said user's vision field;

recognize one or more objects in the user's environment by applying object recognition to images received from the one or more outwardly facing cameras; and based on said object recognition, highlighting a least a portion of the view of said environment in front of the user to the user's eye through said transparent portion.

49. The head-mounted display system of Example 48, wherein highlighting the object comprising superimposing a partially transparent color over the object.

50. The head-mounted display system of Example 48 or 49, wherein highlighting the object comprising highlighting the object other than by displaying images from said one or more outwardly facing cameras.

51. A head-mounted display system configured to project light to an eye of a user to display augmented reality image content in a vision field of said user, said head-mounted display system comprising:

a head-mounted display disposed on a frame, said display configured to project light into said user's eye so as to present image content to said user's vision field, at least a portion of said display being transparent and disposed at a location in front of the user's eye when the user wears said head-mounted display system such that said transparent portion transmits light from a portion of the environment in front of the user and said head-mounted display to the user's eye to provide a view of said portion of the environment in front of the user and said head-mounted display;

an outwardly facing camera configured to image an object in the user's environment; and processing electronics in communication with said display and said outwardly facing camera to control presentation of image content on said display, the processing electronics configured to:

determine that the user is operating a vehicle; and enhancing the object in the user's vision field.

52. display system of Example 51, wherein enhancing the object in the user's vision field comprises moving image content of the object from a first location in the user's vision field to a second location.

53. The display system of Example 51 or 52, wherein enhancing the object in the user's vision field comprises altering a perceived color of the object relative to an original color of the object without the enhancement.

54. The display system of any of Examples 51 to 53, wherein enhancing the object in the user's vision field comprises one or more of increasing contrast, color saturation, brightness, edge visibility, opacity, or sharpness of the displayed image content.

55. The display system of any of Examples 51 to 54, wherein enhancing the object in the user's vision field comprises highlighting the object by superimposing a partially transparent color over the object.

56. A head-mounted display system configured to project light to an eye of a user to display augmented reality image content in a vision field of said user, said head-mounted display system comprising:

a frame configured to be supported on a head of the user;

a database configured to contain one or more user records;

a head-mounted display disposed on the frame, said display configured to project light into said user's eye so as to present image content to said user's vision field, at least a portion of said display being transparent and disposed at a location in front of the user's eye when the user wears said head-mounted display system such that said transparent portion transmits light from a portion of the environment in front of the user and said head-mounted display to the user's eye to provide a view of said portion of the environment in front of the user and said head-mounted display; and processing electronics in communication with said display and said database, the processing electronics configured to reduce an amount of displayed image content based on the user one or more records.

57. The display system of Example 56, wherein the one or more user records comprises at least one of a driving record, an accident record, a citation record, a school performance record, a criminal record, or an arrest record.

58. The display system of Example 56 or 57, wherein the one or more user records comprises the user's age.

59. The display system of any of Examples 56-58, wherein reducing an amount of displayed image content based on the user one or more records comprises selectively enabling user access to a displayed image content.

60. The display system any of Examples 56-59, wherein reducing an amount of displayed image content based on the user's one or more records comprises displaying no image content.

61. The display system any of Examples 56-59, wherein reducing an amount of displayed image content based on the user's one or more records comprises displaying substantially no image content.

62. A head-mounted display system configured to project light to an eye of a user to display augmented reality image content in a vision field of said user, said head-mounted display system comprising:

a frame configured to be supported on a head of the user;

a head-mounted display disposed on the frame, said display configured to project light into said user's eye so as to present image content to said user's vision field, at least a portion of said display being transparent and disposed at a location in front of the user's eye when the user wears said head-mounted display system such that said transparent portion transmits light from a portion of the environment in front of the user and said head-mounted display to the user's eye to provide a view of said portion of the environment in front of the user and said head-mounted display; and processing electronics in communication with said display, the processing electronics configured to:

determine that the user is in the proximity of a vehicle based at least in part on an established communication link with a processor of the vehicle; and reduce an amount of displayed image content based on the established communication link.

63. The head-mounted display system of Example 62, wherein determining that the user is in the proximity of a vehicle comprises at least one of sending and/or receiving a radio frequency signal or an infrared signal.

64. The head-mounted display system of Example 62, wherein determining that the user is in the proximity of a vehicle comprises at least one of sending and/or receiving a radio frequency signal.

65. The head-mounted display system of Example 62, wherein determining that the user is in the proximity of a vehicle comprises at least one of sending and/or receiving a wireless signal.

66. The head-mounted display system of Example 62, wherein determining that the user is in the proximity of a vehicle comprises at least one of sending and/or receiving a blue tooth signal.

67. The head-mounted display system of any of Examples 62 or 66, wherein reducing an amount of displayed image content based on the established communication link comprises not displaying any image content.

68. The head-mounted display system of any of Examples 62 or 66, wherein reducing an amount of displayed image content based on the established communication link comprises not displaying substantially any image content.

69. A head-mounted display system configured to project light to an eye of a user to display augmented reality image content in a vision field of said user, said head-mounted display system comprising:
a frame configured to be supported on a head of the user;
a head-mounted display disposed on the frame, said display configured to project light into said user's eye so as to present image content to said user's vision field, at least a portion of said display being transparent and disposed at a location in front of the user's eye when the user wears said head-mounted display system such that said transparent portion transmits light from a portion of the environment in front of the user and said head-mounted display to the user's eye to provide a view of said portion of the environment in front of the user and said head-mounted display;
an outwardly facing camera configured to image an object in the user's environment;
an environmental sensor configured to identify one or more positions of the object; and
processing electronics in communication with said display, said outwardly facing camera, and said environmental sensor, the processing electronics configured to:
determine whether the user is operating a vehicle;
determine a risk of at least one of the vehicle colliding with the object and the object colliding with the vehicle; and
reduce an amount of displayed image content based on the determined risk.

70. The head-mounted display system of Example 69, wherein determining the collision risk comprises determining a rate at which the object and the vehicle are getting closer based on the one or more positions of the object identified by the environmental sensor.

71. The head-mounted display system of Example 69 or 70, wherein said environmental sensor configured to identify one or more positions of the object comprises at least one of a laser range finder, LIDAR, a radar distance finder, or an ultrasonic ranging device.

72. A head-mounted display system configured to project light to an eye of a user to display augmented reality image content in a vision field of said user, said head-mounted display system comprising:
a display disposed on a frame, said display configured to project light into said user's eye so as to present image content to said user's vision field, at least a portion of said display being transparent and disposed at a location in front of the user's eye when the user wears said head-mounted display system such that said transparent portion transmits light from a portion of the environment in front of the user and said head-mounted display to the user's eye to provide a view of said portion of the environment in front of the user and said head-mounted display;
an outwardly facing camera configured to image an object in the user's environment; and
processing electronics in communication with said display and said outwardly facing camera to control presentation of image content on said display, the processing electronics configured to:
determine that the user is operating a vehicle;
display image content to said user's vision field at different amounts of divergences as if projected from different distances from the user's eye; and
reduce an amount of displayed image content based on the determination that the user is operating a vehicle.

Any of the above examples may include any one or more of the features set forth below to produce any of the following examples.

73. The display system of any of Examples 1 to 72, wherein the processing electronics may be configured to alter the user perception of a virtual object within the vision field of the user by altering image content comprising the object.

74. The display system of Example 73, wherein altering image content comprises altering at least one of contrast, opacity, color, color saturation, color balance, size, brightness, edges, or sharpness of image content comprising the object.

75. The display system of any of Examples 1 to 74, wherein the processing electronics may be configured to alter the user perception of an object by moving the object from a first location to a second location.

76. The display system of Example 75, wherein the first location is the peripheral region and the second location is the central region or wherein the first location is the central region and the second location is the peripheral region.

77. The display system of any of Examples 1 to 76, further configured to provide an alert to the user.

78. The display system of Example 77, wherein the alert is a visual alert or an audio alert.

79. The display system of any of Examples 1 to 78, further comprising one or more environmental sensors.

80. The display system of any of Examples 1 to 79, wherein the one or more environmental sensors comprise a depth sensor, a pair of binocular world cameras, a geolocation sensor, a proximity sensor, or a GPS.

81. The display system of any of Examples 1 to 79, further comprising one or more user sensors.

82. The display system of any of Examples 1 to 81, wherein the one or more user sensors comprise one or more cameras.

83. The display system of any of Examples 1 to 82, wherein the head-mounted display comprises a waveguide comprising diffractive optical elements configured to output the light by extracting the light out of the waveguide, wherein the waveguide is one of a stack of waveguides, wherein different waveguides of the stack of waveguides are configured to output light with different wavefront divergence.

84. The display system of any of Examples 1 to 83, wherein the processing electronics is further configured to determine the user intent for the situation and alter the user perception of the real or virtual object within the vision field of the user based at least in part on the determined user intent.

85. The display system of any of Examples 1 to 84, wherein the processing electronics is further configured to determine the user intent for the situation and alter the user perception of the real or virtual object within the vision field of the user based at least in part on sensing the increased focus.

86. The display system of any of Examples 1 to 85, wherein said environmental sensor comprises a sensor configured to detect a radio signal.

87. The display system of any of Examples 1 to 86, wherein said environmental sensor comprises a sensor configured to detect a blue tooth signal from an automobile.

88. The display system of any of Examples 1 to 87, wherein said processing electronics is configured to determine whether the user is driving a motor vehicle.

89. The display system of any of Examples 1 to 88, wherein said processing electronics are configured to alter user perception of a real or virtual object within the vision field of the user based at least in part on one or more data records regarding the user, said one or more data records comprising a driving record of said user.

90. The display system of Examples 1 to 89, wherein the processing electronics are configured to alter background.

91. The display system of Example 90, wherein altering background comprises increasing homogenization of background thereby reducing visible features in the background.

92. The display system of Example 91, wherein increasing homogenization of background comprises washing out or painting over the background.

93. The display system of any of Examples 1 to 92, wherein the processing electronics are configured to alter the background by increasing the intensity of light in the background such that features in the environment in front of the user and the head-mounted display are less prominent to the user.

94. The display system of any of Examples 1 to 93, wherein the processing electronics are configured to increase the intensity of light such that features in the environment in front of the user and the head-mounted display are less prominent to the user.

95. The display system of any of Examples 1 to 94, wherein the processing electronics is configured to alter the user perception of an object within the vision field of the user by highlighting the object.

96. The display system of Example 95, wherein highlighting the object comprise superimposing a partially transparent color over the object.

97. The display system of any of Example 1 to 96, further comprising one or more light sources configured to direct light into the eye of said user to form images in the eye.

98. The display system of Example 97, wherein said one or more light sources are configured to direct light into one or more waveguides.

99. The display system of any of Examples 97 or 98, wherein said one or more light sources comprise a fiber scanning projector.

100. The display system of any of Example 1 to 99, wherein said at least a portion of said display that is transparent and disposed at a location in front of the user's eye comprises one or more waveguides configured to project the light to the user.

101. The display system of any of Examples 1 to 100, further comprising one or more sensors configured to monitor the environment.

102. The display system of Example 101, wherein said one or more sensors comprise one or more outward-facing image capture systems configured to image said environment.

103. The display system of Example 102, wherein said one or more outward-facing image capture systems configured to image said environment comprise one or more outward-facing cameras.

104. The display system of any of Examples 101-103, wherein one or more sensors comprise a distance measuring system.

105. The display system of Example 104, wherein said distance measuring system comprises a laser rangefinder.

106. The display system of any of Examples 1 to 105, further comprising an eye tracking system configured to track position and/or movement of said user's eye.

107. The display system of any of Examples 1 to 106, further comprising one or more inward-facing image capture systems configured to image said user's eye.

108. The display system of any of Examples 1 to 107, wherein the head-mounted display system is configured to process image content presented to at least a first portion of the user's vision field differently in comparison to image content presented to the a second portion of the user's vision field.

109. The display system of any of Examples 1 to 108, wherein the head-mounted display system is configured to process image content presented to at least a portion of said peripheral region of the user's vision field differently in comparison to image content presented to the central region of the user's vision field.

110. The display system of any of Examples 1 to 109, wherein enhancing provided by said the processing electronics comprises magnifying image content.

111. The display system of any of Examples 1 to 110, wherein enhancing or de-emphasizing provided by said the processing electronics comprises altering brightness.

112. The display system of any of Examples 1 to 111, wherein enhancing provided by said the processing electronics comprises increasing brightness.

113. The display system of any of Examples 1 to 112, wherein de-emphasizing provided by said the processing electronics comprises decreasing brightness.

114. The display system of any of Examples 1 to 113, wherein de-emphasizing provided by said the processing electronics comprises increasing brightness.

115. The display system of any of Examples 1 to 114, wherein enhancing or de-emphasizing provided by said the processing electronics comprises altering contrast.

116. The display system of any of Examples 1 to 115, wherein enhancing provided by said the processing electronics comprises increasing contrast.

117. The display system of any of Examples 1 to 116, wherein de-emphasizing provided by said the processing electronics comprises decreasing contrast.

118. The display system of any of Examples 1 to 117, wherein enhancing or de-emphasizing provided by said the processing electronics comprises altering color saturation.

119. The display system of any of Examples 1 to 118, wherein enhancing provided by said the processing electronics comprises increasing color saturation.

120. The display system of any of Examples 1 to 119, wherein de-emphasizing provided by said the processing electronics comprises decreasing color saturation.

121. The display system of any of Examples 1 to 120, wherein enhancing or de-emphasizing provided by said the processing electronics comprises altering sharpness.

122. The display system of any of Examples 1 to 121, wherein enhancing provided by said the processing electronics comprises increasing sharpness.

123. The display system of any of Examples 1 to 122, wherein de-emphasizing provided by said the processing electronics comprises decreasing sharpness.

124. The display system of any of Examples 1 to 123, wherein enhancing or de-emphasizing provided by said the processing electronics comprises altering opacity.

125. The display system of any of Examples 1 to 124, wherein enhancing provided by said the processing electronics comprises increasing opacity.

126. The display system of any of Examples 1 to 125, wherein de-emphasizing provided by said the processing electronics comprises decreasing opacity.

127. The display system of any of Examples 1 to 126, wherein de-emphasizing provided by said the processing electronics comprises increasing opacity.

128. The display system of any of Examples 1 to 127, wherein enhancing comprises edge enhancing features.

129. The display system of any of Examples 1 to 128, enhancing or de-emphasizing provided by said the processing electronics comprises shifting the color balance.

Additional examples are provided below.

Example Set IA

1. A head-mounted display system configured to project light to an eye of a user to display augmented reality image content, said user's eye having a vision field having a central region and a peripheral region disposed about said central region, said head-mounted display system comprising:
   a frame configured to be supported on a head of the user;
   a display disposed on the frame, said display configured to project light into said user's eye so as to present image content at said central region of said user's vision field, at least a portion of said display being transparent and disposed at a location in front of the user's eye when the user wears said head-mounted display system such that said transparent portion transmits light from a portion of the environment in front of the user to the user's eye to provide a view of said portion of the environment in front of the user;
   processing electronics in communication with said display to control presentation of image content on said display,
   wherein said head-mounted display system is configured to present image content to said peripheral region of the user's vision field that is enhanced in comparison to image content presented to the central region of the user's vision field.

2. The system of Example 1, further comprising one or more light sources configured to direct light into the eye of said user to form images in the eye.

3. The system of Examples 1 or 2, wherein said at least a portion of said display that is transparent and disposed at a location in front of the user's eye comprises one or more waveguides configured to project the light to the user.

4. The system of Example 3, wherein said one or more light sources is configured to direct light into said one or more waveguides.

5. The system of any of Examples 2-4, wherein said light source comprises a fiber scanning projector.

6. The system of any of the above Examples, further comprising one or more sensors configured to monitor the environment.

7. The system of Example 6, wherein said one or more sensors comprise one or more outward-facing image capture devices configured to image said environment.

8. The system of Example 7, wherein said one or more outward-facing image capture devices configured to image said environment comprise one or more outward-facing cameras.

9. The system of any of Examples 6-8, wherein one or more sensors comprise a distance measuring device.

10. The system of Example 9, wherein said distance measuring system comprises a laser rangefinder.

11. The system of any of the above Examples, further comprising an eye tracking device configured to track position and/or movement of said user's eye.

12. The system of Examples 1 or 11, further comprising one or more inward-facing image capture devices configured to image said user's eye.

13. The system of any of the above Examples, wherein the head-mounted display system is configured to process image content presented to at least a portion of said peripheral region of the user's vision field differently in comparison to image content presented to the central region of the user's vision field.

14. The system of Example 13, wherein the head-mounted display system is configured to process image content differently by magnifying image content presented to at least a portion of said peripheral region of the user's vision field in comparison to image content presented to the central region of the user's vision field.

15. The system of any of Examples 13-14, wherein the head-mounted display system is configured to process image content differently by increasing brightness in image content presented to at least a portion of said peripheral region of the user's vision field in comparison to image content presented to the central region of the user's vision field.

16. The system of any of Examples 13-15, wherein the head-mounted display system is configured to process image content differently by increasing contrast of image content presented to at least a portion of said peripheral region of the user's vision field in comparison to image content presented to the central region of the user's vision field.

17. The system of any of Examples 13-16, wherein the head-mounted display system is configured to process image content differently by increasing color saturation of image content presented to at least a portion of said peripheral region of the user's vision field in comparison to image content presented to the central region of the user's vision field.

18. The system of any of Examples 13-17, wherein the head-mounted display system is configured to process image content differently by sharpening of image content presented to at least a portion of said peripheral region of the user's vision field in comparison to image content presented to the central region of the user's vision field.

19. The system of Example 18, wherein sharpening comprises edge enhancing features in image content presented to at least a portion of said peripheral region of the user's vision field in comparison to image content presented to the central region of the user's vision field.

20. The system of any of Examples 13-19, wherein the head-mounted display system is configured to process image content differently by shifting the color balance of image content presented to at least a portion of said peripheral region of the user's vision field in comparison to image content presented to the central region of the user's vision field.

21. A head-mounted display system configured to project light to an eye of a user to display augmented reality image content, said user's eye having a vision field having a central region and a peripheral region disposed about said central region, said head-mounted display system comprising:
   a frame configured to be supported on a head of the user;
   a display disposed on the frame, said display configured to project light into said user's eye so as to present image content at said central and peripheral regions of said user's vision field, at least a portion of said display being transparent and disposed at a location in front of the user's eye when the user wears said head-mounted display system such that said transparent portion transmits light from a portion of the environment in front of the user to the user's eye to provide a view of said portion of the environment in front of the user;
   processing electronics in communication with said display to control presentation of image content on said display,
   wherein said head-mounted display system is configured to present image content to said central region of the user's vision field that is de-emphasized in comparison to image content presented to the peripheral region of the user's vision field.

22. The system of Example 21, further comprising one or more light sources configured to direct light into the eye the user to form images in said eye.

23. The system of Examples 21 or 22, wherein said at least a portion of said display that is transparent and disposed at a location in front of the user's eye comprises one or more waveguides configured to project the light to the user.

24. The system of Example 23, wherein said one or more light sources is configured to direct light into said one or more waveguides.

25. The system of any of Examples 22-24, wherein said light source comprises a fiber scanning projector.

26. The system of any of Examples 21-25, further comprising one or more sensors configured to monitor the environment.

27. The system of Example 26, wherein said one or more sensors comprises one or more outward-facing image capture devices configured to image said environment.

28. The system of Example 27, wherein said one or more outward-facing image capture devices configured to image said environment comprises one or more outward-facing cameras.

29. The system of any of Examples 26-28, wherein one or more sensors comprises a distance measuring device.

30. The system of Example 29, wherein said distance measuring device comprises a laser rangefinder.

31. The system of any of Examples 21-30, further an eye tracking device configured to track position and/or movement of said user's eye.

32. The system of Examples 21-31, further comprising one or more inward-facing image capture devices configured to image said user's eye.

33. The system of any of Examples 21-32, wherein the head-mounted display system is configured to process image content presented to at least a portion of said central region of the user's vision field differently in comparison to image content presented to the peripheral region of the user's vision field 34. The system of Example 33, wherein the head-mounted display system is configured to process image content differently by blurring image content presented to at least a portion of said central region of the user's vision field in comparison to image content presented to the peripheral region of the user's vision field.

35. The system of any of Examples 33-34, wherein the head-mounted display system is configured to process image content differently by darkening or attenuating image content presented to at least a portion of said central region of the user's vision field in comparison to image content presented to the peripheral region of the user's vision field.

36. The system of any of Examples 33-35, wherein the head-mounted display system is configured to process image content differently by reducing contrast of image content presented to at least a portion of said central region of the user's vision field in comparison to image content presented to the peripheral region of the user's vision field.

37. The system of any of Examples 33-36, wherein the head-mounted display system is configured to process image content differently by decreasing color saturation of image content presented to at least a portion of said central region of the user's vision field in comparison to image content presented to the peripheral region of the user's vision field.

38. The system of any of Examples 33-37, wherein the head-mounted display system is configured to process image content differently by decreasing sharpness of image content presented to at least a portion of said central region of the user's vision field in comparison to image content presented to the peripheral region of the user's vision field.

39. The system of Example 38, wherein decreasing sharpness comprises de-enhancing edges of features in image content presented to at least a portion of said central region of the user's vision field in comparison to image content presented to the peripheral region of the user's vision field.

40. The system of any of Examples 33-39, wherein the head-mounted display system is configured to process image content differently by shifting the color balance of image content presented to at least a portion of said central region of the user's vision field in comparison to image content presented to the peripheral region of the user's vision field.

41. The system of any of Examples 33-40, wherein the head-mounted display system is configured to process image content differently by shrinking image content presented to at least a portion of said central region of the user's vision field in comparison to image content presented to the peripheral region of the user's vision field.

42. The system of Example 14, wherein said magnifying is based at least in part on the resolution of the eye.

43. The system of Example 34, wherein said blurring comprises using a same color to blur said image content presented to said at least a portion of said central region of the user's vision field.

44. The system of Example 44, wherein said same color comprises a high contrast color in comparison to a color in said image content presented to said peripheral region of the user's vision field.

45. The system of any of Examples 1-20 or 42, wherein the system is configured to provide an alert to the user to indicate the presented image has been enhanced.

46. The system of any of Examples 21-41 or any of Examples 43-44, wherein the system is configured to provide an alert to the user to indicate the presented image has been de-emphasized.

47. The system of any of Examples 45 or 46, wherein the alert is a visual alert.

48. The system of any of Examples 45 or 46, wherein the alert is an audio alert.

49. The system of any of the above Examples, wherein said head-mounted display system is configured to construct a 3D representation of said at least part of the environment in front of the user and to interpret the representation of said at least part of the environment, said part of said environment comprising a patient, and said head-mounted display further configured to distinguish a first structure associated with the patient from a second structure associated with the patient.

50. The system of any of the above Examples, wherein said at least a portion of said display that is transparent and disposed at a location in front of the user's eye comprises one or more waveguides.

51. The system of Example 50, comprising one or more light sources configured to direct light into said one or more waveguides, the waveguides configured to direct light into the user's eye.

52. The system of any of Examples 50-51, wherein said one or more light sources comprises a fiber scanning projector.

53. The system of any of the above Examples, further comprising one or more sensors configured to monitor the environment.

54. The system of Example 53, wherein said one or more sensors comprise one or more outward-facing image capture devices configured to image said environment.

55. The system of Example 54, wherein said one or more outward-facing image capture devices configured to image said environment comprise one or more outward-facing cameras.

56. The system of any of the above Examples, further comprising a distance measuring device.

57. The system of any of the above Examples, further comprising an eye tracking device configured to track position and/or movement of said user's eye.

58. The system of any of the above Examples, wherein the head-mounted display is configured to estimate a volume of human tissue within the user's field of view.

59. The system of any of the above Examples, wherein the head-mounted display is configured to measure a distance between two objects in the environment.

60. The system of any of the above Examples, wherein the head-mounted display is configured to toggle between a first image modality and a second image modality that is presented on the display.

61. The system of Example 60, wherein the first image modality comprises an MRI scan.

62. The system of any of Examples 60-61, wherein the second image modality comprises an ultrasound.

63. The system of any of Examples 60-62, wherein the first image modality comprises an x-ray scan.

64. The system of any of the above Examples, further comprising an electronic emitter adapted to produce ultrasonic sound waves.

65. The system of any of the above Examples, further comprising a sensor adapted to convert ultrasonic sound waves into electrical signals.

66. The system of any of the above Examples, wherein the head-mounted display is configured to allow a user to place virtual fiducial markers on the portion of the environment in front of the user to the user's eye.

67. The system of any of the above Examples, wherein the head-mounted display is configured to project an image onto the display such that the image appears to be attached to a real-world object in the environment.

68. The system of any of the above Examples, wherein the head-mounted display is configured to display virtual cutting guidelines such that the virtual cutting guidelines appear to a user to be overlaid on a human body region to be cut or gives access to the part to be cut.

69. The system of Example 68, wherein an apparent location of the virtual cutting guidelines appears to be related to a position of a patient's body part.

70. The system of any of the above Examples, wherein the head-mounted display is configured to emit signals to obtain data on positions of objects in the portion of the environment in front of the user.

71. The system of any of the above Examples, wherein the head-mounted display is configured to obtain a position of objects in the portion of the environment in front of the user using a database of object locations.

72. The system of Example 71, wherein the head-mounted display is configured to set a point of reference based on said database of object locations and to project an image into the eye of a user such that the image appears to be fixed with respect to the point of reference.

73. The system of any of the above Examples, wherein the head-mounted display is configured to rotate a view of a 3D image of an object about an axis based on a user input.

74. The system of any of the above Examples, wherein the head-mounted display is configured to translate a view of an image of a 3D object based on a user input.

75. The system of any of the above Examples, wherein the head-mounted display is configured to display a first slice of a 3D image of an object.

76. The system of Example 75, wherein the head-mounted display is configured to sequence through an image of the first slice and an image of a second slice of the 3D image.

77. The system of any of the above Examples, wherein the head-mounted display is configured to transmit an image of a portion of the environment in front of the user such that a second user of head-mounted displays can view said image of said portion of the environment transmitted.

78. The system of any of the above Examples, wherein the head-mounted display is configured to alert a user of a step in a medical procedure.

79. The system of any of the above Examples, wherein the head-mounted display is configured to monitor a user's medical parameter and provide an alert based on the medical parameter.

80. The system of Example 79, wherein the user's medical parameter comprises a vital sign.

81. The system of any of the above Examples, wherein the head-mounted display is configured to emit ultrasound waves and to measure a signal resulting from said ultrasound waves and wherein the head-mounted display is further configured to form an ultrasound image based on the signal.

82. The system of any of the above Examples, wherein the head-mounted display is configured to alert the user of objects and/or events that are outside the user's field of view.

83. The system of any of the above Examples, further comprising one or more light sources configured to direct light into the eye of said user to form images in the eye.

84. The system of any of the above Examples, wherein said one or more light sources comprises a fiber scanning projector.

85. The system of Example 16, wherein increasing contrast comprises adjusting brightness or darkness of at least one color of said image content.

86. The system of Example 16, wherein increasing contrast comprises adding black, grey, white, or other color to at least one color of said image content.

87. The system of any of the above Examples, wherein the head-mounted display is configured to provide a degree of opacity at least in the vicinity of the presented image content.

88. The system of any of the above Examples, wherein the head-mounted display is configured to combine a first image modality with a second image modality different from the first image modality.

89. The system of Example 88, wherein the first image modality and the second image modality each comprises an image from an MRI, CT, PET, MRA, or CTA scan.

90. The system of Example 88 or 89, wherein the head-mounted display is configured to align the combined image of the first and second image modalities over the patient's actual anatomy.

Example Set IB

1. A head-mounted display system configured to project light to an eye of a user to display augmented reality image content, said user's eye having a vision field having a central region and a peripheral region disposed about said central region, said head-mounted display system comprising:
    a frame configured to be supported on a head of the user;
    a display disposed on the frame, said display configured to project light into said user's eye so as to present image content at said central region of said user's vision field, at least a portion of said display being transparent and disposed at a location in front of the user's eye when the user wears said head-mounted display system such that said transparent portion transmits light from a portion of the environment in front of the user to the user's eye to provide a view of said portion of the environment in front of the user;
    processing electronics in communication with said display to control presentation of image content on said display,
    wherein said head-mounted display system is configured to present image content to said central region of the user's vision field that is enhanced in comparison to image content presented to the peripheral region of the user's vision field.

2. The system of Example 1, further comprising one or more light sources configured to direct light into the eye of said user to form images in the eye.

3. The system of Examples 1 or 2, wherein said at least a portion of said display that is transparent and disposed at a location in front of the user's eye comprises one or more waveguides configured to project the light to the user.

4. The system of Example 3, wherein said one or more light sources is configured to direct light into said one or more waveguides.

5. The system of any of Examples 2-4, wherein said light source comprises a fiber scanning projector.

6. The system of any of the above Examples, further comprising one or more sensors configured to monitor the environment.

7. The system of Example 6, wherein said one or more sensors comprise one or more outward-facing image capture devices configured to image said environment.

8. The system of Example 7, wherein said one or more outward-facing image capture devices configured to image said environment comprise one or more outward-facing cameras.

9. The system of any of Examples 6-8, wherein one or more sensors comprise a distance measuring device.

10. The system of Example 9, wherein said distance measuring device comprises a laser rangefinder.

11. The system of any of the above Examples, further comprising an eye tracking device configured to track position and/or movement of said user's eye.

12. The system of Examples 1 or 11, further comprising one or more inward-facing image capture devices configured to image said user's eye.

13. The system of any of the above Examples, wherein the head-mounted display system is configured to process image content presented to at least a portion of said central region of the user's vision field differently in comparison to image content presented to the peripheral region of the user's vision field.

14. The system of Example 13, wherein the head-mounted display system is configured to process image content differently by magnifying image content presented to at least a portion of said central region of the user's vision field in comparison to image content presented to the peripheral region of the user's vision field.

15. The system of any of Examples 13-14, wherein the head-mounted display system is configured to process image content differently by increasing brightness in image content presented to at least a portion of said central region of the user's vision field in comparison to image content presented to the peripheral region of the user's vision field.

16. The system of any of Examples 13-15, wherein the head-mounted display system is configured to process image content differently by increasing contrast of image content presented to at least a portion of said central region of the user's vision field in comparison to image content presented to the peripheral region of the user's vision field.

17. The system of any of Examples 13-16, wherein the head-mounted display system is configured to process image content differently by increasing color saturation of image content presented to at least a portion of said central region of the user's vision field in comparison to image content presented to the peripheral region of the user's vision field.

18. The system of any of Examples 13-17, wherein the head-mounted display system is configured to process image content differently by sharpening of image content presented to at least a portion of said central region of the user's vision field in comparison to image content presented to the peripheral region of the user's vision field.

19. The system of Example 18, wherein sharpening comprises edge enhancing features in image content presented to at least a portion of said central region of the user's vision field in comparison to image content presented to the peripheral region of the user's vision field.

20. The system of any of Examples 13-19, wherein the head-mounted display system is configured to process image content differently by shifting the color balance of image content presented to at least a portion of said central region of the user's vision field in comparison to image content presented to the peripheral region of the user's vision field.

21. A head-mounted display system configured to project light to an eye of a user to display augmented reality image content, said user's eye having a vision field having a central region and a peripheral region disposed about said central region, said head-mounted display system comprising:
    a frame configured to be supported on a head of the user;
    a display disposed on the frame, said display configured to project light into said user's eye so as to present image content at said central and peripheral regions of said user's vision field, at least a portion of said display being transparent and disposed at a location in front of the user's eye when the user wears said head-mounted display system such that said transparent portion transmits light from a portion of the environment in front of the user to the user's eye to provide a view of said portion of the environment in front of the user;

processing electronics in communication with said display to control presentation of image content on said display,
wherein said head-mounted display system is configured to present image content to said peripheral region of the user's vision field that is de-emphasized in comparison to image content presented to the central region of the user's vision field.

22. The system of Example 21, further comprising one or more light sources configured to direct light into the eye the user to form images in said eye.

23. The system of Examples 21 or 22, wherein said at least a portion of said display that is transparent and disposed at a location in front of the user's eye comprises one or more waveguides configured to project the light to the user.

24. The system of Example 23, wherein said one or more light sources is configured to direct light into said one or more waveguides.

25. The system of any of Examples 22-24, wherein said light source comprises a fiber scanning projector.

26. The system of any of Examples 21-25, further comprising one or more sensors configured to monitor the environment.

27. The system of Example 26, wherein said one or more sensors comprises one or more outward-facing image capture devices configured to image said environment.

28. The system of Example 27, wherein said one or more outward-facing image capture devices configured to image said environment comprises one or more outward-facing cameras.

29. The system of any of Examples 26-28, wherein one or more sensors comprises a distance measuring device.

30. The system of Example 29, wherein said distance measuring device comprises a laser rangefinder.

31. The system of any of Examples 21-30, further an eye tracking device configured to track position and/or movement of said user's eye.

32. The system of Examples 21-31, further comprising one or more inward-facing image capture devices configured to image said user's eye.

33. The system of any of Examples 21-32, wherein the head-mounted display system is configured to process image content presented to at least a portion of said peripheral region of the user's vision field differently in comparison to image content presented to the central region of the user's vision field 34. The system of Example 33, wherein the head-mounted display system is configured to process image content differently by blurring image content presented to at least a portion of said peripheral region of the user's vision field in comparison to image content presented to the central region of the user's vision field.

35. The system of any of Examples 33-34, wherein the head-mounted display system is configured to process image content differently by darkening or attenuating image content presented to at least a portion of said peripheral region of the user's vision field in comparison to image content presented to the central region of the user's vision field.

36. The system of any of Examples 33-35, wherein the head-mounted display system is configured to process image content differently by reducing contrast of image content presented to at least a portion of said peripheral region of the user's vision field in comparison to image content presented to the central region of the user's vision field.

37. The system of any of Examples 33-36, wherein the head-mounted display system is configured to process image content differently by decreasing color saturation of image content presented to at least a portion of said peripheral region of the user's vision field in comparison to image content presented to the central region of the user's vision field.

38. The system of any of Examples 33-37, wherein the head-mounted display system is configured to process image content differently by decreasing sharpness of image content presented to at least a portion of said peripheral region of the user's vision field in comparison to image content presented to the central region of the user's vision field.

39. The system of Example 38, wherein decreasing sharpness comprises de-enhancing edges of features in image content presented to at least a portion of said peripheral region of the user's vision field in comparison to image content presented to the central region of the user's vision field.

40. The system of any of Examples 33-39, wherein the head-mounted display system is configured to process image content differently by shifting the color balance of image content presented to at least a portion of said peripheral region of the user's vision field in comparison to image content presented to the central region of the user's vision field.

41. The system of any of Examples 33-40, wherein the head-mounted display system is configured to process image content differently by shrinking image content presented to at least a portion of said peripheral region of the user's vision field in comparison to image content presented to the central region of the user's vision field.

42. The system of Example 14, wherein said magnifying is based at least in part on the resolution of the eye.

43. The system of Example 34, wherein said blurring comprises using a same color to blur said image content presented to said at least a portion of said peripheral region of the user's vision field.

44. The system of Example 44, wherein said same color comprises a high contrast color in comparison to a color in said image content presented to said central region of the user's vision field.

45. The system of any of Examples 1-20 or 42, wherein the system is configured to provide an alert to the user to indicate the presented image has been enhanced.

46. The system of any of Examples 21-41 or any of Examples 43-44, wherein the system is configured to provide an alert to the user to indicate the presented image has been de-emphasized.

47. The system of any of Examples 45 or 46, wherein the alert is a visual alert.

48. The system of any of Examples 45 or 46, wherein the alert is an audio alert.

49. The system of any of the above Examples, wherein said head-mounted display system is configured to construct a 3D representation of said at least part of the environment in front of the user and to interpret the representation of said at least part of the environment, said part of said environment comprising a patient, and said head-mounted display further configured to distinguish a first structure associated with the patient from a second structure associated with the patient.

50. The system of any of the above Examples, wherein said at least a portion of said display that is transparent and disposed at a location in front of the user's eye comprises one or more waveguides.

51. The system of Example 50, comprising one or more light sources configured to direct light into said one or more waveguides, the waveguides configured to direct light into the user's eye.

52. The system of any of Examples 50-51, wherein said one or more light sources comprises a fiber scanning projector.

53. The system of any of the above Examples, further comprising one or more sensors configured to monitor the environment.

54. The system of Example 53, wherein said one or more sensors comprise one or more outward-facing image capture devices configured to image said environment.

55. The system of Example 54, wherein said one or more outward-facing image capture devices configured to image said environment comprise one or more outward-facing cameras.

56. The system of any of the above Examples, further comprising a distance measuring device.

57. The system of any of the above Examples, further comprising an eye tracking device configured to track position and/or movement of said user's eye.

58. The system of any of the above Examples, wherein the head-mounted display is configured to estimate a volume of human tissue within the user's field of view.

59. The system of any of the above Examples, wherein the head-mounted display is configured to measure a distance between two objects in the environment.

60. The system of any of the above Examples, wherein the head-mounted display is configured to toggle between a first image modality and a second image modality that is presented on the display.

61. The system of Example 60, wherein the first image modality comprises an MRI scan.

62. The system of any of Examples 60-61, wherein the second image modality comprises an ultrasound.

63. The system of any of Examples 60-61, wherein the first image modality comprises an x-ray scan.

64. The system of any of the above Examples, further comprising an electronic emitter adapted to produce ultrasonic sound waves.

65. The system of any of the above Examples, further comprising a sensor adapted to convert ultrasonic sound waves into electrical signals.

66. The system of any of the above Examples, wherein the head-mounted display is configured to allow a user to place virtual fiducial markers on the portion of the environment in front of the user to the user's eye.

67. The system of any of the above Examples, wherein the head-mounted display is configured to project an image onto the display such that the image appears to be attached to a real-world object in the environment.

68. The system of any of the above Examples, wherein the head-mounted display is configured to display virtual cutting guidelines such that the virtual cutting guidelines appear to a user to be overlaid on a human body region to be cut or gives access to the part to be cut.

69. The system of Example 68, wherein an apparent location of the virtual cutting guidelines appears to be related to a position of a patient's body part.

70. The system of any of the above Examples, wherein the head-mounted display is configured to emit signals to obtain data on positions of objects in the portion of the environment in front of the user.

71. The system of any of the above Examples, wherein the head-mounted display is configured to obtain a position of objects in the portion of the environment in front of the user using a database of object locations.

72. The system of Example 71, wherein the head-mounted display is configured to set a point of reference based on said database of object locations and to project an image into the eye of a user such that the image appears to be fixed with respect to the point of reference.

73. The system of any of the above Examples, wherein the head-mounted display is configured to rotate a view of a 3D image of an object about an axis based on a user input.

74. The system of any of the above Examples, wherein the head-mounted display is configured to translate a view of an image of a 3D object based on a user input.

75. The system of any of the above Examples, wherein the head-mounted display is configured to display a first slice of a 3D image of an object.

76. The system of Example 76, wherein the head-mounted display is configured to sequence through an image of the first slice and an image of a second slice of the 3D image.

77. The system of any of the above Examples, wherein the head-mounted display is configured to transmit an image of a portion of the environment in front of the user such that a second user of head-mounted displays can view said image of said portion of the environment transmitted.

78. The system of any of the above Examples, wherein the head-mounted display is configured to alert a user of a step in a medical procedure.

79. The system of any of the above Examples, wherein the head-mounted display is configured to monitor a user's medical parameter and provide an alert based on the medical parameter.

80. The system of Example 79, wherein the user's medical parameter comprises a vital sign.

81. The system of any of the above Examples, wherein the head-mounted display is configured to emit ultrasound waves and to measure a signal resulting from said ultrasound waves and wherein the head-mounted display is further configured to form an ultrasound image based on the signal.

82. The system of any of the above Examples, wherein the head-mounted display is configured to alert the user of objects and/or events that are outside the user's field of view.

83. The system of any of the above Examples, further comprising one or more light sources configured to direct light into the eye of said user to form images in the eye.

84. The system of any of the above Examples, wherein said one or more light sources comprises a fiber scanning projector.

85. The system of Example 16, wherein increasing contrast comprises adjusting brightness or darkness of at least one color of said image content.

86. The system of Example 16, wherein increasing contrast comprises adding black, grey, white, or other color to at least one color of said image content.

87. The system of any of the above Examples, wherein the head-mounted display is configured to provide a degree of opacity at least in the vicinity of the presented image content.

88. The system of any of the above Examples, wherein the head-mounted display is configured to combine a first image modality with a second image modality different from the first image modality.

89. The system of Example 88, wherein the first image modality and the second image modality each comprises an image from an MRI, CT, PET, MRA, or CTA scan.

90. The system of Example 88 or 89, wherein the head-mounted display is configured to align the combined image of the first and second image modalities over the patient's actual anatomy.

Example Set IIA

1. A head-mounted display system configured to project light to an eye of a user to display augmented reality image content, said user's eye having a vision field having a central region and a peripheral region disposed about said central region, said head-mounted display system comprising:
a frame configured to be supported on a head of the user;
a display disposed on the frame, said display configured to project light into said user's eye so as to present image content to the user on a plurality of depth planes, at least a portion of said display comprising one or more waveguides, said one or more waveguides being transparent and disposed at a location in front of the user's eye when the user wears said head-mounted display system such that said transparent portion transmits light from a portion of an environment in front of the user to the user's eye to provide a view of said portion of the environment in front of the user, the central region of the vision field of the user's eye corresponding to a central region in the environment in front of the user and the peripheral region of the vision field of the user's eye corresponding to a peripheral region in the environment in front of the user;
an outward-facing image capture device configured to image said at least part of the environment in front of the user;
one or more sensors configured to measure the distance to objects in said at least part of the environment in front of the user;
one or more input devices configured to received input from said user;
processing electronics in communication with said display to control presentation of image content on said display,
wherein said head-mounted display system is configured to select an object in the environment corresponding to the peripheral region of the user's vision field based on input received by said one or more input devices, said one or more sensors is configured to measure the distance to said object after said selection, said outward-facing image capture device is configured to obtain an image of said object and said display is configured to present an enhanced image of said object at a depth plane determined based on said distance measured by said one or more sensors configured to measure distance, said enhanced image being enhanced in comparison to in other portions of the vision field, said enhanced image being presented at a location in the peripheral region of the user's vision field.

2. The system of Example 1, further comprising one or more light sources configured to direct light into an eye of a person to form an image in the eye.

3. The system of Example 2, wherein said one or more light sources are configured to direct light into said one or more waveguides.

4. The system of Examples 2 or 3, wherein said one or more light source comprises a fiber scanning projector.

5. The system of Example 1, wherein said depth planes comprise a first far depth plane and a second near depth plane, said first far depth plane farther from said user's eye than said second near depth plane when said head mounted display is worn by said user.

6. The system of Example 5, wherein said enhanced image is presented on said far depth plane.

7. The system of Example 5 or 6, wherein said display comprises optical elements having optical power such that said light projected into said eye is diverging so as to present image content from said second near depth plane.

8. The system of Example 7, wherein optical elements having optical power comprise lenses.

9. The system of Example 7 or 8, wherein optical elements having optical power comprise diffractive optical elements.

10. The system of Examples 1, wherein said head-mounted display system is configured to present said enhanced image content at a location in said peripheral region of the user's vision field that corresponds to the location in the peripheral region in the environment where said object is located.

11. The system of Examples 1, wherein said head-mounted display system is configured to move said enhanced image content to a location in said peripheral region of the user's vision field that does not correspond to the peripheral region in the environment where said object is located.

12. The system of Example 1, wherein said one or more sensors comprises one or more outward-facing image capture devices configured to image said environment.

13. The system of Example 12, wherein said one or more outward-facing image capture devices configured to image said environment comprises one or more outward-facing cameras.

14. The system of any of Examples 1, wherein one or more sensors comprises a distance measuring device.

15. The system of Example 14, wherein distance measuring device comprises a laser rangefinder.

16. The system of Examples 1, wherein said one or more input devices configured to receive input from said user comprise an inward-facing eye-tracking camera disposed to image said user's eye and track movement thereof.

17. The system of any of the Examples above, wherein said presenting said enhanced image comprises processing the image of said object differently in comparison to other portions of said user's vision field than where said image of said object is formed 18. The system of Example 17, wherein said processing the image differently comprises magnifying said image of said object in comparison to other portions of said user's vision field than where said image of said object is formed.

19. The system of any of Examples 17-18, wherein said processing the image differently comprises increasing brightness in said image of said object in comparison to other portions of said user's vision field than where said image of said object is formed.

20. The system of any of Examples 17-19, wherein said processing the image differently comprises increasing contrast of said image of said object in comparison to other portions of said user's vision field than where said image of said object is formed.

21. The system of any of Examples 17-20, wherein said processing the image differently comprises increasing color saturation of said image of said object in comparison to other portions of said user's vision field than where said image of said object is formed.

22. The system of any of Examples 17-21, wherein said processing the image differently comprises sharpening said image of said object in comparison to other portions of said user's vision field than where said image of said object is formed.

23. The system of Example 22, wherein said sharpening comprises edge enhancing features of said image of said object in comparison to other portions of said user's vision field than where said image of said object is formed.

24. The system of any of Examples 17-23, wherein said processing the image differently comprises shifting the color balance of said image of said object in comparison to other portions of said user's vision field than where said image of said object is formed.

25. The system of any of the Examples above, wherein said other portions of the vision field comprise other portions of said peripheral region of said vision field.

26. The system of any of the Examples above, wherein said other portions of the vision field comprise at least a portion said central region of said vision field.

27. A head-mounted display system configured to project light to an eye of a user to display augmented reality image content, said user's eye having a vision field having a central region and a peripheral region disposed about said central region, said head-mounted display system comprising:
- a frame configured to be supported on a head of the user;
- a display disposed on the frame, said display configured to project light into said user's eye so as to present image content to the user on a plurality of depth planes, at least a portion of said display comprising one or more waveguides, said one or more waveguides being transparent and disposed at a location in front of the user's eye when the user wears said head-mounted display system such that said transparent portion transmits light from a portion of an environment in front of the user to the user's eye to provide a view of said portion of the environment in front of the user, the central region of the vision field of the user's eye corresponding to a central region in the environment in front of the user and the peripheral region of the vision field of the user's eye corresponding to a peripheral region in the environment in front of the user;
- an outward-facing image capture device configured to image said at least part of environment in front of the user;
- one or more sensors configured measure the distance to objects in said at least part of environment in front of the user;
- one or more input devices configured received input from said user;
- processing electronics in communication with said display to control presentation of image content on said display,
- wherein said head-mounted display system is configured to select an object in the environment corresponding to the peripheral region of the user's vision field based on input received by said one or more input devices, said one or more sensors is configured to measure the distance to said object after said selection, said outward-facing image capture device is configured to obtain an image of said object and said display is configured to present an image of said object at a depth plane determined based on said distance measured by said one or more sensors configured to measure distance, said image of said object being presented at a location in the peripheral region of the user's vision field, said display configured to de-emphasize images formed in other portions of the vision field in comparison to said image of said object.

28. The system of Example 27, further comprising one or more light sources configured to direct light into an eye of a person to form an image in the eye.

29. The system of Example 28, wherein said one or more light sources are configured to direct light into said one or more waveguides.

30. The system of Examples 28 or 29, wherein said one or more light source comprises a fiber scanning projector.

31. The system of Example 27, wherein said depth planes comprise a first far depth plane and a second near depth plane, said first far depth plane farther from said user's eye than said second near depth plane when said head mounted display is worn by said user.

32. The system of Example 31, wherein said image of said object is presented on said far depth plane.

33. The system of Example 31 or 32, wherein said display comprises optical elements having optical power such that said light projected into said eye is diverging so as to present image content from said second near depth plane.

34. The system of Example 33, wherein optical elements having optical power comprise lenses.

35. The system of Examples 33 or 34, wherein optical elements having optical power comprise diffractive optical elements.

36. The system of Examples 27, wherein said head-mounted display system is configured to present said image of said object at a location in said peripheral region of the user's vision field that corresponds to the location in the peripheral region in the environment where said object is located.

37. The system of Examples 27, wherein said head-mounted display system is configured to move said image of said object to a location in said peripheral region of the user's vision field that does not correspond to the peripheral region in the environment where said object is located.

38. The system of Example 27, wherein said one or more sensors comprise one or more outward-facing image capture devices configured to image said environment.

39. The system of Example 38, wherein said one or more outward-facing image capture devices configured to image said environment comprises one or more outward-facing cameras.

40. The system of any of Examples 27, wherein said one or more sensors comprises a distance measuring device.

41. The system of Example 40, wherein said distance measuring device comprises a laser rangefinder.

42. The system of Examples 27, wherein said one or more input devices configured to receive input from said user comprise an inward-facing eye-tracking camera disposed to image said user's eye and track movement thereof.

43. The system of any of Examples 27-42, wherein said head mounted display system is configured to process images formed in other portions of said user's vision field than where said image of said object is formed differently that said image of said object.

44. The system of Example 43, wherein said head mounted display system is configured to process images differently by shrinking or reducing size of images formed in other portions of said user's vision field than where said image of said object is formed in comparison to said image of said object.

45. The system of any of Examples 43-44, wherein said head mounted display system is configured to process images differently by darkening or attenuating images formed in other portions of said user's vision field than where said image of said object is formed in comparison to said image of said object.

46. The system of any of Examples 43-45, wherein said head mounted display system is configured to process images differently by reducing contrast of images formed in other portions of said user's vision field than where said image of said object is formed in comparison to said image of said object.

47. The system of any of Examples 43-46, wherein said head mounted display system is configured to process images differently by decreasing color saturation of images formed in other portions of said user's vision field than where said image of said object is formed in comparison to said image of said object.

48. The system of any of Examples 43-47, wherein said head mounted display system is configured to process images differently by decreasing sharpness of images formed in other portions of said user's vision field than where said image of said object is formed in comparison to said image of said object.

49. The system of Example 48, wherein said decreasing sharpness comprises de-enhancing edges of features in said images formed in other portions of said user's vision field than where said image of said object is formed in comparison to said image of said object.

50. The system of Example 48 or 49, wherein said decreasing sharpness comprises blurring images formed in other portions of said user's vision field than where said image of said object is formed in comparison to said image of said object.

51. The system of any of Examples 48-50, wherein said head mounted display system is configured to process images differently by shifting the color balance of images formed in other portions of said user's vision field than where said image of said object is formed in comparison to said image of said object.

52. The system of any of Examples 27-51, wherein said other portions of the vision field comprise other portions of said peripheral region of said vision field.

53. The system of any of Examples 27-52, wherein said other portions of the vision field comprise at least a portion said central region of said vision field.

54. The system of Example 5, wherein said enhanced image is presented on said near depth plane.

55. The system of Example 5 or 54, wherein said display comprises optical elements having optical power such that said light projected into said eye is diverging so as to present image content from said first far depth plane.

56. The system of Example 18, wherein said magnifying is based at least in part on the resolution of the eye.

57. The system of Example 31, wherein said image of said object is presented on said near depth plane.

58. The system of Example 31 or 57, wherein said display comprises optical elements having optical power such that said light projected into said eye is diverging so as to present image content from said first far depth plane.

59. The system of Example 50, wherein said blurring comprises using a same color to blur said images formed in other portions of said user vision field.

60. The system of Example 59, wherein said same color comprises a high contrast color in comparison to a color in said image of said object.

61. The system of any of Examples 1-26 or any of Examples 54-56, wherein the system is configured to provide an alert to the user to indicate the presented image has been enhanced.

62. The system of any of Examples 27-53 or any of Examples 57-60, wherein the system is configured to provide an alert to the user to indicate the presented image has been de-emphasized.

63. The system of any of Examples 61 or 62, wherein the alert is a visual alert.

64. The system of any of Examples 61 or 62, wherein the alert is an audio alert.

65. The system of any of the above Examples, wherein said head-mounted display system is configured to construct a 3D representation of said at least part of the environment in front of the user and to interpret the representation of said at least part of the environment, said part of said environment comprising a patient, and said head-mounted display further configured to distinguish a first structure associated with the patient from a second structure associated with the patient.

66. The system of any of the above Examples, wherein said at least a portion of said display that is transparent and disposed at a location in front of the user's eye comprises one or more waveguides.

67. The system of Example 66, comprising one or more light sources configured to direct light into said one or more waveguides, the waveguides configured to direct light into the user's eye.

68. The system of any of Examples 66-67, wherein said one or more light sources comprises a fiber scanning projector.

69. The system of any of the above Examples, further comprising one or more sensors configured to monitor the environment.

70. The system of Example 69, wherein said one or more sensors comprise one or more outward-facing image capture devices configured to image said environment.

71. The system of Example 70, wherein said one or more outward-facing image capture devices configured to image said environment comprise one or more outward-facing cameras.

72. The system of any of the above Examples, further comprising a distance measuring device.

73. The system of any of the above Examples, further comprising an eye tracking device configured to track position and/or movement of said user's eye.

74. The system of any of the above Examples, wherein the head-mounted display is configured to estimate a volume of human tissue within the user's field of view.

75. The system of any of the above Examples, wherein the head-mounted display is configured to measure a distance between two objects in the environment.

76. The system of any of the above Examples, wherein the head-mounted display is configured to toggle between a first image modality and a second image modality that is presented on the display.

77. The system of Example 76, wherein the first image modality comprises an MRI scan.

78. The system of any of Examples 76-77, wherein the second image modality comprises an ultrasound.

79. The system of any of Examples 76-78, wherein the first image modality comprises an x-ray scan.

80. The system of any of the above Examples, further comprising an electronic emitter adapted to produce ultrasonic sound waves.

81. The system of any of the above Examples, further comprising a sensor adapted to convert ultrasonic sound waves into electrical signals.

82. The system of any of the above Examples, wherein the head-mounted display is configured to allow a user to place virtual fiducial markers on the portion of the environment in front of the user to the user's eye.

83. The system of any of the above Examples, wherein the head-mounted display is configured to project an image onto the display such that the image appears to be attached to a real-world object in the environment.

84. The system of any of the above Examples, wherein the head-mounted display is configured to display virtual cutting guidelines such that the virtual cutting guidelines appear to a user to be overlaid on a human body region to be cut or gives access to the part to be cut.

85. The system of Example 84, wherein an apparent location of the virtual cutting guidelines appears to be related to a position of a patient's body part.

86. The system of any of the above Examples, wherein the head-mounted display is configured to emit signals to obtain data on positions of objects in the portion of the environment in front of the user.

87. The system of any of the above Examples, wherein the head-mounted display is configured to obtain a position of objects in the portion of the environment in front of the user using a database of object locations.

88. The system of Example 87, wherein the head-mounted display is configured to set a point of reference based on said database of object locations and to project an image into the eye of a user such that the image appears to be fixed with respect to the point of reference.

89. The system of any of the above Examples, wherein the head-mounted display is configured to rotate a view of a 3D image of an object about an axis based on a user input.

90. The system of any of the above Examples, wherein the head-mounted display is configured to translate a view of an image of a 3D object based on a user input.

91. The system of any of the above Examples, wherein the head-mounted display is configured to display a first slice of a 3D image of an object.

92. The system of Example 91, wherein the head-mounted display is configured to sequence through an image of the first slice and an image of a second slice of the 3D image.

93. The system of any of the above Examples, wherein the head-mounted display is configured to transmit an image of a portion of the environment in front of the user such that a second user of head-mounted displays can view said image of said portion of the environment transmitted.

94. The system of any of the above Examples, wherein the head-mounted display is configured to alert a user of a step in a medical procedure.

95. The system of any of the above Examples, wherein the head-mounted display is configured to monitor a user's medical parameter and provide an alert based on the medical parameter.

96. The system of Example 95, wherein the user's medical parameter comprises a vital sign.

97. The system of any of the above Examples, wherein the head-mounted display is configured to emit ultrasound waves and to measure a signal resulting from said ultrasound waves and wherein the head-mounted display is further configured to form an ultrasound image based on the signal.

98. The system of any of the above Examples, wherein the head-mounted display is configured to alert the user of objects and/or events that are outside the user's field of view.

99. The system of any of the above Examples, further comprising one or more light sources configured to direct light into the eye of said user to form images in the eye.

100. The system of any of the above Examples, wherein said one or more light sources comprises a fiber scanning projector.

101. The system of Example 20, wherein increasing contrast comprises adjusting brightness or darkness of at least one color of said image content.

102. The system of Example 20, wherein increasing contrast comprises adding black, grey, white, or other color to at least one color of said image content.

103. The system of any of the above Examples, wherein the head-mounted display is configured to provide a degree of opacity at least in the vicinity of the presented image content.

104. The system of any of the above Examples, wherein the head-mounted display is configured to combine a first image modality with a second image modality different from the first image modality.

105. The system of Example 104, wherein the first image modality and the second image modality each comprises an image from an MRI, CT, PET, MRA, or CTA scan.

106. The system of Example 104 or 105, wherein the head-mounted display is configured to align the combined image of the first and second image modalities over the patient's actual anatomy.

Example Set IIB

1. A head-mounted display system configured to project light to an eye of a user to display augmented reality image content, said user's eye having a vision field having a central region and a peripheral region disposed about said central region, said head-mounted display system comprising:
    a frame configured to be supported on a head of the user;
    a display disposed on the frame, said display configured to project light into said user's eye so as to present image content to the user on a plurality of depth planes, at least a portion of said display comprising one or more waveguides, said one or more waveguides being transparent and disposed at a location in front of the user's eye when the user wears said head-mounted display system such that said transparent portion transmits light from a portion of an environment in front of the user to the user's eye to provide a view of said portion of the environment in front of the user, the central region of the vision field of the user's eye corresponding to a central region in the environment in front of the user and the peripheral region of the vision field of the user's eye corresponding to a peripheral region in the environment in front of the user;
    an outward-facing image capture device configured to image said at least part of the environment in front of the user;
    one or more sensors configured to measure the distance to objects in said at least part of the environment in front of the user;
    one or more input devices configured to received input from said user;
    processing electronics in communication with said display to control presentation of image content on said display,
    wherein said head-mounted display system is configured to select an object in the environment corresponding to the central region of the user's vision field based on input received by said one or more input devices, said one or more sensors is configured to measure the distance to said object after said selection, said outward-facing image capture device is configured to obtain an image of said object and said display is configured to present an enhanced image of said object at a depth plane determined based on said distance measured by said one or more sensors configured to measure distance, said enhanced image being enhanced in comparison to in other portions of the vision field, said enhanced image being presented at a location in the central region of the user's vision field.

2. The system of Example 1, further comprising one or more light sources configured to direct light into an eye of a person to form an image in the eye.

3. The system of Example 2, wherein said one or more light sources are configured to direct light into said one or more waveguides.

4. The system of Examples 2 or 3, wherein said one or more light source comprises a fiber scanning projector.

5. The system of Example 1, wherein said depth planes comprise a first far depth plane and a second near depth plane, said first far depth plane farther from said user's eye than said second near depth plane when said head mounted display is worn by said user.

6. The system of Example 5, wherein said enhanced image is presented on said far depth plane.

7. The system of Example 5 or 6, wherein said display comprises optical elements having optical power such that said light projected into said eye is diverging so as to present image content from said second near depth plane.

8. The system of Example 7, wherein optical elements having optical power comprise lenses.

9. The system of Example 7 or 8, wherein optical elements having optical power comprise diffractive optical elements.

10. The system of Examples 1, wherein said head-mounted display system is configured to present said enhanced image content at a location in said central region of the user's vision field that corresponds to the location in the central region in the environment where said object is located.

11. The system of Examples 1, wherein said head-mounted display system is configured to move said enhanced image content to a location in said central region of the user's vision field that does not correspond to the central region in the environment where said object is located.

12. The system of Example 1, wherein said one or more sensors comprises one or more outward-facing image capture devices configured to image said environment.

13. The system of Example 12, wherein said one or more outward-facing image capture devices configured to image said environment comprises one or more outward-facing cameras.

14. The system of any of Examples 1, wherein one or more sensors comprises a distance measuring device.

15. The system of Example 14, wherein distance measuring device comprises a laser rangefinder.

16. The system of Examples 1, wherein said one or more input devices configured to receive input from said user comprise an inward-facing eye-tracking camera disposed to image said user's eye and track movement thereof.

17. The system of any of the Examples above, wherein said presenting said enhanced image comprises processing the image of said object differently in comparison to other portions of said user's vision field than where said image of said object is formed 18. The system of Example 17, wherein said processing the image differently comprises magnifying said image of said object in comparison to other portions of said user's vision field than where said image of said object is formed.

19. The system of any of Examples 17-18, wherein said processing the image differently comprises increasing brightness in said image of said object in comparison to other portions of said user's vision field than where said image of said object is formed.

20. The system of any of Examples 17-19, wherein said processing the image differently comprises increasing contrast of said image of said object in comparison to other portions of said user's vision field than where said image of said object is formed.

21. The system of any of Examples 17-20, wherein said processing the image differently comprises increasing color saturation of said image of said object in comparison to other portions of said user's vision field than where said image of said object is formed.

22. The system of any of Examples 17-21, wherein said processing the image differently comprises sharpening said image of said object in comparison to other portions of said user's vision field than where said image of said object is formed.

23. The system of Example 22, wherein said sharpening comprises edge enhancing features of said image of said object in comparison to other portions of said user's vision field than where said image of said object is formed.

24. The system of any of Examples 17-23, wherein said processing the image differently comprises shifting the color balance of said image of said object in comparison to other portions of said user's vision field than where said image of said object is formed.

25. The system of any of the Examples above, wherein said other portions of the vision field comprise other portions of said central region of said vision field.

26. The system of any of the Examples above, wherein said other portions of the vision field comprise at least a portion said peripheral region of said vision field.

27. A head-mounted display system configured to project light to an eye of a user to display augmented reality image content, said user's eye having a vision field having a central region and a peripheral region disposed about said central region, said head-mounted display system comprising:
    a frame configured to be supported on a head of the user;
    a display disposed on the frame, said display configured to project light into said user's eye so as to present image content to the user on a plurality of depth planes, at least a portion of said display comprising one or more waveguides, said one or more waveguides being transparent and disposed at a location in front of the user's eye when the user wears said head-mounted display system such that said transparent portion transmits light from a portion of an environment in front of the user to the user's eye to provide a view of said portion of the environment in front of the user, the central region of the vision field of the user's eye corresponding to a central region in the environment in front of the user and the peripheral region of the vision field of the user's eye corresponding to a peripheral region in the environment in front of the user;
    an outward-facing image capture device configured to image said at least part of environment in front of the user;
    one or more sensors configured measure the distance to objects in said at least part of environment in front of the user;
    one or more input devices configured received input from said user;
    processing electronics in communication with said display to control presentation of image content on said display, wherein said head-mounted display system is configured to select an object in the environment corresponding to the central region of the user's vision field based on input received by said one or more input devices, said one or more sensors is configured to measure the distance to said object after said selection, said outward-facing image capture device is configured to obtain an image of said object and said display is configured to present an image of said object at a depth plane determined based on said distance measured by said one or more sensors configured to measure distance, said image of said object being presented at a location in the central region of the user's vision field, said display configured to de-emphasize images formed in other portions of the vision field in comparison to said image of said object.

28. The system of Example 27, further comprising one or more light sources configured to direct light into an eye of a person to form an image in the eye.

29. The system of Example 28, wherein said one or more light sources are configured to direct light into said one or more waveguides.

30. The system of Examples 28 or 29, wherein said one or more light source comprises a fiber scanning projector.

31. The system of Example 27, wherein said depth planes comprise a first far depth plane and a second near depth plane, said first far depth plane farther from said user's eye than said second near depth plane when said head mounted display is worn by said user.

32. The system of Example 31, wherein said image of said object is presented on said far depth plane.

33. The system of Example 31 or 32, wherein said display comprises optical elements having optical power such that said light projected into said eye is diverging so as to present image content from said second near depth plane.

34. The system of Example 33, wherein optical elements having optical power comprise lenses.

35. The system of Examples 33 or 34, wherein optical elements having optical power comprise diffractive optical elements.

36. The system of Examples 27, wherein said head-mounted display system is configured to present said image of said object at a location in said central region of the user's vision field that corresponds to the location in the central region in the environment where said object is located.

37. The system of Examples 27, wherein said head-mounted display system is configured to move said image of said object to a location in said central region of the user's vision field that does not correspond to the central region in the environment where said object is located.

38. The system of Example 27, wherein said one or more sensors comprise one or more outward-facing image capture devices configured to image said environment.

39. The system of Example 38, wherein said one or more outward-facing image capture devices configured to image said environment comprises one or more outward-facing cameras.

40. The system of any of Examples 27, wherein said one or more sensors comprises a distance measuring device.

41. The system of Example 40, wherein said distance measuring device comprises a laser rangefinder.

42. The system of Examples 27, wherein said one or more input devices configured to receive input from said user comprise an inward-facing eye-tracking camera disposed to image said user's eye and track movement thereof.

43. The system of any of Examples 27-42, wherein said head mounted display system is configured to process images formed in other portions of said user's vision field than where said image of said object is formed differently that said image of said object.

44. The system of Example 43, wherein said head mounted display system is configured to process images differently by shrinking or reducing size of images formed in other portions of said user's vision field than where said image of said object is formed in comparison to said image of said object.

45. The system of any of Examples 43-44, wherein said head mounted display system is configured to process images differently by darkening or attenuating images formed in other portions of said user's vision field than where said image of said object is formed in comparison to said image of said object.

46. The system of any of Examples 43-45, wherein said head mounted display system is configured to process images differently by reducing contrast of images formed in other portions of said user's vision field than where said image of said object is formed in comparison to said image of said object.

47. The system of any of Examples 43-46, wherein said head mounted display system is configured to process images differently by decreasing color saturation of images formed in other portions of said user's vision field than where said image of said object is formed in comparison to said image of said object.

48. The system of any of Examples 43-47, wherein said head mounted display system is configured to process images differently by decreasing sharpness of images formed in other portions of said user's vision field than where said image of said object is formed in comparison to said image of said object.

49. The system of Example 48, wherein said decreasing sharpness comprises de-enhancing edges of features in said images formed in other portions of said user's vision field than where said image of said object is formed in comparison to said image of said object.

50. The system of Example 48 or 49, wherein said decreasing sharpness comprises blurring images formed in other portions of said user's vision field than where said image of said object is formed in comparison to said image of said object.

51. The system of any of Examples 48-50, wherein said head mounted display system is configured to process images differently by shifting the color balance of images formed in other portions of said user's vision field than where said image of said object is formed in comparison to said image of said object.

52. The system of any of Examples 27-51, wherein said other portions of the vision field comprise other portions of said central region of said vision field.

53. The system of any of Examples 27-52, wherein said other portions of the vision field comprise at least a portion said peripheral region of said vision field.

54. The system of Example 5, wherein said enhanced image is presented on said near depth plane.

55. The system of Example 5 or 54, wherein said display comprises optical elements having optical power such that said light projected into said eye is diverging so as to present image content from said first far depth plane.

56. The system of Example 18, wherein said magnifying is based at least in part on the resolution of the eye.

57. The system of Example 31, wherein said image of said object is presented on said near depth plane.

58. The system of Example 31 or 57, wherein said display comprises optical elements having optical power such that said light projected into said eye is diverging so as to present image content from said first far depth plane.

59. The system of Example 50, wherein said blurring comprises using a same color to blur said images formed in other portions of said user vision field.

60. The system of Example 59, wherein said same color comprises a high contrast color in comparison to a color in said image of said object.

61. The system of any of Examples 1-26 or any of Examples 54-56, wherein the system is configured to provide an alert to the user to indicate the presented image has been enhanced.

62. The system of any of Examples 27-53 or any of Examples 57-60, wherein the system is configured to provide an alert to the user to indicate the presented image has been de-emphasized.

63. The system of any of Examples 61 or 62, wherein the alert is a visual alert.

64. The system of any of Examples 61 or 62, wherein the alert is an audio alert.

65. The system of any of the above Examples, wherein said head-mounted display system is configured to construct a 3D representation of said at least part of the environment in front of the user and to interpret the representation of said at least part of the environment, said part of said environment comprising a patient, and said head-mounted display further configured to distinguish a first structure associated with the patient from a second structure associated with the patient.

66. The system of any of the above Examples, wherein said at least a portion of said display that is transparent and disposed at a location in front of the user's eye comprises one or more waveguides.

67. The system of Example 66, comprising one or more light sources configured to direct light into said one or more waveguides, the waveguides configured to direct light into the user's eye.

68. The system of any of Examples 66-67, wherein said one or more light sources comprises a fiber scanning projector.

69. The system of any of the above Examples, further comprising one or more sensors configured to monitor the environment.

70. The system of Example 69, wherein said one or more sensors comprise one or more outward-facing image capture devices configured to image said environment.

71. The system of Example 70, wherein said one or more outward-facing image capture devices configured to image said environment comprise one or more outward-facing cameras.

72. The system of any of the above Examples, further comprising a distance measuring device.

73. The system of any of the above Examples, further comprising an eye tracking device configured to track position and/or movement of said user's eye.

74. The system of any of the above Examples, wherein the head-mounted display is configured to estimate a volume of human tissue within the user's field of view.

75. The system of any of the above Examples, wherein the head-mounted display is configured to measure a distance between two objects in the environment.

76. The system of any of the above Examples, wherein the head-mounted display is configured to toggle between a first image modality and a second image modality that is presented on the display.

77. The system of Example 76, wherein the first image modality comprises an MRI scan.

78. The system of any of Examples 76-77, wherein the second image modality comprises an ultrasound.

79. The system of any of Examples 76-78, wherein the first image modality comprises an x-ray scan.

80. The system of any of the above Examples, further comprising an electronic emitter adapted to produce ultrasonic sound waves.

81. The system of any of the above Examples, further comprising a sensor adapted to convert ultrasonic sound waves into electrical signals.

82. The system of any of the above Examples, wherein the head-mounted display is configured to allow a user to place virtual fiducial markers on the portion of the environment in front of the user to the user's eye.

83. The system of any of the above Examples, wherein the head-mounted display is configured to project an image onto the display such that the image appears to be attached to a real-world object in the environment.

84. The system of any of the above Examples, wherein the head-mounted display is configured to display virtual cutting guidelines such that the virtual cutting guidelines appear to a user to be overlaid on a human body region to be cut or gives access to the part to be cut.

85. The system of Example 84, wherein an apparent location of the virtual cutting guidelines appears to be related to a position of a patient's body part.

86. The system of any of the above Examples, wherein the head-mounted display is configured to emit signals to obtain data on positions of objects in the portion of the environment in front of the user.

87. The system of any of the above Examples, wherein the head-mounted display is configured to obtain a position of objects in the portion of the environment in front of the user using a database of object locations.

88. The system of Example 87, wherein the head-mounted display is configured to set a point of reference based on said database of object locations and to project an image into the eye of a user such that the image appears to be fixed with respect to the point of reference.

89. The system of any of the above Examples, wherein the head-mounted display is configured to rotate a view of a 3D image of an object about an axis based on a user input.

90. The system of any of the above Examples, wherein the head-mounted display is configured to translate a view of an image of a 3D object based on a user input.

91. The system of any of the above Examples, wherein the head-mounted display is configured to display a first slice of a 3D image of an object.

92. The system of Example 91, wherein the head-mounted display is configured to sequence through an image of the first slice and an image of a second slice of the 3D image.

93. The system of any of the above Examples, wherein the head-mounted display is configured to transmit an image of a portion of the environment in front of the user such that a second user of head-mounted displays can view said image of said portion of the environment transmitted.

94. The system of any of the above Examples, wherein the head-mounted display is configured to alert a user of a step in a medical procedure.

95. The system of any of the above Examples, wherein the head-mounted display is configured to monitor a user's medical parameter and provide an alert based on the medical parameter.

96. The system of Example 95, wherein the user's medical parameter comprises a vital sign.

97. The system of any of the above Examples, wherein the head-mounted display is configured to emit ultrasound waves and to measure a signal resulting from said ultrasound waves and wherein the head-mounted display is further configured to form an ultrasound image based on the signal.

98. The system of any of the above Examples, wherein the head-mounted display is configured to alert the user of objects and/or events that are outside the user's field of view.

99. The system of any of the above Examples, further comprising one or more light sources configured to direct light into the eye of said user to form images in the eye.

100. The system of any of the above Examples, wherein said one or more light sources comprises a fiber scanning projector.

101. The system of Example 20, wherein increasing contrast comprises adjusting brightness or darkness of at least one color of said image content.

102. The system of Example 20, wherein increasing contrast comprises adding black, grey, white, or other color to at least one color of said image content.

103. The system of any of the above Examples, wherein the head-mounted display is configured to provide a degree of opacity at least in the vicinity of the presented image content.

104. The system of any of the above Examples, wherein the head-mounted display is configured to combine a first image modality with a second image modality different from the first image modality.

105. The system of Example 104, wherein the first image modality and the second image modality each comprises an image from an MRI, CT, PET, MRA, or CTA scan.

106. The system of Example 104 or 105, wherein the head-mounted display is configured to align the combined image of the first and second image modalities over the patient's actual anatomy.

Example Set III

1. A head-mounted display system configured to project light to an eye of a user to display augmented reality image content, said user's eye having a vision field having a central region and a peripheral region disposed about said central region, said head-mounted display system comprising:
    a frame configured to be supported on a head of the user;
    a display disposed on the frame, said display configured to project light into said user's eye so as to present image content to the user on a plurality of depth planes, at least a portion of said display comprising one or more waveguides, said one or more waveguides being transparent and disposed at a location in front of the user's eye when the user wears said head-mounted display system such that said transparent portion transmits light from a portion of an environment in front of the user to the user's eye to provide a view of said portion of the environment in front of the user, the central region of the vision field of the user's eye corresponding to a central region in the environment in front of the user and the peripheral region of the vision field of the user's eye corresponding to a peripheral region in the environment in front of the user;
    an outward-facing image capture device configured to image said at least part of environment in front of the user;
    one or more input devices configured received input from said user;
    processing electronics in communication with said display to control presentation of image content on said display,
    wherein said depth planes comprise a first depth plane and a second depth plane, said distance to said object corresponds more to said first depth plane than said second depth plane when said head mounted display is worn by said user,
    wherein said head-mounted display system is configured to select an object in the environment in the user's vision field based on input received by said one or more input devices, said outward-facing image capture device is configured to obtain an image of said object and said display is configured to present an image of said object at said second depth plane.

2. The system of Examples 1, wherein said one or more input devices configured to receive input from said user comprise an inward-facing eye-tracking camera disposed to image said user's eye and track movement thereof.

3. The system of any of the Examples above, wherein said one or more sensors comprises one or more outward-facing image capture devices configured to image said environment.

4. The system of Example 3, wherein said one or more outward-facing image capture devices configured to image said environment comprises one or more outward-facing cameras.

5. The system of any of the Examples above, further comprising one or more sensors configured measure the distance to objects in said at least part of environment in front of the user.

6. The system of Examples 5, wherein said one or more sensors is configured to measure the distance to said object after said selection of said object.

7. The system of any of Examples 5-6, wherein one or more sensors comprises a distance measuring device.

8. The system of Example 7, wherein distance measuring device comprises a laser rangefinder.

9. The system of any of the Examples above, wherein said first depth plane comprises a far depth plane, said second depth plane comprises a near depth plane, said far depth plane farther from said user's eye than said near depth plane when said head mounted display is worn by said user.

10. The system of any of Examples 1-8, wherein said first depth plane comprises a near depth plane, said second depth plane comprises a far depth plane, said far depth plane farther from said user's eye than said near depth plane when said head mounted display is worn by said user.

11. The system of any of the Examples above, wherein said display is configured to present additional image content at said second depth plane.

12. The system of Example 11, wherein said additional image is the selected object.

13. The system of any of the above Examples, wherein said image of said object presented at said second depth plane is magnified.

14. The system of any of the above Examples, wherein said image of said object presented at said second depth plane is not magnified.

15. The system of Example 15, wherein said image of said object presented at said second depth plane is reduced in size.

16. The system of any of the above Examples, wherein said one or more input devices configured to receive input from said user comprise head pose sensors.

17. The system of Example 16, wherein said head pose sensors comprise accelerometers or IMUs.

18. The system of any of the above Examples, wherein said head mounted display system is configured to present said image of said object in said central region.

19. The system of any of the above Examples, wherein said head mounted display system is configured to present said image of said object in said peripheral region.

20. The system of any of the above Examples, wherein said head-mounted display system is configured to construct a 3D representation of said at least part of the environment in front of the user and to interpret the representation of said at least part of the environment, said part of said environment comprising a patient, and said head-mounted display further configured to distinguish a first structure associated with the patient from a second structure associated with the patient.

21. The system of any of the above Examples, wherein said at least a portion of said display that is transparent and disposed at a location in front of the user's eye comprises one or more waveguides.

22. The system of Example 21, comprising one or more light sources configured to direct light into said one or more waveguides, the waveguides configured to direct light into the user's eye.

23. The system of any of Examples 21-22, wherein said one or more light sources comprises a fiber scanning projector.

24. The system of any of the above Examples, further comprising one or more sensors configured to monitor the environment.

25. The system of Example 24, wherein said one or more sensors comprise one or more outward-facing image capture devices configured to image said environment.

26. The system of Example 25, wherein said one or more outward-facing image capture devices configured to image said environment comprise one or more outward-facing cameras.

27. The system of any of the above Examples, further comprising a distance measuring device.

28. The system of any of the above Examples, further comprising an eye tracking device configured to track position and/or movement of said user's eye.

29. The system of any of the above Examples, wherein the head-mounted display is configured to estimate a volume of human tissue within the user's field of view.

30. The system of any of the above Examples, wherein the head-mounted display is configured to measure a distance between two objects in the environment.

31. The system of any of the above Examples, wherein the head-mounted display is configured to toggle between a first image modality and a second image modality that is presented on the display.

32. The system of Example 31, wherein the first image modality comprises an MRI scan.

33. The system of any of Examples 31-32, wherein the second image modality comprises an ultrasound.

34. The system of any of Examples 31-33, wherein the first image modality comprises an x-ray scan.

35. The system of any of the above Examples, further comprising an electronic emitter adapted to produce ultrasonic sound waves.

36. The system of any of the above Examples, further comprising a sensor adapted to convert ultrasonic sound waves into electrical signals.

37. The system of any of the above Examples, wherein the head-mounted display is configured to allow a user to place virtual fiducial markers on the portion of the environment in front of the user to the user's eye.

38. The system of any of the above Examples, wherein the head-mounted display is configured to project an image onto the display such that the image appears to be attached to a real-world object in the environment.

39. The system of any of the above Examples, wherein the head-mounted display is configured to display virtual cutting guidelines such that the virtual cutting guidelines appear to a user to be overlaid on a human body region to be cut or gives access to the part to be cut.

40. The system of Example 39, wherein an apparent location of the virtual cutting guidelines appears to be related to a position of a patient's body part.

41. The system of any of the above Examples, wherein the head-mounted display is configured to emit signals to obtain data on positions of objects in the portion of the environment in front of the user.

42. The system of any of the above Examples, wherein the head-mounted display is configured to obtain a position of objects in the portion of the environment in front of the user using a database of object locations.

43. The system of Example 42, wherein the head-mounted display is configured to set a point of reference based on said database of object locations and to project an image into the eye of a user such that the image appears to be fixed with respect to the point of reference.

44. The system of any of the above Examples, wherein the head-mounted display is configured to rotate a view of a 3D image of an object about an axis based on a user input.

45. The system of any of the above Examples, wherein the head-mounted display is configured to translate a view of an image of a 3D object based on a user input.

46. The system of any of the above Examples, wherein the head-mounted display is configured to display a first slice of a 3D image of an object.

47. The system of Example 46, wherein the head-mounted display is configured to sequence through an image of the first slice and an image of a second slice of the 3D image.

48. The system of any of the above Examples, wherein the head-mounted display is configured to transmit an image of a portion of the environment in front of the user such that a second user of head-mounted displays can view said image of said portion of the environment transmitted.

49. The system of any of the above Examples, wherein the head-mounted display is configured to alert a user of a step in a medical procedure.

50. The system of any of the above Examples, wherein the head-mounted display is configured to monitor a user's medical parameter and provide an alert based on the medical parameter.

51. The system of Example 50, wherein the user's medical parameter comprises a vital sign.

52. The system of any of the above Examples, wherein the head-mounted display is configured to emit ultrasound waves and to measure a signal resulting from said ultrasound waves and wherein the head-mounted display is further configured to form an ultrasound image based on the signal.

53. The system of any of the above Examples, wherein the head-mounted display is configured to alert the user of objects and/or events that are outside the user's field of view.

54. The system of any of the above Examples, further comprising one or more light sources configured to direct light into the eye of said user to form images in the eye.

55. The system of any of the above Examples, wherein said one or more light sources comprises a fiber scanning projector.

56. The system of any of the above Examples, wherein the head-mounted display is configured to combine a first image modality with a second image modality different from the first image modality.

57. The system of Example 56, wherein the first image modality and the second image modality each comprises an image from an MRI, CT, PET, MRA, or CTA scan.

58. The system of Example 56 or 57, wherein the head-mounted display is configured to align the combined image of the first and second image modalities over the patient's actual anatomy.

Example Set IV

1. A head-mounted display system configured to project light to an eye of a user to display augmented reality image content, said user's eye having a vision field having a central region and a peripheral region disposed about said central region, said head-mounted display system comprising:
  a frame configured to be supported on a head of the user;
  a display disposed on the frame, said display configured to project light into said user's eye so as to present image content at said central region of said user's vision field, at least a portion of said display being transparent and disposed at a location in front of the user's eye when the user wears said head-mounted display system such that said transparent portion transmits light from a portion of the environment in front of the user to the user's eye to provide a view of said portion of the environment in front of the user;
  one or more capture devices configured to capture a lighting condition of the environment;
  processing electronics in communication with said display to control presentation of image content on said display,
  wherein said head-mounted display system is configured to present image content to the user's vision field that is enhanced based at least in part on the lighting condition of the environment.

2. The system of Example 1, further comprising one or more light sources configured to direct light into the eye of said user to form images in the eye.

3. The system of Examples 1 or 2, wherein said at least a portion of said display that is transparent and disposed at a location in front of the user's eye comprises one or more waveguides configured to project the light to the user.

4. The system of Example 3, wherein said one or more light sources is configured to direct light into said one or more waveguides.

5. The system of any of Examples 2-4, wherein said light source comprises a fiber scanning projector.

6. The system of any of Examples 1-5, wherein the one or more capture devices comprise one or more image capture devices.

7. The system of Example 6, wherein the one or more image capture devices comprise one or more cameras.

8. The system of any of Examples 1-5, wherein the one or more capture devices comprise one or more light sensors.

9. The system of Example 8, wherein the one or more light sensors comprise one or more light meters.

10. The system of any of the above Examples, wherein the one or more capture devices are configured to measure luminance of the environment.

11. The system of any of the above Examples, further comprising a distance measuring device.

12. The system of Example 11, wherein said distance measuring device comprises a laser rangefinder.

13. The system of any of the above Examples, further comprising an eye tracking device configured to track position and/or movement of said user's eye.

14. The system of any of Examples 1-13, further comprising one or more inward-facing image capture devices configured to image said user's eye.

15. The system of any of the above Examples, wherein the head-mounted display system is configured to magnify the image content based at least in part on the lighting condition of the environment.

16. The system of Example 15, wherein said magnifying is based at least in part on the resolution of the eye.

17. The system of any of the above Examples, wherein the head-mounted display system is configured to increase brightness in the image content based at least in part on the lighting condition of the environment.

18. The system of any of the above Examples, wherein the head-mounted display system is configured to increase contrast in the image content based at least in part on the lighting condition of the environment.

19. The system of any of the above Examples, wherein the head-mounted display system is configured to increase color saturation in the image content based at least in part on the lighting condition of the environment.

20. The system of any of the above Examples, wherein the head-mounted display system is configured to sharpen the image content based at least in part on the lighting condition of the environment.

21. The system of Example 20, wherein sharpening comprises adding edge enhancing features in the image content based at least in part on the lighting condition of the environment.

22. The system of any of the above Examples, wherein the head-mounted display system is configured to shift the color balance of the image content based at least in part on the lighting condition of the environment.

23. The system of any of the above Examples, wherein the system is configured to provide an alert to the user to indicate the image content has been enhanced.

24. The system of Example 23, wherein the alert is a visual alert.

25. The system of Example 23, wherein the alert is an audio alert.

26. A head-mounted display system configured to project light to an eye of a user to display augmented reality image content, said user's eye having a vision field having a central region and a peripheral region disposed about said central region, said head-mounted display system comprising:
  a frame configured to be supported on a head of the user;
  a display disposed on the frame, said display configured to project light into said user's eye so as to present image content at said central region of said user's vision field, at least a portion of said display being transparent and disposed at a location in front of the user's eye when the user wears said head-mounted display system such that said transparent portion transmits light from a portion of the environment in front of the user to the user's eye to provide a view of said portion of the environment in front of the user;
  one or more capture devices configured to capture a lighting condition of the environment;
  processing electronics in communication with said display to control presentation of image content on said display,
  wherein said head-mounted display system is configured to present image content to the user's vision field that is de-emphasized based at least in part on the lighting condition of the environment.

27. The system of Example 26, further comprising one or more light sources configured to direct light into the eye of said user to form images in the eye.

28. The system of Examples 26 or 27, wherein said at least a portion of said display that is transparent and disposed at a location in front of the user's eye comprises one or more waveguides configured to project the light to the user.

29. The system of Example 28, wherein said one or more light sources is configured to direct light into said one or more waveguides.

30. The system of any of Examples 27-29, wherein said light source comprises a fiber scanning projector.

31. The system of any of Examples 26-30, wherein the one or more capture devices comprise one or more image capture devices.

32. The system of Example 31, wherein the one or more image capture devices comprise one or more cameras.

33. The system of any of Examples 26-30, wherein the one or more capture devices comprise one or more light sensors.

34. The system of Example 33, wherein the one or more light sensors comprise one or more light meters.

35. The system of any of Examples 26-34, wherein the one or more capture devices are configured to measure luminance of the environment.

36. The system of any of Examples 26-35, further comprising a distance measuring device.

37. The system of Example 36, wherein said distance measuring device comprises a laser rangefinder.

38. The system of any of Examples 26-37, further comprising an eye tracking device configured to track position and/or movement of said user's eye.

39. The system of any of Examples 26-38, further comprising one or more inward-facing image capture devices configured to image said user's eye.

40. The system of any of Examples 26-39, wherein the head-mounted display system is configured to reduce size of the image content based at least in part on the lighting condition of the environment.

41. The system of Example 40, wherein said reducing size is based at least in part on the resolution of the eye.

42. The system of any of Examples 26-41, wherein the head-mounted display system is configured to darken or attenuate the image content based at least in part on the lighting condition of the environment.

43. The system of any of Examples 26-42, wherein the head-mounted display system is configured to reduce contrast in the image content based at least in part on the lighting condition of the environment.

44. The system of any of Examples 26-43, wherein the head-mounted display system is configured to decrease color saturation in the image content based at least in part on the lighting condition of the environment.

45. The system of any of Examples 26-44, wherein the head-mounted display system is configured to decrease sharpness of the image content based at least in part on the lighting condition of the environment.

46. The system of Example 45, wherein decreasing sharpness comprises de-enhancing edges of features in the image content based at least in part on the lighting condition of the environment.

47. The system of any of Examples 26-46, wherein the head-mounted display system is configured to shift the color balance of the image content based at least in part on the lighting condition of the environment.

48. The system of any of Examples 26-47, wherein the head-mounted display system is configured to blur the image content based at least in part on the lighting condition of the environment.

49. The system of Example 48, wherein said blurring comprises using a same color to blur said image content.

50. The system of any of Examples 26-49, wherein the system is configured to provide an alert to the user to indicate the image content has been de-emphasized.

51. The system of Example 50, wherein the alert is a visual alert.

52. The system of Example 50, wherein the alert is an audio alert.

53. The system of any of the above Examples, wherein said head-mounted display system is configured to construct a 3D representation of said at least part of the environment in front of the user and to interpret the representation of said at least part of the environment, said part of said environment comprising a patient, and said head-mounted display further configured to distinguish a first structure associated with the patient from a second structure associated with the patient.

54. The system of any of the above Examples, wherein said at least a portion of said display that is transparent and disposed at a location in front of the user's eye comprises one or more waveguides.

55. The system of Example 54, comprising one or more light sources configured to direct light into said one or more waveguides, the waveguides configured to direct light into the user's eye.

56. The system of any of Examples 54-55, wherein said one or more light sources comprises a fiber scanning projector.

57. The system of any of the above Examples, further comprising one or more sensors configured to monitor the environment.

58. The system of Example 57, wherein said one or more sensors comprise one or more outward-facing image capture devices configured to image said environment.

59. The system of Example 58, wherein said one or more outward-facing image capture devices configured to image said environment comprise one or more outward-facing cameras.

60. The system of any of the above Examples, further comprising a distance measuring device.

61. The system of any of the above Examples, further comprising an eye tracking device configured to track position and/or movement of said user's eye.

62. The system of any of the above Examples, wherein the head-mounted display is configured to estimate a volume of human tissue within the user's field of view.

63. The system of any of the above Examples, wherein the head-mounted display is configured to measure a distance between two objects in the environment.

64. The system of any of the above Examples, wherein the head-mounted display is configured to toggle between a first image modality and a second image modality that is presented on the display.

65. The system of Example 64, wherein the first image modality comprises an MRI scan.

66. The system of any of Examples 64-65, wherein the second image modality comprises an ultrasound.

67. The system of any of Examples 64-66, wherein the first image modality comprises an x-ray scan.

68. The system of any of the above Examples, further comprising an electronic emitter adapted to produce ultrasonic sound waves.

69. The system of any of the above Examples, further comprising a sensor adapted to convert ultrasonic sound waves into electrical signals.

70. The system of any of the above Examples, wherein the head-mounted display is configured to allow a user to place virtual fiducial markers on the portion of the environment in front of the user to the user's eye.

71. The system of any of the above Examples, wherein the head-mounted display is configured to project an image onto the display such that the image appears to be attached to a real-world object in the environment.

72. The system of any of the above Examples, wherein the head-mounted display is configured to display virtual cutting guidelines such that the virtual cutting guidelines appear to a user to be overlaid on a human body region to be cut or gives access to the part to be cut.

73. The system of Example 72, wherein an apparent location of the virtual cutting guidelines appears to be related to a position of a patient's body part.

74. The system of any of the above Examples, wherein the head-mounted display is configured to emit signals to obtain data on positions of objects in the portion of the environment in front of the user.

75. The system of any of the above Examples, wherein the head-mounted display is configured to obtain a position of objects in the portion of the environment in front of the user using a database of object locations.

76. The system of Example 75, wherein the head-mounted display is configured to set a point of reference based on said database of object locations and to project an image into the eye of a user such that the image appears to be fixed with respect to the point of reference.

77. The system of any of the above Examples, wherein the head-mounted display is configured to rotate a view of a 3D image of an object about an axis based on a user input.

78. The system of any of the above Examples, wherein the head-mounted display is configured to translate a view of an image of a 3D object based on a user input.

79. The system of any of the above Examples, wherein the head-mounted display is configured to display a first slice of a 3D image of an object.

80. The system of Example 79, wherein the head-mounted display is configured to sequence through an image of the first slice and an image of a second slice of the 3D image.

81. The system of any of the above Examples, wherein the head-mounted display is configured to transmit an image of a portion of the environment in front of the user such that a second user of head-mounted displays can view said image of said portion of the environment transmitted.

82. The system of any of the above Examples, wherein the head-mounted display is configured to alert a user of a step in a medical procedure.

83. The system of any of the above Examples, wherein the head-mounted display is configured to monitor a user's medical parameter and provide an alert based on the medical parameter.

84. The system of Example 83, wherein the user's medical parameter comprises a vital sign.

85. The system of any of the above Examples, wherein the head-mounted display is configured to emit ultrasound waves and to measure a signal resulting from said ultrasound waves and wherein the head-mounted display is further configured to form an ultrasound image based on the signal.

86. The system of any of the above Examples, wherein the head-mounted display is configured to alert the user of objects and/or events that are outside the user's field of view.

87. The system of any of the above Examples, further comprising one or more light sources configured to direct light into the eye of said user to form images in the eye.

88. The system of any of the above Examples, wherein said one or more light sources comprises a fiber scanning projector.

89. The system of Example 18, wherein increasing contrast comprises adjusting brightness or darkness of at least one color of said image content.

90. The system of Example 18, wherein increasing contrast comprises adding black, grey, white, or other color to at least one color of said image content.

91. The system of any of the above Examples, wherein the head-mounted display is configured to provide a degree of opacity at least in the vicinity of the presented image content.

92. The system of any of the above Examples, wherein the head-mounted display is configured to combine a first image modality with a second image modality different from the first image modality.

93. The system of Example 92, wherein the first image modality and the second image modality each comprises an image from an MRI, CT, PET, MRA, or CTA scan.

94. The system of Example 92 or 93, wherein the head-mounted display is configured to align the combined image of the first and second image modalities over the patient's actual anatomy.

Example Set IVA

1. A head-mounted display system configured to project light to an eye of a user to display augmented reality image content, said user's eye having a vision field having a central region and a peripheral region disposed about said central region, said head-mounted display system comprising:
   a frame configured to be supported on a head of the user;
   a display disposed on the frame, said display configured to project light into said user's eye so as to present image content at said central region of said user's vision field, at least a portion of said display being transparent and disposed at a location in front of the user's eye when the user wears said head-mounted display system such that said transparent portion transmits light from a portion of the environment in front of the user to the user's eye to provide a view of said portion of the environment in front of the user;
   one or more capture devices configured to capture a lighting condition of the environment;
   processing electronics in communication with said display to control presentation of image content on said display,
   wherein said head-mounted display system is configured to project light to a location of the user's eye so as to present image content to a portion of the central region of the user's vision field that is enhanced based at least in part on the lighting condition of the environment.

2. The system of Example 1, wherein under a photopic lighting condition, the image content is enhanced inversely based on the projected light location's density of cones.

3. The system of Example 2, wherein the photopic lighting condition of the environment has a luminance from 10 $cd/m^2$ to $10^8$ $cd/m^2$.

4. The system of Example 1, wherein under a scotopic lighting condition, the image content is enhanced inversely based on the projected light location's density of rods.

5. The system of Example 4, wherein the scotopic lighting condition of the environment has a luminance from $10^{-3.5}$ cd/m² to $10^{-6}$ cd/m².

6. The system of Example 1, wherein under a mesopic lighting condition, the image content is enhanced based at least in part on time spent in the mesopic lighting condition.

7. The system of Example 6, wherein the mesopic lighting condition of the environment has a luminance from $10^{-3}$ cd/m² to $10^{0.5}$ cd/m².

8. The system of Example 6 or 7, wherein the system is configured to determine whether cones or rods dominate in the user's eye based at least in part on the time spent in the mesopic lighting condition.

9. The system of any of Examples 6-8, wherein the image content is enhanced inversely based on the projected light location's density of cones when the cones dominate in the user's eye.

10. The system of any of Examples 6-8, wherein the image content is enhanced inversely based to the projected light location's density of rods of the user's eye when the rods dominate the user's eye.

11. The system of any of the above Examples, wherein the system comprises a timer or clock to monitor the time spent in the lighting condition.

12. The system of any of the above Examples, further comprising one or more light sources configured to direct light into the eye of said user to form images in the eye.

13. The system of any of the above Examples, wherein said at least a portion of said display that is transparent and disposed at a location in front of the user's eye comprises one or more waveguides configured to project the light to the user.

14. The system of Example 13, wherein said one or more light sources is configured to direct light into said one or more waveguides.

15. The system of any of Examples 12-14, wherein said light source comprises a fiber scanning projector.

16. The system of any of Examples 1-15, wherein the one or more capture devices comprise one or more image capture devices.

17. The system of Example 16, wherein the one or more image capture devices comprise one or more cameras.

18. The system of any of Examples 1-15, wherein the one or more capture devices comprise one or more light sensors.

19. The system of Example 18, wherein the one or more light sensors comprise one or more light meters.

20. The system of any of the above Examples, wherein the one or more capture devices are configured to measure luminance of the environment.

21. The system of any of the above Examples, wherein the one or more capture devices comprise a detector array comprising an array of pixels, wherein the detector array is configured to integrate light level over the pixels to capture the lighting condition.

22. The system of any of the above Examples, wherein the one or more capture devices comprise one or more inward-facing cameras configured to detect a pupil size to capture the lighting condition.

23. The system of any of the above Examples, further comprising a distance measuring device.

24. The system of Example 23, wherein said distance measuring device comprises a laser rangefinder.

25. The system of any of the above Examples, further comprising an eye tracking device configured to track position and/or movement of said user's eye.

26. The system of any of Examples 1-25, further comprising one or more inward-facing image capture devices configured to image said user's eye.

27. The system of any of the above Examples, wherein the head-mounted display system is configured to magnify the image content based at least in part on the lighting condition of the environment.

28. The system of Example 27, wherein said magnifying is based at least in part on the resolution of the eye.

29. The system of any of the above Examples, wherein the head-mounted display system is configured to increase brightness in the image content based at least in part on the lighting condition of the environment.

30. The system of any of the above Examples, wherein the head-mounted display system is configured to increase contrast in the image content based at least in part on the lighting condition of the environment.

31. The system of Example 30, wherein the head-mounted display system is configured to increase contrast based at least in part on the contrast sensitivity of the eye.

32. The system of any of the above Examples, wherein the head-mounted display system is configured to increase color saturation in the image content based at least in part on the lighting condition of the environment.

33. The system of any of the above Examples, wherein the head-mounted display system is configured to sharpen the image content based at least in part on the lighting condition of the environment.

34. The system of Example 33, wherein sharpening comprises adding edge enhancing features in the image content based at least in part on the lighting condition of the environment.

35. The system of any of the above Examples, wherein the head-mounted display system is configured to shift the color balance of the image content based at least in part on the lighting condition of the environment.

36. The system of any of the above Examples, wherein the system is configured to provide an alert to the user to indicate the image content has been enhanced.

37. The system of Example 36, wherein the alert is a visual alert.

38. The system of Example 36, wherein the alert is an audio alert.

39. The system of any of the above Examples, wherein said head-mounted display system is configured to construct a 3D representation of said at least part of the environment in front of the user and to interpret the representation of said at least part of the environment, said part of said environment comprising a patient, and said head-mounted display further configured to distinguish a first structure associated with the patient from a second structure associated with the patient.

40. The system of any of the above Examples, further comprising one or more sensors configured to monitor the environment.

41. The system of Example 40, wherein said one or more sensors comprise one or more outward-facing image capture devices configured to image said environment.

42. The system of Example 41, wherein said one or more outward-facing image capture devices configured to image said environment comprise one or more outward-facing cameras.

43. The system of any of the above Examples, wherein the head-mounted display is configured to estimate a volume of human tissue within the user's field of view.

44. The system of any of the above Examples, wherein the head-mounted display is configured to measure a distance between two objects in the environment.

45. The system of any of the above Examples, wherein the head-mounted display is configured to toggle between a first image modality and a second image modality that is presented on the display.

46. The system of Example 45, wherein the first image modality comprises an MRI scan.

47. The system of any of Examples 45-46, wherein the second image modality comprises an ultrasound.

48. The system of any of Examples 45-47, wherein the first image modality comprises an x-ray scan.

49. The system of any of the above Examples, further comprising an electronic emitter adapted to produce ultrasonic sound waves.

50. The system of any of the above Examples, further comprising a sensor adapted to convert ultrasonic sound waves into electrical signals.

51. The system of any of the above Examples, wherein the head-mounted display is configured to allow a user to place virtual fiducial markers on the portion of the environment in front of the user to the user's eye.

52. The system of any of the above Examples, wherein the head-mounted display is configured to project an image onto the display such that the image appears to be attached to a real-world object in the environment.

53. The system of any of the above Examples, wherein the head-mounted display is configured to display virtual cutting guidelines such that the virtual cutting guidelines appear to a user to be overlaid on a human body region to be cut or gives access to the part to be cut.

54. The system of Example 53, wherein an apparent location of the virtual cutting guidelines appears to be related to a position of a patient's body part.

55. The system of any of the above Examples, wherein the head-mounted display is configured to emit signals to obtain data on positions of objects in the portion of the environment in front of the user.

56. The system of any of the above Examples, wherein the head-mounted display is configured to obtain a position of objects in the portion of the environment in front of the user using a database of object locations.

57. The system of Example 56, wherein the head-mounted display is configured to set a point of reference based on said database of object locations and to project an image into the eye of a user such that the image appears to be fixed with respect to the point of reference.

58. The system of any of the above Examples, wherein the head-mounted display is configured to rotate a view of a 3D image of an object about an axis based on a user input.

59. The system of any of the above Examples, wherein the head-mounted display is configured to translate a view of an image of a 3D object based on a user input.

60. The system of any of the above Examples, wherein the head-mounted display is configured to display a first slice of a 3D image of an object.

61. The system of Example 60, wherein the head-mounted display is configured to sequence through an image of the first slice and an image of a second slice of the 3D image.

62. The system of any of the above Examples, wherein the head-mounted display is configured to transmit an image of a portion of the environment in front of the user such that a second user of head-mounted displays can view said image of said portion of the environment transmitted.

63. The system of any of the above Examples, wherein the head-mounted display is configured to alert a user of a step in a medical procedure.

64. The system of any of the above Examples, wherein the head-mounted display is configured to monitor a medical parameter and provide an alert based on the medical parameter.

65. The system of Example 64, wherein the medical parameter comprises a vital sign.

66. The system of any of the above Examples, wherein the head-mounted display is configured to emit ultrasound waves and to measure a signal resulting from said ultrasound waves and wherein the head-mounted display is further configured to form an ultrasound image based on the signal.

67. The system of any of the above Examples, wherein the head-mounted display is configured to alert the user of objects and/or events that are outside the user's field of view.

68. The system of Example 21, wherein the detector array comprises an outward looking camera configured to image the environment.

69. The system of any of the above Examples, wherein said head-mounted display system is configured to project light to a location of the user's eye so as to present image content to a portion of the central region of the user's vision field that is enhanced with respect to image content presented to a portion of the peripheral region.

70. The system of any of the above Examples, wherein said head-mounted display system is configured to project light to a location of the user's eye so as to present image content to a portion of the central region of the user's vision field that is enhanced with respect to image content presented to another portion of the central region.

71. The system of any of the above Examples, wherein the system is configured to determine how to present the image content in the user's eye based at least in part on a temporal aspect of the lighting condition of the environment.

72. The system of any of the above Examples, wherein said display is configured to project light into said user's eye at different divergences so as to present said image content as if said image content is coming from different depths.

73. The system of Example 30, wherein increasing contrast comprises adjusting brightness or darkness of at least one color of said image content.

74. The system of Example 30, wherein increasing contrast comprises adding black, grey, white, or other color to at least one color of said image content.

75. The system of any of the above Examples, wherein the head-mounted display is configured to provide a degree of opacity at least in the vicinity of the presented image content.

76. The system of any of the above Examples, wherein the head-mounted display is configured to combine a first image modality with a second image modality different from the first image modality.

77. The system of Example 76, wherein the first image modality and the second image modality each comprises an image from an MRI, CT, PET, MRA, or CTA scan.

78. The system of Example 76 or 77, wherein the head-mounted display is configured to align the combined image of the first and second image modalities over the patient's actual anatomy.

Example Set IVB

1. A head-mounted display system configured to project light to an eye of a user to display augmented reality image content, said user's eye having a vision field having a central region and a peripheral region disposed about said central region, said head-mounted display system comprising:
- a frame configured to be supported on a head of the user;
- a display disposed on the frame, said display configured to project light into said user's eye so as to present image content at said peripheral region of said user's vision field, at least a portion of said display being transparent and disposed at a location in front of the user's eye when the user wears said head-mounted display system such that said transparent portion transmits light from a portion of the environment in front of the user to the user's eye to provide a view of said portion of the environment in front of the user;
- one or more capture devices configured to capture a lighting condition of the environment;
- processing electronics in communication with said display to control presentation of image content on said display,
- wherein said head-mounted display system is configured to project light to a location of the user's eye so as to present image content to a portion of the peripheral region of the user's vision field that is enhanced based at least in part on the lighting condition of the environment.

2. The system of Example 1, wherein under a photopic lighting condition, the image content is enhanced inversely based on the projected light location's density of cones.

3. The system of Example 2, wherein the photopic lighting condition of the environment has a luminance from 10 $cd/m^2$ to $10^8$ $cd/m^2$.

4. The system of Example 1, wherein under a scotopic lighting condition, the image content is enhanced inversely based on the projected light location's density of rods.

5. The system of Example 4, wherein the scotopic lighting condition of the environment has a luminance from $10^{-3.5}$ $cd/m^2$ to $10^{-6}$ $cd/m^2$.

6. The system of Example 1, wherein under a mesopic lighting condition, the image content is enhanced based at least in part on time spent in the mesopic lighting condition.

7. The system of Example 6, wherein the mesopic lighting condition of the environment has a luminance from $10^{-3}$ $cd/m^2$ to $10^{0.5}$ $cd/m^2$.

8. The system of Example 6 or 7, wherein the system is configured to determine whether cones or rods dominate in the user's eye based at least in part on the time spent in the mesopic lighting condition.

9. The system of any of Examples 6-8, wherein the image content is enhanced inversely based on the projected light location's density of cones when the cones dominate in the user's eye.

10. The system of any of Examples 6-8, wherein the image content is enhanced inversely based to the projected light location's density of rods of the user's eye when the rods dominate the user's eye.

11. The system of any of the above Examples, wherein the system comprises a timer or clock to monitor the time spent in the lighting condition.

12. The system of any of the above Examples, further comprising one or more light sources configured to direct light into the eye of said user to form images in the eye.

13. The system of any of the above Examples, wherein said at least a portion of said display that is transparent and disposed at a location in front of the user's eye comprises one or more waveguides configured to project the light to the user.

14. The system of Example 13, wherein said one or more light sources is configured to direct light into said one or more waveguides.

15. The system of any of Examples 12-14, wherein said light source comprises a fiber scanning projector.

16. The system of any of Examples 1-15, wherein the one or more capture devices comprise one or more image capture devices.

17. The system of Example 16, wherein the one or more image capture devices comprise one or more cameras.

18. The system of any of Examples 1-15, wherein the one or more capture devices comprise one or more light sensors.

19. The system of Example 18, wherein the one or more light sensors comprise one or more light meters.

20. The system of any of the above Examples, wherein the one or more capture devices are configured to measure luminance of the environment.

21. The system of any of the above Examples, wherein the one or more capture devices comprise a detector array comprising an array of pixels, wherein the detector array is configured to integrate light level over the pixels to capture the lighting condition.

22. The system of any of the above Examples, wherein the one or more capture devices comprise one or more inward-facing cameras configured to detect a pupil size to capture the lighting condition.

23. The system of any of the above Examples, further comprising a distance measuring device.

24. The system of Example 23, wherein said distance measuring device comprises a laser rangefinder.

25. The system of any of the above Examples, further comprising an eye tracking device configured to track position and/or movement of said user's eye.

26. The system of any of Examples 1-25, further comprising one or more inward-facing image capture devices configured to image said user's eye.

27. The system of any of the above Examples, wherein the head-mounted display system is configured to magnify the image content based at least in part on the lighting condition of the environment.

28. The system of Example 27, wherein said magnifying is based at least in part on the resolution of the eye.

29. The system of any of the above Examples, wherein the head-mounted display system is configured to increase brightness in the image content based at least in part on the lighting condition of the environment.

30. The system of any of the above Examples, wherein the head-mounted display system is configured to increase contrast in the image content based at least in part on the lighting condition of the environment.

31. The system of Example 30, wherein the head-mounted display system is configured to increase contrast based at least in part on the contrast sensitivity of the eye.

32. The system of any of the above Examples, wherein the head-mounted display system is configured to increase color saturation in the image content based at least in part on the lighting condition of the environment.

33. The system of any of the above Examples, wherein the head-mounted display system is configured to sharpen the image content based at least in part on the lighting condition of the environment.

34. The system of Example 33, wherein sharpening comprises adding edge enhancing features in the image content based at least in part on the lighting condition of the environment.

35. The system of any of the above Examples, wherein the head-mounted display system is configured to shift the color balance of the image content based at least in part on the lighting condition of the environment.

36. The system of any of the above Examples, wherein the system is configured to provide an alert to the user to indicate the image content has been enhanced.

37. The system of Example 36, wherein the alert is a visual alert.

38. The system of Example 36, wherein the alert is an audio alert.

39. The system of any of the above Examples, wherein said head-mounted display system is configured to construct a 3D representation of said at least part of the environment in front of the user and to interpret the representation of said at least part of the environment, said part of said environment comprising a patient, and said head-mounted display further configured to distinguish a first structure associated with the patient from a second structure associated with the patient.

40. The system of any of the above Examples, further comprising one or more sensors configured to monitor the environment.

41. The system of Example 40, wherein said one or more sensors comprise one or more outward-facing image capture devices configured to image said environment.

42. The system of Example 41, wherein said one or more outward-facing image capture devices configured to image said environment comprise one or more outward-facing cameras.

43. The system of any of the above Examples, wherein the head-mounted display is configured to estimate a volume of human tissue within the user's field of view.

44. The system of any of the above Examples, wherein the head-mounted display is configured to measure a distance between two objects in the environment.

45. The system of any of the above Examples, wherein the head-mounted display is configured to toggle between a first image modality and a second image modality that is presented on the display.

46. The system of Example 45, wherein the first image modality comprises an MRI scan.

47. The system of any of Examples 45-46, wherein the second image modality comprises an ultrasound.

48. The system of any of Examples 45-47, wherein the first image modality comprises an x-ray scan.

49. The system of any of the above Examples, further comprising an electronic emitter adapted to produce ultrasonic sound waves.

50. The system of any of the above Examples, further comprising a sensor adapted to convert ultrasonic sound waves into electrical signals.

51. The system of any of the above Examples, wherein the head-mounted display is configured to allow a user to place virtual fiducial markers on the portion of the environment in front of the user to the user's eye.

52. The system of any of the above Examples, wherein the head-mounted display is configured to project an image onto the display such that the image appears to be attached to a real-world object in the environment.

53. The system of any of the above Examples, wherein the head-mounted display is configured to display virtual cutting guidelines such that the virtual cutting guidelines appear to a user to be overlaid on a human body region to be cut or gives access to the part to be cut.

54. The system of Example 53, wherein an apparent location of the virtual cutting guidelines appears to be related to a position of a patient's body part.

55. The system of any of the above Examples, wherein the head-mounted display is configured to emit signals to obtain data on positions of objects in the portion of the environment in front of the user.

56. The system of any of the above Examples, wherein the head-mounted display is configured to obtain a position of objects in the portion of the environment in front of the user using a database of object locations.

57. The system of Example 56, wherein the head-mounted display is configured to set a point of reference based on said database of object locations and to project an image into the eye of a user such that the image appears to be fixed with respect to the point of reference.

58. The system of any of the above Examples, wherein the head-mounted display is configured to rotate a view of a 3D image of an object about an axis based on a user input.

59. The system of any of the above Examples, wherein the head-mounted display is configured to translate a view of an image of a 3D object based on a user input.

60. The system of any of the above Examples, wherein the head-mounted display is configured to display a first slice of a 3D image of an object.

61. The system of Example 60, wherein the head-mounted display is configured to sequence through an image of the first slice and an image of a second slice of the 3D image.

62. The system of any of the above Examples, wherein the head-mounted display is configured to transmit an image of a portion of the environment in front of the user such that a second user of head-mounted displays can view said image of said portion of the environment transmitted.

63. The system of any of the above Examples, wherein the head-mounted display is configured to alert a user of a step in a medical procedure.

64. The system of any of the above Examples, wherein the head-mounted display is configured to monitor a medical parameter and provide an alert based on the medical parameter.

65. The system of Example 64, wherein the medical parameter comprises a vital sign.

66. The system of any of the above Examples, wherein the head-mounted display is configured to emit ultrasound waves and to measure a signal resulting from said ultrasound waves and wherein the head-mounted display is further configured to form an ultrasound image based on the signal.

67. The system of any of the above Examples, wherein the head-mounted display is configured to alert the user of objects and/or events that are outside the user's field of view.

68. The system of Example 21, wherein the detector array comprises an outward looking camera configured to image the environment.

69. The system of any of the above Examples, wherein said head-mounted display system is configured to project light to a location of the user's eye so as to present image content to a portion of the peripheral region of the user's vision field that is enhanced with respect to image content presented to a portion of the central region.

70. The system of any of the above Examples, wherein said head-mounted display system is configured to project light to a location of the user's eye so as to present image content to a portion of the peripheral region of the user's vision field that is enhanced with respect to image content presented to another portion of the peripheral region.

71. The system of any of the above Examples, wherein the system is configured to determine how to present the image content in the user's eye based at least in part on a temporal aspect of the lighting condition of the environment.

72. The system of any of the above Examples, wherein said display is configured to project light into said user's eye at different divergences so as to present said image content as if said image content is coming from different depths.

73. The system of Example 30, wherein increasing contrast comprises adjusting brightness or darkness of at least one color of said image content.

74. The system of Example 30, wherein increasing contrast comprises adding black, grey, white, or other color to at least one color of said image content.

75. The system of any of the above Examples, wherein the head-mounted display is configured to provide a degree of opacity at least in the vicinity of the presented image content.

76. The system of any of the above Examples, wherein the head-mounted display is configured to combine a first image modality with a second image modality different from the first image modality.

77. The system of Example 76, wherein the first image modality and the second image modality each comprises an image from an MRI, CT, PET, MRA, or CTA scan.

78. The system of Example 76 or 77, wherein the head-mounted display is configured to align the combined image of the first and second image modalities over the patient's actual anatomy.

Example Set IVC

1. A head-mounted display system configured to project light to an eye of a user to display augmented reality image content, said user's eye having a vision field having a central region and a peripheral region disposed about said central region, said head-mounted display system comprising:
   a frame configured to be supported on a head of the user;
   a display disposed on the frame, said display configured to project light into said user's eye so as to present image content to said user's vision field, at least a portion of said display being transparent and disposed at a location in front of the user's eye when the user wears said head-mounted display system such that said transparent portion transmits light from a portion of the environment in front of the user to the user's eye to provide a view of said portion of the environment in front of the user;
   one or more capture devices configured to capture a lighting condition of the environment;
   processing electronics in communication with said display to control presentation of image content on said display,
   wherein said head-mounted display system is configured to present image content from a first portion of the user's vision field to a second portion of the user's vision field based at least in part on the lighting condition of the environment, and wherein under the lighting condition of the environment, the second portion corresponds to a location of the user's eye having a higher visual acuity than the first portion.

2. The system of Example 1, wherein under a photopic lighting condition, the second portion corresponds to a location of the user's eye having a higher density of cones than the first portion.

3. The system of Example 2, wherein the photopic lighting condition of the environment has a luminance from 10 $cd/m^2$ to $10^8$ $cd/m^2$.

4. The system of Example 2 or 3, wherein the first portion comprises a portion in the peripheral region and the second portion comprises a portion in the central region.

5. The system of Example 2 or 3, wherein the first portion comprises a portion in the central region and the second portion comprises another portion in the central region.

6. The system of Example 2 or 3, wherein the first portion comprises a portion in the peripheral region and the second portion comprises another portion in the peripheral region.

7. The system of Example 1, wherein under a scotopic lighting condition, the second portion corresponds to a location of the user's eye having a higher density of rods than the first portion.

8. The system of Example 7, wherein the scotopic lighting condition of the environment has a luminance from $10^{-3.5}$ $cd/m^2$ to $10^{-6}$ $cd/m^2$.

9. The system of Example 7 or 8, wherein the first portion comprises a portion in the central region and the second portion comprises a region in the peripheral region.

10. The system of Example 7 or 8, wherein the first portion comprises a portion in the peripheral region and the second portion comprises another region in the peripheral region.

11. The system of Example 1, wherein under a mesopic lighting condition, the system is configured to present image content from the first portion to the second portion based at least in part on time spent in the mesopic lighting condition.

12. The system of Example 11, wherein the mesopic lighting condition of the environment has a luminance from $10^{-3}$ $cd/m^2$ to $10^{0.5}$ $cd/m^2$.

13. The system of Example 11 or 12, wherein the system is configured to determine whether cones or rods dominate in the user's eye based at least in part on the time spent in the mesopic lighting condition.

14. The system of any of Examples 11-13, wherein the second portion corresponds to a location of the user's eye having a higher density of cones than the first portion when the cones dominate in the user's eye.

15. The system of Example 14, wherein the first portion comprises a portion in the peripheral region and the second portion comprises a portion in the central region.

16. The system of Example 14, wherein the first portion comprises a portion in the central region and the second portion comprises another portion in the central region.

17. The system of Example 14, wherein the first portion comprises a portion in the peripheral region and the second portion comprises another portion in the peripheral region.

18. The system of any of Examples 11-13, wherein the second portion corresponds to a location of the user's eye having a higher density of rods than the first portion when the rods dominate in the user's eye.

19. The system of Example 18, wherein the first portion comprises a portion in the central region and the second portion comprises a portion in the peripheral region.

20. The system of Example 18, wherein the first portion comprises a portion in the peripheral region and the second portion comprises another portion in the peripheral region.

21. The system of any of the above Examples, wherein the system comprises a timer or clock to monitor the time spent in the lighting condition.

22. The system of any of the above Examples, further comprising one or more light sources configured to direct light into the eye of said user to form images in the eye.

23. The system of any of the above Examples, wherein said at least a portion of said display that is transparent and disposed at a location in front of the user's eye comprises one or more waveguides configured to project the light to the user.

24. The system of Example 23, wherein said one or more light sources is configured to direct light into said one or more waveguides.

25. The system of any of Examples 22-24, wherein said light source comprises a fiber scanning projector.

26. The system of any of Examples 1-25, wherein the one or more capture devices comprise one or more image capture devices.

27. The system of Example 26, wherein the one or more image capture devices comprise one or more cameras.

28. The system of any of Examples 1-25, wherein the one or more capture devices comprise one or more light sensors.

29. The system of Example 28, wherein the one or more light sensors comprise one or more light meters.

30. The system of any of the above Examples, wherein the one or more capture devices are configured to measure luminance of the environment.

31. The system of any of the above Examples, wherein the one or more capture devices comprise a detector array comprising an array of pixels, wherein the detector array is configured to integrate light level over the pixels to capture the lighting condition.

32. The system of any of the above Examples, wherein the one or more capture devices comprise one or more inward-facing cameras configured to detect a pupil size to capture the lighting condition.

33. The system of any of the above Examples, further comprising a distance measuring device.

34. The system of Example 33, wherein said distance measuring device comprises a laser rangefinder.

35. The system of any of the above Examples, further comprising an eye tracking device configured to track position and/or movement of said user's eye.

36. The system of any of Examples 1-35, further comprising one or more inward-facing image capture devices configured to image said user's eye.

37. The system of any of the above Examples, wherein the system is configured to provide an alert to the user to indicate the image content has been displaced from the first portion to the second portion.

38. The system of Example 37, wherein the alert is a visual alert.

39. The system of Example 37, wherein the alert is an audio alert.

40. The system of any of the above Examples, wherein said head-mounted display system is configured to construct a 3D representation of said at least part of the environment in front of the user and to interpret the representation of said at least part of the environment, said part of said environment comprising a patient, and said head-mounted display further configured to distinguish a first structure associated with the patient from a second structure associated with the patient.

41. The system of any of the above Examples, further comprising one or more sensors configured to monitor the environment.

42. The system of Example 41, wherein said one or more sensors comprise one or more outward-facing image capture devices configured to image said environment.

43. The system of Example 42, wherein said one or more outward-facing image capture devices configured to image said environment comprise one or more outward-facing cameras.

44. The system of any of the above Examples, wherein the head-mounted display is configured to estimate a volume of human tissue within the user's field of view.

45. The system of any of the above Examples, wherein the head-mounted display is configured to measure a distance between two objects in the environment.

46. The system of any of the above Examples, wherein the head-mounted display is configured to toggle between a first image modality and a second image modality that is presented on the display.

47. The system of Example 46, wherein the first image modality comprises an MRI scan.

48. The system of any of Examples 46-47, wherein the second image modality comprises an ultrasound.

49. The system of any of Examples 46-48, wherein the first image modality comprises an x-ray scan.

50. The system of any of the above Examples, further comprising an electronic emitter adapted to produce ultrasonic sound waves.

51. The system of any of the above Examples, further comprising a sensor adapted to convert ultrasonic sound waves into electrical signals.

52. The system of any of the above Examples, wherein the head-mounted display is configured to allow a user to place virtual fiducial markers on the portion of the environment in front of the user to the user's eye.

53. The system of any of the above Examples, wherein the head-mounted display is configured to project an image onto the display such that the image appears to be attached to a real-world object in the environment.

54. The system of any of the above Examples, wherein the head-mounted display is configured to display virtual cutting guidelines such that the virtual cutting guidelines appear to a user to be overlaid on a human body region to be cut or gives access to the part to be cut.

55. The system of Example 54, wherein an apparent location of the virtual cutting guidelines appears to be related to a position of a patient's body part.

56. The system of any of the above Examples, wherein the head-mounted display is configured to emit signals to obtain data on positions of objects in the portion of the environment in front of the user.

57. The system of any of the above Examples, wherein the head-mounted display is configured to obtain a position of objects in the portion of the environment in front of the user using a database of object locations.

58. The system of Example 57, wherein the head-mounted display is configured to set a point of reference based on said database of object locations and to project an image into the eye of a user such that the image appears to be fixed with respect to the point of reference.

59. The system of any of the above Examples, wherein the head-mounted display is configured to rotate a view of a 3D image of an object about an axis based on a user input.

60. The system of any of the above Examples, wherein the head-mounted display is configured to translate a view of an image of a 3D object based on a user input.

61. The system of any of the above Examples, wherein the head-mounted display is configured to display a first slice of a 3D image of an object.

62. The system of Example 61, wherein the head-mounted display is configured to sequence through an image of the first slice and an image of a second slice of the 3D image.

63. The system of any of the above Examples, wherein the head-mounted display is configured to transmit an image of a portion of the environment in front of the user such that a second user of head-mounted displays can view said image of said portion of the environment transmitted.

64. The system of any of the above Examples, wherein the head-mounted display is configured to alert a user of a step in a medical procedure.

65. The system of any of the above Examples, wherein the head-mounted display is configured to monitor a medical parameter and provide an alert based on the medical parameter.

66. The system of Example 65, wherein the medical parameter comprises a vital sign.

67. The system of any of the above Examples, wherein the head-mounted display is configured to emit ultrasound waves and to measure a signal resulting from said ultrasound waves and wherein the head-mounted display is further configured to form an ultrasound image based on the signal.

68. The system of any of the above Examples, wherein the head-mounted display is configured to alert the user of objects and/or events that are outside the user's field of view.

69. The system of Example 31, wherein the detector array comprises an outward looking camera configured to image the environment.

70. The system of any of the above Examples, wherein the system is configured to determine how to present the image content in the user's eye based at least in part on a temporal aspect of the lighting condition of the environment.

71. The system of any of the above Examples, wherein said display is configured to project light into said user's eye at different divergences so as to present said image content as if said image content is coming from different depths.

72. The system of any of the above Examples, wherein the head-mounted display is configured to combine a first image modality with a second image modality different from the first image modality.

73. The system of Example 72, wherein the first image modality and the second image modality each comprises an image from an MRI, CT, PET, MRA, or CTA scan.

74. The system of Example 72 or 73, wherein the head-mounted display is configured to align the combined image of the first and second image modalities over the patient's actual anatomy.

Example Set IVD

1. A head-mounted display system configured to project light to an eye of a user to display augmented reality image content, said user's eye having a vision field having a central region and a peripheral region disposed about said central region, said head-mounted display system comprising:
 a frame configured to be supported on a head of the user;
 a display disposed on the frame, said display configured to project light into said user's eye so as to present image content to said user's vision field, at least a portion of said display being transparent and disposed at a location in front of the user's eye when the user wears said head-mounted display system such that said transparent portion transmits light from a portion of the environment in front of the user to the user's eye to provide a view of said portion of the environment in front of the user;
 one or more capture devices configured to capture a lighting condition of the environment;
 processing electronics in communication with said display to control presentation of image content on said display,
 wherein said head-mounted display system is configured to project light to a location of the user's eye so as to present image content to a portion of the user's vision field based at least in part on the lighting condition of the environment.

2. The system of Example 1, wherein under a photopic lighting condition, the projected light location is based on the projected light location's density of cones.

3. The system of Example 2, wherein the photopic lighting condition of the environment has a luminance from 10 $cd/m^2$ to $10^8$ $cd/m^2$.

4. The system of any of Examples 2-3, wherein the portion of the user's vision field comprises the central region.

5. The system of any of Examples 2-4, wherein the projected light location is in a range from 0 to 5 degrees off from the fovea.

6. The system of Example 1, wherein under a scotopic lighting condition, the projected light location is based on the projected light location's density of rods.

7. The system of Example 6, wherein the scotopic lighting condition of the environment has a luminance from $10^{-3.5}$ $cd/m^2$ to $10^{-6}$ $cd/m^2$.

8. The system of any of Examples 6-7, wherein the portion of the user's vision field comprises the peripheral region.

9. The system of any of Examples 6-8, wherein the projected light location is in a range from 15 to 20 degrees off from the fovea.

10. The system of any of Examples 6-8, wherein the projected light location is in a range from 25 to 35 degrees off from the fovea.

11. The system of Example 1, wherein under a mesopic lighting condition, the projected light location is based at least in part on time spent in the mesopic lighting condition.

12. The system of Example 11, wherein the mesopic lighting condition of the environment has a luminance from $10^{-3}$ $cd/m^2$ to $10^{0.5}$ $cd/m^2$.

13. The system of Example 11 or 12, wherein the system is configured to determine whether cones or rods dominate in the user's eye based at least in part on the time spent in the mesopic lighting condition.

14. The system of any of Examples 11-13, wherein the projected light location is based on the projected light location's density of cones when the cones dominate in the user's eye.

15. The system of Example 14, wherein the portion of the user's vision field comprises the central region.

16. The system of Example 14, wherein the projected light location is in a range from 0 to 5 degrees off from the fovea.

17. The system of any of Examples 11-13, wherein the projected light location is based to the projected light location's density of rods of the user's eye when the rods dominate the user's eye.

18. The system of Example 17, wherein the portion of the user's vision field comprises the peripheral region.

19. The system of Example 17, wherein the projected light location is in a range from 15 to 20 degrees off from the fovea.

20. The system of Example 17, wherein the projected light location is in a range from 25 to 35 degrees off from the fovea.

21. The system of any of the above Examples, wherein the system comprises a timer or clock to monitor the time spent in the lighting condition.

22. The system of any of the above Examples, further comprising one or more light sources configured to direct light into the eye of said user to form images in the eye.

23. The system of any of the above Examples, wherein said at least a portion of said display that is transparent and disposed at a location in front of the user's eye comprises one or more waveguides configured to project the light to the user.

24. The system of Example 23, wherein said one or more light sources is configured to direct light into said one or more waveguides.

25. The system of any of Examples 22-24, wherein said light source comprises a fiber scanning projector.

26. The system of any of Examples 1-25, wherein the one or more capture devices comprise one or more image capture devices.

27. The system of Example 26, wherein the one or more image capture devices comprise one or more cameras.

28. The system of any of Examples 1-25, wherein the one or more capture devices comprise one or more light sensors.

29. The system of Example 28, wherein the one or more light sensors comprise one or more light meters.

30. The system of any of the above Examples, wherein the one or more capture devices are configured to measure luminance of the environment.

31. The system of any of the above Examples, wherein the one or more capture devices comprise a detector array comprising an array of pixels, wherein the detector array is configured to integrate light level over the pixels to capture the lighting condition.

32. The system of any of the above Examples, wherein the one or more capture devices comprise one or more inward-facing cameras configured to detect a pupil size to capture the lighting condition.

33. The system of any of the above Examples, further comprising a distance measuring device.

34. The system of Example 33, wherein said distance measuring device comprises a laser rangefinder.

35. The system of any of the above Examples, further comprising an eye tracking device configured to track position and/or movement of said user's eye.

36. The system of any of Examples 1-35, further comprising one or more inward-facing image capture devices configured to image said user's eye.

37. The system of any of the above Examples, wherein the system is configured to provide an alert to the user to indicate the image content has been presented.

38. The system of Example 37, wherein the alert is a visual alert.

39. The system of Example 37, wherein the alert is an audio alert.

40. The system of any of the above Examples, wherein said head-mounted display system is configured to construct a 3D representation of said at least part of the environment in front of the user and to interpret the representation of said at least part of the environment, said part of said environment comprising a patient, and said head-mounted display further configured to distinguish a first structure associated with the patient from a second structure associated with the patient.

41. The system of any of the above Examples, further comprising one or more sensors configured to monitor the environment.

42. The system of Example 41, wherein said one or more sensors comprise one or more outward-facing image capture devices configured to image said environment.

43. The system of Example 42, wherein said one or more outward-facing image capture devices configured to image said environment comprise one or more outward-facing cameras.

44. The system of any of the above Examples, wherein the head-mounted display is configured to estimate a volume of human tissue within the user's field of view.

45. The system of any of the above Examples, wherein the head-mounted display is configured to measure a distance between two objects in the environment.

46. The system of any of the above Examples, wherein the head-mounted display is configured to toggle between a first image modality and a second image modality that is presented on the display.

47. The system of Example 46, wherein the first image modality comprises an MRI scan.

48. The system of any of Examples 46-47, wherein the second image modality comprises an ultrasound.

49. The system of any of Examples 46-48, wherein the first image modality comprises an x-ray scan.

50. The system of any of the above Examples, further comprising an electronic emitter adapted to produce ultrasonic sound waves.

51. The system of any of the above Examples, further comprising a sensor adapted to convert ultrasonic sound waves into electrical signals.

52. The system of any of the above Examples, wherein the head-mounted display is configured to allow a user to place virtual fiducial markers on the portion of the environment in front of the user to the user's eye.

53. The system of any of the above Examples, wherein the head-mounted display is configured to project an image onto the display such that the image appears to be attached to a real-world object in the environment.

54. The system of any of the above Examples, wherein the head-mounted display is configured to display virtual cutting guidelines such that the virtual cutting guidelines appear to a user to be overlaid on a human body region to be cut or gives access to the part to be cut.

55. The system of Example 54, wherein an apparent location of the virtual cutting guidelines appears to be related to a position of a patient's body part.

56. The system of any of the above Examples, wherein the head-mounted display is configured to emit signals to obtain data on positions of objects in the portion of the environment in front of the user.

57. The system of any of the above Examples, wherein the head-mounted display is configured to obtain a position of objects in the portion of the environment in front of the user using a database of object locations.

58. The system of Example 57, wherein the head-mounted display is configured to set a point of reference based on said database of object locations and to project an image into the eye of a user such that the image appears to be fixed with respect to the point of reference.

59. The system of any of the above Examples, wherein the head-mounted display is configured to rotate a view of a 3D image of an object about an axis based on a user input.

60. The system of any of the above Examples, wherein the head-mounted display is configured to translate a view of an image of a 3D object based on a user input.

61. The system of any of the above Examples, wherein the head-mounted display is configured to display a first slice of a 3D image of an object.

62. The system of Example 61, wherein the head-mounted display is configured to sequence through an image of the first slice and an image of a second slice of the 3D image.

63. The system of any of the above Examples, wherein the head-mounted display is configured to transmit an image of a portion of the environment in front of the user such that a second user of head-mounted displays can view said image of said portion of the environment transmitted.

64. The system of any of the above Examples, wherein the head-mounted display is configured to alert a user of a step in a medical procedure.

65. The system of any of the above Examples, wherein the head-mounted display is configured to monitor a medical parameter and provide an alert based on the medical parameter.

66. The system of Example 65, wherein the medical parameter comprises a vital sign.

67. The system of any of the above Examples, wherein the head-mounted display is configured to emit ultrasound waves and to measure a signal resulting from said ultrasound waves and wherein the head-mounted display is further configured to form an ultrasound image based on the signal.

68. The system of any of the above Examples, wherein the head-mounted display is configured to alert the user of objects and/or events that are outside the user's field of view.

69. The system of Example 31, wherein the detector array comprises an outward looking camera configured to image the environment.

70. The system of any of the above Examples, wherein the system is configured to determine how to present the image content in the user's eye based at least in part on a temporal aspect of the lighting condition of the environment.

71. The system of any of the above Examples, wherein said head-mounted display system is configured to project light to a location of the user's eye so as to present image content to a portion of the user's vision field based at least in part on the projected light location's density of photoreceptors 72. The system of any of the above Examples, wherein said display is configured to project light into said user's eye at different divergences so as to present said image content as if said image content is coming from different depths.

73. The system of any of the above Examples, wherein the head-mounted display is configured to combine a first image modality with a second image modality different from the first image modality.

74. The system of Example 73, wherein the first image modality and the second image modality each comprises an image from an MRI, CT, PET, MRA, or CTA scan.

75. The system of Example 73 or 74, wherein the head-mounted display is configured to align the combined image of the first and second image modalities over the patient's actual anatomy.

Example Set IVE

1. A head-mounted display system configured to project light to an eye of a user to display augmented reality image content, said user's eye having a vision field having a central region and a peripheral region disposed about said central region, said head-mounted display system comprising:
   a frame configured to be supported on a head of the user;
   a display disposed on the frame, said display configured to project light into said user's eye so as to present image content at said central region of said user's vision field, at least a portion of said display being transparent and disposed at a location in front of the user's eye when the user wears said head-mounted display system such that said transparent portion transmits light from a portion of the environment in front of the user to the user's eye to provide a view of said portion of the environment in front of the user;
   one or more capture devices configured to capture a lighting condition of the environment;
   processing electronics in communication with said display to control presentation of image content on said display,
   wherein said head-mounted display system is configured to project light to a location of the user's eye so as to present image content to a portion of the central region of the user's vision field that is de-emphasized based at least in part on the lighting condition of the environment.

2. The system of Example 1, wherein under a photopic lighting condition, the image content is de-emphasized based on the projected light location's density of cones.

3. The system of Example 2, wherein the photopic lighting condition of the environment has a luminance from 10 $cd/m^2$ to $10^8$ $cd/m^2$.

4. The system of Example 1, wherein under a scotopic lighting condition, the image content is de-emphasized based on the projected light location's density of rods.

5. The system of Example 4, wherein the scotopic lighting condition of the environment has a luminance from $10^{-3.5}$ $cd/m^2$ to $10^{-6}$ $cd/m^2$.

6. The system of Example 1, wherein under a mesopic lighting condition, the image content is de-emphasized based at least in part on time spent in the mesopic lighting condition.

7. The system of Example 6, wherein the mesopic lighting condition of the environment has a luminance from $10^{-3}$ $cd/m^2$ to $10^{0.5}$ $cd/m^2$.

8. The system of Example 6 or 7, wherein the system is configured to determine whether cones or rods dominate in the user's eye based at least in part on the time spent in the mesopic lighting condition.

9. The system of any of Examples 6-8, wherein the image content is de-emphasized based on the projected light location's density of cones when the cones dominate in the user's eye.

10. The system of any of Examples 6-8, wherein the image content is de-emphasized based on the projected light location's density of rods of the user's eye when the rods dominate the user's eye.

11. The system of any of the above Examples, wherein the system comprises a timer or clock to monitor the time spent in the lighting condition.

12. The system of any of the above Examples, further comprising one or more light sources configured to direct light into the eye of said user to form images in the eye.

13. The system of any of the above Examples, wherein said at least a portion of said display that is transparent and disposed at a location in front of the user's eye comprises one or more waveguides configured to project the light to the user.

14. The system of Example 13, wherein said one or more light sources is configured to direct light into said one or more waveguides.

15. The system of any of Examples 12-14, wherein said light source comprises a fiber scanning projector.

16. The system of any of Examples 1-15, wherein the one or more capture devices comprise one or more image capture devices.

17. The system of Example 16, wherein the one or more image capture devices comprise one or more cameras.

18. The system of any of Examples 1-15, wherein the one or more capture devices comprise one or more light sensors.

19. The system of Example 18, wherein the one or more light sensors comprise one or more light meters.

20. The system of any of the above Examples, wherein the one or more capture devices are configured to measure luminance of the environment.

21. The system of any of the above Examples, wherein the one or more capture devices comprise a detector array comprising an array of pixels, wherein the detector array is configured to integrate light level over the pixels to capture the lighting condition.

22. The system of any of the above Examples, wherein the one or more capture devices comprise one or more inward-facing cameras configured to detect a pupil size to capture the lighting condition.

23. The system of any of the above Examples, further comprising a distance measuring device.

24. The system of Example 23, wherein said distance measuring device comprises a laser rangefinder.

25. The system of any of the above Examples, further comprising an eye tracking device configured to track position and/or movement of said user's eye.

26. The system of any of Examples 1-25, further comprising one or more inward-facing image capture devices configured to image said user's eye.

27. The system of any of the above Examples, wherein the head-mounted display system is configured to reduce the size of the image content based at least in part on the lighting condition of the environment.

28. The system of Example 27, wherein said reduction in size is based at least in part on the resolution of the eye.

29. The system of any of the above Examples, wherein the head-mounted display system is configured to decrease brightness in the image content based at least in part on the lighting condition of the environment.

30. The system of any of the above Examples, wherein the head-mounted display system is configured to decrease contrast in the image content based at least in part on the lighting condition of the environment.

31. The system of Example 30, wherein the head-mounted display system is configured to decrease contrast based at least in part on the contrast sensitivity of the eye.

32. The system of any of the above Examples, wherein the head-mounted display system is configured to decrease color saturation in the image content based at least in part on the lighting condition of the environment.

33. The system of any of the above Examples, wherein the head-mounted display system is configured to reduce the sharpness of the image content based at least in part on the lighting condition of the environment.

34. The system of Example 33, wherein sharpening comprises de-emphasizing edges of features in the image content based at least in part on the lighting condition of the environment.

35. The system of any of the above Examples, wherein the head-mounted display system is configured to shift the color balance of the image content based at least in part on the lighting condition of the environment.

36. The system of any of the above Examples, wherein the system is configured to provide an alert to the user to indicate the image content has been de-emphasized.

37. The system of Example 36, wherein the alert is a visual alert.

38. The system of Example 36, wherein the alert is an audio alert.

39. The system of any of the above Examples, wherein said head-mounted display system is configured to construct a 3D representation of said at least part of the environment in front of the user and to interpret the representation of said at least part of the environment, said part of said environment comprising a patient, and said head-mounted display further configured to distinguish a first structure associated with the patient from a second structure associated with the patient.

40. The system of any of the above Examples, further comprising one or more sensors configured to monitor the environment.

41. The system of Example 40, wherein said one or more sensors comprise one or more outward-facing image capture devices configured to image said environment.

42. The system of Example 41, wherein said one or more outward-facing image capture devices configured to image said environment comprise one or more outward-facing cameras.

43. The system of any of the above Examples, wherein the head-mounted display is configured to estimate a volume of human tissue within the user's field of view.

44. The system of any of the above Examples, wherein the head-mounted display is configured to measure a distance between two objects in the environment.

45. The system of any of the above Examples, wherein the head-mounted display is configured to toggle between a first image modality and a second image modality that is presented on the display.

46. The system of Example 45, wherein the first image modality comprises an MRI scan.

47. The system of any of Examples 45-46, wherein the second image modality comprises an ultrasound.

48. The system of any of Examples 45-47, wherein the first image modality comprises an x-ray scan.

49. The system of any of the above Examples, further comprising an electronic emitter adapted to produce ultrasonic sound waves.

50. The system of any of the above Examples, further comprising a sensor adapted to convert ultrasonic sound waves into electrical signals.

51. The system of any of the above Examples, wherein the head-mounted display is configured to allow a user to place virtual fiducial markers on the portion of the environment in front of the user to the user's eye.

52. The system of any of the above Examples, wherein the head-mounted display is configured to project an image onto the display such that the image appears to be attached to a real-world object in the environment.

53. The system of any of the above Examples, wherein the head-mounted display is configured to display virtual cutting guidelines such that the virtual cutting guidelines appear to a user to be overlaid on a human body region to be cut or gives access to the part to be cut.

54. The system of Example 53, wherein an apparent location of the virtual cutting guidelines appears to be related to a position of a patient's body part.

55. The system of any of the above Examples, wherein the head-mounted display is configured to emit signals to obtain data on positions of objects in the portion of the environment in front of the user.

56. The system of any of the above Examples, wherein the head-mounted display is configured to obtain a position of objects in the portion of the environment in front of the user using a database of object locations.

57. The system of Example 56, wherein the head-mounted display is configured to set a point of reference based on said database of object locations and to project an image into the eye of a user such that the image appears to be fixed with respect to the point of reference.

58. The system of any of the above Examples, wherein the head-mounted display is configured to rotate a view of a 3D image of an object about an axis based on a user input.

59. The system of any of the above Examples, wherein the head-mounted display is configured to translate a view of an image of a 3D object based on a user input.

60. The system of any of the above Examples, wherein the head-mounted display is configured to display a first slice of a 3D image of an object.

61. The system of Example 60, wherein the head-mounted display is configured to sequence through an image of the first slice and an image of a second slice of the 3D image.

62. The system of any of the above Examples, wherein the head-mounted display is configured to transmit an image of a portion of the environment in front of the user such that a second user of head-mounted displays can view said image of said portion of the environment transmitted.

63. The system of any of the above Examples, wherein the head-mounted display is configured to alert a user of a step in a medical procedure.

64. The system of any of the above Examples, wherein the head-mounted display is configured to monitor a medical parameter and provide an alert based on the medical parameter.

65. The system of Example 64, wherein the medical parameter comprises a vital sign.

66. The system of any of the above Examples, wherein the head-mounted display is configured to emit ultrasound waves and to measure a signal resulting from said ultrasound waves and wherein the head-mounted display is further configured to form an ultrasound image based on the signal.

67. The system of any of the above Examples, wherein the head-mounted display is configured to alert the user of objects and/or events that are outside the user's field of view.

68. The system of Example 21, wherein the detector array comprises an outward looking camera configured to image the environment.

69. The system of any of the above Examples, wherein said head-mounted display system is configured to project light to a location of the user's eye so as to present image content to a portion of the central region of the user's vision field that is de-emphasized with respect to image content presented to a portion of the peripheral region.

70. The system of any of the above Examples, wherein said head-mounted display system is configured to project light to a location of the user's eye so as to present image content to a portion of the central region of the user's vision field that is de-emphasized with respect to image content presented to another portion of the central region.

71. The system of any of the above Examples, wherein the system is configured to determine how to present the image content in the user's eye based at least in part on a temporal aspect of the lighting condition of the environment.

72. The system of any of the above Examples, wherein said display is configured to project light into said user's eye at different divergences so as to present said image content as if said image content is coming from different depths.

73. The system of any of the above Examples, wherein the head-mounted display is configured to provide a degree of opacity at least in the vicinity of the presented image content.

74. The system of any of the above Examples, wherein the head-mounted display is configured to combine a first image modality with a second image modality different from the first image modality.

75. The system of Example 74, wherein the first image modality and the second image modality each comprises an image from an MRI, CT, PET, MRA, or CTA scan.

76. The system of Example 74 or 75, wherein the head-mounted display is configured to align the combined image of the first and second image modalities over the patient's actual anatomy.

Example Set IVF

1. A head-mounted display system configured to project light to an eye of a user to display augmented reality image content, said user's eye having a vision field having a central region and a peripheral region disposed about said central region, said head-mounted display system comprising:
a frame configured to be supported on a head of the user;
a display disposed on the frame, said display configured to project light into said user's eye so as to present image content at said peripheral region of said user's vision field, at least a portion of said display being transparent and disposed at a location in front of the user's eye when the user wears said head-mounted display system such that said transparent portion transmits light from a portion of the environment in front of the user to the user's eye to provide a view of said portion of the environment in front of the user;
one or more capture devices configured to capture a lighting condition of the environment;
processing electronics in communication with said display to control presentation of image content on said display,
wherein said head-mounted display system is configured to project light to a location of the user's eye so as to present image content to a portion of the peripheral region of the user's vision field that is de-emphasized based at least in part on the lighting condition of the environment.

2. The system of Example 1, wherein under a photopic lighting condition, the image content is de-emphasized based on the projected light location's density of cones.

3. The system of Example 2, wherein the photopic lighting condition of the environment has a luminance from 10 $cd/m^2$ to $10^8$ $cd/m^2$.

4. The system of Example 1, wherein under a scotopic lighting condition, the image content is de-emphasized based on the projected light location's density of rods.

5. The system of Example 4, wherein the scotopic lighting condition of the environment has a luminance from $10^{-3.5}$ $cd/m^2$ to $10^{-6}$ $cd/m^2$.

6. The system of Example 1, wherein under a mesopic lighting condition, the image content is de-emphasized based at least in part on time spent in the mesopic lighting condition.

7. The system of Example 6, wherein the mesopic lighting condition of the environment has a luminance from $10^{-3}$ $cd/m^2$ to $10^{0.5}$ $cd/m^2$.

8. The system of Example 6 or 7, wherein the system is configured to determine whether cones or rods dominate in the user's eye based at least in part on the time spent in the mesopic lighting condition.

9. The system of any of Examples 6-8, wherein the image content is de-emphasized based on the projected light location's density of cones when the cones dominate in the user's eye.

10. The system of any of Examples 6-8, wherein the image content is de-emphasized based to the projected light location's density of rods of the user's eye when the rods dominate the user's eye.

11. The system of any of the above Examples, wherein the system comprises a timer or clock to monitor the time spent in the lighting condition.

12. The system of any of the above Examples, further comprising one or more light sources configured to direct light into the eye of said user to form images in the eye.

13. The system of any of the above Examples, wherein said at least a portion of said display that is transparent and disposed at a location in front of the user's eye comprises one or more waveguides configured to project the light to the user.

14. The system of Example 13, wherein said one or more light sources is configured to direct light into said one or more waveguides.

15. The system of any of Examples 12-14, wherein said light source comprises a fiber scanning projector.

16. The system of any of Examples 1-15, wherein the one or more capture devices comprise one or more image capture devices.

17. The system of Example 16, wherein the one or more image capture devices comprise one or more cameras.

18. The system of any of Examples 1-15, wherein the one or more capture devices comprise one or more light sensors.

19. The system of Example 18, wherein the one or more light sensors comprise one or more light meters.

20. The system of any of the above Examples, wherein the one or more capture devices are configured to measure luminance of the environment.

21. The system of any of the above Examples, wherein the one or more capture devices comprise a detector array comprising an array of pixels, wherein the detector array is configured to integrate light level over the pixels to capture the lighting condition.

22. The system of any of the above Examples, wherein the one or more capture devices comprise one or more inward-facing cameras configured to detect a pupil size to capture the lighting condition.

23. The system of any of the above Examples, further comprising a distance measuring device.

24. The system of Example 23, wherein said distance measuring device comprises a laser rangefinder.

25. The system of any of the above Examples, further comprising an eye tracking device configured to track position and/or movement of said user's eye.

26. The system of any of Examples 1-25, further comprising one or more inward-facing image capture devices configured to image said user's eye.

27. The system of any of the above Examples, wherein the head-mounted display system is configured to reduce the size of the image content based at least in part on the lighting condition of the environment.

28. The system of Example 27, wherein said reduction in the size is based at least in part on the resolution of the eye.

29. The system of any of the above Examples, wherein the head-mounted display system is configured to decrease brightness in the image content based at least in part on the lighting condition of the environment.

30. The system of any of the above Examples, wherein the head-mounted display system is configured to decrease contrast in the image content based at least in part on the lighting condition of the environment.

31. The system of Example 30, wherein the head-mounted display system is configured to decrease contrast based at least in part on the contrast sensitivity of the eye.

32. The system of any of the above Examples, wherein the head-mounted display system is configured to decrease color saturation in the image content based at least in part on the lighting condition of the environment.

33. The system of any of the above Examples, wherein the head-mounted display system is configured to reduce the sharpness of the image content based at least in part on the lighting condition of the environment.

34. The system of Example 33, wherein sharpening comprises de-emphasize the edge of features in the image content based at least in part on the lighting condition of the environment.

35. The system of any of the above Examples, wherein the head-mounted display system is configured to shift the color balance of the image content based at least in part on the lighting condition of the environment.

36. The system of any of the above Examples, wherein the system is configured to provide an alert to the user to indicate the image content has been de-emphasized.

37. The system of Example 36, wherein the alert is a visual alert.

38. The system of Example 36, wherein the alert is an audio alert.

39. The system of any of the above Examples, wherein said head-mounted display system is configured to construct a 3D representation of said at least part of the environment in front of the user and to interpret the representation of said at least part of the environment, said part of said environment comprising a patient, and said head-mounted display further configured to distinguish a first structure associated with the patient from a second structure associated with the patient.

40. The system of any of the above Examples, further comprising one or more sensors configured to monitor the environment.

41. The system of Example 40, wherein said one or more sensors comprise one or more outward-facing image capture devices configured to image said environment.

42. The system of Example 41, wherein said one or more outward-facing image capture devices configured to image said environment comprise one or more outward-facing cameras.

43. The system of any of the above Examples, wherein the head-mounted display is configured to estimate a volume of human tissue within the user's field of view.

44. The system of any of the above Examples, wherein the head-mounted display is configured to measure a distance between two objects in the environment.

45. The system of any of the above Examples, wherein the head-mounted display is configured to toggle between a first image modality and a second image modality that is presented on the display.

46. The system of Example 45, wherein the first image modality comprises an MRI scan.

47. The system of any of Examples 45-46, wherein the second image modality comprises an ultrasound.

48. The system of any of Examples 45-47, wherein the first image modality comprises an x-ray scan.

49. The system of any of the above Examples, further comprising an electronic emitter adapted to produce ultrasonic sound waves.

50. The system of any of the above Examples, further comprising a sensor adapted to convert ultrasonic sound waves into electrical signals.

51. The system of any of the above Examples, wherein the head-mounted display is configured to allow a user to place virtual fiducial markers on the portion of the environment in front of the user to the user's eye.

52. The system of any of the above Examples, wherein the head-mounted display is configured to project an image onto the display such that the image appears to be attached to a real-world object in the environment.

53. The system of any of the above Examples, wherein the head-mounted display is configured to display virtual cutting guidelines such that the virtual cutting guidelines appear to a user to be overlaid on a human body region to be cut or gives access to the part to be cut.

54. The system of Example 53, wherein an apparent location of the virtual cutting guidelines appears to be related to a position of a patient's body part.

55. The system of any of the above Examples, wherein the head-mounted display is configured to emit signals to obtain data on positions of objects in the portion of the environment in front of the user.

56. The system of any of the above Examples, wherein the head-mounted display is configured to obtain a position of objects in the portion of the environment in front of the user using a database of object locations.

57. The system of Example 56, wherein the head-mounted display is configured to set a point of reference based on said database of object locations and to project an image into the eye of a user such that the image appears to be fixed with respect to the point of reference.

58. The system of any of the above Examples, wherein the head-mounted display is configured to rotate a view of a 3D image of an object about an axis based on a user input.

59. The system of any of the above Examples, wherein the head-mounted display is configured to translate a view of an image of a 3D object based on a user input.

60. The system of any of the above Examples, wherein the head-mounted display is configured to display a first slice of a 3D image of an object.

61. The system of Example 60, wherein the head-mounted display is configured to sequence through an image of the first slice and an image of a second slice of the 3D image.

62. The system of any of the above Examples, wherein the head-mounted display is configured to transmit an image of a portion of the environment in front of the user such that a second user of head-mounted displays can view said image of said portion of the environment transmitted.

63. The system of any of the above Examples, wherein the head-mounted display is configured to alert a user of a step in a medical procedure.

64. The system of any of the above Examples, wherein the head-mounted display is configured to monitor a medical parameter and provide an alert based on the medical parameter.

65. The system of Example 64, wherein the medical parameter comprises a vital sign.

66. The system of any of the above Examples, wherein the head-mounted display is configured to emit ultrasound waves and to measure a signal resulting from said ultrasound waves and wherein the head-mounted display is further configured to form an ultrasound image based on the signal.

67. The system of any of the above Examples, wherein the head-mounted display is configured to alert the user of objects and/or events that are outside the user's field of view.

68. The system of Example 21, wherein the detector array comprises an outward looking camera configured to image the environment.

69. The system of any of the above Examples, wherein said head-mounted display system is configured to project light to a location of the user's eye so as to present image content to a portion of the peripheral region of the user's vision field that is de-emphasized with respect to image content presented to a portion of the central region.

70. The system of any of the above Examples, wherein said head-mounted display system is configured to project light to a location of the user's eye so as to present image content to a portion of the peripheral region of the user's vision field that is de-emphasized with respect to image content presented to another portion of the peripheral region.

71. The system of any of the above Examples, wherein the system is configured to determine how to present the image content in the user's eye based at least in part on a temporal aspect of the lighting condition of the environment.

72. The system of any of the above Examples, wherein said display is configured to project light into said user's eye at different divergences so as to present said image content as if said image content is coming from different depths.

73. The system of any of the above Examples, wherein the head-mounted display is configured to provide a degree of opacity at least in the vicinity of the presented image content.

74. The system of any of the above Examples, wherein the head-mounted display is configured to combine a first image modality with a second image modality different from the first image modality.

75. The system of Example 74, wherein the first image modality and the second image modality each comprises an image from an MRI, CT, PET, MRA, or CTA scan.

76. The system of Example 74 or 75, wherein the head-mounted display is configured to align the combined image of the first and second image modalities over the patient's actual anatomy.

Example Set V

1. A head-mounted display system for use in medical treatment and/or diagnostics configured to project light to a user's eye to display augmented reality image content, said user's eye having a vision field having a central region and a peripheral region disposed about said central region, said head-mounted display comprising:
a frame configured to be supported on the head of the user;
a display disposed on the frame, said display configured to project light on a plurality of depth planes into said user's eye, at least a portion of said display being transparent and disposed at a location in front of the user's eye when the user wears said head-mounted display such that said transparent portion transmits light from a portion of the environment in front of the user to the user's eye to provide a view of said portion of the environment in front of the user; and
processing electronics in communication with said display to control presentation of image content on said display.

2. The system of Example 1, wherein said head-mounted display system is configured to construct a 3D representation of said at least part of the environment in front of the user and to interpret the representation of said at least part of the environment, said part of said environment comprising a patient, and said head-mounted display further configured to distinguish a first structure associated with the patient from a second structure associated with the patient.

3. The system of any of the above Examples, wherein said at least a portion of said display that is transparent and disposed at a location in front of the user's eye comprises one or more waveguides.

4. The system of Example 3, comprising one or more light sources configured to direct light into said one or more waveguides, the waveguides configured to direct light into the user's eye.

5. The system of any of Examples 3-4, wherein said one or more light sources comprises a fiber scanning projector.

6. The system of any of the above Examples, further comprising one or more sensors configured to monitor the environment.

7. The system of Example 6, wherein said one or more sensors comprise one or more outward-facing image capture devices configured to image said environment.

8. The system of Example 7, wherein said one or more outward-facing image capture devices configured to image said environment comprise one or more outward-facing cameras.

9. The system of any of the above Examples, further comprising a distance measuring device.

10. The system of any of the above Examples, further comprising an eye tracking device configured to track position and/or movement of said user's eye.

11. The system of any of the above Examples, wherein the head-mounted display is configured to estimate a volume of human tissue within the user's field of view.

12. The system of any of the above Examples, wherein the head-mounted display is configured to measure a distance between two objects in the environment.

13. The system of any of the above Examples, wherein the head-mounted display is configured to toggle between a first image modality and a second image modality that is presented on the display.

14. The system of Example 13, wherein the first image modality comprises an MRI scan.

15. The system of any of Examples 13-14, wherein the second image modality comprises an ultrasound.

16. The system of any of Examples 13-15, wherein the first image modality comprises an x-ray scan.

17. The system of any of the above Examples, further comprising an electronic emitter adapted to produce ultrasonic sound waves.

18. The system of any of the above Examples, further comprising a sensor adapted to convert ultrasonic sound waves into electrical signals.

19. The system of any of the above Examples, wherein the head-mounted display is configured to allow a user to place virtual fiducial markers on the portion of the environment in front of the user to the user's eye.

20. The system of any of the above Examples, wherein the head-mounted display is configured to project an image onto the display such that the image appears to be attached to a real-world object in the environment.

21. The system of any of the above Examples, wherein the head-mounted display is configured to display virtual cutting guidelines such that the virtual cutting guidelines appear to a user to be overlaid on a human body region to be cut or gives access to the part to be cut.

22. The system of Example 21, wherein an apparent location of the virtual cutting guidelines appears to be related to a position of a patient's body part.

23. The system of any of the above Examples, wherein the head-mounted display is configured to emit signals to obtain data on positions of objects in the portion of the environment in front of the user.

24. The system of any of the above Examples, wherein the head-mounted display is configured to obtain a position of objects in the portion of the environment in front of the user using a database of object locations.

25. The system of Example 24, wherein the head-mounted display is configured to set a point of reference based on said database of object locations and to project an image into the eye of a user such that the image appears to be fixed with respect to the point of reference.

26. The system of any of the above Examples, wherein the head-mounted display is configured to rotate a view of a 3D image of an object about an axis based on a user input.

27. The system of any of the above Examples, wherein the head-mounted display is configured to translate a view of an image of a 3D object based on a user input.

28. The system of any of the above Examples, wherein the head-mounted display is configured to display a first slice of a 3D image of an object.

29. The system of Example 28, wherein the head-mounted display is configured to sequence through an image of the first slice and an image of a second slice of the 3D image.

30. The system of any of the above Examples, wherein the head-mounted display is configured to transmit an image of a portion of the environment in front of the user such that a second user of head-mounted displays can view said image of said portion of the environment transmitted.

31. The system of any of the above Examples, wherein the head-mounted display is configured to alert a user of a step in a medical procedure.

32. The system of any of the above Examples, wherein the head-mounted display is configured to monitor a user's medical parameter and provide an alert based on the medical parameter.

33. The system of Example 32, wherein the user's medical parameter comprises a vital sign.

34. The system of any of the above Examples, wherein the head-mounted display is configured to emit ultrasound waves and to measure a signal resulting from said ultrasound waves and wherein the head-mounted display is further configured to form an ultrasound image based on the signal.

35. The system of any of the above Examples, wherein the head-mounted display is configured to alert the user of objects and/or events that are outside the user's field of view.

36. The system of any of the above Examples, further comprising one or more light sources configured to direct light into the eye of said user to form images in the eye.

37. The system of any of the above Examples, wherein said one or more light sources comprises a fiber scanning projector.

38. The system of any of the above Examples, wherein the head-mounted display is configured to emit energy toward the patient and sense returned energy.

39. The system of Example 38, wherein the energy comprises ultrasound.

40. The system of any of the above Examples, wherein the head-mounted display is configured to combine a first image modality with a second image modality different from the first image modality.

41. The system of Example 40, wherein the first image modality and the second image modality each comprises an image from an MRI, CT, PET, MRA, or CTA scan.

42. The system of Example 40 or 41, wherein the head-mounted display is configured to align the combined image of the first and second image modalities over the patient's actual anatomy.

BRIEF DESCRIPTION OF THE DRAWINGS

FIG. 2 illustrates an example of wearable display system.

DETAILED DESCRIPTION

The eyes are complex organs that collect and sense reflected and emitted light from our environment to provide useful information such as the shapes, features, and location of objects about us. Improving our ability to perceive objects with our eyes can help us in our pursuit of a wide range of endeavors. One example where enhanced vision can be particularly beneficial is for the medical practitioner, such as the surgeon, in performing medical tasks such as surgery, diagnosis, and/or treatment. Enhanced vision can also be helpful for everyday tasks requiring concentration, such as operating a motor vehicle or other vehicle.

Figure 1A:
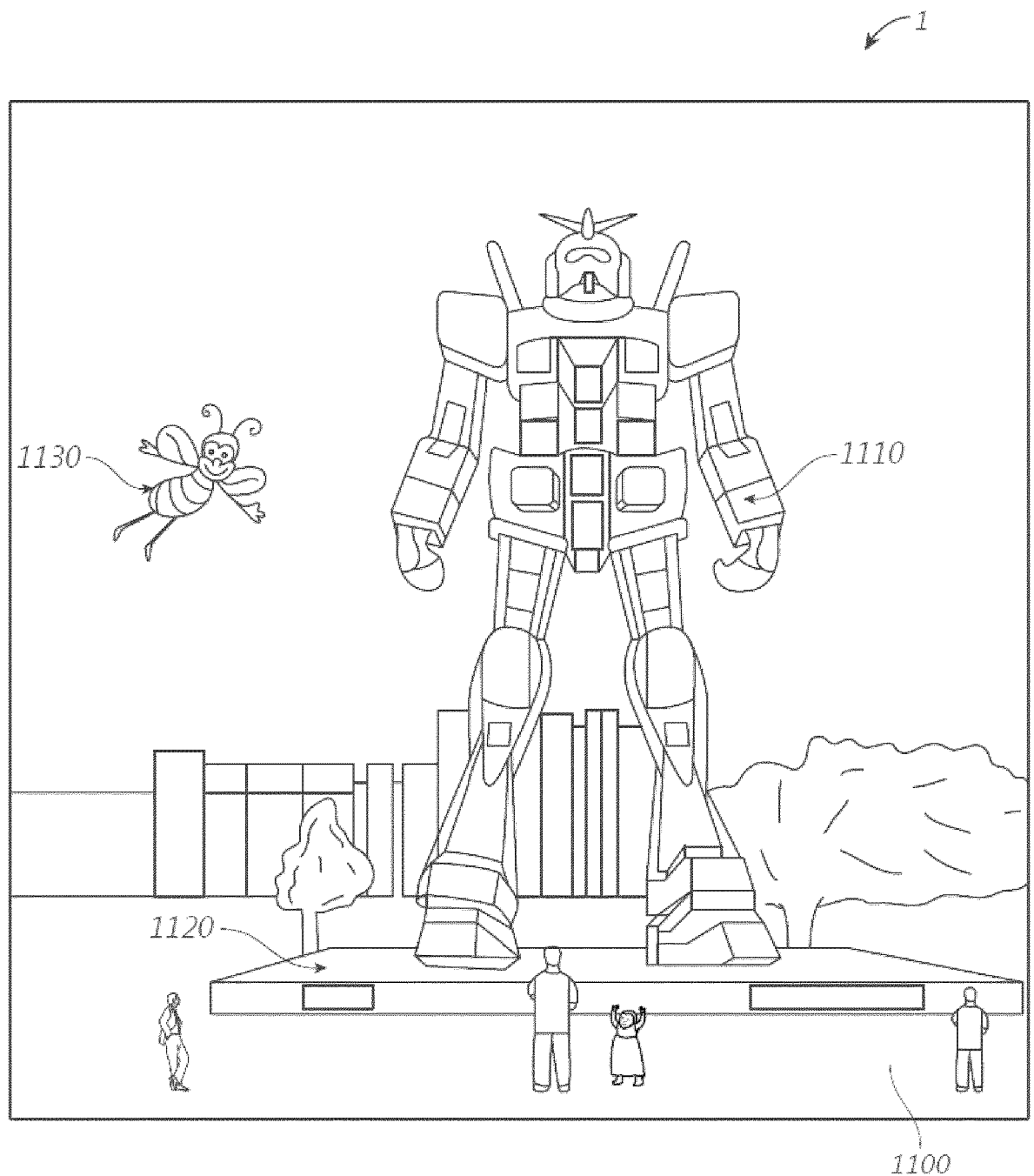
FIG. 1A illustrates a user's view of augmented reality (AR) through an AR device.
Figure 1B:
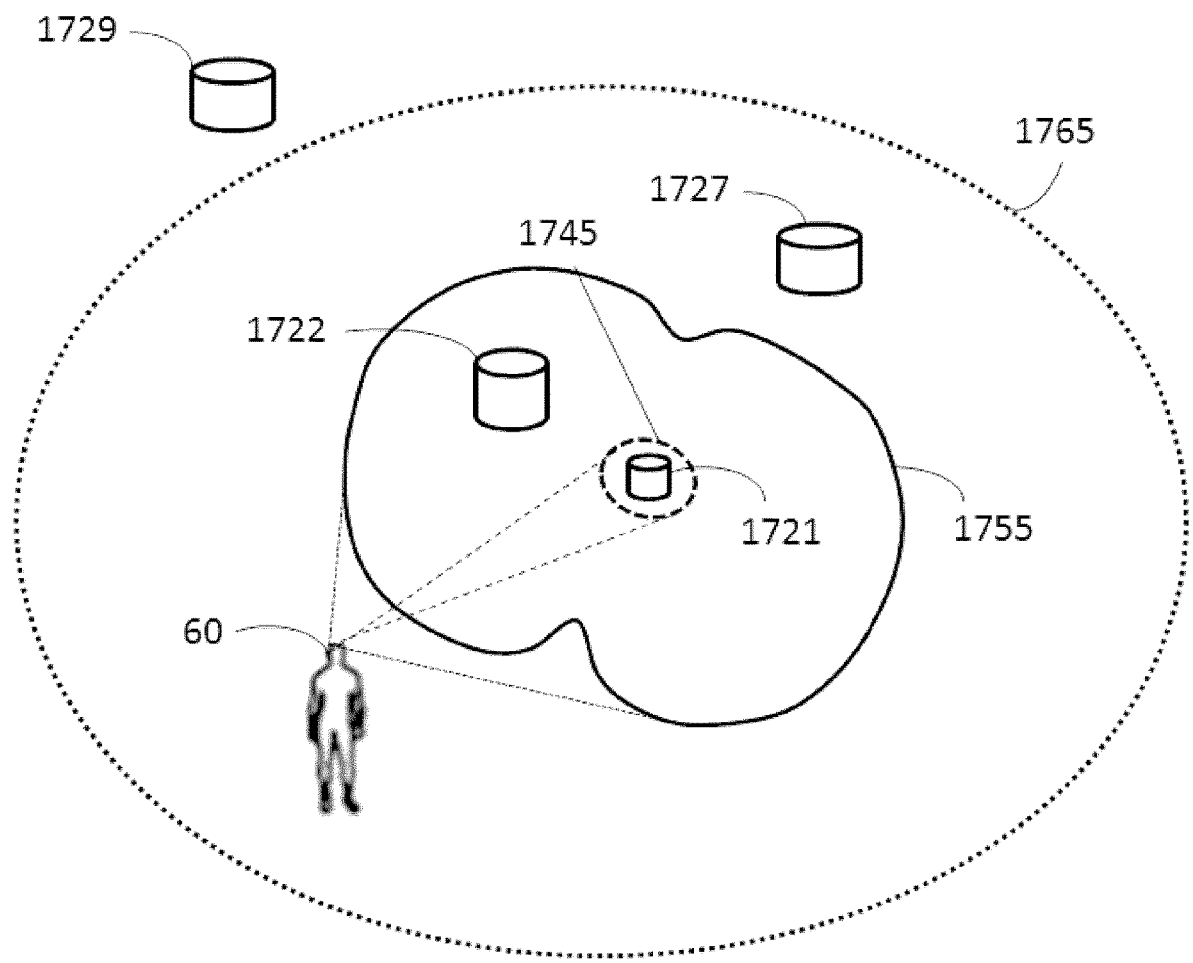
FIG. 1B illustrates a person's field of view and field of regard.

The view a person has of the world or their surrounding environment at any given instant is characterized by a field of view having a central region and a peripheral region. This field of view can change as the person moves about, moves their head, or moves their eyes or gaze. FIG. 1B shows such a field of view 1755 including central and peripheral regions. FIG. 1B also shows the field of regard 1765, which comprises a portion of the environment around a person 60 that is capable of being perceived by the person 60, for example, by turning their head or redirecting their gaze. The center portion of the field of view 1755 of a person's 60 eyes may be referred to as the central field of view 1745. The region within the field of view 1755 but outside the central field of view 1745 may be referred to as the peripheral field of view.

The central field of view will provide a person a corresponding view of objects in a central region of the environmental view. Similarly, the peripheral field of view will provide a person a corresponding view of objects in a peripheral region of the environmental view. In this case, what is considered central and what is considered peripheral, is a function of which direction the person is looking, and hence their field of view.

Figures 1, 1C, 2:
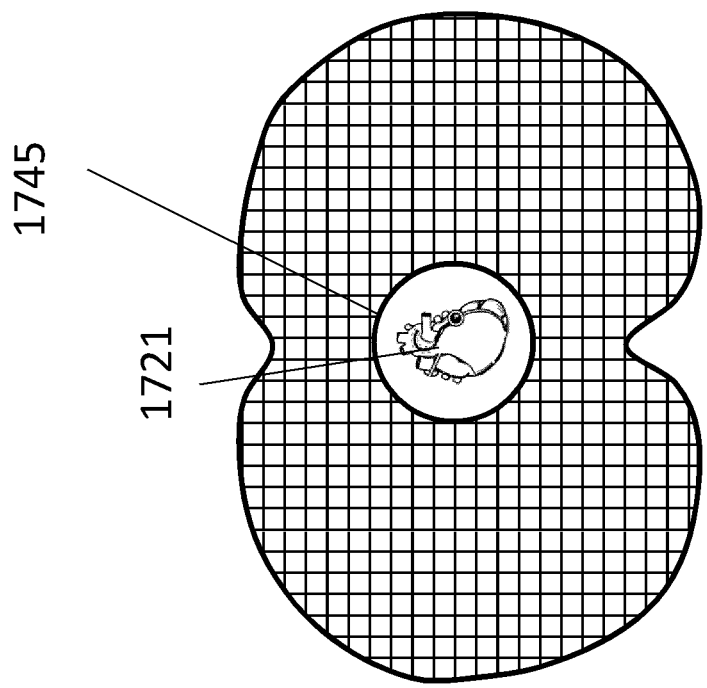
FIGS. 1C-1 and 1C-2 illustrate a first-person perspective of what portions of a scene the central field of view and peripheral field of view may include.
Figures 1, 1C:
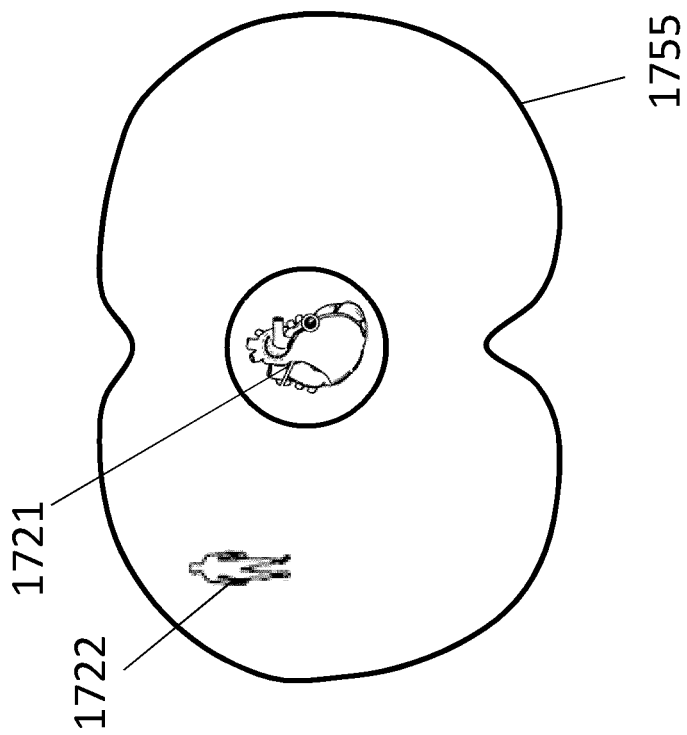

FIGS. 1C-1 and 1C-2 illustrate a first-person perspective of what portions of a scene that the central field of view and peripheral field of view may include. For example, FIG. 1C-1 illustrates an example of what a person may see in his or her field of view 1755. The field of view 1755 may include objects 1721, 1722. As shown in FIG. 1C-2, the central field of view 1745 includes the object 1721, while the other object 1722 shown in FIG. 1C-1 is in the peripheral field of view (e.g., the shaded region).

Figure 1D:
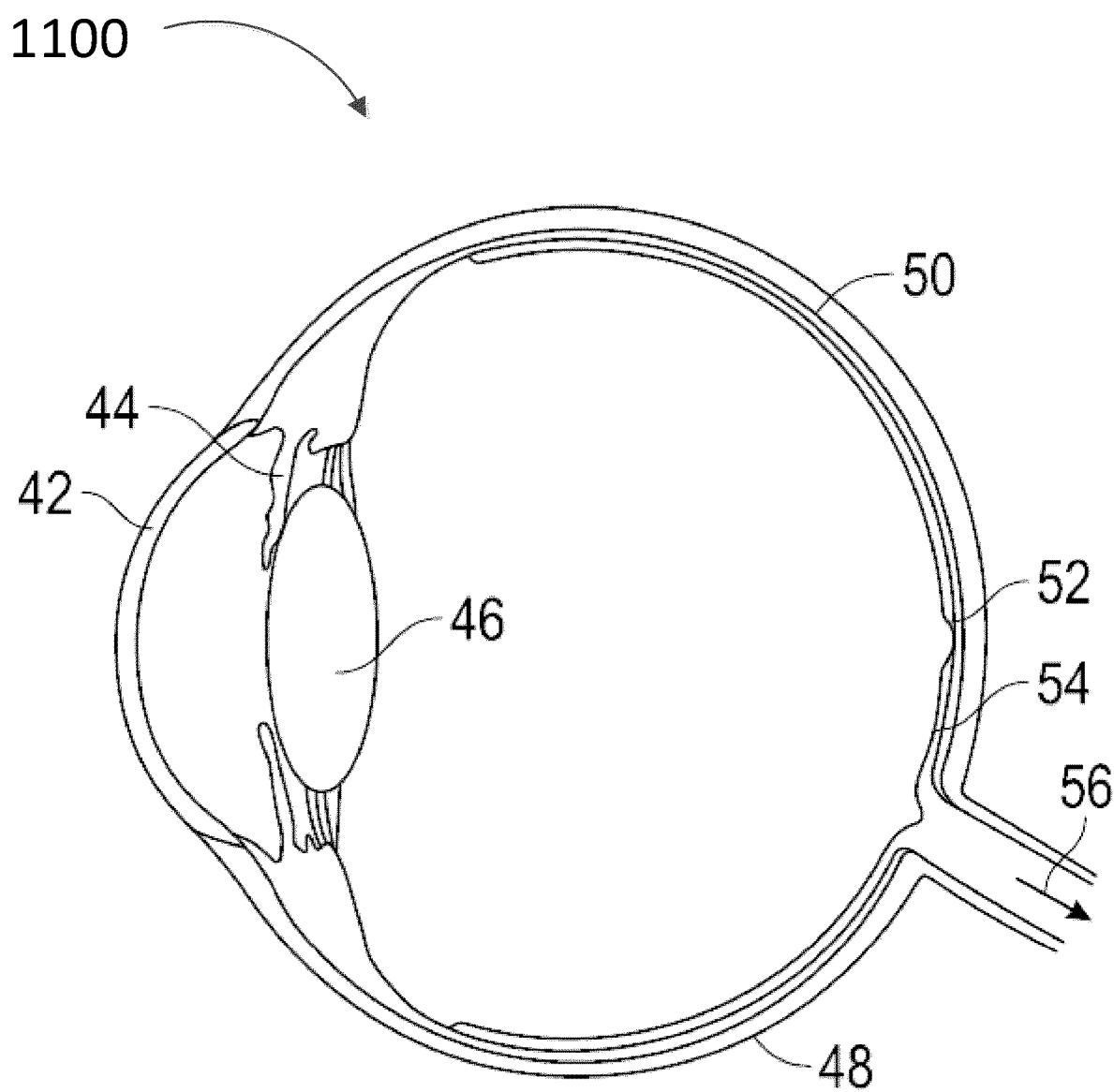
FIG. 1D illustrates a cross-section of a human eye.

As shown in FIG. 1D, a schematic cross-sectional view of a human eye 1100 is depicted featuring a cornea 42, iris 44, lens—or "crystalline lens" 46, sclera 48, choroid layer 50, macula 52, retina 54, and optic nerve pathway 56 to the brain. The cornea 42 and the crystalline lens 46 refract and focus the light toward the retina 54. The macula 52 is the center of the retina 54. At the center of the macula 52 is a portion of the retina 54 that is referred to as the "fovea". The retina 54 contains photoreceptor cells known as cones and rods. Near the inner surface of the retina 54 are ganglion cells that receive and transmit visual information from the cones and rods to the brain. The visual information can include information for forming an image.

Figure 1E:
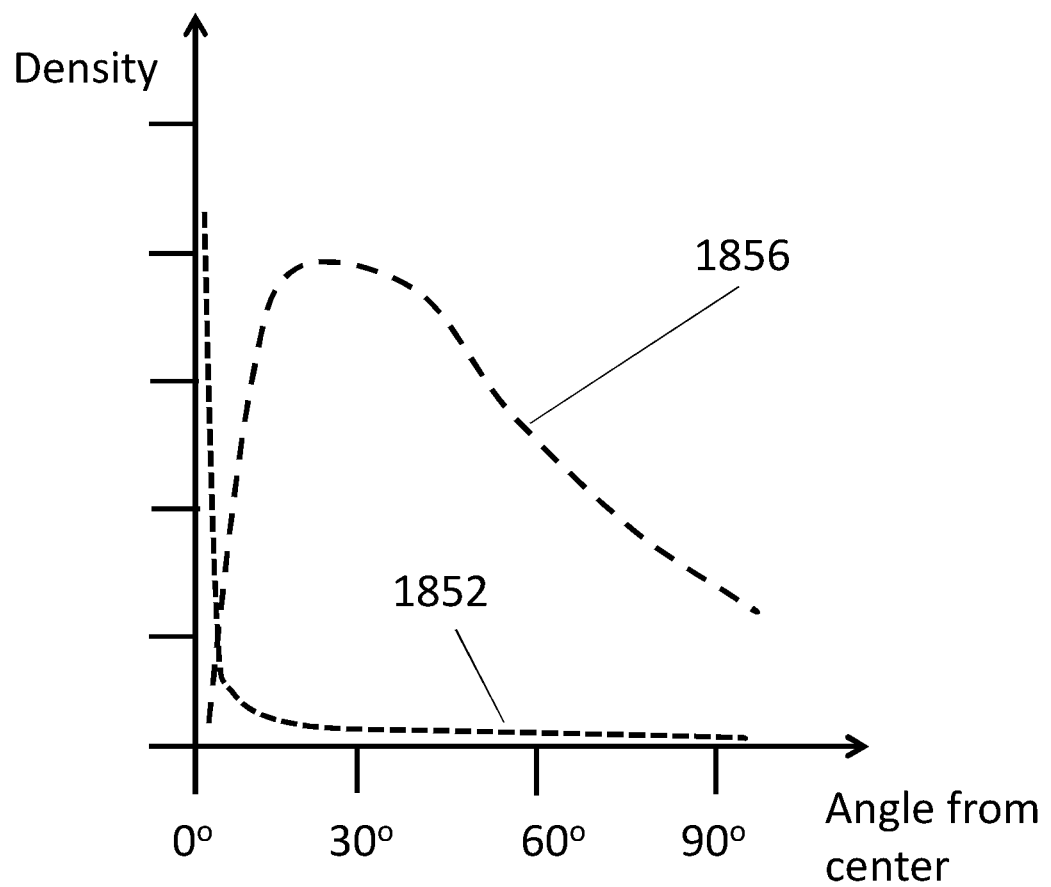
FIGS. 1E and 1F illustrate the relative density and resolution, respectively, of the cones and rods in a typical human eye.

The fovea contains more photoreceptors (approximately 120 cones per visual degree) than any other portion of the retina 54. FIG. 1E illustrates the relative density of cones and rods in a typical human eye, plotted as a function of angle from the center of the retina (e.g., as measured from an optical axis through the lens of the eye to the center of the retina). FIG. 1E shows that the relative density of cones 1852 is the highest at the center of the retina (e.g., the fovea) and decreases dramatically after a few degrees from that center. In contrast, there are substantially no rods in the center, but the density of rods 1856 increases dramatically after a few degrees from the center and decreases over retina.

Figure 1F:
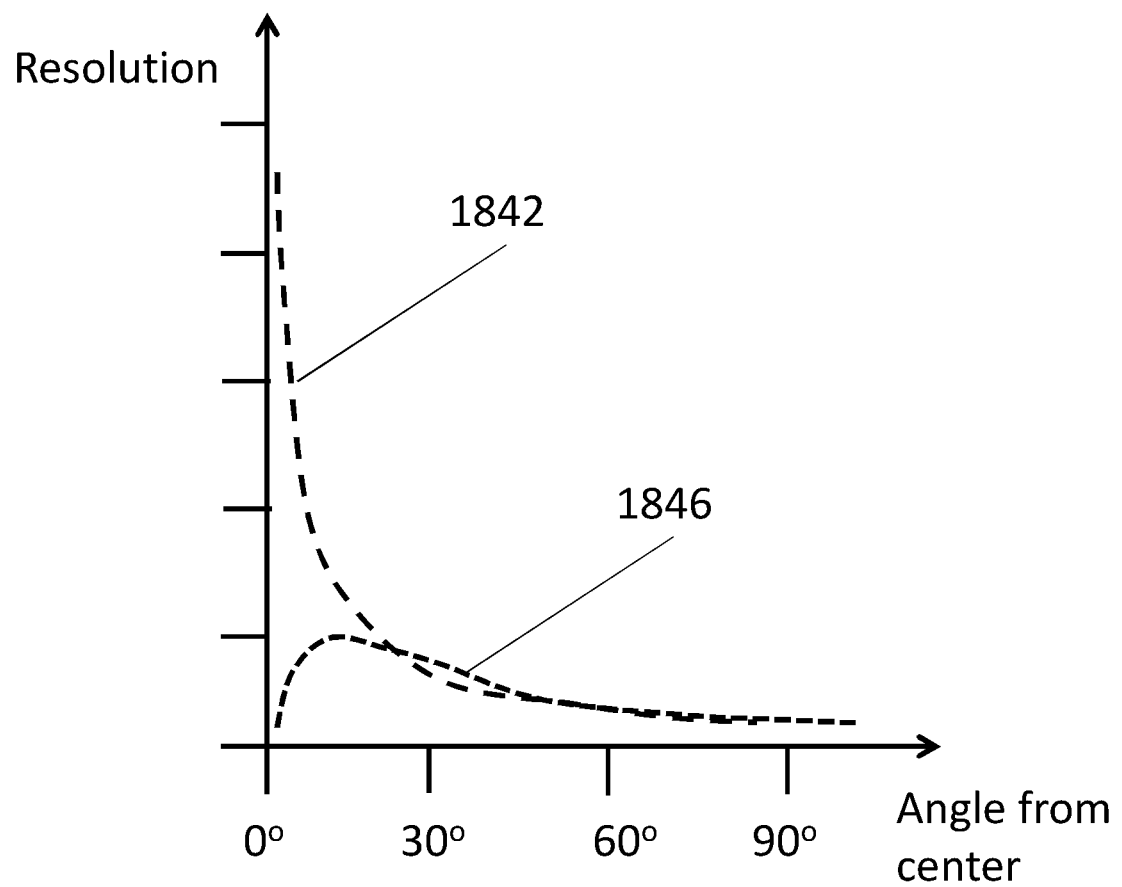

FIG. 1F shows the relative resolution of the cones and rods over the same angular spectrum across the retina. As shown in FIG. 1F, similar to the density of the cones, the resolution of the cones 1842 is the highest at the fovea and declines as the angle from the fovea increases. Similar to the density of the rods, the resolution of the rods 1846 increases initially before tapering off.

Since the fovea is located at the center of the eye, the central field of view falls on the fovea. The cones are generally responsible for color (for example, I-cones or long wavelength sensitive cones may be used for red wavelengths, m-cones or medium wavelength sensitive cones may be used for green wavelengths, and s-cones or short wavelength sensitive cones may be used for blue wavelengths) and spatial resolution. The rods are not sensitive to color and are generally responsible for basic spatial resolution (e.g., for detection of shapes and movement). Since the fovea contains the highest density of cones, it provides the high resolution for objects located in a person's central field of view. Moving away from the fovea, the cone density diminishes, as does the resolution for objects located in a person's peripheral field of view (e.g., from the near peripheral field of view to the far peripheral field of view). Because of the decreasing cone density from the fovea, the peripheral field of view may generally be associated with inferior image quality as compared to that of the central field of view. However, it may be desirable to center one's eyes on an object in the central field of view (e.g., 1745 in FIG. 1B), and also be able to see an object in the peripheral field of view.

Accordingly, various embodiments of a display system described herein may advantageously provide an improved user view of one or more objects in the user's peripheral field of view. For example, certain embodiments may allow the user to focus on one object in the user's central field of view and simultaneously view with increased visibility another object that is located in the user's peripheral field of view. As an example, in a typical surgical setting, a surgeon is either focused on the patient or on a medical image located some distance from the operating table. The surgeon may move his or her eyes (and/or head) back and forth between the two so that one of the patient and the medical image is in the surgeon's central field of view and the other is at a lower resolution in the surgeon's peripheral field of view (or even possibly outside the surgeon's field of view). In various embodiments described herein, the display systems may present image content such that the surgeon may see both the patient and the medical image at the same time and with sufficient visual acuity (e.g. sufficient resolution). For example, some embodiments can be configured to present an augmented or virtual image of the medical image that is enhanced or moved closer to the patient. Some such embodiments may reduce the time spent on shifting attention between the patient and medical image and thus allow more time to be spent on observing and providing medical attention to the patient. Various embodiments described herein may also advantageously provide an improved user view of one or more objects in the user's central field of view. For example, some embodiments can be configured to provide a grey background to de-emphasize the rest of the room relative to the surgical site and/or the medical image.

Figure 1G:
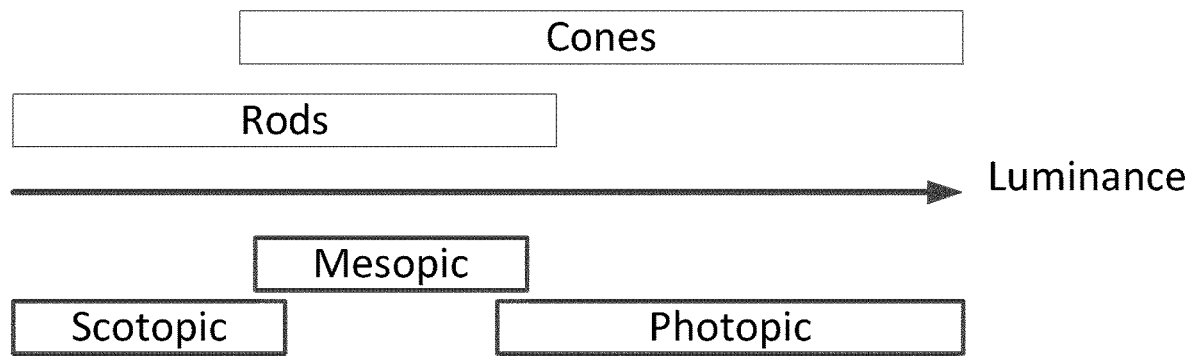
FIG. 1G illustrates visual function under different lighting conditions.
Figure 2:
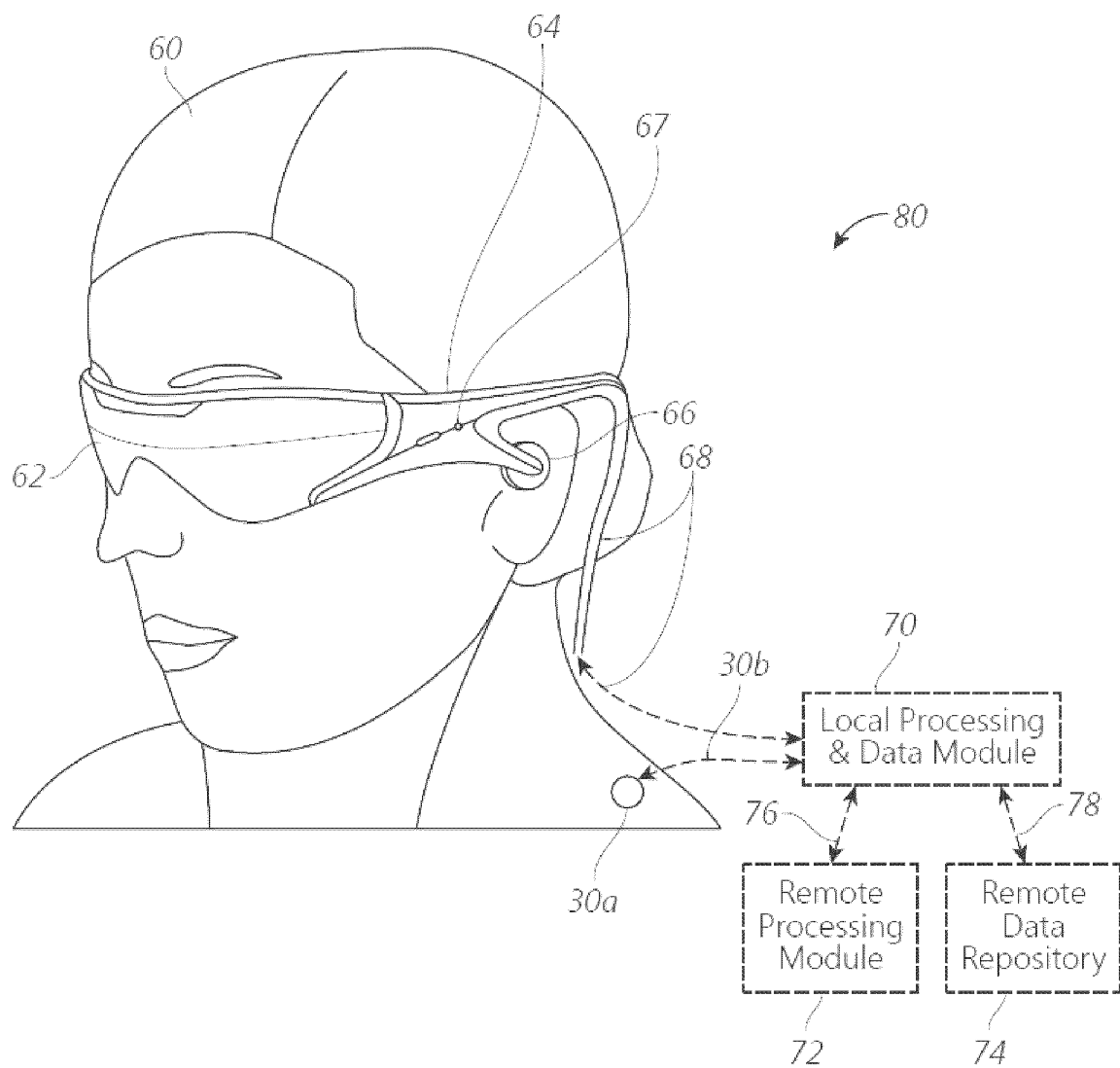

There are three different types of vision: photopic, mesopic, and scotopic vision. Photopic, mesopic, and scotopic vision are the vision of the eye under relatively bright (e.g., from 10 to $10^8$ cd/m$^2$ in some instances), intermediate (e.g., from $10^{-3}$ cd/m$^2$ to $10^{0.5}$ cd/m$^2$ in some instances), and low light (e.g., from $10^{-3.5}$ cd/m$^2$ to $10^{-6}$ cd/m$^2$ in some instances) conditions respectively. For example, depending on the ambient light luminance, cones, rods, or both may be activated. The cones and rods may be inversely related as they are activated during different lighting conditions. As shown in FIG. 1G, cones are activated under high light conditions, while rods are activated during low light conditions. Thus, for photopic vision, cones are mainly used and for scotopic vision, rods are mainly used. Mesopic vision utilizes both cones and rods. Since visual acuity can depend on the resolution or density of the cones and/or rods, visual acuity can also be a function of the illumination level. Accordingly, various embodiments described herein may include one or more capture devices (e.g., one or more cameras, light sensors, light meters, etc.) to capture the lighting condition and/or may present or modify (e.g., enhance, de-emphasize, move, etc.) at least a portion of image content based at least in part on the lighting condition.

As photopic vision turns into mesopic vision, the rods become more active although not necessarily by a linear relationship. For example, the relationship can be dependent upon time spent in the dark environment. The darker the environment, the faster it can be for the transition from cones being active to rods being active. As scotopic vision turns into mesopic vision, the opposite can occur. By monitoring time, luminance level, and luminance level change, the amount of the cones and/or rods being utilized can be determined. Accordingly, various embodiments described herein may include one or more timing devices (e.g., one or more clocks or timers) to monitor the time and/or may present or modify (e.g., enhance, de-emphasize, move, etc.) at least a portion of image content based at least in part on the lighting condition and/or at least in part on the time in the lighting condition.

Although not limited to the medical context, certain embodiments described herein may be implemented for medical imaging, display, and visualization. For example, medical care service professionals receive heavy demands on their physical and mental capabilities in connection with the medical services they provide. Such professionals can include, for example, doctors, surgeons, nurses, technicians, dentists, ophthalmologists, home medical service providers, clinicians, and/or other medical care providers. In many circumstances, the demands of medical care require quick responses and precise action. Professionals outside of the medical context (e.g., athletes, mechanics, and chefs) may also benefit from various embodiments described herein. Moreover, those with occupations and hobbies that require the use of one's hands while requiring information from multiple locations can benefit from the methods and systems disclosed herein. Furthermore, various embodiments described herein can be used in everyday activities, e.g., tasks which may require user focus and concentration such as operating a motor vehicle or other vehicle.

Advantageously, in some embodiments, augmented reality (AR) display systems disclosed herein may be configured to aid medical care providers in their work (e.g., to provide an enhanced user view of one or more objects in the user's peripheral and/or central field of view). The AR systems may display virtual content to a user, or viewer, while still allowing the user to see the world around them. Preferably, this content is displayed on a head-mounted display, e.g., as part of eyewear, that projects image information to the user's eyes. In addition, the display may also transmit light from the surrounding environment to the user's eyes, to allow a view of that surrounding environment. As used herein, it will be appreciated that a "head-mounted" display is a display that may be mounted on the head of a viewer.

A person wearing a head-mounted augmented reality display system or device such as described herein may be provided with a view of the external world or environment through transparent optics, e.g., windows, lens, waveguides, etc., that permit light from objects in the external environment to pass through the transparent optics to the eyes of the user such that those objects in the external environment can be viewed directly. The person wearing the head mounted augmented reality display has a field of view, such as shown in FIG. 1B when viewing the external world directly through the transparent elements of the head mounted display. The AR system, may additionally present images to the users wearing the head mounted display, for example, by projecting light from a modulated light source into the eye of the user. These images may be referred to as "virtual" images as these "virtual" images are generated by a display and not from light from objects in the external world that passes through the transparent elements of the head mounted display to the eye to form an image of the objects on the retina.

As discussed further below, many VR, AR, and MR display devices suffer from accommodation-vergence mismatches when displaying image information. Such mismatches may cause user discomfort and may make long-term wear of the device infeasible. Advantageously, display devices according to embodiments herein allow for long-term wear of the device by, among other things, providing a correct match between accommodation and vergence in the user. As a result, users of the device may be able to wear and use the device substantially continuously for durations of 3 hours or more, 4 hours or more, 5 hours or more, 6 hours or more, or all day, without removing the device for more than 25%, more than 20%, more than 15%, more than 10%, or more than 5% of the duration. In some embodiments, the display device may display augmented reality images substantially continuously for the above-noted durations.

The wearability of display systems disclosed herein and the long-term nature of that wearability, coupled with the close proximity of the display system (including sensory components) to the user, advantageously facilitate the use of the display system or device before, during, and after medical procedures and treatments. In some embodiments, the display system may be configured to provide images of real world objects in the field of view of the user (e.g., tangible objects in the environment forward the user, etc.). In certain embodiments, the display system can render the images of the real-world objects as enhanced images for the viewer. Enhanced images may include, for example, images projected by a light source into the eye that have improved magnification, location in the field of view of the user, depth plane allocation, color saturation, contrast, brightness, sharpness, measurement proportions, white balance, shadows, highlights, image orientation relative to the user, color or shadow balance, and/or clarity, relative to the image of the actual real-world object in the environment in front of the user wearing the head mounted display and/or relative to other images provided by the display and/or other objects in the environment in front of the user wearing the head mounted display. For example, the display system may be configured to identify an object in the real world and display a magnified image of the object. In various embodiments, the display system may be configured to magnify a portion of the image in comparison to other portions of the image or other objects in the field of view of the user viewing objects in the environment ahead through the transparent optical elements (windows, lenses, waveguides) of the head mounted display.

In some embodiments, the display system may be configured to determine an approximate distance that the object appears to be from a user. In certain embodiments, the display system can render an image of the object at a depth field based at least in part on the approximate determined distance. It will be appreciated that the display system may display visual content for each eye, and may alter various visual parameters, including the location of the visual content, the depth plane on which the content is displayed, the duration of exposure to the visual content, etc. By varying the visual content and these visual parameters, the real-world object can be rendered by the display system in a variety of manners, as described herein. In some embodiments, the display system may alter various visual parameters of visual content for other objects in the environment and/or for the surrounding environment.

The human visual system is not a passive sensor type of system; it is configured to actively scan the environment. In a manner somewhat akin to use of a flatbed scanner to capture an image, or use of a finger to read Braille from a paper, the photoreceptors of the eye fire in response to changes in stimulation, rather than constantly responding to a constant state of stimulation.

The visual cortex of the brain gains valuable perception information from the motion of both eyes and components thereof relative to each other, as discussed herein. Moreover, movement of the head, which houses the eyes, also has a key impact upon visualization of objects. Humans move their heads to visualize the world around them; they often are in a fairly constant state of repositioning and reorienting the head relative to an object of interest. Further, most people prefer to move their heads when their eye gaze needs to move more than about 20 degrees off center to focus on a particular object (e.g., people do not typically like to look at things "from the corner of the eye"). Humans also typically scan or move their heads in relation to sounds—to improve audio signal capture and utilize the geometry of the ears relative to the head. The human visual system gains powerful depth cues from what is called "head motion parallax", which is related to the relative motion of objects at different distances as a function of head motion and eye vergence distance (e.g., if a person moves his head from side to side and maintains fixation on an object, items farther out from that object will move in the same direction as the head; items in front of that object will move opposite the head motion; these are very salient cues for where things are spatially in the environment relative to the person—perhaps as powerful as stereopsis). Head motion also is utilized to look around objects, of course.

The reliance on head movements by a user, however, may be disadvantageous in a situation where the user requires heightened levels of focus, concentration, and/or attention (e.g., during a surgery or while driving a car). In such situations, a user may find it helpful to have images presented more conveniently (e.g., personalized for the user) or enhanced, such as magnified, more centrally, for example, closer to his or her central field of view or closer to the optical axis and/or fovea, or in other ways as described herein. The user may also find it helpful to have possibly distracting content de-emphasized, such as reduced in size or moved to the periphery.

In some embodiments, the ability of the display system to display images on multiple depth planes may advantageously be applied to determine which of multiple images that a viewer is perceiving or reacting to, advantageously without requiring direct user input or complex external instrumentation to measure brain activity. For example, real-world images may be rendered on different depth planes of the display system, and the accommodation and/or vergence of the user's eyes may be measured (e.g., using eye-tracking cameras on the display device). It will be appreciated that images on different depth planes that are perceived by the viewer will cause the eye to assume different accommodation and/or vergence states. Consequently, the image that is perceived by the user may be inferred by determining: 1) the accommodation and/or vergence states of the user's eyes; and 2) matching that accommodation and/or vergence state with the images or depth planes of the images being displayed. The image corresponding to the measured accommodation and/or vergence states of the user is then interpreted to be the image that is perceived by the user. In some embodiments, the images may be displayed on widely disparate depth planes (e.g., infinity and the closest depth plane outputted by the display system) to increase the expected difference in accommodation and/or vergence states between the images. In some embodiments, the duration of the user's fixation on an image (e.g., the amount of time that the user's eyes assume a particular accommodation and/or vergence state may also be measured to infer whether the user is actively perceiving a particular image, or whether the change in accommodation and/or vergence states is, e.g., an involuntary reflex. It will be appreciated that such a scheme for detecting user perception may be utilized for various perception tests, including without limitation, tests related to rivalry, dominance and/or suppression, backward masking, and forward masking.

As discussed above, the field of regard comprises a portion of the environment around the user that is capable of being perceived by the user. Accordingly, for a user wearing a head-mounted augmented reality device (ARD), the field of regard may include substantially all of the 4π steradian solid angle surrounding the wearer, because the wearer can move his or her body, head, or eyes to perceive substantially any direction in space. In other contexts, the user's movements may be more constricted, and accordingly the user's field of regard may subtend a smaller solid angle.

In FIG. 1B, the field of regard 1765 can contain a group of objects (e.g., objects 1721, 1722, 1727) which can be perceived by the user wearing the AR system. In some embodiments, objects 1729 may be outside the user's field of view looking through the transparent optics of the head mounted display but may nonetheless potentially be perceived by at least one sensor (e.g., cameras) on the AR system (depending on their location and field of view) and displayed for the user 60.

The AR system can add virtual elements to the existing physical objects viewed through the transparent optics of the head mounted display, thereby permitting user interaction with the physical objects. For example, the AR system may add a virtual menu associated with a medical monitor in the room, where the virtual menu may give the user the option to turn on or adjust medical imaging equipment or dosing controls using the AR system.

Accordingly, the display may present additional virtual image content to the wearer in addition to the virtual image of the object in the environment in front of the user. The virtual objects may include, for example, operating system objects such as e.g., a terminal for inputting commands, a file manager for accessing files or directories, an icon, a menu, an application for audio or video streaming, a notification from an operating system, and so on. The virtual objects may also include objects in an application such as e.g., avatars, virtual objects in games, graphics or images, etc. Some virtual objects can be both an operating system object and an object in an application.

The field of view 1755 can contain multiple objects (e.g. objects 1721, 1722). The field of view 1755 can depend on the size or optical characteristics of the AR system, for example clear aperture size of the transparent window or lens of the head mounted display through which light passes from the real world in front of the user to the user's eyes. In some embodiments, as the user's 60 pose changes (e.g., head pose, body pose, and/or eye pose), the field of view 1755 can correspondingly change, and the objects within the field of view 1755 may also change. As described herein, the AR system may include sensors such as cameras that monitor or image objects in the field of regard 1765 as well as objects in the field of view 1755. In some such embodiments, the AR system may alert the user of unnoticed objects or events occurring in the user's field of view 1755 and/or occurring outside the user's field of view but within the field of regard 1765. In some embodiments, the AR system can also distinguish between what a user 60 is or not directing attention to.

FIG. 2 illustrates an example of wearable display system 80. The display system 80 includes a display 62, and various mechanical and electronic modules and systems to support the functioning of that display 62. The display 62 may be coupled to a frame 64, which is wearable by a display system user or viewer 60 and which is configured to position the display 62 in front of the eyes of the user 60. The display 62 may be considered eyewear in some embodiments. In some embodiments, a speaker 66 is coupled to the frame 64 and positioned adjacent the ear canal of the user 60 (in some embodiments, another speaker, not shown, is positioned adjacent the other ear canal of the user to provide for stereo/shapeable sound control). In some embodiments, the display system may also include one or more microphones 67 or other devices to detect sound. In some embodiments, the microphone is configured to allow the user to provide inputs or commands to the system 80 (e.g., the selection of voice menu commands, natural language questions, etc.), and/or may allow audio communication with other persons (e.g., with other users of similar display systems. The microphone may further be configured as a peripheral sensor to continuously collect audio data (e.g., to passively collect from the user and/or environment). Such audio data may include user sounds such as heavy breathing, or environmental sounds, such as a loud bang indicative of a nearby event. The display system may also include a peripheral sensor 30*a*, which may be separate from the frame 64 and attached to the body of the user 60 (e.g., on the head, torso, an extremity, etc. of the user 60). The peripheral sensor 30*a* may be configured to acquire data regarding the user 60 in some embodiments, as described further herein.

With continued reference to FIG. 2, the display 62 is operatively coupled by communications link 68, such as by a wired lead or wireless connectivity, to a local data processing module 70 which may be mounted in a variety of configurations, such as fixedly attached to the frame 64, fixedly attached to a helmet or hat worn by the user, embedded in headphones, or otherwise removably attached to the user 60 (e.g., in a backpack-style configuration, in a belt-coupling style configuration). Similarly, the sensor 30*a* may be operatively coupled by communications link 30*b*, e.g., a wired lead or wireless connectivity, to the local processor and data module 70. The local processing and data module 70 may comprise a hardware processor, as well as digital memory, such as non-volatile memory (e.g., flash memory or hard disk drives), both of which may be utilized to assist in the processing, caching, and storage of data. The data include data a) captured from sensors (which may be, e.g., operatively coupled to the frame 64 or otherwise attached to the user 60), such as image capture devices (such as cameras), microphones, inertial measurement units, accelerometers, compasses, GPS units, radio devices, gyros, depth sensors, pairs of binocular world cameras, geolocation sensors, proximity sensors, and/or other sensors disclosed herein; and/or b) acquired and/or processed using remote processing module 72 and/or remote data repository 74 (including data relating to virtual content), possibly for passage to the display 62 after such processing or retrieval. The local processing and data module 70 may be operatively coupled by communication links 76, 78, such as via a wired or wireless communication links, to the remote processing module 72 and remote data repository 74 such that these remote modules 72, 74 are operatively coupled to each other and available as resources to the local processing and data module 70. In some embodiments, the local processing and data module 70 may include one or more of the image capture devices, microphones, inertial measurement units, accelerometers, compasses, GPS units, radio devices, gyros, depth sensors, pairs of binocular world cameras, geolocation sensors, proximity sensors, etc. In some other embodiments, one or more of these sensors may be attached to the frame 64, or may be standalone structures that communicate with the local processing and data module 70 by wired or wireless communication pathways.

With continued reference to FIG. 2, in some embodiments, the remote processing module 72 may comprise one or more processors configured to analyze and process data and/or image information. In some embodiments, the remote data repository 74 may comprise a digital data storage facility, which may be available through the internet or other networking configuration in a "cloud" resource configuration. In some embodiments, the remote data repository 74 may include one or more remote servers, which provide information, e.g., information for generating augmented reality content, to the local processing and data module 70 and/or the remote processing module 72. In some embodiments, all data is stored and all computations are performed in the local processing and data module, allowing fully autonomous use from a remote module.

Figure 3:
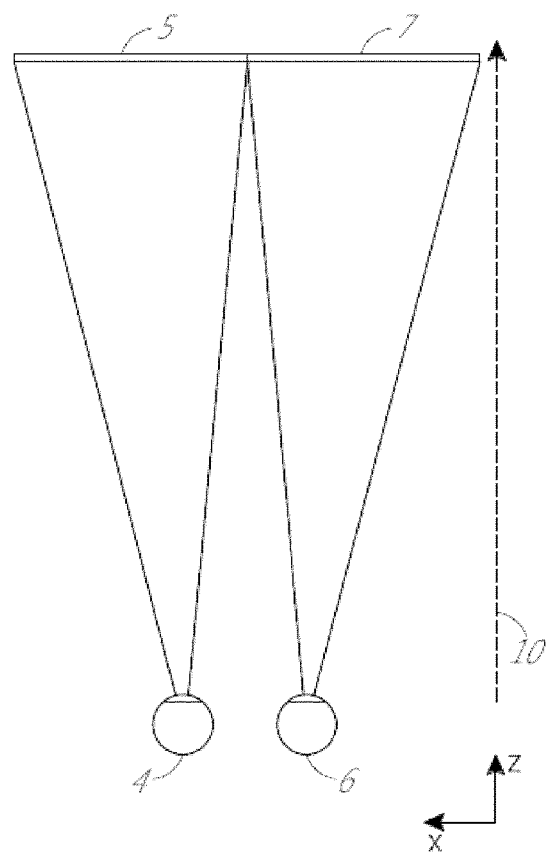
FIG. 3 illustrates a conventional display system for simulating three-dimensional imagery for a user.

The perception of an image as being "three-dimensional" or "3-D" may be achieved by providing slightly different presentations of the image to each eye of the viewer. FIG. 3 illustrates a conventional display system for simulating three-dimensional imagery for a user. Two distinct images 5, 7—one for each eye 4, 6—are outputted to the user. The images 5, 7 are spaced from the eyes 4, 6 by a distance 10 along an optical or z-axis parallel to the line of sight of the viewer. The images 5, 7 are flat and the eyes 4, 6 may focus on the images by assuming a single accommodated state. Such systems rely on the human visual system to combine the images 5, 7 to provide a perception of depth and/or scale for the combined image.

It will be appreciated, however, that the human visual system is more complicated and providing a realistic perception of depth is more challenging. For example, many viewers of conventional "3-D" display systems find such systems to be uncomfortable or may not perceive a sense of depth at all. Without being limited by theory, it is believed that viewers of an object may perceive the object as being "three-dimensional" due to a combination of vergence and accommodation. Vergence movements (i.e., rotation of the eyes so that the pupils move toward or away from each other to converge the lines of sight of the eyes to fixate upon an object) of the two eyes relative to each other are closely associated with focusing (or "accommodation") of the lenses and pupils of the eyes. Under normal conditions, changing the focus of the lenses of the eyes, or accommodating the eyes, to change focus from one object to another object at a different distance will automatically cause a matching change in vergence to the same distance, under a relationship known as the "accommodation-vergence reflex," as well as pupil dilation or constriction. Likewise, a change in vergence will trigger a matching change in accommodation of lens shape and pupil size, under normal conditions. As noted herein, many stereoscopic or "3-D" display systems display a scene using slightly different presentations (and, so, slightly different images) to each eye such that a three-dimensional perspective is perceived by the human visual system. Such systems are uncomfortable for many viewers, however, since they, among other things, simply provide a different presentation of a scene, but with the eyes viewing all the image information at a single accommodated state, and work against the "accommodation-vergence reflex." Display systems that provide a better match between accommodation and vergence may form more realistic and comfortable simulations of three-dimensional imagery contributing to increased duration of wear and in turn compliance to diagnostic and therapy protocols.

Figure 4:
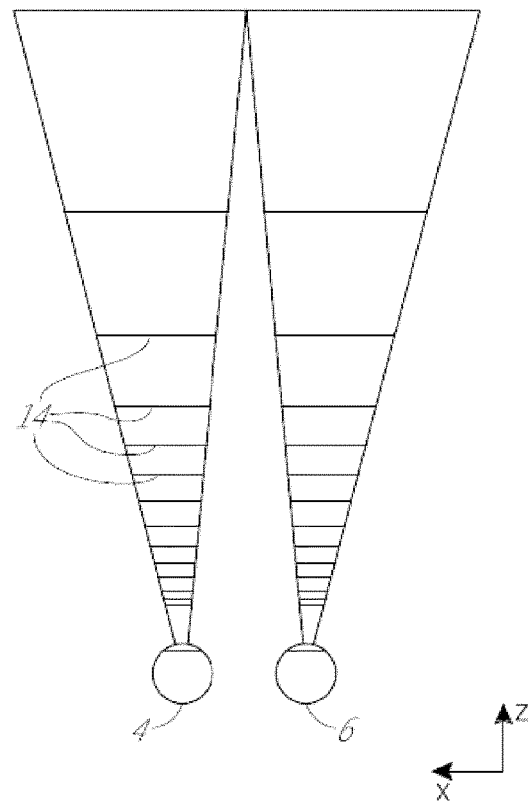
FIG. 4 illustrates aspects of an approach for simulating three-dimensional imagery using multiple depth planes.

FIG. 4 illustrates aspects of an approach for simulating three-dimensional imagery using multiple depth planes. With reference to FIG. 4, objects at various distances from eyes 4, 6 on the z-axis are accommodated by the eyes 4, 6 so that those objects are in focus. The eyes (4 and 6) assume particular accommodated states to bring into focus objects at different distances along the z-axis. Consequently, a particular accommodated state may be said to be associated with a particular one of depth planes 14, which has an associated focal distance, such that objects or parts of objects in a particular depth plane are in focus when the eye is in the accommodated state for that depth plane. In some embodiments, three-dimensional imagery may be simulated by providing different presentations of an image for each of the eyes 4, 6, and also by providing different presentations of the image corresponding to each of the depth planes. While shown as being separate for clarity of illustration, it will be appreciated that the fields of view of the eyes 4, 6 may overlap, for example, as distance along the z-axis increases. In addition, while shown as flat for ease of illustration, it will be appreciated that the contours of a depth plane may be curved in physical space, such that all features in a depth plane are in focus with the eye in a particular accommodated state.

Figure 5A:
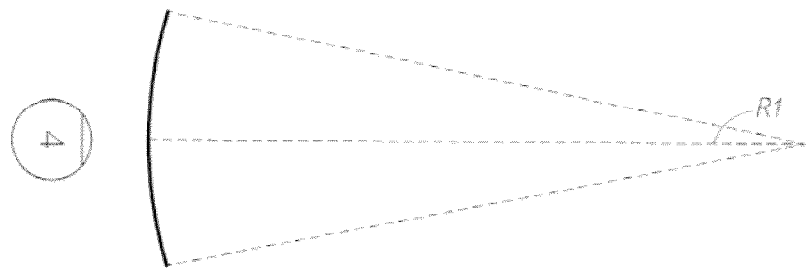
FIGS. 5A-5C illustrate relationships between radius of curvature and focal radius.
Figure 5B:
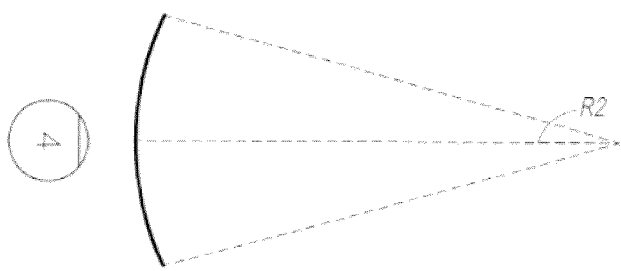
Figure 5C:
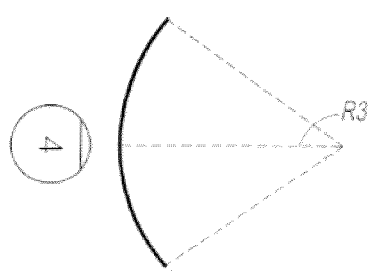

The distance between an object and the eye 4 or 6 may also change the amount of divergence of light from that object, as viewed by that eye. FIGS. 5A-5C illustrate relationships between distance and the divergence of light rays. The distance between the object and the eye 4 is represented by, in order of decreasing distance, R1, R2, and R3. As shown in FIGS. 5A-5C, the light rays become more divergent as distance to the object decreases. As distance increases, the light rays become more collimated. Stated another way, it may be said that the light field produced by a point (the object or a part of the object) has a spherical wavefront curvature, which is a function of how far away the point is from the eye of the user. The curvature increases with decreasing distance between the object and the eye 4. Consequently, at different depth planes, the degree of divergence of light rays is also different, with the degree of divergence increasing with decreasing distance between depth planes and the viewer's eye 4. While only a single eye 4 is illustrated for clarity of illustration in FIGS. 5A-5C and other figures herein, it will be appreciated that the discussions regarding eye 4 may be applied to both eyes 4 and 6 of a viewer.

Without being limited by theory, it is believed that the human eye typically can interpret a finite number of depth planes to provide depth perception. Consequently, a highly believable simulation of perceived depth may be achieved by providing, to the eye, different presentations of an image (e.g., scene) corresponding to each of these limited number of depth planes. The different presentations may be separately focused by the viewer's eyes, thereby helping to provide the user with depth cues based on the accommodation of the eye required to bring into focus different image features for the scene located on different depth plane and/or based on observing different image features on different depth planes being out of focus.

Figure 6:
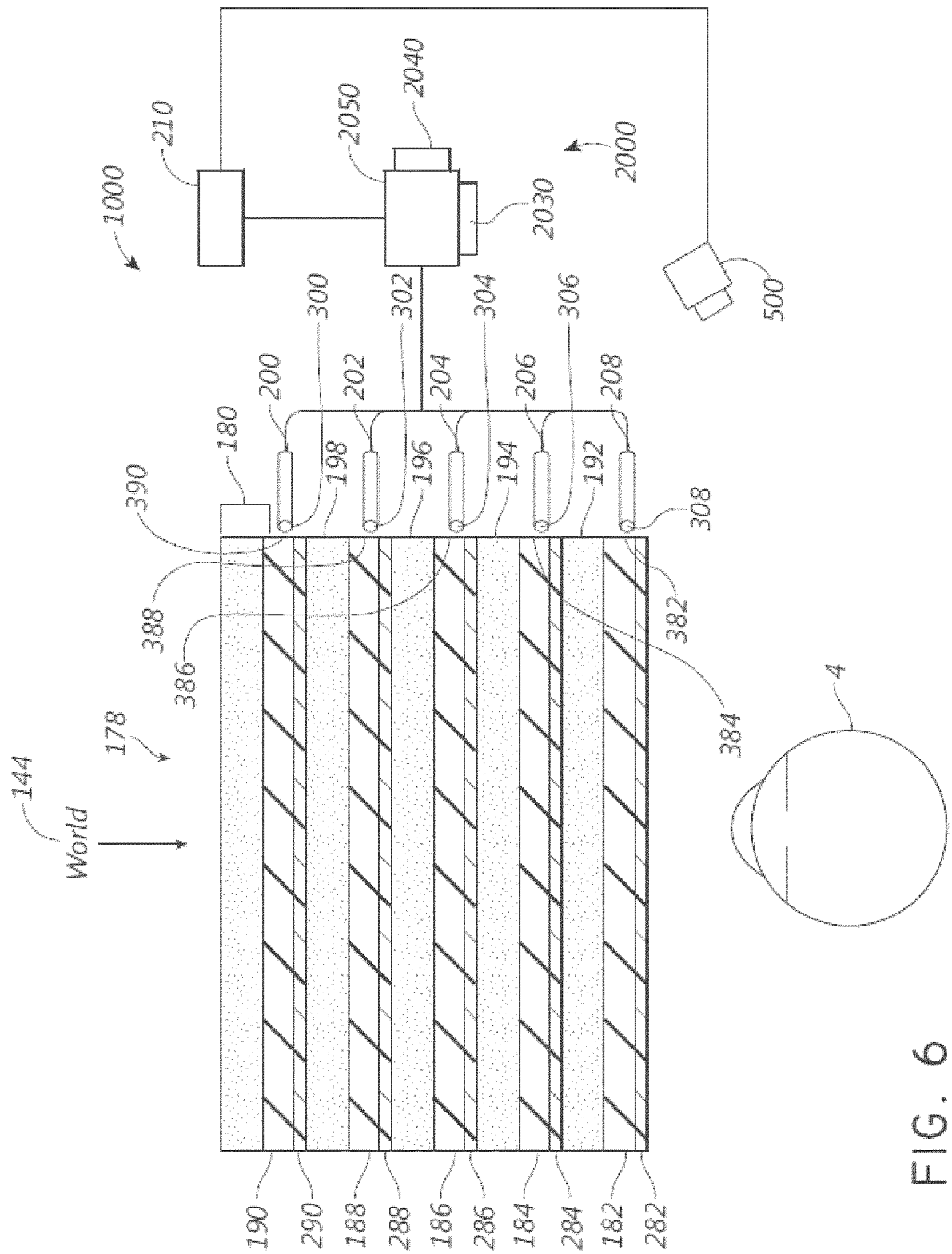
FIG. 6 illustrates an example of a waveguide stack for outputting image information to a user.

FIG. 6 illustrates an example of a waveguide stack for outputting image information to a user. A display system 1000 includes a stack of waveguides, or stacked waveguide assembly, 178 that may be utilized to provide three-dimensional perception to the eye/brain using a plurality of waveguides 182, 184, 186, 188, 190. In some embodiments, the display system 1000 is the system 80 of FIG. 2, with FIG. 6 schematically showing some parts of that system 80 in greater detail. For example, the waveguide assembly 178 may be part of the display 62 of FIG. 2. It will be appreciated that the display system 1000 may be considered a light field display in some embodiments.

With continued reference to FIG. 6, the waveguide assembly 178 may also include a plurality of features 198, 196, 194, 192 between the waveguides. In some embodiments, the features 198, 196, 194, 192 may be one or more lenses. The waveguides 182, 184, 186, 188, 190 and/or the plurality of lenses 198, 196, 194, 192 may be configured to send image information to the eye with various levels of wavefront curvature or light ray divergence. Each waveguide level may be associated with a particular depth plane and may be configured to output image information corresponding to that depth plane. Image injection devices 200, 202, 204, 206, 208 may function as a source of light for the waveguides and may be utilized to inject image information into the waveguides 182, 184, 186, 188, 190, each of which may be configured, as described herein, to distribute incoming light across each respective waveguide, for output toward the eye 4. Light exits an output surface 300, 302, 304, 306, 308 of the image injection devices 200, 202, 204, 206, 208 and is injected into a corresponding input surface 382, 384, 386, 388, 390 of the waveguides 182, 184, 186, 188, 190. In some embodiments, the each of the input surfaces 382, 384, 386, 388, 390 may be an edge of a corresponding waveguide, or may be part of a major surface of the corresponding waveguide (that is, one of the waveguide surfaces directly facing the world 144 or the viewer's eye 4). In some embodiments, a single beam of light (e.g. a collimated beam) may be injected into each waveguide to output an entire field of cloned collimated beams that are directed toward the eye 4 at particular angles (and amounts of divergence) corresponding to the depth plane associated with a particular waveguide. In some embodiments, a single one of the image injection devices 200, 202, 204, 206, 208 may be associated with and inject light into a plurality (e.g., three) of the waveguides 182, 184, 186, 188, 190.

In some embodiments, the image injection devices 200, 202, 204, 206, 208 are discrete displays that each produce image information for injection into a corresponding waveguide 182, 184, 186, 188, 190, respectively. In some other embodiments, the image injection devices 200, 202, 204, 206, 208 are the output ends of a single multiplexed display which may, e.g., pipe image information via one or more optical conduits (such as fiber optic cables) to each of the image injection devices 200, 202, 204, 206, 208. It will be appreciated that the image information provided by the image injection devices 200, 202, 204, 206, 208 may include light of different wavelengths, or colors (e.g., different component colors, as discussed herein).

In some embodiments, the light injected into the waveguides 182, 184, 186, 188, 190 is provided by a light projector system 2000, which comprises a light module 2040, which may include a light emitter, such as a light emitting diode (LED). The light from the light module 2040 may be directed to and modified by a light modulator 2030, e.g., a spatial light modulator, via a beam splitter 2050. The light modulator 2030 may be configured to change the perceived intensity of the light injected into the waveguides 182, 184, 186, 188, 190. Examples of spatial light modulators include liquid crystal displays (LCD) including a liquid crystal on silicon (LCOS) displays.

In some embodiments, the display system 1000 may be a scanning fiber display comprising one or more scanning fibers configured to project light in various patterns (e.g., raster scan, spiral scan, Lissajous patterns, etc.) into one or more waveguides 182, 184, 186, 188, 190 and ultimately to the eye 4 of the viewer. In some embodiments, the illustrated image injection devices 200, 202, 204, 206, 208 may schematically represent a single scanning fiber or a bundles of scanning fibers configured to inject light into one or a plurality of the waveguides 182, 184, 186, 188, 190. In some other embodiments, the illustrated image injection devices 200, 202, 204, 206, 208 may schematically represent a plurality of scanning fibers or a plurality of bundles of scanning, fibers each of which are configured to inject light into an associated one of the waveguides 182, 184, 186, 188, 190. It will be appreciated that the one or more optical fibers may be configured to transmit light from the light module 2040 to the one or more waveguides 182, 184, 186, 188, 190. It will be appreciated that one or more intervening optical structures may be provided between the scanning fiber, or fibers, and the one or more waveguides 182, 184, 186, 188, 190 to, e.g., redirect light exiting the scanning fiber into the one or more waveguides 182, 184, 186, 188, 190.

A controller 210 controls the operation of one or more of the stacked waveguide assembly 178, including operation of the image injection devices 200, 202, 204, 206, 208, the light source 2040, and the light modulator 2030. In some embodiments, the controller 210 is part of the local data processing module 70. The controller 210 includes programming (e.g., instructions in a non-transitory medium) that regulates the timing and provision of image information to the waveguides 182, 184, 186, 188, 190 according to, e.g., any of the various schemes disclosed herein. In some embodiments, the controller may be a single integral device, or a distributed system connected by wired or wireless communication channels. The controller 210 may be part of the processing modules 70 or 72 (FIG. 2) in some embodiments.

With continued reference to FIG. 6, the waveguides 182, 184, 186, 188, 190 may be configured to propagate light within each respective waveguide by total internal reflection (TIR). The waveguides 182, 184, 186, 188, 190 may each be planar or have another shape (e.g., curved), with major top and bottom surfaces and edges extending between those major top and bottom surfaces. In the illustrated configuration, the waveguides 182, 184, 186, 188, 190 may each include outcoupling optical elements 282, 284, 286, 288, 290 that are configured to extract light out of a waveguide by redirecting the light, propagating within each respective waveguide, out of the waveguide to output image information to the eye 4. Extracted light may also be referred to as outcoupled light and the outcoupling optical elements light may also be referred to light extracting optical elements. An extracted beam of light is outputted by the waveguide at locations at which the light propagating in the waveguide strikes a light extracting optical element. The outcoupling optical elements 282, 284, 286, 288, 290 may, for example, be gratings, including diffractive optical features, as discussed further herein. While illustrated disposed at the bottom major surfaces of the waveguides 182, 184, 186, 188, 190 for ease of description and drawing clarity, in some embodiments, the outcoupling optical elements 282, 284, 286, 288, 290 may be disposed at the top and/or bottom major surfaces, and/or may be disposed directly in the volume of the waveguides 182, 184, 186, 188, 190, as discussed further herein. In some embodiments, the outcoupling optical elements 282, 284, 286, 288, 290 may be formed in a layer of material that is attached to a transparent substrate to form the waveguides 182, 184, 186, 188, 190. In some other embodiments, the waveguides 182, 184, 186, 188, 190 may be a monolithic piece of material and the outcoupling optical elements 282, 284, 286, 288, 290 may be formed on a surface and/or in the interior of that piece of material.

With continued reference to FIG. 6, as discussed herein, each waveguide 182, 184, 186, 188, 190 is configured to output light to form an image corresponding to a particular depth plane. For example, the waveguide 182 nearest the eye may be configured to deliver collimated light, as injected into such waveguide 182, to the eye 4. The collimated light may be representative of the optical infinity focal plane. The next waveguide up 184 may be configured to send out collimated light which passes through the first lens 192 (e.g., a negative lens) before it can reach the eye 4; such first lens 192 may be configured to create a slight convex wavefront curvature so that the eye/brain interprets light coming from that next waveguide up 184 as coming from a first focal plane closer inward toward the eye 4 from optical infinity. Similarly, the third up waveguide 186 passes its output light through both the first 192 and second 194 lenses before reaching the eye 4; the combined optical power of the first 192 and second 194 lenses may be configured to create another incremental amount of wavefront curvature so that the eye/brain interprets light coming from the third waveguide 186 as coming from a second focal plane that is even closer inward toward the person from optical infinity than was light from the next waveguide up 184.

The other waveguide layers 188, 190 and lenses 196, 198 are similarly configured, with the highest waveguide 190 in the stack sending its output through all of the lenses between it and the eye for an aggregate focal power representative of the closest focal plane to the person. To compensate for the stack of lenses 198, 196, 194, 192 when viewing/interpreting light coming from the world 144 on the other side of the stacked waveguide assembly 178, a compensating lens layer 180 may be disposed at the top of the stack to compensate for the aggregate power of the lens stack 198, 196, 194, 192 below. Such a configuration provides as many perceived focal planes as there are available waveguide/lens pairings. Both the outcoupling optical elements of the waveguides and the focusing aspects of the lenses may be static (i.e., not dynamic or electro-active). In some alternative embodiments, either or both may be dynamic using electro-active features.

In some embodiments, two or more of the waveguides 182, 184, 186, 188, 190 may have the same associated depth plane. For example, multiple waveguides 182, 184, 186, 188, 190 may be configured to output images set to the same depth plane, or multiple subsets of the waveguides 182, 184, 186, 188, 190 may be configured to output images set to the same plurality of depth planes, with one set for each depth plane. This can provide advantages for forming a tiled image to provide an expanded field of view at those depth planes.

With continued reference to FIG. 6, the outcoupling optical elements 282, 284, 286, 288, 290 may be configured to both redirect light out of their respective waveguides and to output this light with the appropriate amount of divergence or collimation for a particular depth plane associated with the waveguide. As a result, waveguides having different associated depth planes may have different configurations of outcoupling optical elements 282, 284, 286, 288, 290, which output light with a different amount of divergence depending on the associated depth plane. In some embodiments, the light extracting optical elements 282, 284, 286, 288, 290 may be volumetric or surface features, which may be configured to output light at specific angles. For example, the light extracting optical elements 282, 284, 286, 288, 290 may be volume holograms, surface holograms, and/or diffraction gratings. In some embodiments, the features 198, 196, 194, 192 may not be lenses; rather, they may simply be spacers (e.g., cladding layers and/or structures for forming air gaps).

In some embodiments, the outcoupling optical elements 282, 284, 286, 288, 290 are diffractive features that form a diffraction pattern, or "diffractive optical element" (also referred to herein as a "DOE"). Preferably, the DOE's have a sufficiently low diffraction efficiency so that only a portion of the light of the beam is deflected away toward the eye 4 with each intersection of the DOE, while the rest continues to move through a waveguide via total internal reflection. The light carrying the image information is thus divided into a number of related exit beams that exit the waveguide at a multiplicity of locations and the result is a fairly uniform pattern of exit emission toward the eye 4 for this particular collimated beam bouncing around within a waveguide.

In some embodiments, one or more DOEs may be switchable between "on" states in which they actively diffract, and "off" states in which they do not significantly diffract. For instance, a switchable DOE may comprise a layer of polymer dispersed liquid crystal, in which microdroplets comprise a diffraction pattern in a host medium, and the refractive index of the microdroplets may be switched to substantially match the refractive index of the host material (in which case the pattern does not appreciably diffract incident light) or the microdroplet may be switched to an index that does not match that of the host medium (in which case the pattern actively diffracts incident light).

In some embodiments, a camera assembly 500 (e.g., a digital camera, including visible light and infrared light cameras) may be provided to capture images of the eye 4 and/or tissue around the eye 4 to, e.g., detect user inputs. As used herein, a camera may be any image capture device. In some embodiments, the camera assembly 500 may include an image capture device and a light source to project light (e.g., infrared light) to the eye, which may then be reflected by the eye and detected by the image capture device. In some embodiments, the camera assembly 500 may be attached to the frame 64 (FIG. 2) and may be in electrical communication with the processing modules 70 and/or 72, which may process image information from the camera assembly 500. In some embodiments, one camera assembly 500 may be utilized for each eye, to separately monitor each eye.

Figure 7:
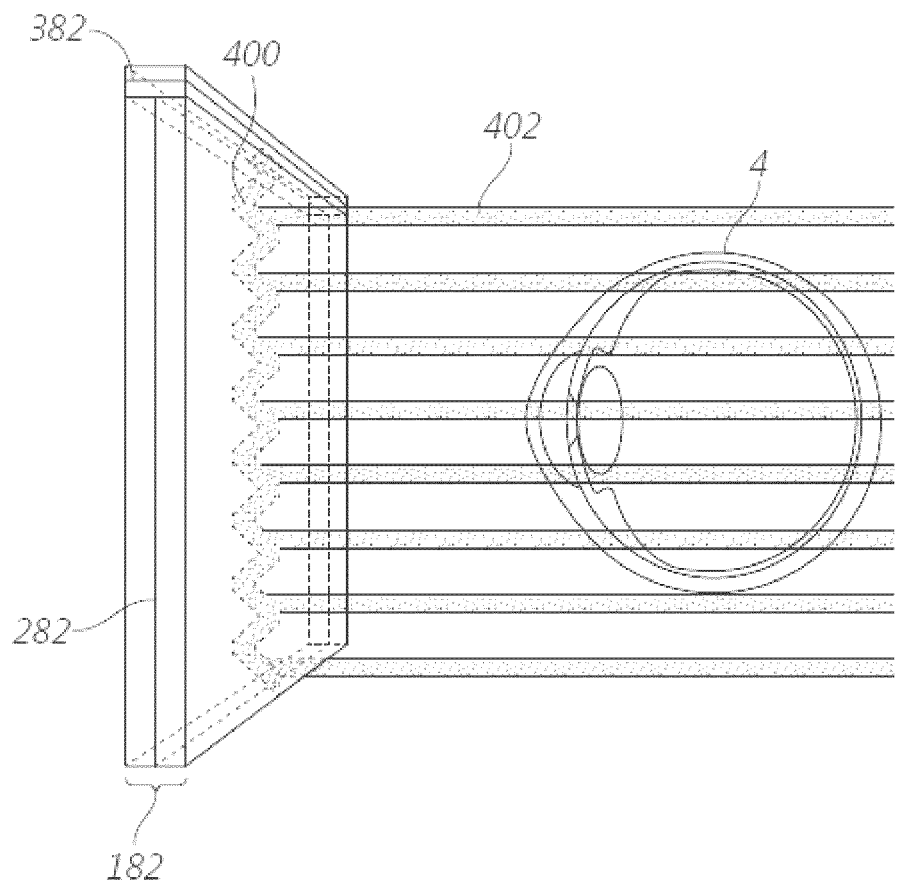
FIG. 7 illustrates an example of exit beams outputted by a waveguide.

With reference now to FIG. 7, an example of exit beams outputted by a waveguide is shown. One waveguide is illustrated, but it will be appreciated that other waveguides in the waveguide assembly 178 (FIG. 6) may function similarly, where the waveguide assembly 178 includes multiple waveguides. Light 400 is injected into the waveguide 182 at the input surface 382 of the waveguide 182 and propagates within the waveguide 182 by TIR. At points where the light 400 impinges on the DOE 282, a portion of the light exits the waveguide as exit beams 402. The exit beams 402 are illustrated as substantially parallel but, as discussed herein, they may also be redirected to propagate to the eye 4 at an angle (e.g., forming divergent exit beams), depending on the depth plane associated with the waveguide 182. It will be appreciated that substantially parallel exit beams may be indicative of a waveguide with outcoupling optical elements that outcouple light to form images that appear to be set on a depth plane at a large distance (e.g., optical infinity) from the eye 4. Other waveguides or other sets of outcoupling optical elements may output an exit beam pattern that is more divergent, which would require the eye 4 to accommodate to a closer distance to bring it into focus on the retina and would be interpreted by the brain as light from a distance closer to the eye 4 than optical infinity.

Figure 8:
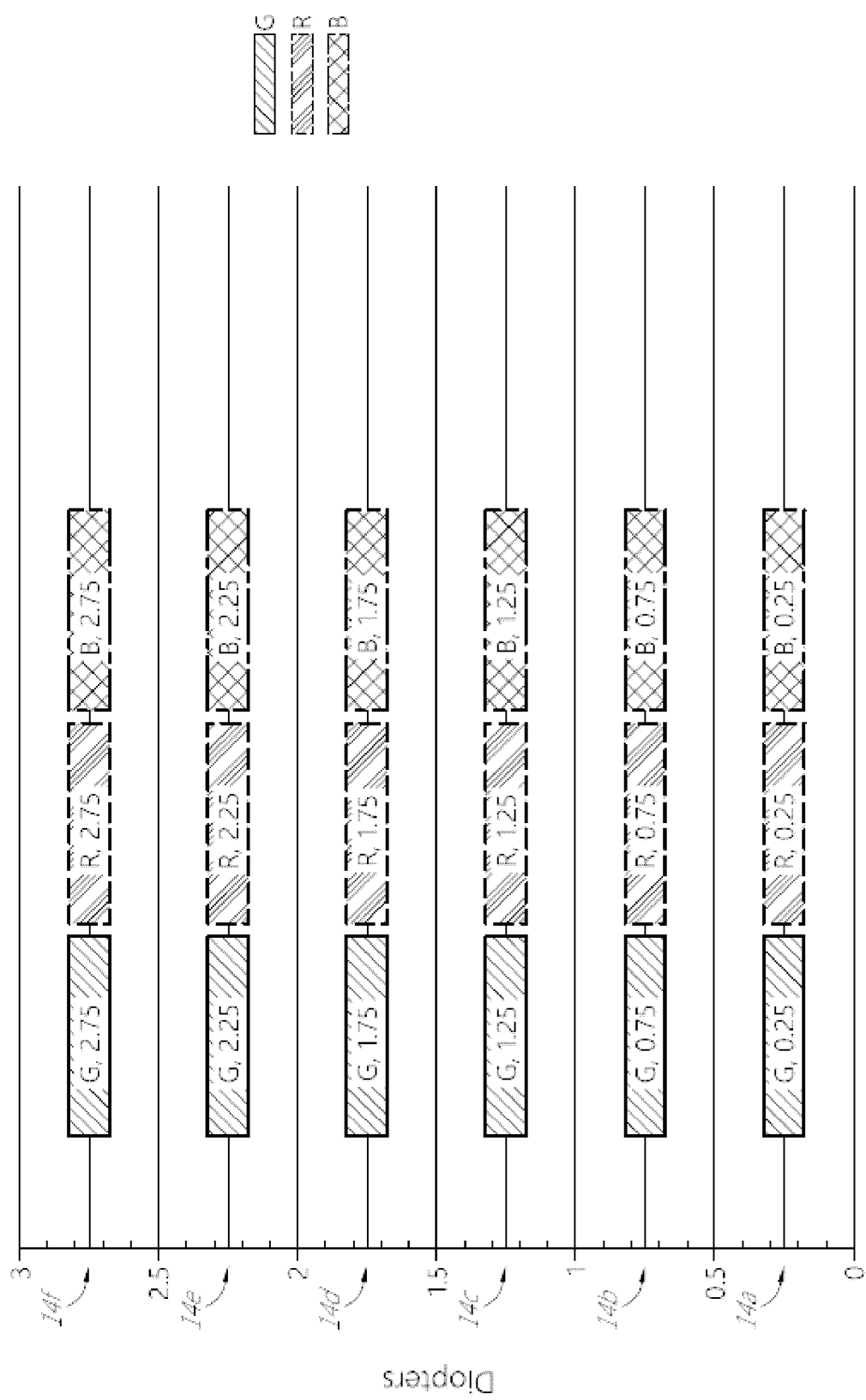
FIG. 8 illustrates an example of a stacked waveguide assembly in which each depth plane includes images formed using multiple different component colors.

In some embodiments, a full color image may be formed at each depth plane by overlaying images in each of the component colors, e.g., three or more component colors. FIG. 8 illustrates an example of a stacked waveguide assembly in which each depth plane includes images formed using multiple different component colors. The illustrated embodiment shows depth planes 14a-14f, although more or fewer depths are also contemplated. Each depth plane may have three component color images associated with it: a first image of a first color, G; a second image of a second color, R; and a third image of a third color, B. Different depth planes are indicated in the figure by different numbers for diopters (dpt) following the letters G, R, and B. Just as examples, the numbers following each of these letters indicate diopters (1/m), or inverse distance of the depth plane from a viewer, and each box in the figures represents an individual component color image. In some embodiments, to account for differences in the eye's focusing of light of different wavelengths, the exact placement of the depth planes for different component colors may vary. For example, different component color images for a given depth plane may be placed on depth planes corresponding to different distances from the user. Such an arrangement may increase visual acuity and user comfort and/or may decrease chromatic aberrations.

In some embodiments, light of each component color may be outputted by a single dedicated waveguide and, consequently, each depth plane may have multiple waveguides associated with it. In such embodiments, each box in the figures including the letters G, R, or B may be understood to represent an individual waveguide, and three waveguides may be provided per depth plane where three component color images are provided per depth plane. While the waveguides associated with each depth plane are shown adjacent to one another in this drawing for ease of description, it will be appreciated that, in a physical device, the waveguides may all be arranged in a stack with one waveguide per level. In some other embodiments, multiple component colors may be outputted by the same waveguide, such that, e.g., only a single waveguide may be provided per depth plane.

With continued reference to FIG. 8, in some embodiments, G is the color green, R is the color red, and B is the color blue. In some other embodiments, other colors associated with other wavelengths of light, including magenta and cyan, may be used in addition to or may replace one or more of red, green, or blue. In some embodiments, features 198, 196, 194, and 192 may be active or passive optical filters configured to block or selectively light from the ambient environment to the viewer's eyes.

It will be appreciated that references to a given color of light throughout this disclosure will be understood to encompass light of one or more wavelengths within a range of wavelengths of light that are perceived by a viewer as being of that given color. For example, red light may include light of one or more wavelengths in the range of about 620-780 nm, green light may include light of one or more wavelengths in the range of about 492-577 nm, and blue light may include light of one or more wavelengths in the range of about 435-493 nm.

In some embodiments, the light source 2040 (FIG. 6) may be configured to emit light of one or more wavelengths outside the visual perception range of the viewer, for example, infrared and/or ultraviolet wavelengths. In addition, the incoupling, outcoupling, and other light redirecting structures of the waveguides of the display 1000 may be configured to direct and emit this light out of the display towards the user's eye 4, e.g., for imaging and/or other applications.

Figure 9A:
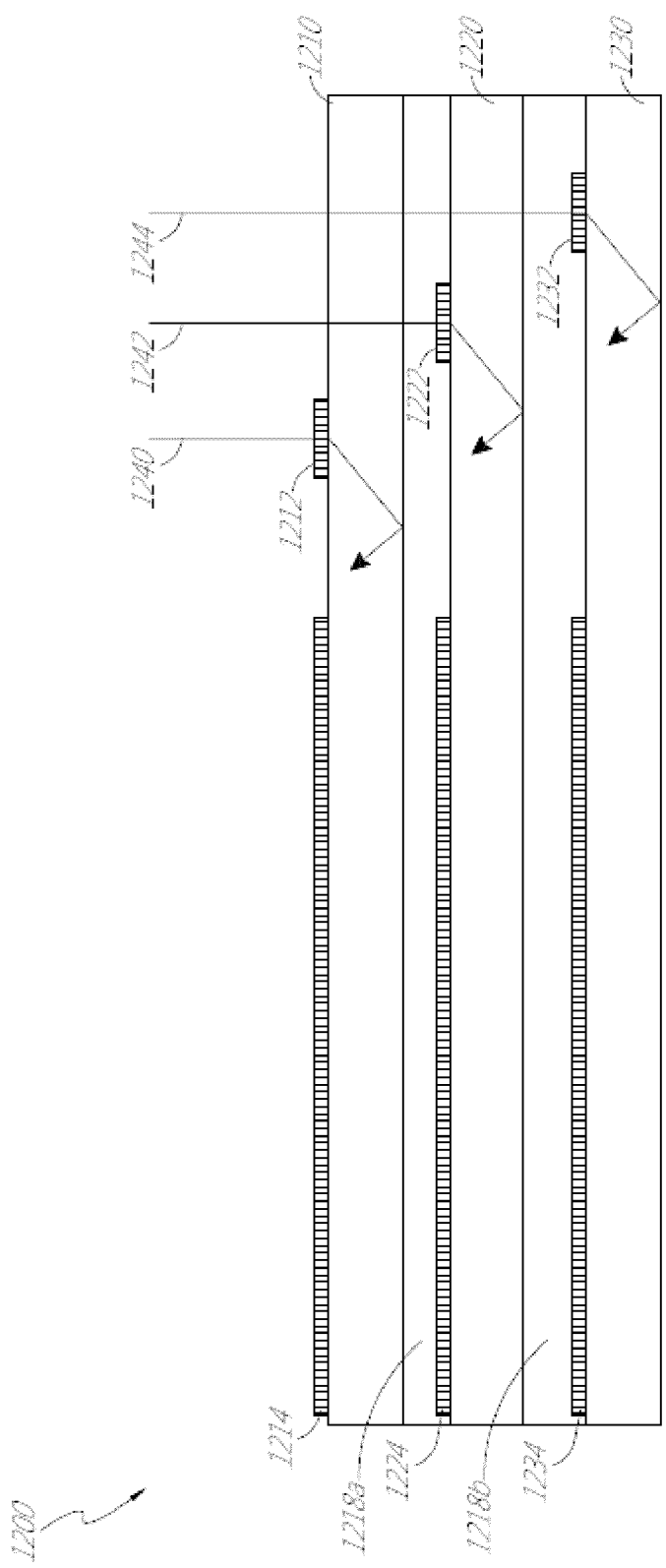
FIG. 9A illustrates a cross-sectional side view of an example of a set of stacked waveguides that each includes an incoupling optical element.

With reference now to FIG. 9A, in some embodiments, light impinging on a waveguide may need to be redirected to incouple that light into the waveguide. An incoupling optical element may be used to redirect and incouple the light into its corresponding waveguide. FIG. 9A illustrates a cross-sectional side view of an example of a plurality or set 1200 of stacked waveguides that each includes an incoupling optical element. The waveguides may each be configured to output light of one or more different wavelengths, or one or more different ranges of wavelengths. It will be appreciated that the stack 1200 may correspond to the stack 178 (FIG. 6) and the illustrated waveguides of the stack 1200 may correspond to part of the plurality of waveguides 182, 184, 186, 188, 190, except that light from one or more of the image injection devices 200, 202, 204, 206, 208 is injected into the waveguides from a position that requires light to be redirected for incoupling.

The illustrated set 1200 of stacked waveguides includes waveguides 1210, 1220, and 1230. Each waveguide includes an associated incoupling optical element (which may also be referred to as a light input area on the waveguide), with, e.g., incoupling optical element 1212 disposed on a major surface (e.g., an upper major surface) of waveguide 1210, incoupling optical element 1224 disposed on a major surface (e.g., an upper major surface) of waveguide 1220, and incoupling optical element 1232 disposed on a major surface (e.g., an upper major surface) of waveguide 1230. In some embodiments, one or more of the incoupling optical elements 1212, 1222, 1232 may be disposed on the bottom major surface of the respective waveguide 1210, 1220, 1230 (particularly where the one or more incoupling optical elements are reflective, deflecting optical elements). As illustrated, the incoupling optical elements 1212, 1222, 1232 may be disposed on the upper major surface of their respective waveguide 1210, 1220, 1230 (or the top of the next lower waveguide), particularly where those incoupling optical elements are transmissive, deflecting optical elements. In some embodiments, the incoupling optical elements 1212, 1222, 1232 may be disposed in the body of the respective waveguide 1210, 1220, 1230. In some embodiments, as discussed herein, the incoupling optical elements 1212, 1222, 1232 are wavelength selective, such that they selectively redirect one or more wavelengths of light, while transmitting other wavelengths of light. While illustrated on one side or corner of their respective waveguide 1210, 1220, 1230, it will be appreciated that the incoupling optical elements 1212, 1222, 1232 may be disposed in other areas of their respective waveguide 1210, 1220, 1230 in some embodiments.

As illustrated, the incoupling optical elements 1212, 1222, 1232 may be laterally offset from one another. In some embodiments, each incoupling optical element may be offset such that it receives light without that light passing through another incoupling optical element. For example, each incoupling optical element 1212, 1222, 1232 may be configured to receive light from a different image injection device 200, 202, 204, 206, and 208 as shown in FIG. 6, and may be separated (e.g., laterally spaced apart) from other incoupling optical elements 1212, 1222, 1232 such that it substantially does not receive light from the other ones of the incoupling optical elements 1212, 1222, 1232.

Each waveguide also includes associated light distributing elements, with, e.g., light distributing elements 1214 disposed on a major surface (e.g., a top major surface) of waveguide 1210, light distributing elements 1224 disposed on a major surface (e.g., a top major surface) of waveguide 1220, and light distributing elements 1234 disposed on a major surface (e.g., a top major surface) of waveguide 1230. In some other embodiments, the light distributing elements 1214, 1224, 1234, may be disposed on a bottom major surface of associated waveguides 1210, 1220, 1230, respectively. In some other embodiments, the light distributing elements 1214, 1224, 1234, may be disposed on both top and bottom major surface of associated waveguides 1210, 1220, 1230, respectively; or the light distributing elements 1214, 1224, 1234, may be disposed on different ones of the top and bottom major surfaces in different associated waveguides 1210, 1220, 1230, respectively.

The waveguides 1210, 1220, 1230 may be spaced apart and separated by, e.g., gas, liquid, and/or solid layers of material. For example, as illustrated, layer 1218*a* may separate waveguides 1210 and 1220; and layer 1218*b* may separate waveguides 1220 and 1230. In some embodiments, the layers 1218*a* and 1218*b* are formed of low refractive index materials (that is, materials having a lower refractive index than the material forming the immediately adjacent one of waveguides 1210, 1220, 1230). Preferably, the refractive index of the material forming the layers 1218*a*, 1218*b* is 0.05 or more, or 0.10 or more less than the refractive index of the material forming the waveguides 1210, 1220, 1230. Advantageously, the lower refractive index layers 1218*a*, 1218*b* may function as cladding layers that facilitate total internal reflection (TIR) of light through the waveguides 1210, 1220, 1230 (e.g., TIR between the top and bottom major surfaces of each waveguide). In some embodiments, the layers 1218*a*, 1218*b* are formed of air. While not illustrated, it will be appreciated that the top and bottom of the illustrated set 1200 of waveguides may include immediately neighboring cladding layers.

Preferably, for ease of manufacturing and other considerations, the material forming the waveguides 1210, 1220, 1230 are similar or the same, and the material forming the layers 1218*a*, 1218*b* are similar or the same. In some embodiments, the material forming the waveguides 1210, 1220, 1230 may be different between one or more waveguides, and/or the material forming the layers 1218*a*, 1218*b* may be different, while still holding to the various refractive index relationships noted above.

With continued reference to FIG. 9A, light rays 1240, 1242, 1244 are incident on the set 1200 of waveguides. It will be appreciated that the light rays 1240, 1242, 1244 may be injected into the waveguides 1210, 1220, 1230 by one or more image injection devices 200, 202, 204, 206, 208 (FIG. 6).

In some embodiments, the light rays 1240, 1242, 1244 have different properties, e.g., different wavelengths or different ranges of wavelengths, which may correspond to different colors. The incoupling optical elements 1212, 1222, 1232 each deflect the incident light such that the light propagates through a respective one of the waveguides 1210, 1220, 1230 by TIR.

For example, incoupling optical element 1212 may be configured to deflect ray 1240, which has a first wavelength or range of wavelengths. Similarly, the transmitted ray 1242 impinges on and is deflected by the incoupling optical element 1222, which is configured to deflect light of a second wavelength or range of wavelengths. Likewise, the ray 1244 is deflected by the incoupling optical element 1232, which is configured to selectively deflect light of third wavelength or range of wavelengths.

With continued reference to FIG. 9A, the deflected light rays 1240, 1242, 1244 are deflected so that they propagate through a corresponding waveguide 1210, 1220, 1230; that is, the incoupling optical elements 1212, 1222, 1232 of each waveguide deflects light into that corresponding waveguide 1210, 1220, 1230 to incouple light into that corresponding waveguide. The light rays 1240, 1242, 1244 are deflected at angles that cause the light to propagate through the respective waveguide 1210, 1220, 1230 by TIR. The light rays 1240, 1242, 1244 propagate through the respective waveguide 1210, 1220, 1230 by TIR until impinging on the waveguide's corresponding light distributing elements 1214, 1224, 1234.

Figure 9B:
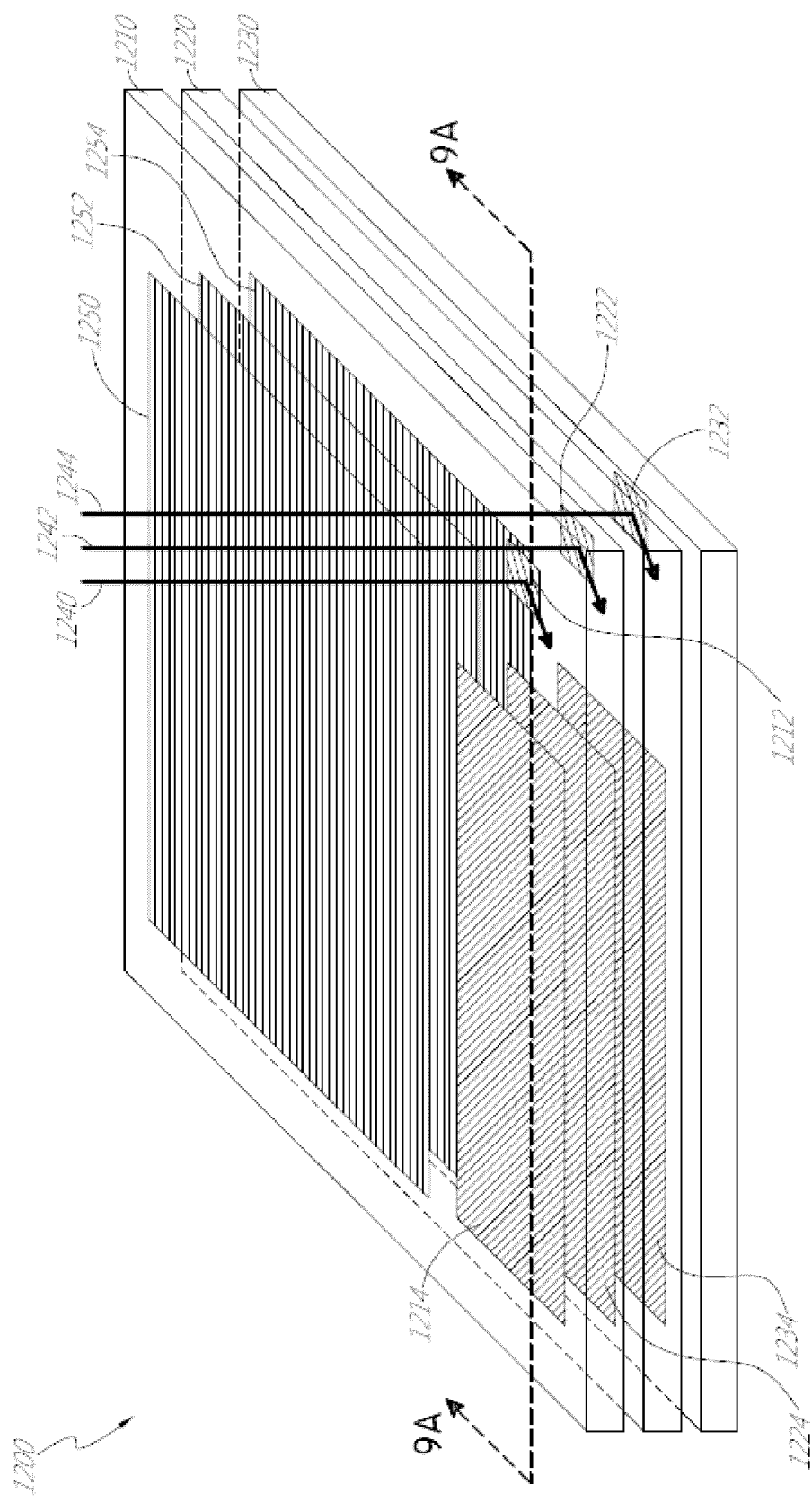
FIG. 9B illustrates a perspective view of an example of the plurality of stacked waveguides of FIG. 9A.

With reference now to FIG. 9B, a perspective view of an example of the plurality of stacked waveguides of FIG. 9A is illustrated. As noted above, the incoupled light rays 1240, 1242, 1244, are deflected by the incoupling optical elements 1212, 1222, 1232, respectively, and then propagate by TIR within the waveguides 1210, 1220, 1230, respectively. The light rays 1240, 1242, 1244 then impinge on the light distributing elements 1214, 1224, 1234, respectively. The light distributing elements 1214, 1224, 1234 deflect the light rays 1240, 1242, 1244 so that they propagate towards the outcoupling optical elements 1250, 1252, 1254, respectively.

In some embodiments, the light distributing elements 1214, 1224, 1234 are orthogonal pupil expanders (OPE's). In some embodiments, the OPE's both deflect or distribute light to the outcoupling optical elements 1250, 1252, 1254 and also increase the beam or spot size of this light as it propagates to the outcoupling optical elements. In some embodiments, e.g., where the beam size is already of a desired size, the light distributing elements 1214, 1224, 1234 may be omitted and the incoupling optical elements 1212, 1222, 1232 may be configured to deflect light directly to the outcoupling optical elements 1250, 1252, 1254. For example, with reference to FIG. 9A, the light distributing elements 1214, 1224, 1234 may be replaced with outcoupling optical elements 1250, 1252, 1254, respectively. In some embodiments, the outcoupling optical elements 1250, 1252, 1254 are exit pupils (EP's) or exit pupil expanders (EPE's) that direct light in a viewer's eye 4 (FIG. 7).

Accordingly, with reference to FIGS. 9A and 9B, in some embodiments, the set 1200 of waveguides includes waveguides 1210, 1220, 1230; incoupling optical elements 1212, 1222, 1232; light distributing elements (e.g., OPE's) 1214, 1224, 1234; and outcoupling optical elements (e.g., EP's) 1250, 1252, 1254 for each component color. The waveguides 1210, 1220, 1230 may be stacked with an air gap/cladding layer between each one. The incoupling optical elements 1212, 1222, 1232 redirect or deflect incident light (with different incoupling optical elements receiving light of different wavelengths) into its waveguide. The light then propagates at an angle which will result in TIR within the respective waveguide 1210, 1220, 1230. In the example shown, light ray 1240 (e.g., blue light) is deflected by the first incoupling optical element 1212, and then continues to bounce down the waveguide, interacting with the light distributing element (e.g., OPE's) 1214 and then the outcoupling optical element (e.g., EPs) 1250, in a manner described earlier. The light rays 1242 and 1244 (e.g., green and red light, respectively) will pass through the waveguide 1210, with light ray 1242 impinging on and being deflected by incoupling optical element 1222. The light ray 1242 then bounces down the waveguide 1220 via TIR, proceeding on to its light distributing element (e.g., OPEs) 1224 and then the outcoupling optical element (e.g., EP's) 1252. Finally, light ray 1244 (e.g., red light) passes through the waveguide 1220 to impinge on the light incoupling optical elements 1232 of the waveguide 1230. The light incoupling optical elements 1232 deflect the light ray 1244 such that the light ray propagates to light distributing element (e.g., OPEs) 1234 by TIR, and then to the outcoupling optical element (e.g., EPs) 1254 by TIR. The outcoupling optical element 1254 then finally outcouples the light ray 1244 to the viewer, who also receives the outcoupled light from the other waveguides 1210, 1220.

Figure 9C:
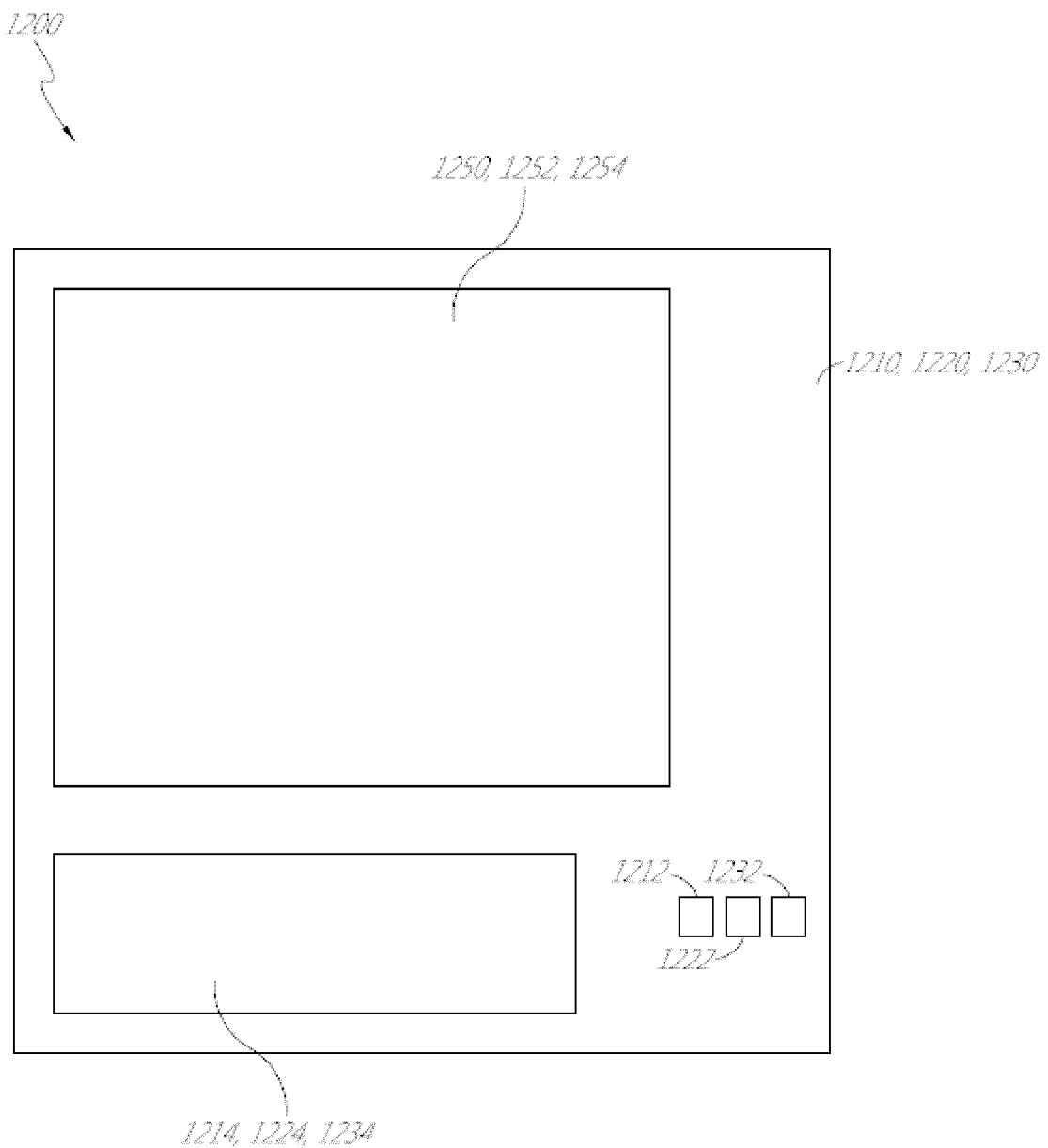
FIG. 9C illustrates a top-down plan view of an example of the plurality of stacked waveguides of FIGS. 9A and 9B.

FIG. 9C illustrates a top-down plan view of an example of the plurality of stacked waveguides of FIGS. 9A and 9B. As illustrated, the waveguides 1210, 1220, 1230, along with each waveguide's associated light distributing element 1214, 1224, 1234 and associated outcoupling optical element 1250, 1252, 1254, may be vertically aligned. However, as discussed herein, the incoupling optical elements 1212, 1222, 1232 are not vertically aligned; rather, the incoupling optical elements are preferably non-overlapping (e.g., laterally spaced apart as seen in the top-down view). As discussed further herein, this nonoverlapping spatial arrangement facilitates the injection of light from different resources into different waveguides on a one-to-one basis, thereby allowing a specific light source to be uniquely coupled to a specific waveguide. In some embodiments, arrangements including nonoverlapping spatially-separated incoupling optical elements may be referred to as a shifted pupil system, and the in coupling optical elements within these arrangements may correspond to sub pupils.

Figure 10A:
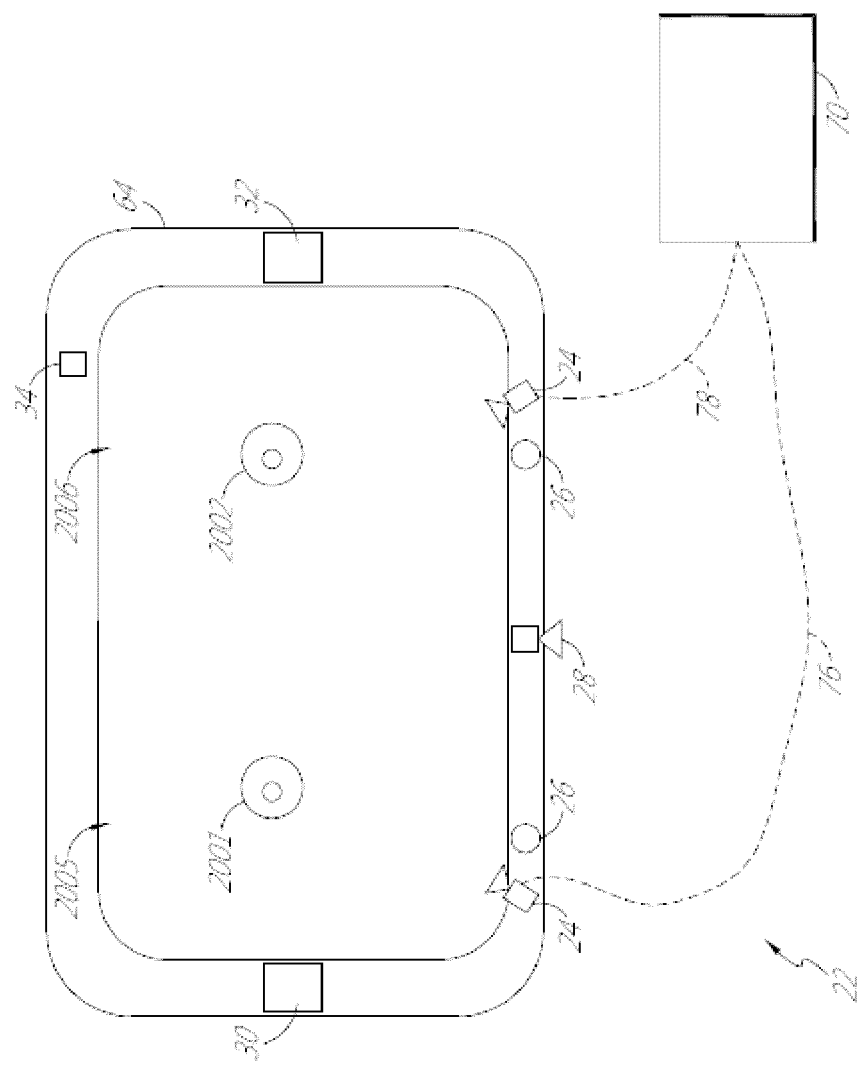
FIG. 10A shows a schematic view of an example of various components of an augmented reality system comprising environmental and user sensors.

With reference now to FIG. 10A, which shows a schematic view of an example of various components of an augmented reality display system comprising user sensors 24, 28, 30, 32 and environmental sensors 34. In some embodiments, the augmented reality display system may be a mixed reality display system. As shown, the user sensors 24, 28, 30, 32 may be configured to detect data regarding the user, and the environmental sensors 34 may be configured to collect data regarding parameters external to the user. In some embodiments, the display system may be configured to store data related to and/or characterizing AR content delivered to the user (e.g., the time, location, color make-up, sound volume etc., of the AR content).

The user sensors will be discussed first. As illustrated, an augmented reality display system 2010 may include various user sensors. The augmented reality display system 2010 may correspond to the system 80 of FIG. 2 and may include a viewer imaging system 22. The system 22 may include cameras 24 (e.g., infrared, UV, and/or visible light cameras) paired with light sources 26 (e.g., infrared light sources) directed at and configured to monitor the user (e.g., the eyes 2001, 2002 and/or surrounding tissues of the user). The cameras 24 and light sources 26 may be operatively coupled to the local processing module 70. Such cameras 24 may be configured to monitor one or more of the orientation, shape, and symmetry of pupils (including pupil sizes) or irises of the respective eyes, and/or tissues surrounding the eye, such as eyelids or eyebrows to conduct the various analyses disclosed herein. In some embodiments, imaging of the iris and/or retina of an eye may be used for secure identification of a user.

With continued reference to FIG. 10A, cameras 24 may further be configured to image the retinas of the respective eyes, such as for diagnostic purposes and/or for orientation tracking based on the location of retinal features, such as the fovea or features of the fundus. Iris and retina imaging or scanning may be performed for secure identification of users for, e.g., correctly associating user data with a particular user and/or to present private information to the appropriate user. In some embodiments, in addition to or as an alternative to the cameras 24, one or more cameras 28 may be configured to detect and/or monitor various other aspects of the status of a user. For example, one or more cameras 28 may be inward-facing and configured to monitor the shape, position, movement, color, and/or other properties of features other than the eyes of the user, e.g., one or more facial features (e.g., facial expression, voluntary movement, involuntary tics). In another example, one or more cameras 28 may be downward-facing and configured to monitor the position, movement, and/or other features or properties of the arms, hands, legs, feet, and/or torso of a user.

In some embodiments, as disclosed herein, the display system 2010 may include a spatial light modulator that variably projects, through a fiber scanner (e.g., the image injection devices in FIG. 6-200, 202, 204, 206, 208), light beams across the retina of the user to form an image. In some embodiments, the fiber scanner may be used in conjunction with, or in place of, the cameras 24 or 28 to, e.g., track or image the user's eyes. For example, as an alternative to or in addition to the scanning fiber being configured to output light, the health system may have a separate light-receiving device to receive light reflected from the user's eyes, and to collect data associated with that reflected light.

With continued reference to FIG. 10A, the cameras 24, 28 and light sources 26 may be mounted on the frame 64, which may also hold the waveguide stacks 2005, 2006. In some embodiments, sensors and/or other electronic devices (e.g., the cameras 24, 28 and light sources 26) of the display system 2010 may be configured to communicate with the local processing and data module 70 through communication links 76, 70.

In some embodiments, in addition to providing data regarding the user, one or both of the cameras 24 and 28 may be utilized to track the eyes to provide user input. For example, the viewer imaging system 22 may be utilized to select items on virtual menus, and/or provide other input to the display system 2010, such as for providing user responses in the various tests and analyses disclosed herein.

In some embodiments, the display system 2010 may include motion sensors 32, such as one or more accelerometers, gyros, gesture sensors, gait sensors, balance sensors, and/or IMU sensors. The sensors 30 may include one or more inwardly directed (user directed) microphones configured to detect sounds, and various properties of those sound, including the intensity and type of sounds detected, the presence of multiple signals, and/or signal location.

The sensors 30 are schematically illustrated as being connected to the frame 64. It will be appreciated that this connection may take the form of a physical attachment to the frame 64 and may be anywhere on the frame 64, including the ends of the temples of the frame 64 which extend over the user's ears. For example, the sensors 30 may be mounted at the ends of the temples of the frame 64, at a point of contact between the frame 64 and the user. In some other embodiments, the sensors 30 may extend away from the frame 64 to contact the user 60 (FIG. 2). In yet other embodiments, the sensors 30 may not be physically attached to the frame 64; rather, the sensors 30 may take the form of peripheral sensors 30a (FIG. 2), which may be spaced apart from the frame 64.

In some embodiments, the display system 2010 may further include one or more environmental sensors 34 configured to detect objects, stimuli, people, animals, locations, or other aspects of the world around the user. For example, environmental sensors 34 may include one or more cameras, altimeters, barometers, chemical sensors, humidity sensors, temperature sensors, external microphones, light sensors (e.g., light meters), timing devices (e.g., clocks or calendars), or any combination or subcombination thereof. In some embodiments, multiple (e.g., two) microphones may be spaced-apart, to facilitate sound source location determinations. In various embodiments including environment sensing cameras, cameras may be located, for example, facing outward (e.g., forward-looking) so as to capture images similar to at least a portion of an ordinary field of view of a user. Environmental sensors may further include emissions devices configured to receive signals such as laser, visible light, invisible wavelengths of light, sound (e.g., audible sound, ultrasound, or other frequencies). In some embodiments, one or more environmental sensors (e.g., cameras or light sensors) may be configured to measure the ambient light (e.g., luminance) of the environment (e.g., to capture the lighting conditions of the environment). Physical contact sensors, such as strain gauges, curb feelers, or the like, may also be included as environmental sensors.

In some embodiments, the display system 2010 may further be configured to receive other environmental inputs, such as GPS location data, weather data, date and time, or other available environmental data which may be received from the internet, satellite communication, or other suitable wired or wireless data communication method. The processing module 70 may be configured to access further information characterizing a location of the user, such as pollen count, demographics, air pollution, environmental toxins, information from smart thermostats, lifestyle statistics, or proximity to other users, buildings, or a healthcare provider. In some embodiments, information characterizing the location may be accessed using cloud-based or other remote databases. The processing module 70 may be configured to obtain such data and/or to further analyze data from any one or combinations of the environmental sensors.

The display system 2010 may be configured to collect and store data obtained through any of the sensors and/or inputs described above for extended periods of time. Data received at the device may be processed and/or stored at the local processing module 70 and/or remotely (e.g., as shown in FIG. 2, at the remote processing module 72 or remote data repository 74). In some embodiments, additional data, such as date and time, GPS location, or other global data may be received directly at the local processing module 70. Data regarding content being delivered to the user by the system, such as images, other visual content, or auditory content, may be received at the local processing module 70 as well.

Figure 10B:
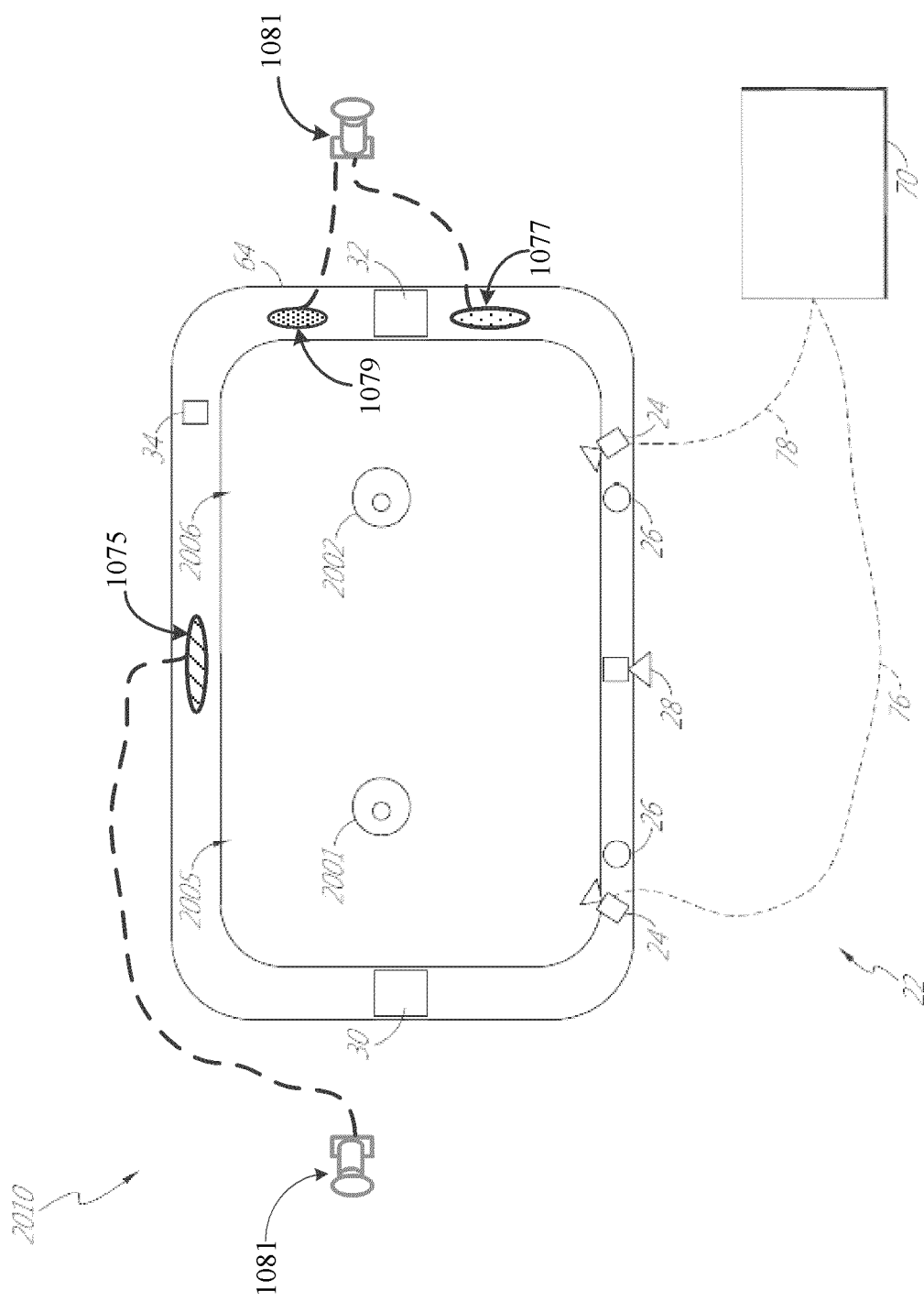
FIG. 10B shows a schematic view of another example of various components of an augmented reality system comprising environmental and user sensors.

FIG. 10B shows another example augmented reality display system. In some embodiments, the display system 2010 may transmit and receive ultrasound waves to present images of a patient based on the ultrasound information. Similar to FIG. 10A, the example in FIG. 10B comprises environmental 34 and user 24, 28, 30, 32 sensors. In addition, as shown in FIG. 10B, the display system 2010 can further include one or more outwardly facing ultrasonic probes 1081 configured to direct acoustical energy to the patient's body. The one or more probes 1081 may be configured to transmit ultrasound to various regions of the user's body as well as receive ultrasound reflected from various regions of the user's body. For example, the one or more probes 1081 may be connected to an ultrasonic transmitter 1077 configured to emit ultrasonic energy to the patient's body, and an ultrasonic receiver 1079 configured to receive ultrasonic energy reflected and/or scattered back from various structures of the patient's body. In some embodiments, the one or more probes 1081 may be connected to an ultrasonic transceiver 1075 that combines both the ultrasonic transmitter and receiver. Various embodiments can present images of the patient based on the reflected information. In some embodiments, the display system 2010 may be configured to determine tissue density of a patient based on the reflected ultrasound waves. In some embodiments, the display system 2010 may be configured to map blood flow (e.g., velocity of the blood flow through the blood vessels) based on the reflected ultrasound waves.

Enhanced Vision Field

As disclosed herein, a display system incorporating user and/or environmental sensors such as outward looking cameras and/or light sensors may advantageously provide an improved user view of image content of the environment, for example, in the user's peripheral field of view (e.g., a peripheral region of the user's vision field). For example, certain embodiments may allow the user to focus on one object in the user's central field of view (e.g., a central region of the user's vision field) and simultaneously view with increased visibility another object that is located in the user's peripheral field of view.

In various embodiments, the central region of the user's vision field may include an area in a range (in half angles) from 0 to 15 degrees, 1 to 15 degrees, 2 to 15 degrees, 5 to 15 degrees, 0 to 12 degrees, 1 to 12 degrees, 2 to 12 degrees, 5 to 12 degrees, 0 to 10 degrees, 1 to 10 degrees, 2 to 10 degrees, 5 to 10 degrees from the center of the fovea (or from an optical axis from the center of the pupil), any combination of these ranges, or any range formed by any value from 0 to 15 degrees from the center of the fovea (e.g., 0 to 7 degrees, 1 to 7 degrees, 2 to 7 degrees from the center of the fovea, etc.)

The peripheral region of the user's vision field may include an outer area of the vision field outside of the corresponding area of the central region. For example, the peripheral region of the user's vision field may include an area of the vision field in a range (in half angles) from 16 to 60 degrees, 18 to 60 degrees, 20 to 60 degrees, 25 to 60 degrees, 30 to 60 degrees, 35 to 60 degrees, 40 to 60 degrees, 45 to 60 degrees, 50 to 60 degrees, 55 to 60 degrees from the center of the fovea (or from an optical axis from the center of the pupil), any combination of these ranges, or any range formed by any value from 16 to 60 degrees from the center of the fovea (e.g., 16 to 50 degrees, 20 to 50 degrees, 16 to 55 degrees, 30 to 55 degrees from the center of the fovea, etc.).

In some embodiments, the central region of the user's vision field may include 1 to 5 percent, 1 to 10 percent, 5 to 10 percent, 1 to 15 percent, 5 to 15 percent, 5 to 20 percent, 10 to 20 percent, 5 to 25 percent, 10 to 25 percent of the user's vision field, any combination of these ranges, or any range formed by any value from 0 to 25 percent of the user's vision field (e.g., 1 to 17 percent, 3 to 18 percent, 7 to 25 percent, 15 to 25 percent of the user's vision field, etc.).

The peripheral region of the user's vision field may include the remaining percent of the user's vision field. For example, the peripheral region of the user's vision field may include 75 to 99.9 percent, 75 to 99 percent, 75 to 95 percent, 75 to 90 percent, 80 to 99.9 percent, 80 to 99 percent, 80 to 95 percent, 80 to 90 percent of the user's vision field, any combination of these ranges, or any range formed by any value from 75 to 99.9 percent of the user's vision field (e.g., 77 to 98 percent, 75 to 85 percent, 85 to 95 percent of the user's vision field, etc.).

Figure 11A:
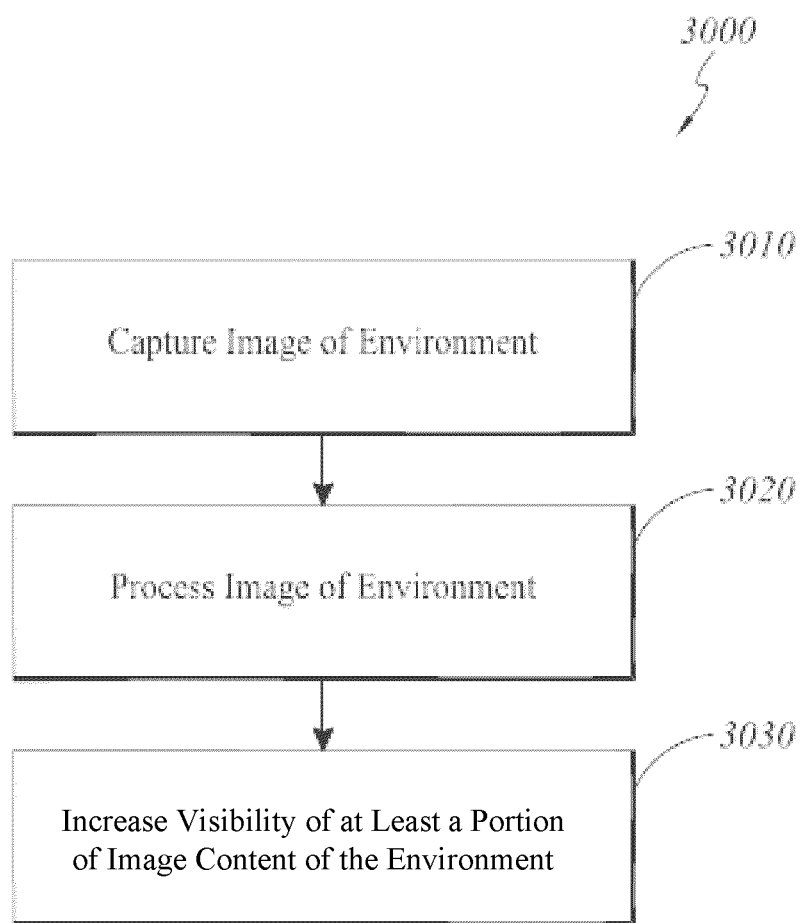
FIG. 11A is a flowchart illustrating an example of a method for enhancing user view of image content of the environment.

With reference now to FIG. 11A, an example method 3000 of improving user view of at least a portion of image content of the environment, for example, in the user's peripheral field of view using a display system is illustrated. The display system may include the display systems 80, 1000, or 2010 in FIGS. 2, 6, and 10A-10B, respectively. The display system may include, for example, a head-mounted display device that projects image content to the user's eyes.

In some embodiments, a head-mounted display device is configured to present to the user augmented reality image content using a display. In certain embodiments, the display is disposed on the frame of the head-mounted display. As described herein, the display can include one or more transparent waveguides disposed at a location in front of the user's eyes. Accordingly, a user may be able to see through the display. Light from objects in the environment in front of the user wearing the head mounted display device are transmitted through the display, e.g., through the one or more transparent waveguides into the users eye such that images of the environment in front of the user or at least a portion thereof is formed on the retina of the user's eye. The user's vision may be characterized by a vision field having a central region and a peripheral region. The peripheral region can be disposed around or about the central region. The central region and peripheral region can correspond to the central field of view and peripheral field of view, respectively, as discussed herein. The central region of the user's vision field may include a portion of the environment directly in front of the user, for example, if the user's gaze is directed directly forward. Similarly, the peripheral region of the vision field of the user's eye can correspond to a peripheral region in the environment in front of the user in such an example. Objects in the center of the portion of the environment forward of the user's gaze may be included in the central field whereas object in the periphery of the portion of the environment forward of the user's gaze may be included in the peripheral field. For example, a user may view a surgery where the user is directing attention on the patient being operated on such as on a surgical site. The patient and in particular the surgical site could correspond, for example, to the user's central region of the user's vision field. Likewise in this example, the user may see in a peripheral region of the vision field other members of the medical staff, anatomy of the patient surrounding the surgical site, furniture in the operating room such as tables and or trays with surgical objects (e.g., instruments) thereon, other surgical and/or diagnostic equipment, the walls and/or floor of the operating room, and/or the lights and other items in a peripheral region of the environment (e.g., scene).

At block 3010, the display system or device may be configured to capture one or more images of the environment. For example, as described herein, various embodiments may include one or more environmental sensors 34 such as one or more image capture devices (for example, video cameras) facing outward to capture images similar to at least a portion of an ordinary field of view of the user. In other words, outward-facing image capture devices may capture images corresponding to the user's view of the environment. Such cameras may, for example, be forward facing so as to capture images of the environment forward of the user. These cameras may, however be tilted or angled at least partially with respect to the directly forward facing direction in various embodiments. These cameras individual and/or together may also have fields of view, which may be larger or smaller than the field of view of the eye of the user.

Accordingly, as discussed herein, a head-mounted display device can include an outward-facing image capture device that can be configured to image or scan a part of the environment in front of the user. In some embodiments, the outward-facing camera is configured to scan portions of the user's environment that are not in front of the user, such as objects or images in the user's field of regard but not in the user's field of view. In certain cases, for example, the head mounted display system can include multiple cameras, such as one or more video cameras directed more towards the portion of the environment in front of the user and one or more video cameras directed more towards the portion of the environment on the sides of the user. In some cases, the head mounted display system can include one or more cameras directed towards the portion of the environment behind of the user. In certain embodiments, the outward-facing camera can be configured to operate continuously for extended periods of time capturing video such as activity in the hospital, operating room, or other environment. In some configurations, the outward-facing camera can determine what the user is directing his or her gaze at, such as an object in the environment. In some embodiments, a head-mounted display device may include one or more capture devices to capture information regarding the environment. For example, a camera or a light sensor (e.g., a light meter) may be used to capture the light condition(s) of the environment.

At block 3020, various embodiments may process an image of the environment. For example, an image may be processed using the local processing and data module 70, or the remote processing module 72 shown in FIG. 2. In some such embodiments, the processing electronics may be in communication with a display 62 to control presentation of image content to the display. The display may include the waveguide assembly 178 shown in FIG. 6 to project light into the user's eye to present images such as the image of the environment from one or more outward-facing video cameras for viewing. As described herein, the waveguide assembly 178 can also be optical transmissive, e.g., transparent, so as to provide a direct view of a portion of the environment in front of the user wearing the head mounted display device via light from objects in the environment propagating through the transparent waveguide assembly to the retina of the user's eye.

With continued reference to FIG. 11A, at block 3030, the display system may be configured to improve visibility of at least a portion of the environment, for example, in the peripheral field of view (e.g., to increase visibility of at least a portion of image content of the environment by presenting an augmented reality image of a portion of the environment). Some embodiments may provide image modification relative to photoreceptor cell density in the eye (e.g., the highest cone density in the fovea for central vision and decreasing cone density away from the fovea for peripheral vision). As illustrated in FIGS. 1E and 1F, based on the cone density in the eye, visual acuity is generally the highest at the fovea (e.g., center of the eye) and declines moving away from the fovea. For example, visual acuity may decrease about 50% every 2.5 degrees away from the center of the eye up (for example, as measured from an optical axis through the lens of the eye to the center of the retina) to about 30 degrees from the center of the eye (e.g., this optical axis). For rays of an even higher angle (e.g., with respect to this optical axis), the decline in visual acuity may be much greater (e.g., a hyperbolic function). The fovea, which has the highest cone density and visual acuity, is used for viewing in the central field of view. Moving away from the fovea, as the cone density and visual acuity decline, viewing moves from the central field of view to the peripheral field of view.

Thus, it is generally more difficult to distinguish between details of an object in the user's peripheral field of view than for objects in the user's central field of view. It is also generally more difficult to distinguish between details of an object in the user's far peripheral field of view than for objects in the user's near peripheral field of view. In terms of resolution, the minimum distance for two-point distinction (e.g., the minimum spacing to distinguish between two features) that can be resolved by the eye increases (and spatial resolution decreases) with distance from the fovea. Thus, in general, image content presented to the eye farther from the center of the field of view may need to be larger in order for them to be seen. Additionally, objects farther from the eye may need to be larger (e.g., magnified) to be seen. As described herein, image content may be modified based on one or more of these relationships.

In various embodiments, the display system may be configured to present image content, for example, to the user's peripheral field of view that is enhanced (e.g., in one or more ways) in relation to how the content would otherwise be perceived by the user (e.g., if not enhanced). In some embodiments, the display system may be configured to present image content, for example, to the user's peripheral field of view that is enhanced in comparison to image content presented to the user's central field of view. In various embodiments, the content perceived by the user, which may include real world content, can appear enhanced by using one or more augmented images and/or by using one or more augmented images in combination with the actual real world content. In some embodiments, the display system can present one or more augmented images having a degree of opacity (e.g., 30%, 40%, 50%, 60%, 70%, 80%, 90%, 95%, etc.). The presented image(s) having a degree of opacity can, in some instances, obscure some of the actual real world content. In some embodiments, enhanced image content can be presented to the eye as one or more virtual images (e.g., with actual real world content obscured by opacity or substantial opacity (e.g., 98%, 99%, or 100% opacity)). In some embodiments, the extent of enhancement may be based at least in part on the distance from the center of the field and/or fovea, the distance from the eye, and/or the minimum distance for two-point distinction, and/or an inverse relationship to the spatial resolution of the eye, and/or an inverse relationship to the cone density, rod density, ganglion cell density, and/or visual acuity of the eye. For example, moving away from the fovea, the minimum distance for two-point distinction increases while the cell density and/or visual acuity of the eye decreases. In some such embodiments, more enhancement may be provided to image content presented to the far peripheral region (e.g., farthest from the central region where cell density and visual acuity decrease and the minimum distance for two-point distinction increases) than to image content presented to the near peripheral region (e.g., closest to the central region).

As an example, the image content presented to the user's peripheral field of view may be enhanced in size. For example, in some embodiments, the image content may be magnified in comparison to the content when viewed without using the display system (e.g., if not magnified). As another example, the display system may be configured to magnify at least a portion of image content presented to the user's peripheral field of view in comparison to image content presented to the user's central field of view. Since the image content presented to the peripheral field of view may be enlarged, certain embodiments may increase the visibility of such image content. The amount of magnification may be based at least in part on the distance from the eye, the distance from the center of the vision field (e.g., distance from fovea), and/or the minimum distance for two-point distinction, and/or an inverse relationship to the spatial resolution of the eye, and/or an inverse relationship to the cell density and/or visual acuity of the eye. For example, more magnification may be provided to image content presented to the far peripheral region and less magnification may be provided to image content presented to the near peripheral region.

As another example, the presented image content to the user's peripheral field of view may be enhanced by altering (e.g., increasing) light intensity or brightness in relation to how the content would appear without intensifying the content (e.g., without increasing the light intensity) and/or compared to image content presented to the user's central field of view. In some such embodiments, one or more light sources may be used to increase the light intensity or brightness of image content. In general, brighter images may be easier to see. Since the image content presented to the peripheral field of view may be brighter, certain embodiments may increase the visibility of such image content. In some embodiments, more light intensity or brightness may be provided to image content presented to the far peripheral region and less intensity or brightness may be provided to image content presented to the near peripheral region. In some embodiments, the light intensity may be based at least in part on the distance from the eye and/or an inverse relationship to the cell density (e.g., rod density) and/or visual acuity of the eye (e.g., with distance from the center of the vision field or fovea.

As another example, the presented image content to the user's peripheral field of view may be enhanced by increasing contrast in relation to how the content would appear without increasing contrast and/or compared to image content presented to the user's central field of view. An increase in contrast may be indicated by a comparison of the contrast ratio. In some such embodiments, the contrast ratio may be based on the ratio between the luminance of the brightest color and the darkest color. In some embodiments, the amount of increase may be such that the contrast ratio is above a threshold for the eye to distinguish the contrast. For example, the retina may have static contrast ratio of about 100:1 and may extend up to about $10^6$:1. Accordingly, various embodiments may increase the contrast ratio in at least a portion of the presented image to about 100:1, $10^3$:1, $10^4$:1, $10^5$:1, or $10^6$:1 or any ranges between any combination of these values. The amount of increase in the contrast ratio may be based on the existing contrast ratio in the image content that will be presented to the user's peripheral field of view, and/or in the image content presented to the user's central field of view.

The increase in contrast may be provided by adjusting the brightness and/or darkness of adjacent colors (e.g., high contrasting colors). In some embodiments, providing black (e.g., value 0) next to white (e.g., value 255 in 8-bit greyscale) may be used. For example, a grey object adjacent to a black object(s) or background may appear lighter than adjacent to a white object(s) or background. In some embodiments, the presented image content may include an augmented image(s) that in combination with the actual real world content provide the adjusted contrast ratio compared to how the content would appear without adjustment and/or compared to image content presented to other portions of the user's field of view. In some examples, the brightness and/or darkness of adjacent colors may be adjusted by adjusting the brightness and/or darkness of at least one color (e.g., adjusting the brightness and/or darkness of the color of an object, color of at least two adjacent objects, color of a background, color of an object and color of the background, the color of part of an object, the color of two adjacent parts of an object, etc.). In some instances, the brightness and/or darkness of a color may be adjusted by providing additional color or colors (e.g., black, grey, white, or other color, etc.) to an object or background such that when viewed with the actual real world content, the combination of the real and additional colors provides the adjusted contrast ratio. In some instances, the brightness and/or darkness of a color may be adjusted by providing one or more augmented images having a degree of opacity (e.g., 30%, 40%, 50%, 60%, 70%, 80%, 90%, 95%, etc.) such that when viewed with the obscured actual real world content, the combination provides the adjusted contrast ratio.

In some embodiments, the presented image content may include a virtual image(s) (e.g., with a portion of the actual real world content obscured by opacity or substantial opacity) with the adjusted contrast ratio compared to how the content would appear without adjustment and/or compared to image content presented to other portions of the user's field of view. In some examples, the brightness and/or darkness of adjacent colors may be adjusted by adjusting the brightness and/or darkness of at least one color (e.g., adjusting the brightness and/or darkness of the color of an object, color of at least two adjacent objects, color of a background, color of an object and color of the background, the color of part of an object, the color of two adjacent parts of an object, etc.). The brightness and/or darkness of a color may be adjusted by adding black, grey, white, or other color to the color or by subtracting black, grey, white, or other color from the color. The brightness and/or darkness of a color may additionally or alternatively be adjusted by substituting a color with black, grey, white, or other color.

Since images with more contrast may be more easily seen, the image content with a higher contrast ratio presented to the peripheral field of view may increase the visibility of such image content. As an example, a surgeon may be viewing the surgical site (e.g., in the surgeon's central field of view), while the patient may begin to bleed elsewhere (e.g., in the surgeon's peripheral field of view). Some embodiments can increase the contrast ratio in the peripheral area such that the red blood "pops" out to the surgeon. For example, as described herein, some embodiments can present an augmented image providing additional red color so that the peripheral area perceived by the user is enhanced. As another example, some embodiments may block out background surrounding the blood with color that produces large contrast with the blood. As another example, some embodiments can present a virtual image of the peripheral area with an increased contrast ratio (e.g., a graphic image of the blood and area surrounding the blood that produces high contrast or increased contrast compared to the actual blood and area surrounding the blood). The surgeon can keep an eye on both the surgical site and the additional bleeding location. In some embodiments, the amount of contrast increase may be based at least in part on an inverse relationship to the cell density (ganglion cell density, cone density, and/or rod density of the eye) as described herein. For example, more contrast may be provided to image content presented to the far peripheral region and less contrast may be provided to image content presented to the near peripheral region.

As another example, the presented image content to the user's peripheral field of view may be enhanced by color or color saturation in relation to how the content would appear without enhanced color or color saturation and/or compared to image content presented to the user's central field of view. In some such embodiments, one or more light sources may be used to increase color saturation in image content. In general, images with higher color saturation may be easier to see. Since the image content presented to the peripheral field of view may have higher color saturation or increase in color saturation compared to image content presented to the central field of view, certain embodiments may increase the visibility of such image content. In some embodiments, the amount of color saturation may be based at least in part on the distance from the eye, distance from the center of the vision field (or fovea) and/or an inverse relationship to the cell density and/or visual acuity of the eye as described herein. For example, more color saturation may be provided to image content presented to the far peripheral region and less color saturation may be provided to image content presented to the near peripheral region (e.g., based on an inverse in cone density).

Other examples of processing image content, for example, provided to the user's peripheral vision field in a manner so as to enhance the peripheral image that can be sensed by the retina in relation to how the content would appear without being enhanced and/or in comparison to image content presented to the user's central vision field are possible. For example, the presented image content to the user's peripheral vision field may be enhanced by shifting the color balance (e.g., red/green balance), and/or white balance (e.g., color temperature). In general, colors appear differently under different light sources (e.g., candlelight v. fluorescent office light), adjacent to different colors, and/or against different backgrounds. The visual system may be based on the eye's sensory response and the brain's interpretation of signals to accommodate variations in color and intensity. If the white is perceived correctly, the other colors can also be perceived correctly. Accordingly, some embodiments may be enhanced by shifting the color balance.

Further, special effects may also be used to enhance image content provided to the peripheral vision field or field of view. For example, some embodiments may be configured to sharpen image content presented to the user's peripheral field of view in relation to how the content would appear without being sharpened and/or compared to image content presented to the user's central field of view. For example, the image content may include edge enhancements. In some such embodiments, the display system may include an edge detector or processing electronics configured to identify edges in the environment. For example, the edge detector or processing electronics configured may be configured to identify edges by detecting abrupt changes in color, by detecting abrupt changes in intensity, and/or by applying a k-means clustering algorithm. The presented image content may be sharpened by including outlines, contours, backgrounds, and/or contrasting techniques to enhance certain edges, shapes, and/or features. As another example, the presented image content may be presented against a background (e.g., a surrounding back screen in some instances) so that at least in the vicinity of the presented image content, the user mainly views the presented image content (e.g., and the surrounding real world content is de-emphasized). In some instances, a background can be provided with a degree of opacity and/or in some instances, with opacity or substantial opacity. As other examples, the image content presented to the user's peripheral field of view may be enhanced based on exposure, lightness, shadows, highlights, flipping (e.g., inverting), straightening, rotating, measuring image portions (e.g., including volumes), and/or using other techniques. In some embodiments, the image content may be presented more conveniently to the user. For example, an image may be easier to view when aligned with the head. Accordingly, some embodiments may enhance image content by straightening and/or rotating the image content based on the user's head pose. Accordingly, the image content presented to the user's peripheral vision field may be image processed differently compared to image content presented to the user's central field of view.

It would be appreciated that instead of (or in combination with) presenting image content to the user's peripheral field of view that is enhanced in relation to how the content would appear without being enhanced and/or in comparison to image content presented to the user's central field of view, various embodiments may be configured to present image content to the user's central field of view that is de-emphasized in relation to how the content would appear without being de-emphasized and/or in comparison to image content presented to the user's peripheral field of view. As an example, the presented image content to the user's central field of view may be de-emphasized by reducing size (e.g., shrinking), blurring, darkening/attenuating, reducing contrast, decreasing color saturation, decreasing sharpness, obscuring, and/or de-enhancing edges compared to image content presented to the user's peripheral field of view. One example of blurring includes presenting image content to the user's central field of view in substantially the same color. The image may comprise variations in tone of a similar color, e.g., blue or green, etc. Thus, the image may appear monotone in the central field with the image in the central field remaining discernable. The user may still be able to view the content in the central field of view (e.g., by the edges of objects), while enhancing the view of objects in the peripheral field of view. The image content presented to the user's central field of view may also be de-emphasized based on exposure, lightness, shadows, highlights, flipping (e.g., inverting), straightening, rotating, measuring image portions (e.g., including volumes), shifting color balance (or white balance), and/or using other techniques. Using lightness, exposure, shadows, highlights, etc. or any combination of these may in some instances help increase contrast. Accordingly, the image content presented to the user's central vision field may be image processed differently compared to image content presented to the user's peripheral field of view. Certain types of image processing can include, for example, common techniques known to those of skill in the art of image processing. Some embodiments may use a combination of various enhancing and/or de-emphasizing techniques.

When an image has been enhanced or de-emphasized, certain embodiments may provide an indicator of the modification to the user. In some instances, the presented image may itself provide the alert to draw the user's attention to the modified image content (e.g., rapid growth in size, the high contrast in the presented image, blurring the image content with one color, a flash, etc.) As other examples, some embodiments may provide a visual (e.g., a pop-up alert or a blinking light) or an audio alert (e.g., a bell or a voice) to the user.

In certain configurations, the extent of the enhancement can be based on various factors. For example, the extent of the enhancement can be determined by the object's distance from the user. In some embodiments, the extent of the enhancement can be based at least in part on the amount of light received from the object or on the amount of light received from other nearby objects in the display.

Although certain examples described herein disclose enhancing image content presented to the user's peripheral field of view and/or de-emphasizing image content presented to the user's central field of view (e.g., to increase visibility of image content of the environment in the user's peripheral field of view), various embodiments may enhance image content presented to the user's central field of view and/or de-emphasize image content presented to the user's peripheral field of view (e.g., to increase visibility of image content of the environment in the user's central field of view) using the enhancing and/or de-emphasizing techniques described herein. For example, a radiologist or other medical practitioner may view an X-ray or content imaged with fluorescence (e.g., stained cells, tumors, amyloid plaques, etc.) in his or her central field of view. Some embodiments may increase contrast, increase light intensity, increase size, obscure background, etc. of the image content presented to the user's central field of view and/or decrease contrast, decrease light intensity, reduce size, blur, darken, obscure, etc. image content presented to the user's peripheral field of view. Some embodiments may also shift the color balance (e.g., red/green balance) of image content as described herein. In such examples, the details in the X-ray or content imaged with fluorescence may be more easily seen. As another example, some embodiments may provide a view of the active surgical site (e.g., in the user's central field of view) against a blurred background (e.g., in the user's peripheral field of view) such that the user can have an enhanced view of the surgical site (e.g., removing visual crowding). As yet another example, some embodiments may obscure content in the background (e.g., with a portion of the background having a degree of opacity or having opacity/substantial opacity) such that the active surgical site is visible and the rest of the real world is obscured.

Moreover, additional "virtual" image content can be presented to the peripheral and/or central vision fields of view. Such additional or "augmented" content can also include further text, arrows, user commands, duplicate images, etc. In some cases, such additional or "augmented" content can comprise images such as two-dimensional (2D) or three-dimensional (3D) images such as x-rays, CT, MRI, PET, ultrasound images or other images from imaging technologies. Such additional image content can also include data from diagnostic monitoring devices or other instrumentation as well as from other sources.

Figure 11B:
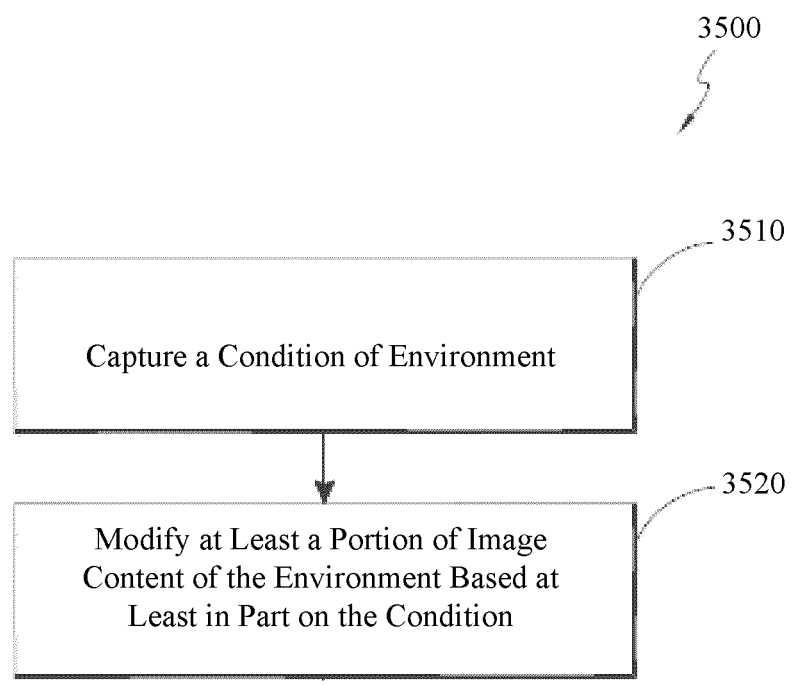
FIG. 11B is a flowchart illustrating another example of a method for enhancing user view of image content of the environment.

With reference now to FIG. 11B, another example method 3500 of improving user view of at least a portion of image content of the environment using a display system is illustrated. The display system may include the display systems 80, 1000, or 2010 in FIGS. 2, 6, and 10A-10B, respectively. The display system may include, for example, a head-mounted display device that projects image content to the user's eyes.

At block 3510, the display system may be configured to capture a condition of the environment. As described herein, some embodiments may include one or more capture devices to capture a condition of the environment. As one example, the display system may include one or more cameras or light sensors (e.g., light meters) to sense the lighting condition(s) of the environment. The one or more cameras or light sensors may measure the luminance of the ambient light.

At block 3520, various embodiments may modify at least a portion of image content of the environment based at least in part on the condition. For example, various embodiments may modify image content based on the lighting condition in the environment.

As described herein, cones are generally responsible for color and spatial resolution. Rods are not sensitive to color and are generally responsible for basic spatial resolution. Cones are most active in bright light conditions, while rods are more active in low light conditions. Thus, as the lighting condition (e.g., luminance) decreases, resolution of the cones also decreases.

Accordingly, some embodiments may present image content based at least in part on an inverse relationship to the lighting condition. In some examples, image content presented to the user may be enhanced with the techniques described herein. The extent of enhancement may be based at least in part on the inverse relationship to the luminance of the environment. For example, more enhancement such as magnification, increased brightness, increased contrast, or other types of enhancement such as described herein or combinations thereof, may be provided to image content in environments with lower lighting conditions. As described herein, a different portion of the image content may also be de-emphasized based at least in part on the lighting condition. Advantageously, certain embodiments described herein may enhance image content based on the lighting condition through one or more of a variety of enhancement/de-emphasizing techniques as described herein. For example, by increasing brightness of image content presented to the display in a dark environment, the user may have decreased visibility of the real-world environment being viewed through the display. Accordingly, various embodiments may utilize one or more of other techniques for enhancing (e.g., other than increasing brightness such as increasing size, increasing contrast, increasing color saturation, increasing sharpness, incorporating backgrounds, etc.) or de-emphasizing (e.g., reducing size, blurring, reducing contrast, decreasing color saturation, decreasing sharpness, obscuring, etc.) image content based on the lighting condition. In some cases, more enhancing or de-emphasizing may be provided to image content in environments with lower lighting conditions.

Certain embodiments may also advantageously enhance image content based on the visual function under the environment's lighting condition (e.g., see FIG. 1G). For example, various embodiments may exploit variations in use of cones and/or rods in the user's eye for different lighting conditions. In some such embodiments, the display system may be configured to project light to a location of the user's eye so as to present image content to a portion of the central or peripheral region of the user's vision field that is enhanced based at least in part on whether the user is utilizing photopic, mesopic, or scoptic vision. Photopic, mesopic, and scotopic vision are the vision of the eye under relatively bright, intermediate, and low light conditions respectively. For photopic vision, cones are mainly used and for scotopic vision, rods are mainly used. Mesopic vision utilizes both cones and rods. As described herein, the corresponding lighting conditions may be referred to as a photopic, mesopic, or scotopic lighting condition. Under a certain lighting condition, when cone activity dominates over rod activity in the eye, some embodiments may enhance image content based on the corresponding cone density as described herein. In some such instances, the image content may be enhanced inversely based on the density of cones. For example, more enhancing (e.g., more of an increase in size, contrast, color saturation, sharpness, etc.) may be provided to image content presented to a location of the eye having lower cone density. In addition, under a certain lighting condition, when rod activity dominates over cone activity in the eye, some embodiments may enhance image content based on the corresponding rod density as described herein. In some such instances, image content may be enhanced inversely based on the density of rods. For example, more enhancing (e.g., more of an increase in size, contrast, color saturation, sharpness, etc.) may be provided to image content presented to a location of the eye having lower rod density.

As described herein, some embodiments may include one or more capture devices to capture information regarding the environment. For example, an image capture device (e.g., a camera) may be used to capture the light condition (e.g., luminance) of the environment. As another example, a detector array comprising an array of pixels (e.g., an array of light sensors, detectors, or active sensor areas) may be used to capture the lighting condition of the environment (e.g., by integrating the light level over the pixels to capture the lighting condition of the environment). As yet another example, one or more capture devices may include an inward-facing image capture device or an eye tracking device to detect a pupil size. Depending on the luminance, pupil size can change. For low light conditions, pupils may dilate while for high light conditions, pupils may constrict. Accordingly, some embodiments may determine the lighting condition based at least in part on the pupil size. Some embodiments may include one or more timing devices (e.g., clocks or timers) to monitor the time spent in the lighting condition. One or more of the timing devices may include the timing device (e.g., a clock) incorporated in the device's electronics such as processing electronics (e.g., the local processing and data module 70 or the remote processing module 72 shown in FIG. 2).

Under a photopic lighting condition, the luminance can be greater than or equal to 10 $cd/m^2$, greater than or equal to 12 $cd/m^2$, greater than or equal to 15 $cd/m^2$, greater than or equal to 20 $cd/m^2$, greater than or equal to 50 $cd/m^2$, or greater than or equal to any value therebetween (e.g., greater than or equal to 10.5 $cd/m^2$, greater than or equal to 13 $cd/m^2$, etc.). The luminance range can be from 10 $cd/m^2$ to $10^8$ $cd/m^2$, 12 $cd/m^2$ to $10^8$ $cd/m^2$, 15 $cd/m^2$ to $10^8$ $cd/m^2$, 10 $cd/m^2$ to $10^7$ $cd/m^2$, 12 $cd/m^2$ to $10^7$ $cd/m^2$, 15 $cd/m^2$ to $10^7$ $cd/m^2$, 10 $cd/m^2$ to $10^6$ $cd/m^2$, or any ranges formed by any value from 10 $cd/m^2$ to $10^8$ $cd/m^2$ (e.g., 10.5 $cd/m^2$ to $10^8$ $cd/m^2$, 10.5 $cd/m^2$ to $10^7$ $cd/m^2$, etc.).

Under some such lighting conditions, since cones are activated, the image content may be enhanced (e.g., magnified, increased in brightness, increased in contrast, increased in color saturation, increased in sharpness, etc.) inversely based on the projected light location's density of cones. For example, in projected light locations (e.g., corresponding to the central or peripheral vision fields) with less cone density (e.g., farther from the fovea), more enhancement (e.g., more of an increase in size, contrast, color saturation, sharpness, etc.) may be needed.

Under a scotopic lighting condition, the luminance can be less than or equal to $10^{-3.5}$ cd/m², less than or equal to $10^{-3.6}$ cd/m², less than or equal to $10^{-3.7}$ cd/m², less than or equal to $10^{-3.8}$ cd/m² less than or equal to $10^{-4}$ cd/m², less than or equal to $10^{-4.5}$ cd/m², or less than or equal to any value less than $10^{-3.5}$ cd/m² (e.g., less than or equal to $10^{-3.9}$ cd/m², less than or equal to $10^{-5}$ cd/m², etc.). The luminance range can be from $10^{-3.5}$ cd/m² to $10^{-6}$ cd/m², $10^{-3.6}$ cd/m² to $10^{-6}$ cd/m², $10^{-3.7}$ cd/m² to $10^{-6}$ cd/m², $10^{-3.8}$ cd/m² to $10^{-6}$ cd/m², $10^{-4}$ cd/m² to $10^{-6}$ cd/m², $10^{-4.5}$ cd/m² to $10^{-6}$ cd/m², $10^{-3.5}$ cd/m² to $10^{-5}$ cd/m², $10^{-3.6}$ cd/m² to $10^{-5}$ cd/m², $10^{-3.6}$ cd/m² to $10^{-5}$ cd/m², $10^{-4}$ cd/m² to $10^{-5}$ cd/m², or any range formed by any value from $10^{-3.5}$ cd/m² to $10^{-6}$ cd/m² (e.g., $10^{-3.9}$ cd/m² to $10^{-6}$ cd/m², $10^{-4.2}$ cd/m² to $10^{-6}$ cd/m², $10^{-5}$ cd/m² to $10^{-6}$ cd/m², etc.).

Under some such lighting conditions, since rods are activated, the image content may be enhanced inversely based on the projected light location's density of rods. In projected light locations (e.g., corresponding to within the central vision field) with less rod density (and more cone density), more enhancement (e.g., more of an increase in size, contrast, color saturation, sharpness, etc.) may be needed, e.g., to "wake up" the rods and/or cones. For example, rods and cones can be activated based on differences. Movement or edges on shapes can be differences that can be detected by rods. Presenting any such differences can wake up the rods and possibly make the rods more sensitive to detecting the image. Since cones are responsible for color, but are not activated for scotopic vision, presenting color or contrast enhanced images (e.g., images with increased color saturation or contrast) to the cones, e.g., in the central region, during scotopic vision may in some embodiments, activate the cones. Further, the rod density can peak at about 18 degrees from the center of the fovea with a smaller peak at about 30 degrees from the center of the fovea. In some embodiments, the enhancement may be based at least in part on a distance from one of these peaks. For example, in projected light locations (e.g., corresponding to within the peripheral vision field) farther away from one of these peaks, more enhancement may be needed.

Under a mesopic lighting condition, the luminance can be from $10^{-3}$ cd/m² to $10^{0.5}$ cd/m² from $10^{-2.9}$ cd/m² to $10^{0.5}$ cd/m², from $10^{-2}0.8$ cd/m² to $10^{0.5}$ cd/m², from $10^{-3}$ cd/m² to $10^{0.45}$ cd/m², from $10^{-2}0.9$ cd/m² to $10^{0.45}$ cd/m², from $10^{-2.8}$ cd/m² to $10^{0.45}$ or any range formed by any value from $10^{-3}$ cd/m² to $10^{0.5}$ cd/m² (e.g., from $10^{-2.9}$ cd/m² to $10^{0.4}$ cd/m², from $10^{-2.8}$ cd/m² to $10^{0.4}$ cd/m², from $10^{-2}$ cd/m² to $10^{0.4}$ cd/m² etc.).

Under some such lighting conditions, both cones and rods can be used. The darker the lighting condition (e.g., going from photopic vision to mesopic vision), more rods (and less cones) may become activated. Additionally, in some such instances, the longer the time spent in the mesopic lighting condition, more rods (and less cones) may become activated. The lighter the lighting condition (e.g., going from scotopic vision to mesopic vision), more cones (and less rods) may become activated. In some such instances, the longer the time spent in the mesopic lighting condition, more cones (and less rods) may become activated. By monitoring the time (e.g., in real time) and luminance level, certain embodiments can determine the amount of the cones and rods that are active and/or whether cones or rods dominate in the user's eye. Generally, the darker the environment, the faster it may be for the transition of rods to dominate over cones. Also, the greater the change in luminance (e.g., more darker or more lighter), the rods or cones may become activated more quickly.

Accordingly, in some embodiments, the image content may be enhanced based at least in part on the lighting condition and at least in part on the time spent in the lighting condition (e.g., in a mesopic lighting condition). When the cones dominate, the image content may be enhanced inversely based on the projected light location's density of cones, e.g., as in the photopic condition. For example, more enhancing (e.g., more of an increase in size, contrast, color saturation, sharpness, etc.) may be provided to image content presented to a location of the eye having lower cone density. When the rods dominate, the image content may be enhanced inversely based on the projected light location's density of rods, e.g., as in the scotopic condition. For example, more enhancing (e.g., more of an increase in size, contrast, color saturation, sharpness, etc.) may be provided to image content presented to a location of the eye having lower rod density.

Additionally, enhancement may be based at least in part on the resolution of the active photoreceptors (e.g., cones for photopic vision, rods for scotopic vision, and cones and/or rods for mesopic vision). Resolving two points of image content may depend on the eye's spatial and/or contrast sensitivity (or spatial resolution). In addition, the minimum spatial distance and/or minimum contrast that the eye may sense may depend on the luminance level. For example, the minimum spatial distance and/or minimum contrast that the eye may sense may be smaller for well-lit environments compared to dark environments. Accordingly, various embodiments may enhance image content in order to be resolved by the eye based at least in part on the resolution of the eye for a given lighting condition. For example, image content may be enlarged to an extent to at least meet the minimum spatial resolution of the active cones and/or rods. As another example, image content may have increased contrast to an extent to at least meet the minimum contrast sensitivity of the active cones and/or rods. Some embodiments may utilize more than one technique for enhancing (e.g., enlarging, increasing brightness, increasing contrast, increasing color saturation, increasing sharpness, adding backgrounds, etc.).

It would be appreciated that various embodiments may utilize one or more techniques for de-emphasizing (e.g., reducing size, blurring, darkening/attenuating, reducing contrast, decreasing color saturation, decreasing sharpness, obscuring, etc.) image content based on the visual function under the environment's lighting condition and/or based on the resolution of the active photoreceptors. For example, in higher luminance levels (e.g., compared to lower luminance levels), cones can be more sensitive. In some such cases, image content presented to a portion of the user's vision field corresponding to a light projected location having a high cone density can be de-emphasized and still be detected. Accordingly, in photopic lighting conditions, some embodiments may de-emphasize image content presented to the central vision field so that the user may be able to better view image content presented to the peripheral vision field while still being able to view the de-emphasized image content presented in the central vision field. In lower luminance levels (e.g., compared to higher luminance levels), rods can be more sensitive. In some such cases, image content presented to a portion of the user's vision field corresponding to a light projected location having a high rod density can be de-emphasized and still be detected. Accordingly, in scotopic lighting conditions, some embodiments may de-emphasize image content presented to the peripheral vision field so that the user may be able to better view image content presented to the central vision field while still being able to view the de-emphasized image content presented in the peripheral vision field. In addition, in mesopic lighting conditions, some embodiments may determine whether cones or rods dominate in the user's eye (e.g., based at least in part on the time spent in the lighting condition) and present image content accordingly. For example, some embodiments can de-emphasize image content based on the density of cones when the cones dominate, e.g., as in the photopic condition. Some embodiments can de-emphasize image content based on the density of rods when the rods dominate, e.g., as in the scotopic condition. Furthermore, some embodiments as described herein may advantageously alert the user of the enhanced/de-emphasized image content via a visual or audio alert.

Image Modification

Figure 12A:
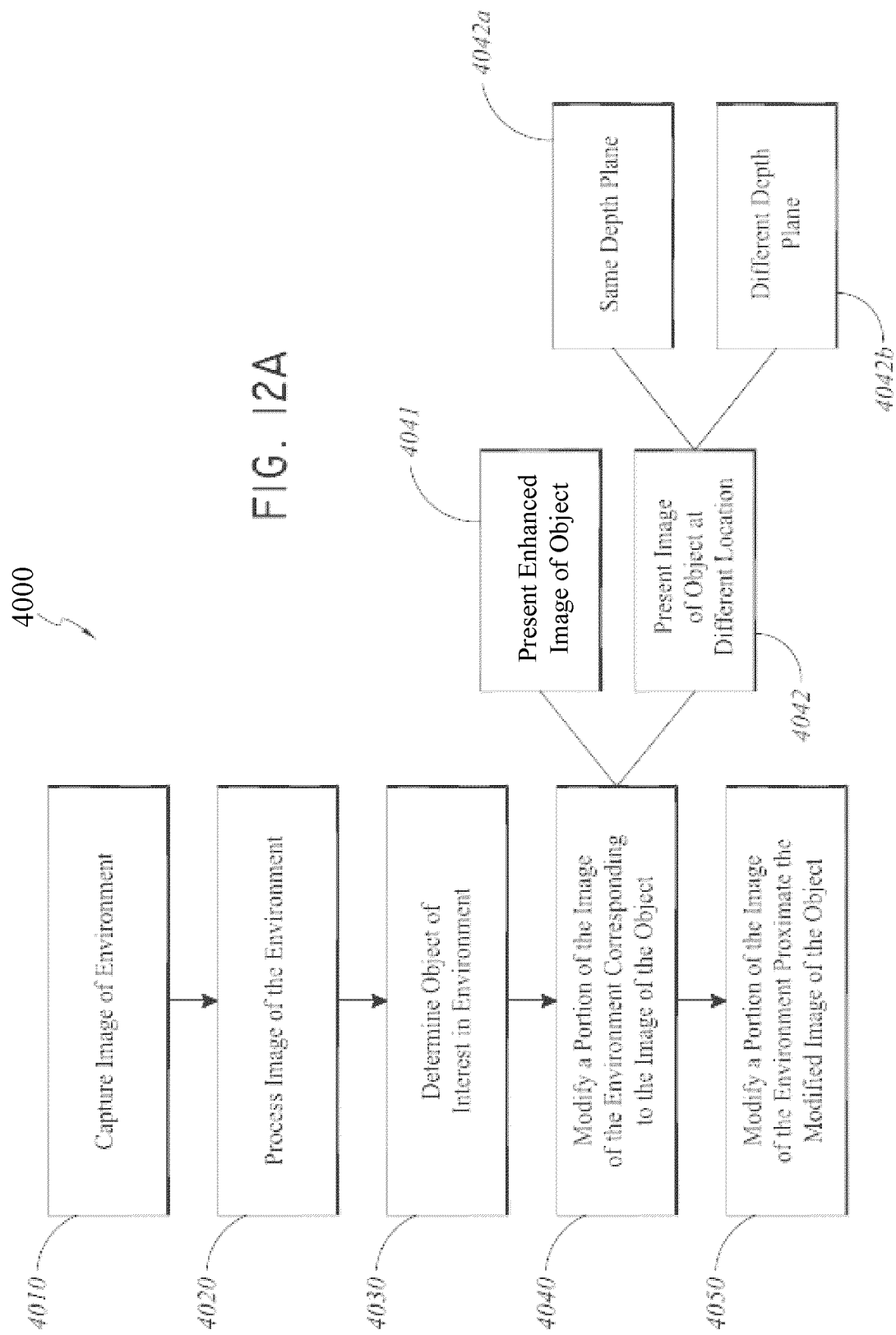
FIG. 12A is a flowchart illustrating an example of a method for image modification.
Figure 12B:
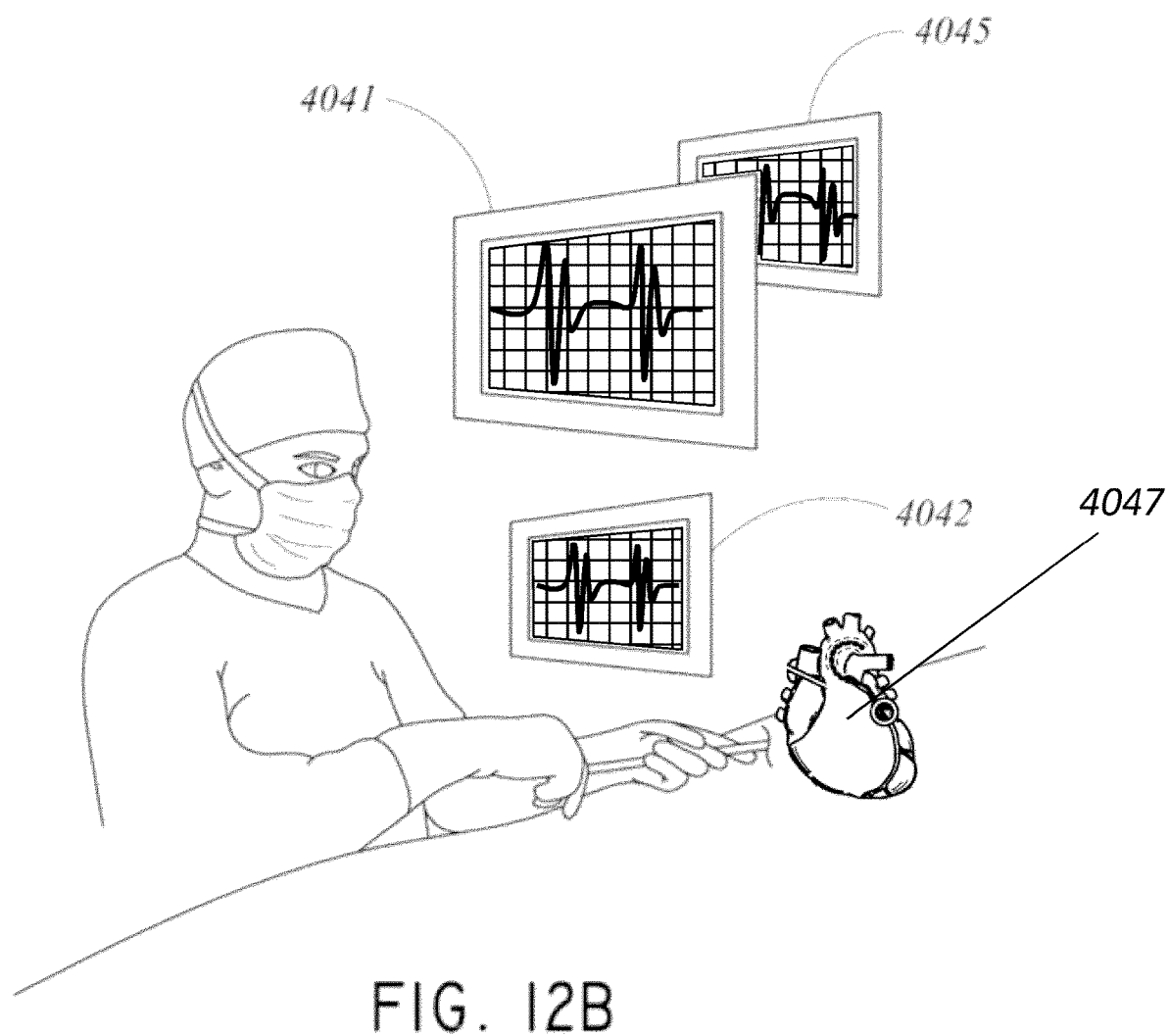
FIG. 12B illustrates example applications of some embodiments described herein.

Referring now to FIGS. 12A and 12B, a display system incorporating user and/or environmental sensors can advantageously provide image modification of an object in the environment. In other words, certain embodiments may allow the user to view with better visibility an object that is located in the user's field of view.

FIGS. 12A and 12B illustrates an example method 4000 of image modification of an object in the user's field of view using a display system. The display system may include the display systems 80, 1000, or 2010 in FIGS. 2, 6, and 10A-10B, respectively. Similar to blocks 3010 and 3020 of FIG. 11A, the display system may be configured to capture one or more images of the environment as shown in block 4010 and may process an image of the environment as shown in block 4020. In some embodiments, capture devices may capture other information regarding the environment (e.g., a camera or a light sensor can be used to capture the lighting condition (e.g., average brightness) of the environment).

At block 4030, various embodiments may determine an object of interest in the environment. In some embodiments, the object of interest may be an object in the user's peripheral field of view. In general, the user will typically focus their attention on an object or objects in the user's central field of view. In some such embodiments, the display system may automatically determine an object of interest to the user that is located in the user's peripheral field of view.

Various embodiments, for example, may identify at least a portion of the environment in the user's peripheral field of view that may be of interest to the user (e.g., one or more objects, part of one or more objects, or at least part of an object and part of its proximate environment). In some embodiments, the display system may automatically identify the portion of the environment by monitoring the user to determine which portion of the environment the user is interested in viewing. The time and/or effort that the user focuses in a certain viewing direction may be interpreted as the user's level of interest. For example, a user interested in a particular region in the user's peripheral field of view, may direct one's head and/or eyes toward a certain direction on multiple occasions and/or may spend a longer period of time viewing that direction. As another example, a user interested in a particular portion of the environment may squint one's eyes when observing in a certain direction indicating effort/interest in trying to view for example, an object that may have low resolution located in that direction. The user also may struggle to accommodate. Measurement of the accommodation of the lens in the eye may therefore be monitored to ascertain if the user is attempting to look at an object, but is having some difficulty.

Accordingly, as shown in FIGS. 10A-10B, the display system may include one or more input devices configured to receive input from the user. The input device may include inward-facing cameras 24, 28 and/or sensors for eye tracking, such as to detect eye position, movement, gaze, or pupil size. Inward-facing cameras 24, 28 and/or sensors may further be configured to monitor other facial indicators such as eyelid position, surrounding eye tissue position, facial muscle movement (e.g., crunching or squeezing facial muscles, squinting, etc.) or other facial position or movement. Sensors and/or cameras such as described herein (e.g., head pose sensors such as accelerometers, gyros, IMU's, and/or cameras 24, 28, 30, 32, 34) may be used to determine the user's head pose, such as the direction the head is positioned (e.g., straight or tilted with respect to the horizon). By using one or more of such information (e.g., information on eye tracking, facial indicators, and/or head pose) in conjunction with information regarding user environment from outward-facing cameras 34, local processing and data module 70 (and/or remote processing module 72 from FIG. 2) may be configured to determine a region of interest in the user's peripheral field of view.

In some embodiments, the display system may identify a portion of the environment in the user's peripheral field of view by the user actively indicating the region of interest. For example, the inward-facing sensors and/or cameras 24, 28 may include a detection system to detect certain user eye-based commands. For example, some embodiments may select a region of interest with user commands involving gaze, squint, or patterns of one or more winks or blinks. As other examples, the display system may include a physical user interface (e.g., a touch sensor such as a touch pad, a mouse, a pointing device, or one or more buttons on a surface of the display system), a virtual user interface (e.g., a virtual touch pad, a virtual mouse, a virtual pointing device, or one or more icons on a virtual touch screen), an audio recognition system (e.g., one or more microphones to detect voice commands, sighs, yawn, etc.), gesture recognition system (e.g., video camera and processing electronics to identify gesture) and/or a movement recognition system (e.g., a motion detector) to allow the user to select the region of interest.

Some embodiments may include one or more indicators or device alerts (e.g., a flashing light or a pop-up alert or using an audio signal) to draw the user's attention to a situation in the peripheral field of view (e.g., unnoticed bleeding in a peripheral region). In response, the user may actively select whether to enhance an image of the relevant portion in the user's peripheral field of view. In some such embodiments, the user may interact with the peripheral field of view without breaking gaze from the instant central field of view (such as a voice command or waving a hand to close a pop-up alert in the periphery).

In various embodiments, the identified portion of the environment in the user's peripheral field of view may include one or more physical objects, part of one or more physical objects, or at least part of a physical object and part of its nearby environment. For example, the identified portion may include one or more tools on a nearby table. As another example, the object may include a pre-recorded or a real-time medical image presented on a physical screen in the operating room. The medical image may include information such as a data file, a computed tomography (CT) scan (or also known as a computed axial tomography (CAT) scan), magnetic resonance imaging (MRI), a positron emission tomography (PET) scan, ultrasound imaging, an x-ray, etc. In some such examples, the portion of the environment does not necessarily include the entire image on the screen, but may comprise a part of the image. Further, the display system may be configured to identify more than one non-adjacent portions of the environment (e.g., a medical image on the left side of the surgeon and a different medical image on the right left of the surgeon).

In various embodiments, the one or more outward-facing sensors 34 may be configured to measure a distance to the object of interest in the identified portion of the environment. The one or more sensors 34 may include a distance measuring device (e.g., a laser rangefinder). The distance to the object of interest may be used to determine a depth plane at which to present image content of the object.

With reference to FIG. 12A, at block 4040, the display system may be configured to modify a portion of the image of the environment corresponding to the image of the object. As shown in block 4041, the display system may present an enhanced image of the object (e.g., a magnified image at a depth plane determined based at least in part on a distance to the object, and/or the minimum distance for two-point distinction, and/or an inverse relationship to the spatial resolution of the eye) or as shown in block 4042, the display system may present an image of the object in a different location. FIG. 12B shows example applications of some such embodiments. In FIG. 12B, a surgeon may be operating on a patient in his or her central field of view. Some distance away from the operating table may be a medical image 4045 (e.g., an electrocardiogram on a heart monitor). Some embodiments, as indicated by 4041 in FIG. 12B, may advantageously present an enhanced medical image (e.g., enhanced in size in this example). In some instances, the enhanced image may appear in substantially the same location as the actual medical image (for clarity, the enhanced image is not shown in the same location in FIG. 12B). For example, the medical image may remain in its actual location or thereabout but may appear enhanced (e.g., larger or smaller than its actual size). When the surgeon looks at the enhanced medical image, the surgeon may be able to see the medical image with better visibility. Some embodiments, as indicated by 4042 in FIG. 12B, may advantageously change the location of the medical image. For example, the medical image that was in the surgeon's peripheral field of view may be displaced closer to the patient so that the surgeon doesn't have to continuously adjust head pose. This way, the surgeon may be able to see both the patient and the medical image at the same time. Various embodiments may also present additional images to the user. For example, as shown in FIG. 12B, an additional AR image 4047 may be provided (e.g., a 3D image of a heart presented close to the patient).

Referring back to block 4041 of FIG. 12A, as described herein, the image of the object may be enhanced on the same depth plane as the corresponding depth plane of the object or on a depth plane that is close to the depth plane corresponding to the object. For example, in some embodiments, the display system may be configured to present a enhanced image of the object of interest at a depth plane determined based at least in part on a distance to the object. The depth plane that the image is projected from may not coincide exactly with the distance from the user to the object in the real world. Instead, in some cases, a depth plane is selected that is close to the distance of the object in the real world from the user, such as the closes depth plane available or at least closer than one or more other depth planes that the head mounted display device is configured to provide images from. Because the image of the object of interest in the user's peripheral field of view is enhanced, the user may have better visibility of that object without having to re-direct the user's field of view towards that object. Although in the example shown in FIG. 12B, the image 4041 of the object 4045 is magnified, the image 4041 of the object 4045 may be enhanced in other ways.

A variety of ways can be used to measure the distance from the user to the object in the real world. For example, U.S. Provisional Application No. 62/294,147 describes one method of taking physical measurements. In some embodiments, the head-mounted display device may include one or more sensors configured to measure distance to objects in the environment. Such a sensor could be a distance measuring device or ranging device such as, for example, a laser rangefinder (e.g., lidar), a radar distance finder, an ultrasonic ranging device (using, e.g., sonar or echo sounds). Other methods such as triangulation may also possibly be used. As described herein, an image of the object can be displayed on the head-mounted display to create the effect on the user that the image of the object appears to be at the same location as a real location. This effect can be achieved by determining a depth plane from which the imaged object can be presented so as to appear to be located as the same distance as the actual location of the object. The depth plane that the head mounted display provides may not necessary exactly match the distance to the object. A depth plane that approximates that distance may be selected. Or maybe the most suitable depth plane is the depth plane that can be provided by the head mounted display device that is closer to the distance from the user to the object than other depth planes that can be provided by the head mounted display device. In some embodiments, for example, the display device includes at least two depth planes, a far depth plane and a near depth plane. The most suitable depth plane may be selected depending on the distance from the object to the user. For example, if the distance from the object to the user is closer to a first depth plane rather than a second depth plane that is provided by a particular head mounted display, the image of that object may be presented on the first depth plane. In some embodiments, the far depth plane may display images of objects that appear farther than a threshold distance from the user, and the near depth plane may display images of objects that appear closer than the threshold distance. In various embodiments, more than just two depth planes are available for presenting images. Again, as described above, in such embodiments, the most suitable depth plane may be selected that is closer to the depth plane corresponding to the object in the real-world.

In some embodiments, the display system may be configured to magnify image content of the object and present that magnified image on a depth plane based at least in part on the distance to the object, and/or the minimum distance for two-point distinction, and/or an inverse relationship to the spatial resolution of the eye. In certain embodiments, the display system may present a magnified (or enhanced) image of the object in relation to how the object would appear without the magnification (or enhancement). In some embodiments, the magnification (or enhancement) of the image can be in relation to surrounding objects in the real world and/or other images presented on the display.

Figure 12C:
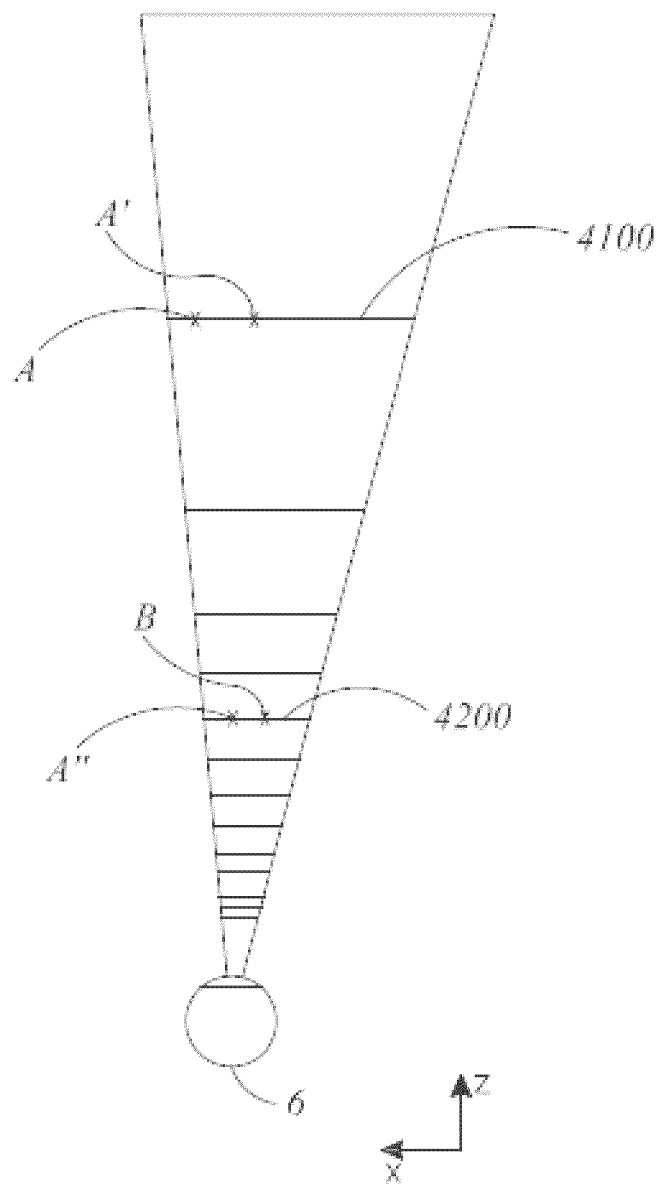
FIG. 12C illustrates examples of image modification based on location.

Referring now to block 4042 in FIG. 12A, as described herein, the display system may present an image of the object of interest at a different location as the object. In some examples, the display system may present the image of the object at a different location at the same depth plane corresponding to the distance to the object as shown in block 4042*a*, or at a depth plane different from the depth plane corresponding to the distance to the object as shown in block 4042*b*. For example, block 4042*a* may be illustrated with reference to FIG. 12C. FIG. 12C shows the depth planes from FIG. 4 from one eye 6. The object of interest may be originally associated with a depth plane 4100 at location A (e.g., at 10 feet from the user). As shown in FIG. 12C, the display system may present the image of the object at location A' (e.g., project rays of light into the retina as if the object from which the rays emanate were located 10 feet from the user or in some embodiments), which is laterally displaced from location A, but at the same depth plane 4100. As an example, the medical image may be located almost outside of the surgeon's field of view (e.g., in the peripheral field of view). In some embodiments, the medical image may be presented at a laterally displaced location such that the medical image appears to be closer to the surgeon's central field of view. In some such embodiments, the surgeon may be able to see the medical image with better visibility than if the medical image were not presented in a laterally displaced location.

Block 4042b may also be illustrated in reference to FIG. 12C. As mentioned above, the object of interest may be originally associated with a depth plane 4100 at location A. As shown in FIG. 12C, the display system may present the image of the object at a location A", which is at a depth plane 4200 different from the depth plane associated with location A. As an example, the medical image located at location A may be presented at a different depth plane 4200 closer to the depth plane 4200 associated with the patient and/or surgical site (e.g., at location B).

In various embodiments, presenting the medical image on a depth plane closer, if not the same, depth plane associated with the patient may ease accommodation in the surgeon (e.g., brings the accommodation state of the medical image closer to that of the patient). In addition, the surgeon may be able to see the medical image with better visibility than if the medical image were not presented at a different location. For example, the medical image may be presented adjacent to the patient. As another example, the medical image may be superimposed onto the patient. In some instances, superimposed images on the patient may provide guidance to the surgeon during surgery.

In some embodiments, the image of the object of interest may be presented at a depth plane closer to or farther from the eye 6. For example, the depth planes may include a far depth plane 4100 and near depth plane 4200. The far depth plane 4100 may be farther from the user's eye 6 than the near depth plane 4200. As described herein, various embodiments may include one or more outward-facing sensors 34 configured to determine a distance to an object of interest. The distance to the object of interest may correspond more to the far depth plane 4100 than the near depth plane 4200. In some instances, the image of the object may be presented at the near depth plane 4200. The image of the object presented at the near depth plane 4200 may in some cases, be presented to the user's central field of view or in proximity thereto. The presented image may or may not be magnified (or otherwise enhanced). In some other embodiments, the object of interest may correspond more to the near depth plane 4200 than the far depth plane 4100, and the image of the object may be presented at the far depth plane 4100 (e.g., to reduce visual crowding caused by too many imaged details that introduce distraction or clutter near the object(s) of interest). Furthermore, in some embodiments, the image of the object may be laterally displaced at the same depth plane as the corresponding depth plane as the object (e.g., laterally displaced from the peripheral field of view to the central field of view). Some embodiments may present an enhanced image laterally displaced at the same depth plane as the corresponding depth plane of the object. As one example, a magnified image of a label on a bottle in the user's peripheral field of view may be presented laterally displaced above the actual labeled bottle.

It would be appreciated that the image for the object of interest may be modified based on aspects other than (or in combination with) magnification and/or location. For example, the portion of the image of the environment corresponding to the image of the object (e.g., in the peripheral field of view) may be modified in intensity/brightness, contrast, color saturation, sharpness, edge enhancement, incorporating backgrounds, color balance, and/or white balance such that it is enhanced in relation to how the object would appear without being modified and/or compared to another portion of the image of the environment (e.g., to another portion of the image of the environment in the peripheral field of view such as one proximate to the modified image or to a portion of the image of the environment in the central field of view). The portion of the image of the environment corresponding to the image of the object may also be enhanced based on exposure, lightness, shadows, highlights, flipping, straightening, rotating, measuring image portions, and/or using other approaches. Accordingly, in various embodiments, portion of the image of the environment corresponding to the image of the object may be processed differently compared to another portion of the image of the environment. The presented image content is additional augmented content and/or can include further additional augmented content (e.g., text, arrows, user commands, duplicate images, 3D-images of objects such as organs that can be manipulated, etc.).

It would be also appreciated that instead of or in addition to modifying the portion of the image or view of the environment corresponding to the object of interest, another portion of the environment may be de-emphasized by shrinking, blurring, darkening/attenuating, reducing contrast, decreasing color saturation, decreasing sharpness, de-enhancing edges, obscuring, etc., of images or views of the environment or of other images displayed by the display. For example, such image content may be blurred to reduce visual crowding or clutter. Some embodiments may blur content by presenting adjacent portions of the image in substantially all of the same color (e.g., monotone). In some such instances, the color may be a color with high contrast to colors in the portion of the image corresponding to the object of interest. De-emphasized images or views of the environment or of other images displayed by the display may also be accomplished based on exposure, lightness, shadows, highlights, flipping (e.g., inverting), straightening or reducing straightness, rotating, measuring image portions (e.g., including volumes), shifting color balance (or white balance), and/or otherwise being image processed differently compared to the portion of the image of the environment corresponding to the image of the object of interest.

It would further be appreciated that the object determined to be of interest may correspond to an object in the user's central field of view, and that the portion of the image of the environment corresponding to the image of the object may be enhanced and/or moved in location as described herein. Further, another portion of the image of the environment may be de-emphasized as described herein.

As yet another example, some embodiments may present an image of an object from the user's central field of view to another location in the user's central field of view. Image content from a far depth plane may be brought to a near depth plane for increased visibility in the user's central field of view. Also, image content corresponding to a near depth plane may be brought to a far depth plane, e.g., to reduce clutter and/or visual crowding in the user's near field of view. Some embodiments may also present an image of an object from the user's central field of view to the user's peripheral field of view (e.g., to reduce visual crowding).

With continued reference to FIG. 12A, at block 4050, some embodiments may be configured to modify a portion of the image of the environment proximate the modified image of the object. For example, some embodiments may de-emphasize an aspect (e.g., reducing size, decrease color saturation, decrease intensity, blurring of image content, darkening/attenuating of image content, changing the color or hue, etc.) of the image of the environment proximate the modified image of the object (e.g., to reduce distracting visual detail or visual crowding). As another example, some embodiments may adjust the portions of the image of the environment proximate the modified image of the object to cover any underlying image. For example, if the modified image of the object were displaced to a different location and/or were a magnified image, certain embodiments may adjust the regions underneath the modified image to prevent presentation of double images. In some instances, the image of the environment may also be modified to include a border surrounding the modified image of the object. Providing a border may help the user know that he or she is viewing a modified image of the object (e.g., an augmented virtual image) and not an image of the object as it exists in the actual world. Further as shown in FIG. 12B, additional augmented reality images (e.g., pre-planned surgical guides, instructions, etc.) may be presented near the modified image of the object.

As described herein, the display device can be configured to highlight images of objects in the environment around the user. Such objects may appear in a variety of sensing regions of the user, such as within the user's field of view. In such instances, the object may be in the user's central field of view or in the peripheral field of view. Alternatively, the objects may be within the user's field of regard but outside the user's field of view field of view. For example, in some embodiments, bringing an image of an object that is outside the user's field of view, into the user's field of view may be useful, to alert the user. In the case of surgery, a screen that is not within the surgeon's field of view when focusing attention on the surgical site may include vital signs of the patient. When such vital signs reach a certain level, the surgeon may be alerted by providing an image of the screen on the head mounted display device display. This screen may be imaged by a video camera placed on the head mounted display device. This camera (or cameras) may be a forward directed camera or possibly even a side directed camera or rear directed camera. As another example, the alert may include an icon (e.g., a copy of the image) or an audio to indicate the potential situation to the surgeon. As yet another example, an icon (e.g., a heart or a thermometer) may appear on the display to remind the surgeon to check certain vital signs (e.g., heart rate or temperature) of the patient. A small icon may provide less distraction. The surgeon may then choose either to move his or head to view the actual object or to view the object as an AR image.

As another example, in the case of an emergency (e.g., at the airport), the object of interest may be a defibrillator. The display device may locate the defibrillator through a network system or object recognition algorithm and provide general directions to its location (e.g., visuals, audio, text, etc.). After the outward-facing cameras locate the defibrillator (e.g., within the user's field of regard), the display device may present an enhanced image of the defibrillator (e.g., a magnified image of it) along with additional augmented images such as more precise directions (e.g., arrows, texts, etc.) to the defibrillator. Further, when using the defibrillator, the display device may present an enhanced image of the instructions booklet next to the patient. Additional content may also be presented near the patient (e.g., location of where to place the defibrillator pads). Numerous other examples are possible. As discussed above, communication with a network system may be useful to provide additional information, such as the location of the defibrillator in this example. Pattern recognition such as provided by processing electronics, may be used to process the image captured by the outward-facing camera, for example, to determine the location of or identify an object, such as the defibrillator in this example.

Further Embodiments of Image Modification Based on Lighting Condition

As described herein, certain embodiments may modify at least a portion of image content of the environment based at least in part on the lighting condition (see e.g., FIG. 11B). As also described herein, various embodiments may identify an object of interest in the environment and modify a portion of the image of the environment corresponding to the object (e.g., present an enhanced image of the object or present an image of the object at a different location as shown in FIGS. 12A-12B.) The portion of the image may be modified based at least in part on the lighting condition.

In some embodiments where image content is presented at a different location, the display system may be configured to present image content from a first portion of the user's vision field to a second portion of the user's vision field based at least in part on the lighting condition of the environment. Under the lighting condition of the environment, the second portion may correspond to a projected light location of the user's eye having a higher visual acuity than the first portion. By moving image content to a location corresponding to a projected light location of the user's eye having a higher visual acuity, certain embodiments described herein may present image content to a display without having to increase the brightness of the image content. Advantageously, using some such embodiments in dark environments may maintain the user's ability to view the real-world through the display in the natural dark environment.

Under a photopic lighting condition, since cones are activated, the second portion may correspond to a projected light location of the user's eye having a higher density of cones than the first portion. For example, the first portion may comprise a portion in the peripheral region and the second portion may comprise a portion in the central region. As another example, the first portion may comprise a portion in the central region and the second portion may comprise another portion in the central region (e.g., corresponding to a projected light location of the user's eye closer to the fovea). As yet another example, the first portion may comprise a portion in the peripheral region and the second portion may comprise another portion in the peripheral region (e.g., corresponding to a projected light location of the user's eye closer to the fovea). The second portion may, in some instances, correspond to a projected light location of the user's eye at the fovea where the cones have the highest acuity for optimal viewing. In some examples, the second portion may correspond to a projected light location of the user's eye in a range from 0 to 10 degrees, 1 to 10 degrees, 2 to 10 degrees, 0 to 8 degrees, 1 to 8 degrees, 2 to 8 degrees, 0 to 5 degrees, 1 to 5 degrees, 2 to 5 degrees from the center of the fovea, or any range formed by any value from 0 to 10 degrees from the center of the fovea (e.g., 1 to 4 degrees, 1 to 6 degrees, 2 to 7 degrees from the center of the fovea, etc.).

Under a scotopic lighting condition, since rods are activated, the second portion may correspond to a projected light location of the user's eye having a higher density of rods than the first portion. For example, a person can try to see detail in dim light using averted vision. Since there are substantially no rods in the fovea, a person can change gaze to peripheral vision while concentrating on the object of interest. Accordingly, the first portion may comprise a portion in the central region and the second portion may comprise a portion in the peripheral region.

As described herein, the rod density can peak at about 18 degrees from the center of the fovea with a smaller peak at about 30 degrees from the center of the fovea. In some examples, the first portion may comprise a portion in the peripheral region and the second portion may comprise another portion in the peripheral region (e.g., corresponding to a projected light location of the user's eye closer to one of the rod density peaks). In some instances, the second portion may correspond to a projected light location of the user's eye at one of the rod density peaks for optimal viewing. In some examples, the second portion may correspond to a projected light location of the user's eye in a range from 10 to 25 degrees, 12 to 22 degrees, 15 to 20 degrees from the center of the fovea, or any range formed by any value from 10 to 25 degrees from the center of the fovea (e.g., 13 to 23 degrees, 14 to 22 degrees, 16 to 20 degrees from the center of the fovea, etc.). In some examples, the second portion may correspond to a projected light location of the user's eye in a range from 20 to 40 degrees, 22 to 38 degrees, 25 to 35 degrees from the center of the fovea, or any range formed by any value from 20 to 40 degrees from the center of the fovea (e.g., 23 to 37 degrees, 26 to 32 degrees, 27 to 33 degrees from the center of the fovea, etc.).

Under a mesopic lighting condition, both cones and rods can be used. In some embodiments, under a mesopic lighting condition, the device may be configured to present image content from the first portion to the second portion based at least in part on the lighting condition and at least in part on the time spent in the lighting condition. The darker the lighting condition, more rods (and less cones) may become activated. Additionally, the longer the time spent in the mesopic lighting condition, more rods (and less cones) may become activated. By monitoring the time (e.g., in real time) and luminance level, certain embodiments can determine the amount of the cones and rods that are being used and whether cones or rods dominate in the user's eye. Generally, the darker the environment, the faster it is for the transition of rods to dominate over cones.

When the cones dominate the user's eye, the second portion may correspond to a projected light location of the user's eye having a higher density of cones than the first portion, e.g., as in the photopic condition. For example, the first portion may comprise a portion in the peripheral region and the second portion may comprise a portion in the central region. As another example, the first portion may comprise a portion in the central region and the second portion may comprise another portion in the central region (e.g., corresponding to a projected light location of the user's eye closer to the fovea). As yet another example, the first portion may comprise a portion in the peripheral region and the second portion may comprise another portion in the peripheral region (e.g., corresponding to a projected light location of the user's eye closer to the fovea). In some instances, the second portion may correspond to a projected light location of the user's eye at the fovea where the cones have the highest acuity for optimal viewing, e.g., as described herein for the photopic condition.

When the rods dominate the user's eye, the second portion may correspond to a projected light location of the user's eye having a higher density of rods than the first portion, e.g., as in the scotopic condition. For example, the first portion may comprise a portion in the central region and the second portion may comprise a portion in the peripheral region. In some examples, the first portion may comprise a portion in the peripheral region and the second portion may comprise another portion in the peripheral region (e.g., corresponding to a projected light location of the user's eye closer to or at one of the rod density peaks as described for the scotopic condition).

Since the display system may be configured to present image content from a first portion of the user's vision field to a second portion of the user's vision field, some embodiments may advantageously alert the user of the changed image content via a visual or audio alert.

It would be appreciated that some embodiments may not necessarily move image content from one location to another, but may use similar principles described herein to determine a location to present augmented image content based at least in part on the lighting condition of the environment and at least in part on the projected light location's density of photoreceptors (e.g., for optimal viewing at the lighting condition).

For example, under a photopic lighting condition, the image content may be presented to a portion of the user's vision field based on the projected light location's density of cones. The image content may be presented to a portion of the user's vision field corresponding to a location of the user's eye having a relatively high density of cones. In some instances, the light may be projected to a location of the user's eye so as to present image content to the central region of the user's vision field. In some instances, the projected light location may be at or close to the fovea.

As another example, under a scotopic lighting condition, the image content may be presented to a portion of the user's vision field based on the projected light location's density of rods as described herein. The image content may be presented to a portion of the user's vision field corresponding to a location of the user's eye having a relatively high density of rods. In some instances, the light may be projected to a location of the user's eye so as to present image content to the peripheral region of the user's vision field. In some instances, the projected light location may be at or close to one of the rod density peaks.

As yet another example, under a mesopic lighting condition, certain embodiments may be configured to determine whether cones or rods dominate in the user's eye under the lighting condition. As described herein, this determination may be based on the time spent in the lighting condition. When the cones dominate the user's eye, the image content may be presented to a location as described for the photopic condition. When the rods dominate the user's eye, the image content may be presented to a location as described for the scotopic condition. As also described herein, some embodiments may advantageously alert the user of the presented augmented image content via a visual or audio alert.

Example Display Systems for Medical Imaging, Display, and Visualization

Many individuals experience a medical condition or disease that requires diagnosis and treatment at some point in their lives. These conditions may take myriad forms, including, for example, heart disease, cancer, spinal conditions, and orthopedic injuries among others. Advantageously, in some embodiments, the augmented reality (AR) display systems disclosed herein may be configured to assist medical professionals in the assessment and treatment of their patients, and may do so at any stage of care. The AR display systems may be used in any suitable context for which medical imaging, medical display, and/or medical visualization is useful. For example, the AR display systems may be used in emergency rooms, operating rooms, clinics, doctor offices, patient homes, and the like. In some embodiments, the AR display systems may be configured to image, display images, manipulate images, diagnose diseases and abnormalities, provide treatment options, prevent certain health issues, and/or provide assistance during medical procedures. It will be appreciated that the AR display systems may assist or supplement one or more medical professionals in any suitable manner. In the medical context, patients and users at home may also benefit from various embodiments.

In some embodiments, the display system may be a "near-to-eye" display, e.g., a display that may be positioned close to and in front of a user's eyes. The display may be a three-dimensional volumetric display that projects images directly into a user's eyes by, for example, scanning beams of intensity-modulated light with varying focus distances in various patterns across the retina. The scanning patterns may include raster, spiral, and/or Lissajous, among others. To project such various patterns to the eye, the display may comprise a scanning fiber display that includes one or more scanning fibers. The display may produce images at various depths by generating both collimated and diverging beams to the eye, which can advantageously allow for a more normal accommodation when displaying objects to a viewer. In some embodiments, the depth or focal distance of an image may be adjusted by optical elements, mechanical structures, processing algorithms, or any combination thereof. The display may comprise an augmented reality display that permits the viewer to see the environment in front through transparent windows, lenses and/or other transparent optics and may also add to that view of the environment with imagery presented by a display comprising a light source that directs light into the eye to enable the formation of such additional or "augmented" imagery.

As discussed below, additional images may include medical images such as X-rays, CT, PET, or MRI scans, ultrasound images, etc. In some embodiments, the contrast level of a medical image can be adjusted. For example, a medical image can be in greyscale and the level of greyscale can be intrinsic of the tissue type. Sometimes the number of levels of a medical image can be greater than the human eye can distinguish. For example, an 8-bit image can have 256 levels, which may be greater than the human eye can distinguish. Some embodiments can adjust contrast levels such that they can be distinguished by the human eye.

Additional images also may comprise medical data or other information, for example, from medical instrumentation or other sources. In some embodiments, image processing and/or machine vision technology included in the display system may be configured to contour and/or measure changes in shape and/or volume and/or measure fluid flow based on such images or other signals or data. Other types of information can also be displayed. The display system may be configured for real-time and/or post-processing of such imaged and sensed data. This can advantageously allow the display system to augment real-time imagery and/or post-viewing imagery with pertinent information such as, for example, instructions, measurements, calculations, and other visible imagery.

As described herein, the display system may include one or more outward-facing cameras. In some embodiments, machine vision may be used to analyze the visual content from the user's environment and may include, for example, one or more of the following, a color sensor, a depth sensor, a pattern recognizer, an edge detector, and/or a world camera, among other features or components. Images from these one or more cameras may be presented on the display. As discussed above and elsewhere herein, the display technology may use depth planes, discrete content viewing, and image placement so that the user may see the content clearly and, as discussed herein, grounded to the earth in various cases (pixel stick).

Such systems may additionally include one or more sensors such as for example image sensors, accelerometers, gyros, temperature sensors, electrodes, pressure sensors, etc. In some embodiments, the display system may include an altimeter, a barometer, a chemical sensor, a humidity/temperature sensor, a microphone, a speaker, a GPS system, a weather map, a calendar and/or other sources of information, each of which may contribute to the type of content the user sees and interacts with on their device.

The system may additionally include one or more recorders and/or one or more other external inputs and/or outputs. As discussed above, machine vision may allow the display system to receive inputs corresponding to the various inputs (e.g., sensors) of the machine vision system and display them in the user's field of view. The images and other information may be stored and/or passed to the other users.

In some embodiments, the results may be collected and/or analyzed, either contemporaneously or through comparison of historical data. In some embodiments, the display system may include machine vision technology to diagnosis medical conditions. In some embodiments, for example, outward-facing cameras may be used to gather information regarding the patient's condition. Also, in some embodiments, ultrasound, x-ray, MRI, PET, CT, imaging may be analyzed to provide a diagnosis. In some embodiments, for example, the device may output ultrasound waves from a transducer as an ultrasound emission source and measure returned ultrasound waves to determine tissue density as a response to obtain information about the patient. See, e.g., FIG. 10B. Accordingly, in some embodiments, the head mounted display device may include a source of ultrasound waves. The head-mounted display may also include a receiver configured to receive, measure, and/or interpret a return signal from the emitted ultrasound waves. Some embodiments use Doppler effect or time of flight as part of the measuring and/or interpretation of the received signal. In certain embodiments, the display system comprises a sensor adapted to convert ultrasonic sound waves into electrical signals. Processing electronics, as disclosed herein, may be used to process such signals. In some embodiments, the source and/or receiver can comprise one or more transducers. In some embodiments, the one or more transducers of the source and/or receiver can be mounted onto the display system. In some embodiments, the display device is configured to emit ultrasounds such that they propagate through a propagation medium (e.g., air, skin, liquid, gel, etc.). Other inputs may also include imported data, for example, images, patient history files, emergency medical records, or surgical case notes which can later be used to help in diagnosis. In some embodiments, the device may use pattern recognition and processing electronics, for example, to perform measurements (e.g., lesion length, time of flight data from ultrasound) to evaluate a patient's condition. In certain embodiments, population norms can be stored such that they can be used to compare with real-time measurements and/or observations made by the device. Using information received by such comparisons, certain embodiments can identify abnormalities from image data. Such diagnoses and/or determinations may employ one or more of an emission, a response, a measurement, and/or an analysis process. Such diagnoses can also be used to prevent certain health issues from occurring. In some embodiments, the information gathered (e.g., history-based reactions, population norms, etc.) can be used in forming more accurate representations and/or images of objects (e.g., a bone structure). In response to collected and/or analyzed data, the display system may, in some embodiments, be configured to provide informational cues, send alerts, or initiate other responses. It will be appreciated that the sensing and display capabilities of the display system may be modified in any suitable manner (e.g., with sensors and/or other devices) to have utility in any medical and consumer application used by researchers, clinicians, patients, consumers, and the like.

The one or more inward-facing cameras can be configured to detect a user's input. In some embodiments, the one or more inward-facing cameras may be configured to track eye movements, surrounding eye tissue, and/or track a user's pupils. The inward-facing cameras may include a retinal camera configured to detect a user's input. In some instances, the feedback can be used to assess user performance and display content (e.g., color, size, location, etc.) accordingly. For example, squinting eyes or drooping eye lids may indicate signs of user fatigue. The display system of some embodiments can be configured to automatically adjust display content by zooming in certain content and/or increasing contrast to re-engage the user in the task. As another example, in some embodiments, the time that a pupil remains focused on an object may be measured and may be interpreted as the user's level of interest. The display system may include gesture recognition. The one or more outward-facing cameras may, for example, use machine vision, edge detection, object recognition, and/or an inertial measurement unit (IMU), etc. to understand the user's gestures, head pose, movement patterns, etc. In some embodiments, the display system may include a microphone capable of recognizing, for example, one or more signals, the location of the one or more signals, audio (e.g., voice) input, and/or the intensity of noise. In some embodiments, the display system may include a speaker for providing audio feedback, for example, to the user.

Generating 3D Virtual Images from Patient Medical Scans

As discussed above, the display system may be combined with various medical imaging modalities (e.g., CT, MRI, PET, and/or ultrasound, etc.) to visualize a variety of anatomical features, including, for example, bone, organs, cartilage, blood, cancerous tissue, etc. For example, in some embodiments, the display system may be configured to measure tissue volume (e.g. tumor volume) and measure the extent of healthy versus unhealthy tissue (e.g., obtain the ratio or percentage of healthy versus unhealthy tissue). In some embodiments, various aspects of the visualized tissue may be analyzed and displayed. When combined with one or more medical imaging modalities, the display system may advantageously generate 3D virtual images of objects from one or more 3D datasets and display them to the user for medical applications. This can, for example, allow for more realistic images, a more accurate and natural viewing experience for the viewer (e.g., since the object image appears in 3D) and improved accuracy in medical procedures. For example, in some such combined embodiments, doctors may use the display system for more precise pre-operative planning and operations. Increasing procedural precision may advantageously reduce patient recovery time as well as conserve more surrounding healthy tissue.

As an example, aggressive surgical interventions such as gross total resection have been the standard treatment for most benign brain tumors. Accurate pre-operative scanning and planning of tumor location using the display system in combination with one or more imaging modalities may allow for more localization tumor resection, and more conservation of healthy surrounding tissue. As another example, the systems described herein may be used to diagnose joint disorders. For example, in a generated joint image, a doctor may be able to zoom and view fluid inside the joint. The doctor may diagnose painful joints. For example, the doctor may take a fluid sample, which may reveal bacteria in the fluid (indicating that the painful joint may be due to infection). In some embodiments, the display system may be configured to recommend a fluid sample be taken based on the image and/or the doctor's interaction with the image.

As described above, the display system may be combined with patient scan modalities such as CT, MRI, PET, ultrasound, or a combination of such imaging modalities (e.g. MRI and PET, CT and PET, MRI and ultrasound, and/or any other suitable combination) to generate a variety of 3D virtual images. Without the display device, physicians previously had to view 2D images and "build" the true 3D images in their imaginations. The display system described herein may be configured to advantageously render 3D images which look like the patient's anatomy or which are renditions of the patient's actual anatomy. These 3D images may be beneficial for diagnosing medical conditions, as well as for educational purposes in which it might be challenging for students to render these 2D images from different perspectives into a 3D model in their heads.

In some embodiments, the display system may include artificial intelligence to analyze the images generated from the patient scan modalities. In this way, diseases such as cancer, diabetes, or cognitive heart failure, among others, may be diagnosed early on using, for example, machine learning technology. In some embodiments, the display system can download or access one or more databases of a population where a population norm is identified. The population norm can be compared with images to aid in, for example, diagnosis of an ailment, analysis of a symptom, and/or prescription of a remedy.

3D Virtual Image Manipulation and Interacting

As discussed above, the display system may display three-dimensional images using, for example, a plurality of depth planes and waveguide stacks. This may give users the ability to focus on images of objects rendered as if at various distances from the eyes with proper accommodation and vergence.

In some embodiments, users do not need to use a remote or finger to manipulate the virtual content in the display field. Instead, as described above, the display device may include one or more inward-facing cameras capable of tracking eye movement, surrounding eye tissue, tracking pupils, and the like. In some embodiments, the display system may include a retinal camera to detect user input. The time that the pupil remains focused on an object can be interpreted as the user's level of interest. In some embodiments, eye tracking technology can allow the user to manipulate the virtual content with a gaze, a squint, and/or one or more blinks of the eye and/or in other ways. In certain embodiments, the display device can detect fluctuations in accommodation and/or vergence. This information can be used to identify that the user is struggling to view an image. In some configurations, the display device can use this information to select a portion of an image to enhance (e.g., magnify). Microphones and/or speaker inputs can be used to manipulate the virtual content.

A wide variety of 3D visual manipulation is possible and such manipulation has many uses. For example, in some embodiments, users may be able to segment (e.g. draw a contour around white matter or tumor), extract body parts, extract portions of body parts, select tissue layers to focus on certain anatomy in a scan (e.g. only show bone, no soft tissue), zoom, translate, rotate, and/or re-position the virtual anatomical image to modify it and/or to examine it more closely. Some embodiments can categorize and/or segment different tissue types using information gathered from medical imaging results. For example, in various instances, the similar value of the grey scale of an image indicates similar tissue type. Accordingly, areas comprising the same tissue type can be identified. In some configurations, for example, k-means clustering can be used to identify, highlight and/or segment certain tissues or tissue sharing a common feature. For example, some embodiments allow a user to "turn off" (e.g., turn dark) a selected section of tissue. For example, if only blood and blood vessel want to be shown, other tissue and sections need not be displayed. Virtual image manipulation such as this may be especially beneficial, for example, in the case of spinal surgery where the image manipulation described herein may enable a user to accurately plan the incisions and trajectories of their instruments. As another example, a user may rotate the virtual image of the heart to better see an occluded artery. The user may magnify or move the image of the heart to his or her liking. Using MRI, CT, PET imaging modalities, in some embodiments, the display system may be configured to display the locations of abnormalities (e.g., the locations of occluded arteries) in the virtual 3D image for quick, efficient, and minimally-invasive visual reference, which may advantageously lead to faster procedures and a more informed doctor. Using 3D visual manipulation may be also beneficial, for example, for stent placement, locating a tumor for removal, taking biopsy samples, among other medical uses.

In some embodiments, the 3D visual manipulation feature may be used for implant planning by manipulating a portion of juxtaposed 3D and 2D images on a screen (e.g., side-by-side, superimposed, etc.). Accurate 2D and 3D images may advantageously allow the user to position implants more safely, especially in critical areas like the spine. As another example, the 3D visual manipulation feature may allow for more accurate orthopedic implant placement and planning. For example, 3D rendering and/or manipulation of image sets based on Digital Imaging and Communications in Medicine (DICOM), a standard of medical imaging, of a patient's hip/knee/leg may be referenced to better plan the leg length, offset, and version of the acetabular cup to be used to more accurately select the artificial components to be implanted in the hip in comparison to planning with a 2D CT image. The display system advantageously may allow users to see their pre-operative plan in 3D, keeping them better informed. The foregoing may also be applied to implant removal planning, as well as to other medical procedures. In some embodiments, the display system may include a user interface. For example, in some embodiments, the user interface can be used much like a menu to adjust the implant size, position, inclination, version, rotation, translation, placement strategy, and/or the like.

As discussed above, the display system may be used to diagnose medical conditions, anatomical and physiological movements, and/or interactions inside the body, including blood circulation in real-time (and/or via post-processing). As an example, diabetes complications often include nerve damage and poor blood circulation. These problems may make the feet vulnerable to skin ulcers that may worsen quickly and be hard to treat. A non-healing ulcer may require amputation of a toe, foot, or part of the leg. Careful foot care is generally therefore important to prevent ulcers. The display systems described herein can include a sensor or imaging system (e.g., ultrasound imaging) and processing electronics to evaluate the data may be configured to monitor circulation and enable users to timely identify poor circulation before or after an ulcer forms. For example, the display system can rely on MRI scans for blood flow concentrations and/or ultrasound for real-time flow of blood in a patient. In some embodiments, early detection of poor circulation using the display system may advantageously allow doctors to prescribe circulation-enhancing supplements before medical circulation-related complications develop (e.g., from diabetes or smoking).

Image Slicing

As described above, the display system may be configured to provide images as one or more depth planes so that users may navigate through slices of various patient scan modalities (e.g., MRI, CT, PET, etc.) and see each slice clearly. In some embodiments, the display system may be configured with and/or may be configured to use depth planes that allow the user to properly focus on the image thereby reducing fatigue and/or eyestrain. The presentation of different image content associated with different depths as if originating from different depth planes can promote proper accommodation and vergence thereby reducing eyestrain and/or fatigue. An additional benefit is that the user may possibly be able to manipulate an image by going "slice-by-slice" through each slice or at least a plurality of slices of the patient scan. The user may, for example, viewing separate slices at different times, possibly at different depth planes and/or slice angles. The user may view the slice in sequence or out of sequence. In some embodiments, more than one patient scan can be presented in the display system. The user may be able to navigate and/or toggle through various slices of one or more patient scans. The user may, in some cases, be presented with the 3D image that permits the user to scroll through 2D slices of the 3D image. This feature may, for example, allow for more accurate implant positioning. This "slice-by-slice" approach may be beneficial, for example, in viewing tumors across multiple tissue layers or for viewing various brain abnormalities, although any suitable use is appreciated.

Image Display Above the Patient

In some embodiments, the display system may display a 2D and/or 3D image above a patient's anatomy. See for example, FIG. 12B. In some embodiments, the 2D and/or 3D virtual image may be grounded to the world (e.g., the environment, to the immobile patient, etc.). To display the virtual image above the appropriate anatomy site of the patient, one or more outward-facing cameras on the display system may be configured to image and processing electronics may be configured with image processing to recognize various aspects of a patient's anatomy. For example, the display system may be able to identify various systems (e.g., circulatory system, limbic system, nervous system), organs (e.g., liver, stomach, heart, lungs, brain, gallbladder, pancreas, appendix, kidneys, etc.), extremities (e.g., arms, legs), tissues (e.g., bone, muscle, fat, etc.) or any other suitable anatomical feature or attribute with or without the aid of one or more of the imaging modalities described above (e.g., CT, PET, MRI, etc.). In some embodiments, the display system may be configured to know where each body part, organ, etc. is located to place the virtual image accurately according to the anatomy, environment, etc. For example, in some embodiments, the display system may include edge detection (e.g., integrated with one or more of the one or more cameras or imaging devices and/or processing electronics) to correctly position the virtual image relative to the patient (e.g., above the organ or relevant anatomical structure). In some embodiments, one or more users may view the virtual image relative to their perspective of the virtual image (e.g., from where each user is standing/viewing the image).

In some embodiments, the 2D and/or 3D image may be manipulated as described above. For example, surgeons may be able to manipulate the image to provide better visualization during surgery (or any other procedure). As some examples, the image may be configured to allow doctors to rotate the virtual image to better see an occlusion in an artery or damage to a spinal disc prior to surgery and/or during surgery.

In some embodiments, as described above, users may manipulate the 2D and/or 3D image without having to look at a separate computer screen, and without having to use hand gestures or a remote control. This can be particularly beneficial for surgeons where sterility during a procedure is crucial. For example, in some embodiments, the display system may be configured to allow users to adjust various features of the virtual image using their eyes or oral (e.g., voice) communication, including for example, the lighting on the virtual image, the contrast between the virtual image and the environment, the orientation of the image, the size of the image, or any other suitable feature. In some embodiments, one or more users may simultaneously view and manipulate the same image. In some cases, if one user manipulated the virtual image, the other viewers can see that virtual image as manipulated. In some cases, however, different user can independently manipulate the virtual image without affecting the other viewer's view of the virtual image.

In some embodiments, for example, images of soft tissue organs such as the breasts, the prostate, and the heart may be viewed and manipulated above the patient to help the user visualize what the procedure might entail and/or provide important information such as spatial relationships with other organs, tumor location, correct anatomy, etc. As another example, one or more images of broken or fractured vertebrae may be viewed and manipulated above the patient's anatomy to allow for more accurate measurements and diagnoses relating to spinal injuries, although any type of bone breakage/fracture is appreciated. Measurement, for example of distances and angle may be obtained. Advantageously, the display system may be configured to allow users to theoretically realign broken bones and superimpose the image over the actual anatomy to simulate the procedure and/or the expected surgical outcome. For example, spinal surgeons may be able to superimpose their targeted outcome over their patient's broken vertebra before beginning the surgery or any time thereafter. As another example, patients considering plastic surgery could have the augmentation superimposed over their actual anatomy as a means of "trying-on" their new look. In some embodiments, the virtual content may also comprise of a menu in which the user can manipulate the virtual content (e.g. size, position, shape, etc.) using the menu. In some embodiments, this feature may allow the user to see which vertebra they may operate on. For broken or fractured bones, using images from the suitable imaging modality, such as for example, X-rays, MRI, etc., and suitable image processing via processing electronics, the display system may detect the bone and then detect abnormalities and obtain measurements from the image. The display system may also be configured to project a simulated correct bone alignment (with pre-operative planning) over the patient's anatomy to assist the user in repairing the break. As another example, the display system may be used to assist users with vertebroplasty, a pain-reducing procedure for fractured vertebra in which bone cement is injected into one or more vertebra. The imaging of the display system may advantageously allow for more precise cement placement in the vertebra.

Displaying augmented and/or virtual content over the patient may be displayed as a combination of images (e.g., a combination of patient scans). For example, some embodiments may be configured to align a medical image with different diagnostic modality (e.g., image-to-image registration) to provide combined information to the user. In some instances, one or more images from MRI, CT, PET, single-photon emission computed tomography (SPECT), magnetic resonance angiography (MRA), computed tomography angiography (CTA), etc. may be combined (e.g., superimposed). As one example, MRI and PET images may display anatomical information and metabolic activity overlaid in one image. Such combined information can assist the user in diagnosing abnormalities more quickly and accurately. Various embodiments can include algorithms to mesh the multiple imaging modalities into a combined virtual visual image for the user to view and in some instances, manipulate. In some embodiments, the combined images can also be aligned with the patient's actual anatomy as described herein.

In some embodiments, the display system may ergonomically project the virtual image in the user's field of view of the patient so that the user does not have to look back and forth between a screen and the surgical site (e.g., for image navigation or for taking patient landmarks to register the patient's actual anatomy). For example, the image may be projected right above the patient anatomy of the patient and increase ease and efficiency of the procedure, such as shown in FIG. 12B. This can allow a caregiver (e.g., doctor) to direct more attention and time to the patient. In other embodiments, the image may be projected on the patient anatomy (e.g., registration points display on the actual patient anatomy) so the doctor knows where to probe/ register the anatomy.

In some embodiments, the display system may be configured to assist users with manual total knee replacement, which may include, for example, 5 cuts on the femur and 1 cut on the tibia. For the 5 cuts on the femur, the last 4 cuts may be based on the first cut. For this reason, position the cutting block accurately for the first cut can be important. The display system may advantageously provide real-time positioning assistance to position the manual resection block according to the pre-operative plan. Various embodiments may be used to assist in positioning virtual content since the display system may be configured to recognize the anatomy of the knee. Some embodiments may also be used for positioning of the cutting blocks. For example, in some embodiments, the cutting guidelines may be grounded to the world (e.g., the knee) so that the position of the user relative to the knee is irrelevant. In some embodiments, the virtual content may be projected from the point of reference (e.g., the knee). Edge detection or other image processing technique may be used, for example, such that the display system may recognize the edge of the patient's bone for proper placement. Another example of edge detection can be applied to the device recognizing the edge of surgical tool tip (e.g. scalpel, drill tip, etc.).

Some embodiments may advantageously display the virtual content above the patient's anatomy such as the related anatomical feature (e.g., by recognizing objects/anatomy), and ground the incision guidelines to the patient, not the user. In some embodiments, incision guidelines may be projected over the patient for more precise incision, which may reduce recovery time. For example, in some embodiments, virtual image content may be displayed above or superimposed on one or more parts of the patient's anatomy indicating where to cut and may include labels (e.g. 5 mm port, 5 mm assistant port, 10 mm camera port, etc.) for what the different cuts are. Other uses are also possible.

Real-Time Virtual Imaging and Display

Various embodiments of the display system can provide the user with real-time, 3D images of real objects. As discussed above, the signals for the images may be received outward looking video camera and/or from instruments or sensors that utilize electromagnetic waves or other energy sources, such as sound waves, to probe the target such as portions of the human body. In some embodiments, the display system may present images of an object based on supersonic or ultrasound information. See, e.g., FIG. 10B. An ultrasonic wave source that generates ultrasonic waves may be disposed to direct those ultrasonic waves onto an object to be imaged. A transducer sensitive to ultrasonic waves may detect and measure the received ultrasonic waves after being directed to the object. This object may be a patient and these ultrasonic waves may be employed to image the anatomy and/or physiology of the human body. For example, in some embodiments, the display device can sense the flow of blood through a person's blood vessels using ultrasound technology. The display device may therefore be configured to image the blood flow of a person. Consequently, the display may potentially allow a user to see and/or measure the pulse of an individual without physically contacting the person. As discussed above, the display device may be configured to present an image that appears to be 3D to the user. This image may be a real-time image in some cases and/or may appear overlaid on the patient. Additionally, as discussed above, the user can potentially manipulate the image, for example, to select a desired view of the rendered image.

As describe above, the display device can combine data from multiple images and/or scans (e.g., X-ray images, CT, PET, or MRI scans, etc.) of an object to render a 3D image of the object. In some cases, the 3D images are created from data obtained from multiple images in the same imaging modality or from the same type of scan (e.g., ultrasound or X-ray). In some instances, information from multiple modalities (e.g., ultrasound plus MRI scan data) can be combined to render a 3D image. As discussed above, the display device may be configured to detect the type of object or objects within the field of view of the user. In some embodiments, the display device can determine an image modality that would be suitable to a user's desires or needs. For example, when imaging a cervix during a medical procedure, the display device may be configured to automatically detect that providing a 3D, real time image to the user is the best modality for use during the surgery. The display system may also be configured to select the modality, such as whether to use ultrasound, X-ray, MRI, etc. to image the particular anatomical feature(s), in the field of view (e.g., central view of view) of the user. The image modality can, for certain designs, be determined automatically and/or in advance. This image may be a real-time image in some cases. In some embodiments, the display device may construct a 3D rendering of an object based on a previous imaging modality (e.g., MRI) and can update in real time the 3D rendering based on new data (e.g., ultrasound). X-rays can also be used in real time such as for example in angioplasty and stent placement.

As described above, the display device may be configured to automatically determine which body part a particular image of an object represents. For example, the display device can be capable of discerning between different organs, bones, or other anatomical parts. As another example, the display device can be capable of discerning between cancer tissue and healthy tissue. In some embodiments, the display device can discern boundaries of neighboring tissues based on an intrinsic quality (e.g., tissue density, absorption, attenuation) and the resultant affect while imaging (e.g., grayscale of an image). As another example, the display device can be capable of discerning anomalies in the body such as broken bone, a tumor, and/or polyp.

In some embodiments, the display device can detect and measure an amount of material that has been added or removed from an object. For example, in some embodiments, the display device can automatically ascertain the amount of cancer tissue that has been removed during a surgery (e.g., based on the angle and/or trajectory of the cutting tool) and can determine how much cancerous tissue is left to be removed. In certain embodiments, the display device can provide feedback (e.g., visual, audio, etc.) to the user if a procedure is incomplete (e.g., if not all cancer tissue has been removed).

The display device can be configured to work in tandem with various external devices. In some embodiments, the display device can receive data from an external device and display it to the user. For example, in some embodiments, a doctor may use an endoscope to view a nasal cavity for cancerous polyps. In this case, the display device can be configured to receive the imaging data from the endoscope and render endoscope images for the user on the display and/or track the position of the endoscope (e.g., using a 6 DOF device attached to the endoscope). In some embodiments, the image can be projected in a convenient location on the display so as to reduce or minimize difficulty in seeing the overlaid image while performing other tasks (e.g., performing a medical operation). The display device could render real-time images and/or provide updates to the doctor as a procedure to remove a nasal polyp progresses. In another example, certain embodiments of the display device can image a portion of a patient's vascular system. Such imagining could be displayed in real-time as a superposition over a user's view of the patient through the display device. This real-time image may be juxtaposed with respect to a surgical site (e.g., adjacent to) or a relevant portion of the body of the patient. This could aid the user, for example, in performing a procedure (e.g., delivery of a dose of drugs, surgical navigation, etc.). In a similar example, an ultrasound image of a fetus above the abdomen or midsection of the pregnant mother can be projected into the eye by the display of the medical practitioner to provide a real-time, 3D image of the ultrasound. As discussed above, in some embodiments, the user can manipulate the overlaid image with, for example, a command using an eye movement, facial expression, finger movement, or other signal as described herein. In some cases, the user can manipulate the object by rotating about or translating along any axis (or a combination thereof). Thus, in some embodiments, the user can manipulate images using six degrees of freedom.

Sharing Virtual Content

In certain embodiments, information received by a display device can be transmitted to other users or non-users of such devices. In some embodiments, the display device can render an image of an object (e.g., using outward-facing cameras on the display device or other sensor or imaging systems) and provide this image to multiple users simultaneously. In some cases, the image may be a 3D image, for example, compiled from 2D scans like those gathered from x-ray, MRI, CT technology. In some embodiments, each display device can present the images of the same object to each user as if each user is viewing the object from different positions relative to the object. For example, a group of doctors can be viewing a virtual image of a patient scan, anatomy, etc. in each of their devices from the perspective from which they are standing because the image would be grounded to the earth via pixel-stick. This would assist with diagnosis by having multiple opinions, educational/training assistance, expert advice, surgical planning, etc. In some configurations, a user can select a virtual location relative to the object from which to view the object. For example, a user could view a surgery as if directly behind or near the surgeon performing the operation, even if the user is not present for the surgery. Moreover, in such embodiments, the virtual location of the users could be changed at the direction of the user so as to achieve a different viewing angle. In various embodiments, therefore, head mounted displays may be in communication with each other or connected to a network that may or may not include other components. Images obtained from a user's display device as well as other information could be transmitted electronically to non-users as well. For example, one or more cameras mounted on one or more head mounted displays can image the environment (e.g., operating room) and gather information on the location of objects (operating table, instruments, patient, surrounding people, etc.) within the environment (possibly using a range finder or distance measurement system) so as to build a database of objects and locations in an environment. With known position, for example of the head mounted display device (e.g., using GPS) and the distance of the object to the head mounted display, the location of the object in 3D space (e.g., x, y, z, coordinates) can be known and stored in a database. Different head mounted devices can send out a map of sparse points to build a 3D map of the environment. The database grows the more time is spent in the environment. In certain cases, edge detection can determine objects, e.g., operating table, instrument tray, equipment or patient.

In various instances, the display device can set a reference point in the real world from which to assign and/or calculate spatial relationships. For example, the display device may be able to identify a point of interest in a room (e.g., chest or knee of patient) and determine measurements in relation to the point of interest, in certain configurations. Image content associated with that object (e.g., a 3D graphic rendition of knee implant) can be presented knowing that object's position relative to the user and other object also in the room. Such image content can be fixed with respect to the reference point or object. For example, the 3D graphic of the knee implant can be fixed above the knee even if the knee is moved. Also, different viewer wearing such head mounted displays, may also see the image content (e.g., 3D graphic) fixed with respect to the reference point (e.g., knee) but may see the image content, which may be 3D image content, from a different perspective because the different viewer is located at a different location and/or oriented differently. See also FIG. 12B and graphic of heart disposed above patient, wherein the graphic of the heart could be fixed above a specific location above the patient and move with the patient if the patient moves, in some cases. As discussed above, to assembly the database of locations some embodiments of the display device can emit signals (e.g., as in sparse point mapping) to obtain data on spatial positions and/or movements in the real world. Effectively, the head mounted display device(s) can image objects in an environment and record their location in a database and a location in that database of locations (e.g., the patient's knee or chest) can used as the frame of reference from which the location and orientation of one or more displayed images are determined based on their selected perspective/location with respect to that frame of reference. Different users with different locations and hence perspectives with respect to the object may also see different image content or views thereof depending on their location.

Similarly, in some embodiments, multiple users could manipulate a common virtual object. For example, in some embodiments, a user viewing a surgery with other virtual users could indicate a particular region of interest (e.g., by highlighting, enlarging) of an object. Such an indication could be simultaneously and/or automatically displayed on each display of other users. In this way, one user could advantageously communicate about precise objects through visual signals with other users. In some embodiments, a user may manipulate a displayed object, such as by rotation or translation. Such manipulation could be displayed on other users' displays, thus easing the way in which two or more users discuss an imaged object that appears to be 3D. Similarly, the display device can be configured to allow users to communicate using other mediums, such as by voice chat, text, or otherwise. In some embodiments, the display device could be configured to detect at which step a user is when performing a procedure (e.g., surgery). For example, certain embodiments could detect which step in a surgery would come next for a doctor and could display the upcoming step to other users in the room. Similarly, the display device could present content (e.g., video, audio, images, text, etc.) to aid the doctor through a particular step of the surgery.

Interventional Radiology

In certain embodiments, the display device can aid medical personnel in viewing and interpreting interventional radiology images. For example, in some embodiments, the device can be configured to render an image on the display before or during a procedure using one or more imaging modalities (e.g., CT, x-rays, MRI, etc.). Using a variety of methods (e.g., machine learning, manual algorithms), in some embodiments, the display device can be trained to properly identify scans or images of normal or healthy patient's, tissue, organs, anatomical structures, etc. as compared to unhealthy or anomalous scan or images. Accordingly, in various embodiments, the display device can automatically determine whether a patient image (e.g., scan) is anomalous or not and potentially determine the medical and/or pathological significance of the image and draw conclusions or diagnoses therefrom. For example, in certain embodiments, the device can recognize fractured bones, anomalies in brain scans such as a tumor, and extra teeth based on x-rays, or the location of a tumor growth based on an image.

In some embodiments, the display device can detect edges of body parts on the surface (e.g., locations of hairs, the edge of knee, etc.) and/or under the skin (e.g., bone, organs, or blood vessels). The display device may be able to render an image of a body part on a user's display while performing a surgical operation. A user may be able to place virtual markers (e.g., fiducial markers) over an image of an object, for example, to indicate which portions should receive radiation treatment, the location for a surgical cut, etc. A user (e.g., physician) may determine the location of the virtual markers, but certain embodiments of the display system can identify and/or place the fiducial markers. Processing electronics associated with the head mounted display device can use pattern recognition to identify the location of structures and where to place fiducial markers. As a further example, the display device can render on the display a 3D image of a blockage in a blood vessel after a contrasting agent has been injected into the patient and scanned with MRI or x-ray. As discussed above, the display system display of multiple depths (e.g., as different slices) associated with different portions of the blockage. Presentation of the 3D image as slices can assist a physician in making accurate pre-operative decisions. Such images are also useful after surgery to evaluate the surgery and progress of the patient thereafter and may be used to make subsequent healthcare decisions.

Accordingly, the display device can aid users (e.g., physicians, nurses, technicians, students) before, during, and/or after various medical procedures by rendering 3D images of an object. In some cases, such images may be juxtaposed with respect to the patient, for example, adjacent to or superimposed above, a surgical or treatment site, or location near where diagnostic testing is being conducted. In some embodiments, this rendering can be based on information from multiple types of scans (e.g., ultrasound plus MRI) and be provided in real-time during a procedure. One application is for arteriovenous malformations or blood vessel abnormalities (e.g., in the brain). Another application is for visualizing a balloon angioplasty, where a balloon is inserted and inflated in a blood vessel in order to unblock a narrowing/clog of an artery or blood vessel. Another application is for biliary draining and stenting, in which a stent is inserted to open blocked ducts and allow bile to drain from the liver. Another example is the case of internal bleeding, in which case the device could be configured to locate an area of internal bleeding and/or aid a user in inserting a clotting substance such as a gel, foam, or coil. Another application is for a chemoembolization, in which a cancer fighting agent is directly delivered to the site of the cancer tumor. The display device could also be useful in the insertion (or virtual practicing of insertion) of a gastronomy tube in the proper place in a patient.

The display device could also aid users in performing or preparing for other procedures. One such application is maintaining hemodialysis access, where angioplasty or thrombolysis is used to open blocked grafts during kidney failure. Another application is radiofrequency ablation, where radiation energy is used to cook and kill cancerous tumors. Another application is the placement of stents, where a catheter is used to position a stent to open a clogged blood vessel or other passageway. Another application is Transjugular Intrahepatic Portosystemic Shunt (TIPS), a lifesaving procedure in which a doctor places an artificial channel within the liver between the inflow portal vein and outflow haptic vein. As a further example, the device could help a user with the uterine fibroid embolization, in which the doctor cuts off blood supply to the fibroid, thus causing the fibroid to shrink and die. In this procedure, a doctor places a catheter in the femoral artery, injects contrast material into the catheter, and guides a catheter through the artery to find the arteries supplying blood to the fibroid. Likewise, the device can advantageously provide views of 3D images for improved visualization, in the preparation of, during, or after medical procedures.

Computer Vision and Object Detection

An object can be detected using a variety of techniques. For example, an object can be detected using computer vision techniques. For example, the display device can analyze the images acquired by the outward-facing imaging system to perform scene reconstruction, event detection, video tracking, object recognition, object pose estimation, learning, indexing, motion estimation, or image restoration, etc. One or more computer vision algorithms may be used to perform these tasks. Some limiting examples of computer vision algorithms include: Scale-invariant feature transform (SIFT), speeded up robust features (SURF), oriented FAST and rotated BRIEF (ORB), binary robust invariant scalable keypoints (BRISK), fast retina keypoint (FREAK), Viola-Jones algorithm, Eigenfaces approach, Lucas-Kanade algorithm, Horn-Schunk algorithm, Mean-shift algorithm, visual simultaneous location and mapping (vSLAM) techniques, a sequential Bayesian estimator (e.g., Kalman filter, extended Kalman filter, etc.), bundle adjustment, Adaptive thresholding (and other thresholding techniques), Iterative Closest Point (ICP), Semi Global Matching (SGM), Semi Global Block Matching (SGBM), Feature Point Histograms, various machine learning algorithms (such as e.g., support vector machine, k-nearest neighbors algorithm, Naive Bayes, neural network (including convolutional or deep neural networks), or other supervised/unsupervised models, etc.), and so forth.

One or more of these computer vision techniques can also be used together with data acquired from other environmental sensors (such as, e.g., microphone, temperature sensor, light sensor, timing device, physical contact sensor, etc.) to detect the presence of the object.

The object may be detected based on one or more criteria. These criteria may be defined by a user (or another person). For example, the user may set a heart monitor in the user's environment (e.g., in the operating room) as a possible object of interest. The user may define the criteria as the signal of the heart monitor being less than a certain value or when the heart monitor beeps. Therefore, when the device detects the heart monitor meeting the criteria using a computer vision algorithm and/or using data received from one or more environmental sensors, the device can then signal the presence of the heart monitor (e.g., an icon as an alert) and/or automatically provide an enhanced view of the heart monitor (e.g., a magnified image of the heart monitor).

Figure 13A:
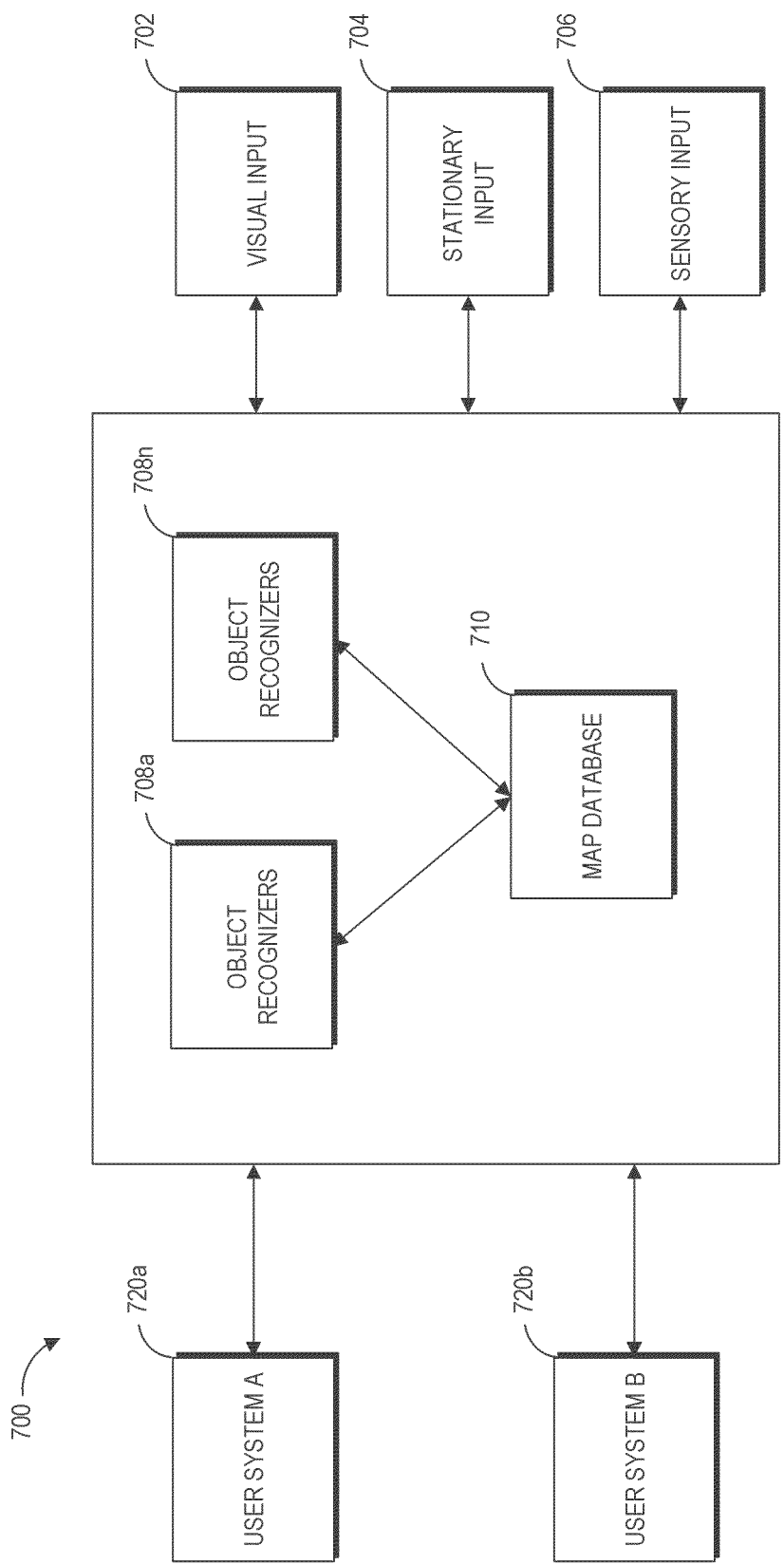
FIG. 13A is a block diagram of an example of a wearable system.

FIG. 13A is a block diagram of an example of a mixed reality ("MR") environment 700. The MR environment 700 may be configured to receive input (e.g., visual input 702 from the user's wearable system, stationary input 704 such as room cameras, sensory input 706 from various sensors, gestures, totems, eye tracking, user input from the user input device 504, etc.) from one or more user wearable systems (e.g., wearable system 80 or display system 62) or stationary room systems (e.g., room cameras, etc.). The wearable systems can use various sensors (e.g., accelerometers, gyroscopes, temperature sensors, movement sensors, depth sensors, GPS sensors, inward-facing imaging system, outward-facing imaging system, etc.) to determine the location and various other attributes of the environment of the user. This information may further be supplemented with information from stationary cameras in the room that may provide images or various cues from a different point of view. The image data acquired by the cameras (such as the room cameras and/or the cameras of the outward-facing imaging system) may be reduced to a set of mapping points.

One or more object recognizers 708 can crawl through the received data (e.g., the collection of points) and recognize or map points, tag images, attach semantic information to objects with the help of a map database 710. The map database 710 may comprise various points collected over time and their corresponding objects. The various devices and the map database can be connected to each other through a network (e.g., LAN, WAN, etc.) to access the cloud.

Based on this information and collection of points in the map database, the object recognizers 708a to 708n may recognize objects and supplement objects with semantic information to give life to the objects. For example, if the object recognizer recognizes a set of points to be a door, the system may attach some semantic information (e.g., the door has a hinge and has a 90 degree movement about the hinge). If the object recognizer recognizes a set of points to be a mirror, the system may attach semantic information that the mirror has a reflective surface that can reflect images of objects in the room. Over time the map database grows as the system (which may reside locally or may be accessible through a wireless network) accumulates more data from the world. Once the objects are recognized, the information may be transmitted to one or more wearable systems. For example, the MR environment 700 may include information about a scene in California. The environment 700 may be transmitted to one or more users in New York. Based on data received from an FOV camera and other inputs, the object recognizers and other software components can map the points collected from the various images, recognize objects etc., such that the scene may be accurately "passed over" to a second user, who may be in a different part of the world. The environment 700 may also use a topological map for localization purposes.

Figure 13B:
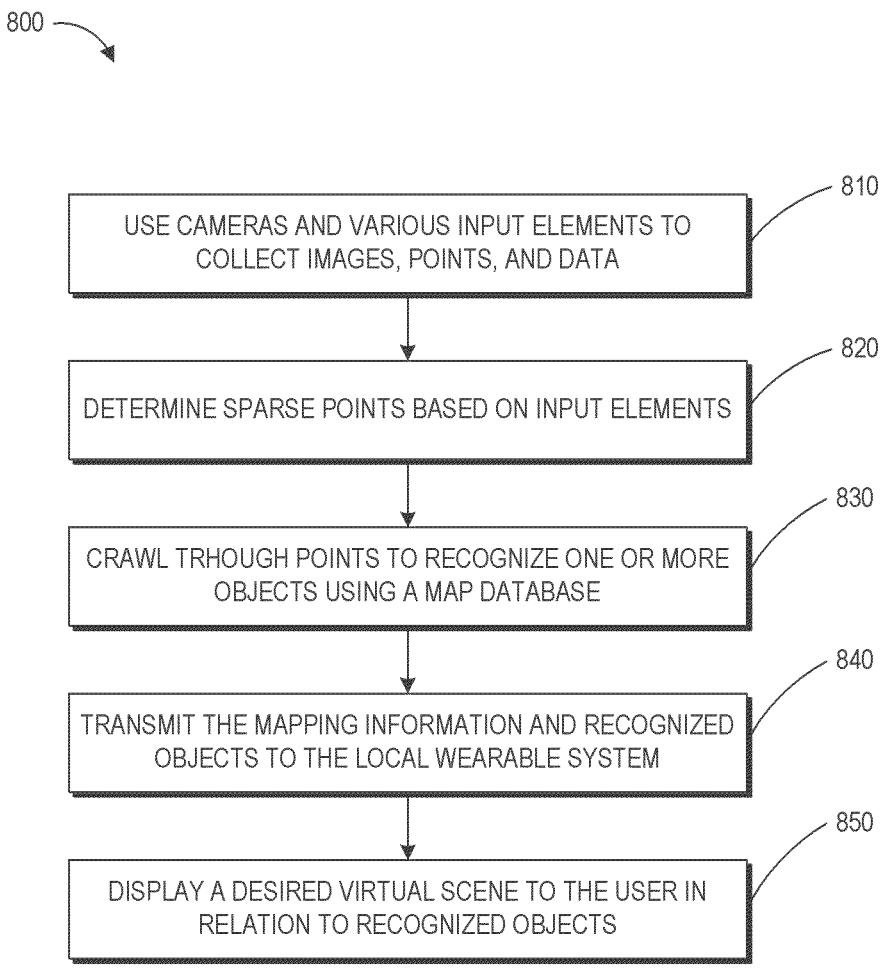
FIG. 13B is a process flow diagram of an example of a method of rendering virtual content in relation to recognized objects.

FIG. 13B is a process flow diagram of an example of a method 800 of rendering virtual content in relation to recognized objects. The method 800 describes how a virtual scene may be represented to a user of the wearable system. The user may be geographically remote from the scene. For example, the user may be New York, but may want to view a scene that is presently going on in California, or may want to go on a walk with a friend who resides in California.

At block 810, the AR system may receive input from the user and other users regarding the environment of the user. This may be achieved through various input devices, and knowledge already possessed in the map database. The user's FOV camera, sensors, GPS, eye tracking, etc., convey information to the system at block 810. The system may determine sparse points based on this information at block 820. The sparse points may be used in determining pose data (e.g., head pose, eye pose, body pose, or hand gestures) that can be used in displaying and understanding the orientation and position of various objects in the user's surroundings. The object recognizers 708a-708n may crawl through these collected points and recognize one or more objects using a map database at block 830. This information may then be conveyed to the user's individual wearable system at block 840, and the desired virtual scene may be accordingly displayed to the user at block 850. For example, the desired virtual scene (e.g., user in CA) may be displayed at the appropriate orientation, position, etc., in relation to the various objects and other surroundings of the user in New York.

Figure 13C:
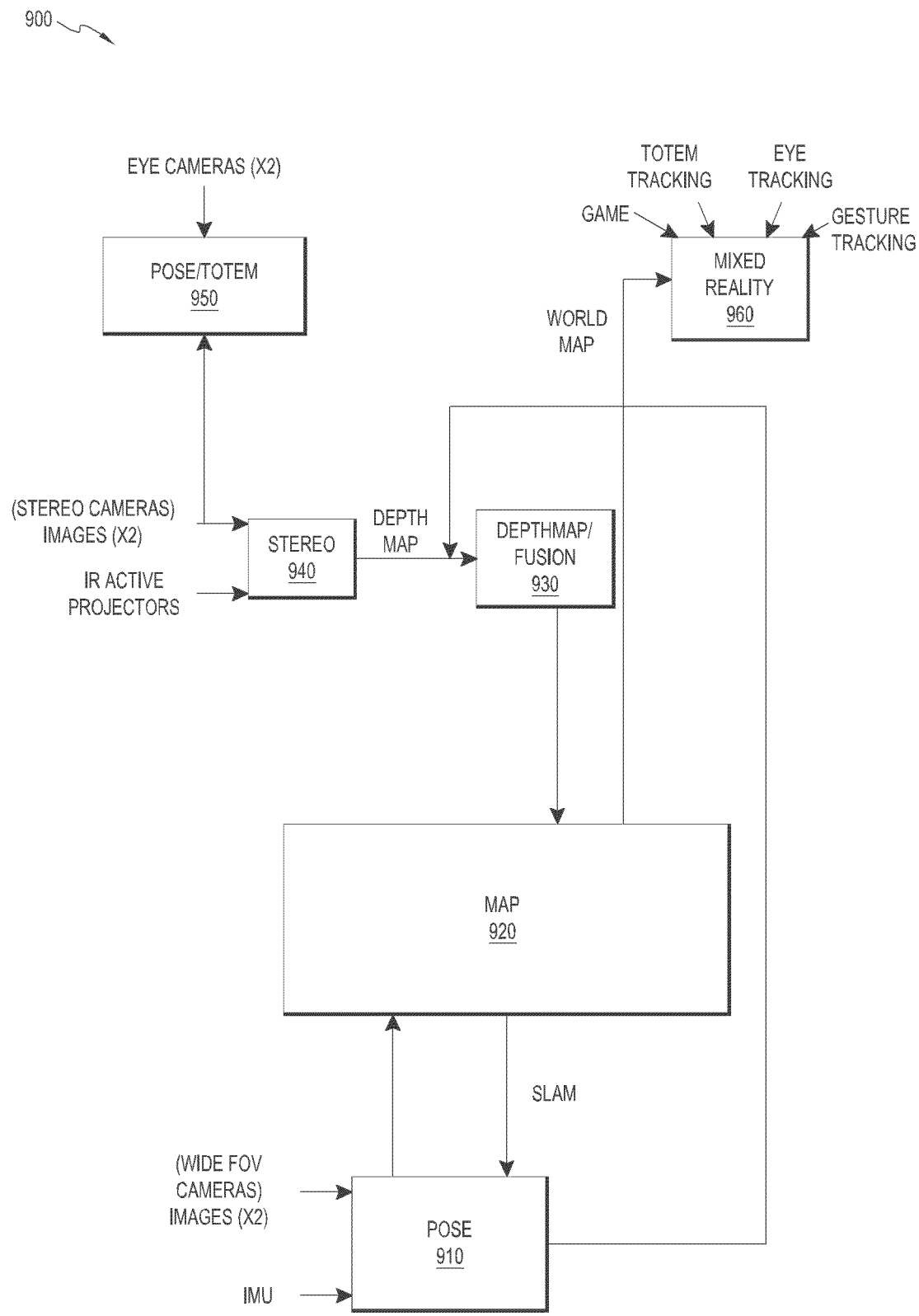
FIG. 13C is a block diagram of another example of a wearable system.

FIG. 13C is a block diagram of another example of a wearable system. In this example, the wearable system 900 comprises a map, which may include map data for the world. The map may partly reside locally on the wearable system, and may partly reside at networked storage locations accessible by wired or wireless network (e.g., in a cloud system). A pose process 910 may be executed on the wearable computing architecture (e.g., processing module 260 or controller 460) and utilize data from the map to determine position and orientation of the wearable computing hardware or user. Pose data may be computed from data collected on the fly as the user is experiencing the system and operating in the world. The data may comprise images, data from sensors (such as inertial measurement units, which generally comprise accelerometer and gyroscope components) and surface information pertinent to objects in the real or virtual environment.

A sparse point representation may be the output of a simultaneous localization and mapping (SLAM or V-SLAM, referring to a configuration wherein the input is images/visual only) process. The system can be configured to not only find out where in the world the various components are, but what the world is made of. Pose may be a building block that achieves many goals, including populating the map and using the data from the map.

Sparse point positions may be supplemented to produce a multifocal AR, VR, or MR experience. Dense representations, generally referring to depth map information, may be utilized to fill this gap at least in part. Such information may be computed from a process referred to as stereo 940, wherein depth information is determined using a technique such as triangulation or time-of-flight sensing. Image information and active patterns (such as infrared patterns created using active projectors) may serve as input to the stereo process 940. A significant amount of depth map information may be fused together, and some of this may be summarized with a surface representation. For example, mathematically definable surfaces may be efficient (e.g., relative to a large point cloud) and digestible inputs to other processing devices like game engines. Thus, the output of the stereo process (e.g., a depth map) 940 may be combined in the fusion process 930. Pose may be an input to this fusion process 930 as well, and the output of fusion 930 becomes an input to populating the map process 920. Sub-surfaces may connect with each other, such as in topographical mapping, to form larger surfaces, and the map becomes a large hybrid of points and surfaces.

To resolve various aspects in a mixed reality process 960, various inputs may be utilized. For example, in the embodiment depicted in FIG. 13C, Game parameters may be inputs to determine that the user of the system is performing a surgery with one or more virtual doctors at various locations around the room. The virtual doctors may be reacting to various conditions within the room. The world map may include information regarding where such objects are relative to each other, to be another valuable input to mixed reality. Pose relative to the world becomes an input as well and plays a key role to almost any interactive system.

Controls or inputs from the user are another input to the wearable system 900. As described herein, user inputs can include visual input, gestures, totems, audio input, sensory input, etc. In order to move around or play a game, for example, the user may need to instruct the wearable system 900 regarding what he or she wants to do. Beyond just moving oneself in space, there are various forms of user controls that may be utilized. A totem (e.g. a user input device), or an object such as a surgical instrument may be held by the user and tracked by the system. The system preferably will be configured to know that the user is holding the item and understand what kind of interaction the user is having with the item (e.g., if the totem or object is a pair of surgical scissors, the system may be configured to understand location and orientation, as well as whether the user is compressing the handles which may be equipped with a sensor, such as an IMU, which may assist in determining what is going on, even when such activity is not within the field of view of any of the cameras.)

Hand gesture tracking or recognition may also provide input information. The wearable system 900 may be configured to track and interpret hand gestures for button presses, for gesturing left or right, stop, grab, hold, etc. For example, in one configuration, the user may want to flip through emails or a calendar in a non-gaming environment, or do a "fist bump" with another person or player. The wearable system 900 may be configured to leverage a minimum amount of hand gesture, which may or may not be dynamic. For example, the gestures may be simple static gestures like open hand for stop, thumbs up for ok, thumbs down for not ok; or a hand flip right, or left, or up/down for directional commands.

Eye tracking is another input (e.g., tracking where the user is looking to control the display technology to render at a specific depth or range). Vergence of the eyes may be determined using triangulation, and then using a vergence/accommodation model developed for that particular person, accommodation may be determined.

With regard to the camera systems, the example wearable system 900 shown in FIG. 13C can include three pairs of cameras: a relative wide FOV or passive SLAM pair of cameras arranged to the sides of the user's face, a different pair of cameras oriented in front of the user to handle the stereo imaging process 940 and also to capture hand gestures and totem/object tracking in front of the user's face. The FOV cameras and the pair of cameras for the stereo process 940 may be a part of the one or more outward-facing imaging sensors 34 (shown in FIG. 10A). The wearable system 900 can include eye tracking cameras (which may be one or more of the user sensors 24, 28, 30, 32 shown in FIG. 10A) oriented toward the eyes of the user in order to triangulate eye vectors and other information. The wearable system 900 may also comprise one or more textured light projectors (such as infrared (IR) projectors) to inject texture into a scene.

As another example, the object of interest may be defibrillator. The user may describe what a defibrillator looks like in general, or may describe a specific defibrillator. In some instances, the device may access an internal or external system that includes pictures of defibrillators. Therefore, when the device detects the defibrillator using a computer vision algorithm and/or using data received from one or more environmental sensors, the device can then signal the presence of the defibrillator and automatically provide an enhanced view of the defibrillator's location. In various embodiments, the device can also store in memory an image of the defibrillator and/or its location for future use.

Such algorithms and methods as well as similar ones may be applied to any of the various applications and/or embodiments described herein.

Machine Learning

A variety of machine learning algorithms can be implemented in some embodiments to detect possible objects of interest (e.g., a heart monitor having a signal below a certain value). Once trained, the machine learning algorithm can be stored by the device. Some examples of machine learning algorithms can include supervised or non-supervised machine learning algorithms, including regression algorithms (such as, for example, Ordinary Least Squares Regression), instance-based algorithms (such as, for example, Learning Vector Quantization), decision tree algorithms (such as, for example, classification and regression trees), Bayesian algorithms (such as, for example, Naive Bayes), clustering algorithms (such as, for example, k-means clustering), association rule learning algorithms (such as, for example, a-priori algorithms), artificial neural network algorithms (such as, for example, Perceptron), deep learning algorithms (such as, for example, Deep Boltzmann Machine, or deep neural network), dimensionality reduction algorithms (such as, for example, Principal Component Analysis), ensemble algorithms (such as, for example, Stacked Generalization), and/or other machine learning algorithms. In some embodiments, individual models can be customized for individual data sets. For example, the wearable device can generate or store a base model. The base model may be used as a starting point to generate additional models specific to a data type (e.g., a particular user), a data set (e.g., a set of additional images obtained), conditional situations, or other variations. In some embodiments, the wearable device can be configured to utilize a plurality of techniques to generate models for analysis of the aggregated data. Other techniques may include using pre-defined thresholds or data values.

The criteria can include a threshold condition. If the analysis of the data acquired by the environmental sensor indicates that the threshold condition is passed, the device may detect the presence of an object of interest. The threshold condition may involve a quantitative and/or qualitative measure. For example, the threshold condition can include a score or a percentage associated with the likelihood of an object of interest. The device can compare the score calculated from the environmental sensor's data with the threshold score. If the score is higher than the threshold level, the device may detect the presence of an object of interest. In other embodiments, the device can signal the presence of the object of interest if the score is lower than the threshold.

The threshold condition may also include letter grades such as "A", "B", "C", "D", and so on. Each grade may represent a severity of the situation. For example, "A" may be the most severe (e.g., a heart monitor beeping) while "D" may be least severe. When the device determines that an event in the user's environment is severe enough (as compared to the threshold condition), the device may indicate the presence of an object of interest or event and take action (e.g., provide an alert, or an enhanced view of the object of interest/event).

The threshold condition may be determined based on objects (or people) in the user's physical environment. For example, the threshold condition may be based on the patient's blood loss, the patient's heart rate, or other physiological parameters. As described with reference to FIGS. 2 and 10A-10B, the device can acquire the data of the patient from the environmental sensors (e.g., an outward-facing camera that images the surgical site) or from an external source (such as, e.g., ECG data monitored by an electrocardiograph or heart monitor).

The threshold condition may also be determined based on the real world objects in the user's environment or on the virtual objects being displayed to the user. As one example, the threshold condition may be based on the user's interaction with an object (e.g. the number of times the user glances at an object, the duration of the user watching an object, etc.). For example, the threshold condition may be determined based on eye-tracking of the user.

In some embodiments, the threshold conditions, the machine learning algorithms, or the computer vision algorithms may be specialized for a specific context. For example, in a surgical context, the computer vision algorithm may be specialized to detect certain surgical events. As another example, the device may execute facial or body recognition algorithms to detect a person (e.g., the patient or other medical personnel) in the user's environment.

Such algorithms and methods as well as similar ones may be applied to any of the various applications and/or embodiments described herein.

Altering Perception Based on User Intent

In various embodiments, a display system may advantageously alter user perception of real or virtual content based at least in part on user intent. For example, certain embodiments may allow the user to focus on a situation or task by enhancing (or de-emphasizing) image content and/or presenting image content at a different location.

Figure 14:
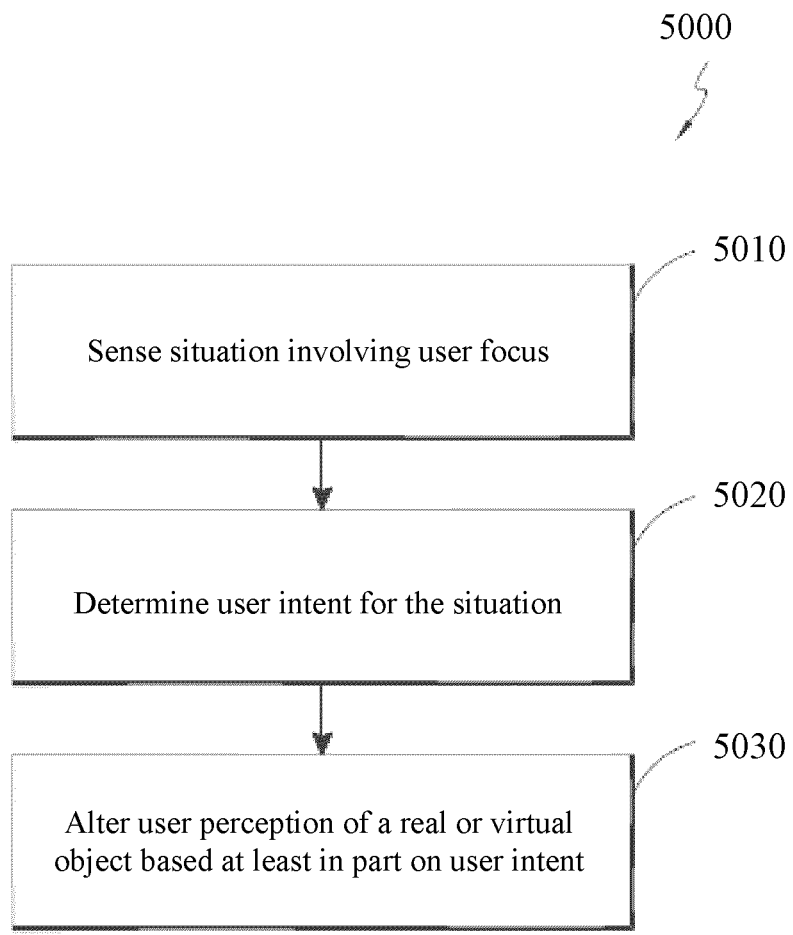
FIG. 14 is a flowchart illustrating an example of a method for altering user perception of a real or virtual object within the user's vision field based at least in part on user intent.

With reference now to FIG. 14, an example method 5000 of altering user perception of a real or virtual object based at least in part on user intent and/or perceived user intent using a display system is illustrated. Determining a perceived user intent may include, for example, imaging one or more objects in the user's environment, determining where the user's eye is viewing, and/or determining an object at which the user's eye is directed. The display system may include any of the display systems described herein, such as the display systems 80, 1000, or 2010 in FIGS. 2, 6, and 10A-10B, respectively. The display system may also include any of the features described herein. For example, as described herein, in some embodiments, a head-mounted display device can be configured to present to the user augmented reality image content using a display. The head-mounted display can be mountable on the head of a user. In certain embodiments, the display can be disposed on a frame (e.g., frame 64 in FIGS. 2 and 10A-10B), e.g., as part of eyewear.

The head-mounted display can project virtual image content to an eye of the user, while still allowing the user to see and interact with the real world. For example, the display can include one or more transparent waveguides (e.g., waveguide assembly 178 in FIG. 6 and/or waveguide stack 1200 in FIGS. 9A-9C) disposed at a location in front of the user's eyes. The display can allow a user to see through the display. The display may transmit light from the real world environment to the user's eyes such that images of the environment can be formed on the user's retina. The display can also project augmented and/or virtual image content to the user's eyes, e.g., by projecting light from a modulated light source. For example, a waveguide in the waveguide assembly may be injected with image information and can direct the image information to the eye of the user.

In some embodiments, the waveguides can be configured to send the image information with different wavefront divergence. The head-mounted display can be configured to project light to an eye of a user to display augmented reality image content to the user at different amounts of divergences as if projected from different distances from the user's eye. Accordingly, the waveguides can be associated with one or more depth planes such that the light can provide image content from different depths (e.g. on different depth planes) to aid in providing, for example, comfortable three-dimensional depth perception. In some embodiments, the waveguides may include one or more optical elements (e.g., outcoupling optical elements 282, 284, 286, 288, 290 in FIG. 6) configured to redirect the light out of a waveguide (e.g., light propagating within a waveguide) and into an eye of the user (e.g., FIG. 7). In some instances, the one or more optical elements can include one or more diffractive optical elements configured to extract light out of a waveguide. The design however need not be limited to using waveguides and/or diffractive optical elements. Nevertheless, in various embodiments, a head-mounted display can be configured to project light to an eye of the user to display augmented reality image content to the user.

The user's vision may be characterized by a vision field having a central region and a peripheral region. The peripheral region can be disposed around or about the central region. The central region and peripheral region can correspond to the central field of view and peripheral field of view, respectively, as discussed herein.

The display system or device can include and/or be coupled to one or more user sensors (e.g., user sensors 24, 28, 30, 32 in FIGS. 10A and 10B) configured to sense the user. In some embodiments, the one or more user sensors are disposed on a frame of the display system. The one or more user sensors can include one or more inward-facing and/or downward-facing sensors. The one or more user sensors can be configured to determine where a user's eye is viewing. An example of a user sensor can include an image capture device such as a camera. As described herein, such sensors can monitor the user including monitoring the user's eyes, facial features, and/or other body parts such as arms, hands, legs, etc. The one or more user sensor for example may comprise inwardly facing camera that image the eye and/or face and may provide eye tracking. Other types of eye tracking devices can also be used. The user sensors (e.g., eye tracking sensors) can be configured to assist in controlling presentation of image content on the display of the display system. Controlling presentation of image content may include, for example, sending sensory images to the processing electronics which then control the presentation of the image content, what image content is displayed, where and the characteristics of the images, e.g., contrast, sharpness, brightness, color, color balance, color saturation, opacity, etc.

The display system or device can also include and/or be coupled to one or more environmental sensors (e.g., environmental sensor 34 in FIGS. 10A and 10B) configured to sense the surroundings of the user. The one or more environmental sensors can include one or more outward-facing sensors. The one or more environmental sensors can be configured to image one or more objects in a user's environment. Examples of environmental sensors can include a depth sensor, one or more cameras such as a pair of binocular world cameras, a geolocation sensor, a proximity sensor, a GPS, etc. The one or more environmental sensors can also include a microphone (e.g., microphone 67 in FIG. 2) configured to sense sounds in the environment. As described herein, environmental sensors can detect and/or monitor objects, motions, and/or sounds in the user's environment, e.g., to help determine what the user may be directing attention to and/or interacting with. Such sensor can provide an indication of actions that the user may be undertaking and/or the user's intent to undertake an action As also described herein, some embodiments may include one or more light sensors, e.g., to determine the light condition of the environment.

Various embodiments can include and/or be coupled to one or more processors (e.g., local processing and data module 70 and/or remote processing module 72 in FIG. 2) having processing electronics in communication with the display, the one or more user sensors, and/or the one or more environmental sensors. In some embodiments, as described herein, the processing electronics can also be in communication with a network system. The processing electronics can be configured to analyse the information obtained from the one or more user and/or environmental sensors and provide instructions to the display, for example, regarding image content to display to the user. For example, the processing electronics can be configured to perform the example method 5000 shown in FIG. 14. The processing electronics can be configured to sense a situation involving increased user focus, optionally determine user intent for the situation, and alter user perception of image content (e.g., a real or virtual object) within the user's vision field based at least in part the user's increased focus and/or on the user intent. As a further example, the processing electronics can be configured to determine an object at which the eye of a user is directed. In some embodiments, the processing electronics are configured to determine more than one object (e.g., in the central field of view and/or in the peripheral field of view) at which the eye is directed. Determining an object at which the eye of the user is directed may include recognizing one or more objects in the user's environment by applying object recognition to images received from the one or more environmental sensors (e.g., outwardly facing cameras). Identifying the object at which the user's view is particularly directed may facilitate determination that the user has increased focus, and/or may assist in determining the user intents. Also or alternatively, identifying the object at which the user is looking at may allow the processing electronics to make that object easier to view, for example, by enhancing the perception of that object and/or by de-emphasizing the perception of other objects. Object recognition may include simply determining the presence of an object and/or isolating the object from the surrounding features. Object recognition may alternatively or additionally include associated with the object some meaning such as recognition of what that object is and/or characteristics or functions of the object. For example, object recognition may simply determine that there is some object in the foreground that is separate from the background. In another example, however, object recognition may additionally include determining what the object is, such as that this object is a persons face, a heart monitor, a steering wheel and possibly associating characteristics and/or meaning with that object. A more sophisticated level of analysis may be to couple determination of a plurality of objects to develop a more advance understanding of the environment. For example, is the processing electronics recognizes a scalpel, a heart rate monitor, and a person prone on a table, the conclusion might be that the user is in an operating room. Combinations of other objects recognized and/or inputs, such as steering wheel in front and center of the user, a dashboard, a windshield, and/or a hood of a car just beyond the windshield as well as possibly other input signals such as receiving a blue tooth signal may indicate that the user is in the driver's seat of a vehicle possibly driving or ready to start a motor vehicle.

Accordingly, at block 5010, the processing electronics can be configured to optionally sense a situation involving user focus. As discussed above, sensing a situation involving user focus can include detecting one or more objects, e.g., from the information provided by the one or more user and/or environmental sensors. Sensing a situation involving user focus can include determining (at least generally) an object at which the user's eye is directed. The processing electronics may be configured to detect objects using any of the computer vision and object detection techniques, such as those described herein (see, e.g, above). Sensing a situation involving user focus can also include detecting one or more motions or sounds, e.g., from the information provided by the one or more user and/or environmental sensors. Sensing a situation involving user focus can also include detecting one or more other types of signals such as radio or RF signals (e.g., a Bluetooth signal emitted by a car). Radio signals emitted in different rooms can also inform that a user is in a particular room and may provide an indication of what action the user may be undertaking. Sensing a situation involving user focus can further include determining whether the one or more detected objects, motions, and/or sounds are associated with a particular situation, such as an action or a situation involving user focus. Alternatively or additionally, sensing a situation involving user focus may include providing various situations involving user focus that are of interest and searching, e.g., in the information provided by the one or more user and/or environmental sensors, for certain objects, motions, and/or sounds associated with those situations.

As an example, the user wearing the head-mounted display device may walk into a surgical room. The images captured by one or more of the user and/or environmental sensors may include images of an operating room and/or associated objects (e.g., operating table, gurney, trays, surgical instruments, heart monitor, patient, medical assistants, etc.). The processing electronics may determine that the surgeon is directing his or her eye at, for example, surgical instruments. The surgeon may have the surgical instrument in his or her hand. The surgical instrument may be acting on the patient. Based on the detected objects, the particular circumstances detected (e.g., surgical instrument approaching patient) and/or where the surgeon has directed his or her eye, the processing electronics may sense that the user is involved in an upcoming surgery.

As described above, various designs of the display system or device may be configured for certain contexts and can sense certain situations in those contexts. For example, a display system or device configured for medical care professionals may be configured to sense situations in the medical context (e.g., a medical diagnosis or procedure). In some instances, the display system or device may or may not be customized for a particular user. Machine learning algorithms can be used in some embodiments as described herein.

After a situation involving user focus has been sensed, the processing electronics can continue to block 5020. In some embodiments, the processing electronics can also continue to sense other situations involving user focus.

At block 5020, the processing electronics can optionally be configured to determine user intent for the situation. Determining user intent can include detecting one or more objects, motions, and/or sounds (e.g., from the information provided by the one or more user and/or environmental sensors) indicative of the user's intent to act. Alternatively or additionally, determining user intent can include providing various possible objects, motions, and/or sounds indicative of the user's intent to act, e.g., in a database, and searching, e.g., in the information provided by the one or more user and/or environmental sensors, for those objects, motions, and/or sounds. For some designs and/or in some situations, the display system or device may or may not act based on the detected objects, motions, and/or sounds until the user intent has been determined.

As an example, the user may talk briefly with a surgical assistant. A microphone may capture the conversation between the surgeon and assistant. The audio data may confirm the upcoming surgery, but may not trigger any action to be taken. The user may then walk over to the patient and pick up a surgical instrument. Based on determining such actions from information provided by the one or more user and/or environmental sensors, the processing electronics may determine user intent to begin the operation. Such actions may trigger the processing electronics to continue to block 5030. As described herein, some designs may be customized for a particular user. For example, a particular surgeon may have a certain habit, ritual or procedure before performing surgery (e.g., saying "Let's begin.") and such habits, procedures, or rituals may be stored on the display system or device.

After user intent has been determined, the processing electronics can continue to perform according to block 5030. In some embodiments, the processing electronics can also continue to determine other user intents in a sensed situation.

At block 5030, the processing electronics can be configured to alter user perception of real or virtual objects, e.g., within the vision field of the user, possibly based at least in part on the user intent and/or user focus etc. Such real or virtual objects may comprise real objects in the user's environment in front of the head mounted display from which light is reflected or emitted that transmits through the eyewear to the eye or virtual content displayed by the display. The processing electronics can be configured to alter user perception of real or virtual content, for example, by altering virtual image content comprising the virtual object using any of the image modification techniques described herein. Altering a user perception of real or virtual content may include at least one of enhancing the rendering of the object at which the eye is directed or de-emphasizing one or more features surrounding the object (e.g., real or virtual object) at which the eye is directed. As an example, the display system or device, e.g., via instructions provided by the processing electronics, can be configured to present image content in a different location. In some instances, real or virtual objects in the user's peripheral vision field may be presented or rerendered in the user's central vision field, e.g., for easier viewing. Alternatively, real or virtual objects in the user's central vision field may be rerendered or presented in the user's peripheral vision field, e.g., to remove clutter. Real or virtual objects in the user's peripheral vision field may also be presented or rendered in another region of the user's peripheral vision field (e.g., far peripheral vision field to near peripheral vision field or vice versa, or far central vision field to near central vision field or vice versa). In some instances, the display system or device, e.g., via instructions provided by the processing electronics, can be configured to present image content from a first depth plane to a second depth plane (e.g., a farther depth plane to a nearer depth plane or vice versa). As also described herein, the image content may be laterally displaced on the same depth plane (e.g., laterally displaced closer or farther to the user's central vision field).

As another example, the display system or device, e.g., via instructions provided by the processing electronics, can be configured to modify image content using any of the enhancing (or de-emphasizing) techniques described herein. For example, the processing electronics can be configured to alter (e.g., increase, decrease) one or more image attributes, such as contrast, opacity, color, color saturation, color balance, size, background, brightness, edge visibility, sharpness, etc. of image content (such as image content comprising the real or virtual object). Emphasizing image content may include increasing certain ones of the one or more image attributes (e.g., brightness, sharpness, contrast, etc.) of the image content. For example, emphasizing image content may include altering a color of the image content, increasing the opacity of the image content. De-emphasizing image content may include decreasing certain ones of said one or more image attributes (e.g., brightness, sharpness, contrast, etc.). For example, de-emphasizing image content may include altering a color of the image content, decreasing the opacity of the image content. In some cases, features surrounding an object may be de-emphasized to make the object more prominent. De-emphasizing features surrounding an object may include decreasing certain ones of the one or more image attributes of the surrounding image content. For example, de-emphasizing surrounding features may include de-emphasizing surrounding virtual image content, and/or increasing the opacity of the surrounding virtual image content to thereby attenuate a view of the surrounding environment in front of the user's head mounted display.

In some designs, image content can be emphasized (e.g., enhanced) or de-emphasized by displaying the image content as if originating at a different depth from the user (e.g., at a different depth plane). For example, emphasizing image content may include displaying the image content on a closer depth and/or displaying surrounding image content on a farther depth. De-emphasizing image content may include displaying the image content on a farther depth and/or displaying surrounding image content on a closer depth. The perceived depth may be provided, possibly at least in part, by varying the divergence of the light. In some instances, the image content can be enhanced or de-emphasized in comparison to how the content would otherwise be perceived by the user (e.g., if not enhanced or de-emphasized) and/or in comparison to other objects in the user's vision field. For example, image content and/or objects in the peripheral field of view of the user may be de-emphasized relative to image content and/or objects in the user's central field of view. As described herein, the degree of enhancement or de-emphasis can be based at least in part on one or more of distance from the central vision field or fovea, minimum distance for two-point distinction, spatial resolution of the eye, cone density, rod density, lighting condition, etc.

Other examples of enhancing include highlighting. For example, yellow highlighting may be superimposed over a virtual object such as an image of an object in the environment rerendered using the outwardly facing camera and display. Another example is to superimpose yellow highlighting in front of an real object that can be seen through the transmissive display. Yellow highlight, may not be too bright so as to washout the object (e.g., speed limit sign) seen through the transmissive display but may be enough to supplement the view of the object through the transmissive display yet the combination of the yellow virtual content (highlighting) and the really object, speed limit sign, may draw the user's attention to the speed limit sign.

Furthermore, certain embodiments can repeat blocks 5020 and 5030 for a given situation involving user focus to determine other user intents in the situation and alter user perception of image content based on those other user intents.

As an example, based on the user intent to begin performing surgery, a grey background can be provided to help the user focus on the surgical site and de-emphasize the rest of the room relative to the surgical site. The sufficiently intense grey light can be projected into the eye such that real objects or features in the environment in front of the user and the head-mounted display that would otherwise constitute background features are less prominent to the user. This grey background can also be homogenous so as to reduce or remove distracting detail. The projection of other image content in the background such as other images/other virtual image content can be reduced or removed as well. In this manner, features in the background can be washed out or painted over sufficiently that such features are not a distraction to the user performing surgery on a surgical site.

Another user intent during surgery may include viewing a medical image on a peripherally located heart monitor (e.g., based on eye-tracking). Based on such user intent, certain embodiments can present an image of the medical image closer to the surgical site for easier viewing.

Various examples described herein are in the medical context. Various embodiments can also be applied to other contexts, e.g., including everyday activities and tasks. One example includes operating a vehicle (e.g., car, taxi, bus, motorcycle, train, construction vehicle, tractor, farm equipment, watercraft, airplane, etc.) in which user focus and concentration can be helpful for the operator and those around the operator. For example, by emphasizing stop signs, traffic lights, pedestrian crossings, and other traffic features, augmented reality enhancements can alert drivers to situations they may not have otherwise seen or noticed, thereby improving safety.

With continued reference to FIG. 14, at block 5010, the processing electronics may sense a situation involving user focus. Sensing a situation involving user focus may include determining an object at which the user's eye is directed. Determing an object at which the user's eye is directed may be based on part on sensory information received from eye tracking sensors configured to determine where the user's eye is viewing. For example, the user wearing the head-mounted display device may leave his or her house and walk outside heading to a vehicle (e.g., car). The images captured by one or more of the user and/or environmental sensors may include images of inside a building, interaction with a door, images of the outdoors, and/or the vehicle. Such images may or may not trigger any action to be taken. The user may then open the vehicle door. Based on information provided by the one or more user or environmental sensors, the processing electronics may sense a situation involving user focus. The display system may image objects and object recognition may be used to identify those objects and possibly movement of those objects. The display system may for example using object recognition identify that the driver is turning on the vehicle or putting the vehicle into gear (e.g., drive or reverse). The display system may obtain wireless internet (e.g., WiFi), Bluetooth, and/or other information gathering systems. The display system may connect to (e.g., be "paired" with) the vehicle through a Bluetooth connection, which may be an indication that the user is within the vehicle (or at least in proximity to the vehicle). The display system may be able to detect whether the display system has previously paired with this particular vehicle. The display system may simply detect the wireless signal (e.g., blue tooth) or other signal such as other radio or RF signal and determine that the user is in the car or in proximity thereto. The display system may determine that the user is about to drive the car or is driving the car, for example, by recognizing the view and objects in the view of the user. Other types of sensors may also be used to determine that the driver is driving or intends to drive. Sensing audio such as voice commands to the car's navigation system or other control systems (e.g., heating and/or cooling), the sound locking the car or of the engine turning on can indicate the user is about to begin driving the car. Acceleration and/or motion data from GPS or accelerometers may be used to determine whether the vehicle is at rest or in motion. A combination of inputs such as the audio inputs (sound of engine starting) coupled with images from outward facing camera of the head mounted display showing the steering wheel or the view through the windshield from the driver's side, may indicate that the user is about to drive or is driving.

The processing electronics may determine that the user may be involved in driving a car and/or identify situations associated with driving, e.g., that the user is about to come to an abrupt stop. The one or more user and/or environmental sensors may detect that a vehicle ahead is gradually slowing or stopping abruptly, etc. Sensors that determine the position of objects such as range finders (laser range finders), LIDAR, radar, ultrasonic ranging devices or other position sensing systems may be able to determine the position and/or change in position. A rate at which the object and the user or user's vehicle are getting closer maybe be determined based on the one or more positions (e.g., change in positions) of the object identified by the environmental sensor. A risk of at least one of the user or user's vehicle colliding with the object or the object colliding with the user or user's vehicle may be ascertained. The display system can display image content and/or enhance and/or de-emphasize objects or image content as appropriate. For example, a virtual stop, warning, or alert sign may be displayed and may be enhanced and/or other objects or image content can be de-emphasized. Additionally, the amount of displayed image content can be reduced based on the determined risk. For example, no or substantially no image content may be displayed in some cases to reduce the likelihood of distraction and to allow the user to focus on the situation (possible collision if action is not taken, e.g., brakes applied, car steered away from object).

In some embodiments, the processing electronics may determine based on automatically received signals that the situation involves focus. For example, the processing electronics may determine that two hands on the steering wheel of a car indicates a situation involving user focus. The one or more sensors such as inward facing sensor such as eye tracking sensor or camera may detect at least a minimum frequency of changes in gaze direction. The sensor(s) may be configured to detect action by the user that may indicate focus by the user, such as, for example, squinting of the eyes, speech above a threshold volume, changes in skin color due to pressure above a threshold level exerted by the user's body (e.g., tightly grasping a steering control), and/or a rise in pulse rate, as determined, e.g., by the one or more environmental or inwardly directed sensors. As a further example, the sensor(s) of the display system may detect that the user has grasped one or more particular controls of the vehicle (e.g., car, construction vehicle), which may be indicative that the situation involves increased user focus.

As part of block 5010, the display system may be able to take into account one or more conditions surrounding the operation of the vehicle in sensing user focus. The display system may include a memory storage device (e.g., hard drive, RAM) that stores information, such as data records, about a user. The one or more sensors of the display system may also be able to sense one or more characteristics of the user. The memory device may retain one or more data records and/or characteristics of a user, such as an age of the user, size and/or height of the user, identity of the user, operating credentials of the user (e.g., driver's license, learner's permit, limited-use permit), operating record of the user (e.g., number and/or cause of citations/tickets, arrests, and/or suspensions, restrictions, and/or revocations of a license), performance record (e.g., school GPA, criminal record), and/or capability of the user (e.g., existence of physical and/or psychological ailments or limitations).

The one or more sensors may be configured to detect characteristics and/or data related to one or more characteristics of the user, such as those listed above. Other examples include, an outward facing camera may scan a user operating credential (e.g., learner's permit), detect a user position and/or orientation (e.g., whether the user is in the driver's seat), and/or sense a physical and/or mental characteristic of the user (e.g., height, weight, etc.). The processing electronics may potentially determine that one or more of these factors indicates a situation involving focus and may adjust user access permissions to system applications (e.g., e-mail, texts, etc.), as described more fully below.

At block 5020, the processing electronics can optionally be configured to determine user intent for the situation. For example, the user may sit down in the car. Such information may or may not trigger any action to be taken. In some embodiments, the one or more sensors may detect and/or search for the presence of certain objects and the relative positions to the user to confirm whether the user is in a position to operate the vehicle (e.g., drive the car). For example, the processing electronics may determine the presence and relative positions of objects indicating that the user is in the driver's seat (e.g., driver side door and/or a side view mirror on the user's left side, a passenger on the user's right side, a dashboard and steering wheel forward of the user, a rear-view mirror to the user's upper right side, etc.). The processing electronics may determine that the user is about to start driving when the one or more sensors provide information consistent with such intent (e.g., the user turns on the engine, the sound of the engine, the user puts the car in drive or in reverse, the user gazes toward the rear, at the rear-view mirror, or at the rear-view camera images, etc.).

At block 5030, the processing electronics can be configured to alter user perception of real or virtual objects (such as real objects in the environment in front of the head mounted display or virtual content), e.g., within the vision field of the user, based at least in part on increased user focus and/or at least in part on the user intent. Various display systems can continuously monitor, e.g., via the one or more sensors, for objects that may be helpful to emphasize to the user. For example, the display system or device may search for traffic signs, road signs, pedestrian crossings, and/or other objects (e.g., traffic lights, stop signs, speed limit signs, etc.) and add augmented or virtual content to the user's vision field. For example, a sign may be enhanced and/or re-rendered possibly enhanced and may possibly be presented closer to the central vision field to help the driver drive safer. As discussed above, the sign may be highlighted with color highlighting. The display system may also de-emphasize distractions, such as, for example, alerts (e.g., emails, phone calls, text or other messages, social media notifications), audio and/or video presentations, and/or peripheral sounds. De-emphasizing distractions may include limiting or removing access to the distractions. For example, functionality of and/or access to certain software applications (e.g., "apps"), the internet, and/or other communication services (e.g., email, phone) may be reduced, restricted, or prohibited during certain actions (e.g., operating the vehicle) and/or under certain circumstances (e.g., for an operator under a certain age). De-emphasizing distractions may include dimming or removing a visual stimulus (e.g., from displaying on the display system) and/or lowering the volume or muting an aural stimulus (e.g., a song, a tone, a voice). Virtual content may therefore be removed or reduces in some cases while other virtual content may be added in some cases. Accordingly, the display system may be configured to enhance the safety of operation of a vehicle (e.g., car).

Although the block diagram in FIG. 14 references sensing a situation involving user focus and determining the user intent, either or both of these may optionally be included or both may be excluded.

In some designs, the processing electronics may determine a plurality of applications (e.g., system applications, third-party applications) that are permissible and/or a plurality of applications that are impermissible during operation of the motor vehicle. The processing electronics may determine which applications are available and/or have reduced access/functionality based on one or more factors discussed above (e.g., user characteristics, environmental readings). For example, a user who is below a certain age, above a certain age, or has no permissible credential to operate the vehicle may have restricted access to applications of the display system. One or more sensors may be configured to detect motion such as objects like cars or people in motion. As an example, based on the detected motion, the processing electronics may be configured to determine the presence of a vehicle stopping abruptly, a slow moving vehicle, a bicycle, and/or pedestrian. In such potentially dangerous situations, relevant content may be enhanced (and/or less relevant details, such as the surroundings, de-emphasized) to help the driver avoid accidents. The object of interest, e.g., vehicle, bicycle, pedestrian could be re-rendered brightly in a color that provides high contrast, for example. An alarm may also sound based on the eyewear detecting the situation. Other background features may be de-emphasized, for example, by projecting bright color light in the eye to wash out or paint over those feature in the real environment or feature of virtual content. A homogenous region may be provided to reduce distracting details. Other examples are possible.

Various embodiments may also include other features as described herein. For example, the display system or device may provide an alert to the user, e.g., to indicate a change in image content. The alert may include a visual alert (e.g., a pop-up, an icon, a blinking light, etc.), a tactile alert (e.g., a vibration), and/or an audio alert (e.g., a bell, music, a voice, etc.).

Accordingly, depending on the design, the head-mounted display device may comprise one or more outwardly facing cameras configured to image objects in the user's environment and processing electronics in communication with said display and said outwardly facing cameras. The processing electronics may be configured to display image content to the user's vision field, recognize one or more objects in the user's environment by applying object recognition to images received from the one or more outwardly facing cameras; and based on said object recognition, at least one of enhancing the rendering of the image content or de-emphasizing the rendering of the image content displayed by the display. Enhancing may comprise one or more of increasing contrast, color saturation, brightness, edges visibility, opacity, sharpness or alter the color or color balance of the rendered image content. De-emphasizing may comprise one or more of decreasing contrast, color saturation, brightness, edges visibility, opacity, or sharpness, or altering the color or color balance of the rendered image content. The one or more outwardly facing cameras may be disposed on the frame.

In some designs, the head-mounted display device comprises one or more outwardly facing cameras configured to image objects in the user's environment and processing electronics in communication with the display and the outwardly facing cameras. The processing electronics may be configured to display image content to the user's vision field, recognize one or more objects in the user's environment by applying object recognition to images received from the one or more outwardly facing cameras; and based on said object recognition, de-emphasize a least a portion of the view of the environment in front of the user to the user's eye through said transparent portion. De-emphasizing may comprise one or more of decreasing brightness, visibility, sharpness, or contrast of the view of the environment through the transparent portion or altering the color of the environment through said transparent portion. De-emphasizing may comprising increasing opacity or brightness to attenuate the view of the environment through said transparent portion, other than by displaying images from said one or more outwardly facing cameras.

Also in some head mounted display designs, processing electronics may be in communication with the display wherein the processing electronics are configured to display image content to the user's vision field and at least one of enhancing the rendering of the image content or de-emphasizing the rendering of the image content displayed by the display. The enhancing may comprise one or more of increasing contrast, color saturation, brightness, edges visibility, opacity, sharpness or altering the color or color balance of the rendered image content relative to other image content displayed by the display. The de-emphasizing may comprise one or more of decreasing contrast, color saturation, brightness, edges visibility, opacity, or sharpness, or altering the color or color balance of the rendered image content relative to other image content displayed by the display. Accordingly, the processing electronics can be configured to enhance the rendering of the image content displayed by the display. Alternatively or in addition, the processing electronics are configured to de-emphasize the rendering of image content displayed by said display. The processing electronics can be configured to enhance the rendering of the image content displayed by said display relative to surrounding image content displayed by the display. The processing electronics can be configured to de-emphasize the rendering of the image content displayed by the display relative to image content displayed by the display that is surrounded by the de-emphasized image content.

Also, depending on the design of the head mounted display device, the device may include one or more outwardly facing cameras configured to image objects in the user's environment, one or more eye tracking sensors configured to determine where the user's eye is viewing, processing electronics in communication with the display, the outwardly facing camera, and the eye tracking sensors to control presentation of image content on said display. The processing electronics may be configured to display image content to said user's vision field, determine the object at which the eye is directed; and at least one of enhancing the rendering of the object at which the eye is directed or de-emphasizing one or more features in the image on the display surrounding the object at which the eye is directed. The display device can thus identify the object that the user is focusing on and can enhance that object as rendered on the display and/or de-emphasize others objects that are rendered on the display. The processing electronics can be configured to display on the display the one or more features surrounding the object at which the user's is focusing but to de-emphasize said one or more features surrounding the object at which the eye is directed as rendered on the display.

As discussed above, object recognition may comprise simply discerning an object amid the background. Other forms of object recognition may comprise identifying what the object is and associated therewith functions and/or characteristics.

A wide variety of other variations and designs are possible. For example, the display system may include an outwardly facing camera that is configured to image an object in the user's environment. The display system may further include processing electronics that are in communication with the display described herein (e.g., above) and/or with the outwardly facing camera. The processing electronics may be configured to determine that a user is operating a vehicle (e.g., a car). The processing electronics may be configured to enhance the object in the user's vision field. Enhancing the object in the user's vision field may include moving image content of the object from a first location in the user's vision field to a second location. Alternatively or additionally, enhancing the object in the user's vision field may comprise altering a perceived color of the object relative to an original color of the object without the enhancement. Enhancing the object in the user's vision field may include one or more of increasing contrast, color saturation, brightness, edge visibility, opacity, or sharpness of the displayed image content. Enhancing the object in the user's vision field may include highlighting the object by superimposing a partially transparent color over the object.

De-emphasizing may also potentially be provided. Such de-emphasizing of real object in the environment may comprise directing light into the eye of sufficient brightness such that the real objects are less visible. De-emphasizing virtual objects may comprise reducing contrast, color saturation, brightness, edge visibility, opacity, or sharpness of the displayed virtual image content.

Depending on the design, a head-mounted display device may include a database that is configured to contain one or more user records (e.g., performance records). The display device may also include processing electronics that are configured to reduce the amount of displayed image content based on the one or more user records. The processing electronics may or may not allow a user access to one or more system and/or user applications based on the one or more user records. Examples of such applications may include email, texts, phone calls, social media connections, etc. The processing electronics may allow a designated amount of image content to be displayed based on the one or more user records. For example, without a determination of an access credential, the user may be restricted in what applications can be used. Alternatively or additionally, without a determination of an access credential, a designated amount of image content may be restricted from being displayed. Based on the user access credential, the amount of displayed image content may be reduced. The one or more user records may include but is not limited to at least one of a driving record, an accident record, a citation record, a school performance record, a criminal record, or an arrest record. Alternatively or additionally, the record may comprise a record of the user's age. Reducing an amount of displayed image content based on the one or more user records may include selectively enabling user access to a displayed image content (e.g., allowing the user access to certain applications or virtual content, but not others). In some cases, reducing an amount of displayed image content may include displaying no image content or substantially no image content.

A display device may include processing electronics that are configured to determine that the user is in the proximity of a vehicle based at least in part on an established communication link with a processor of the vehicle. The processing electronics may be configured to reduce an amount of displayed image content based on the established communication link. Determining that the user is in the proximity of the vehicle may include determining that the user is in the vehicle and/or that the user is operating the vehicle. Determining that the user is operating the vehicle may include determining that the user is driving the vehicle (e.g., a car, a boat). The processing electronics may make a determination that the user is in the proximity of a vehicle based in part on a signal received by one of the environmental sensors, e.g., a radio receiver, an optical receiver. Determining that the user is in the proximity of a vehicle may include at least one of receiving and/or sending a radio frequency signal or sending an infrared signal. The processing electronics may also use an image received by one of the one or more outward facing image sensors (e.g., cameras) together with the establishment of the communication link to make a determination that the user is in the proximity of a vehicle. Reducing an amount of displayed image content based on the established communication link may include not displaying any image content or not displaying substantially any image content.

According to the design of the display device, the display device may include an outwardly facing sensor (e.g., camera) that is configured to image an object in the user's environment. The display device may include one or more environmental sensors that are configured to identify one or more positions of the object. Processing electronics in the display device may be configured to determine whether the user is operating a vehicle. The processing electronics may be configured to determine a risk of at least one of the vehicle colliding with the object and the object colliding with the vehicle. Alternatively or additionally, the processing electronics can be configured to reduce an amount of displayed image content while the user is determined to be inside the vehicle. Depending on the design, the processing electronics can be configured to reduce an amount of displayed image content based on the determined collision risk. Determining the collision risk may include determining a rate at which the object and the vehicle are getting closer based on the one or more positions of the object identified by the one or more environmental sensors.

According to the design of the display device may include an outwardly facing camera configured to image an object in the user's environment and processing electronics in communication with the display and the outwardly facing camera to control presentation of image content on the display. The processing electronics configured to determine that the user is operating a vehicle, display image content to the user's vision field at different amounts of divergences as if projected from different distances from the user's eye, and reduce an amount of displayed image content based on the determination that the user is operating a vehicle.

Accordingly, a wide variety of variations in designs are possible. In some designs, for example, functionality of and/or access to one or more applications (e.g., user applications, system applications) and/or amount of displayed image content may be managed by an access management system. The access management system may be configured to require a login and/or password before one or more applications may be used and/or before image content may be displayed. Additionally or alternatively, the access management system may limit access to a user based on system settings. The access management system may be configured to grant a different set of access permissions (e.g., which applications can be used, what image content will be displayed). Access permissions may be provided as a "white list" (e.g., a list of allowed applications and/or displayed image content) and/or a "black list" (e.g., a list of restricted applications and/or displayed image content). According to the design, the access management system may have access permissions that cannot be changed. Access permissions may be overridden by superior access permissions. For example, a parent may override a child's access permissions. Alternatively, access permissions may be unable to be overridden. Depending on the design, an emergency override may allow a user access (e.g., limited access) to certain applications and/or image content. The access management system may grant access to certain applications and/or image content based at least in part on the type of vehicle that is being operated. For example, certain functionality might be provided for a user driving a boat that would not be allowed during the driving of a car. The access management system may grant user-specific access permissions based on user records (e.g., age, driving record, grade point average (GPA), criminal record, DWD arrests, etc.) The access management system may or may not grant access to applications and/or image content based on a variety of factors, including, but not limited to, vehicle type, user, device, laws of the local jurisdiction, override control policy, population density of the location, extent of user activity (e.g., a user sitting in a car instead of driving the car), etc.

Additionally, it will be appreciated that each of the processes, methods, and algorithms described herein and/or depicted in the figures may be embodied in, and fully or partially automated by, code modules executed by one or more physical computing systems, hardware computer processors, application-specific circuitry, and/or electronic hardware configured to execute specific and particular computer instructions. For example, computing systems may include general purpose computers (e.g., servers) programmed with specific computer instructions or special purpose computers, special purpose circuitry, and so forth. A code module may be compiled and linked into an executable program, installed in a dynamic link library, or may be written in an interpreted programming language. In some embodiments, particular operations and methods may be performed by circuitry that is specific to a given function.

Further, certain embodiments of the functionality of the present disclosure are sufficiently mathematically, computationally, or technically complex that application-specific hardware or one or more physical computing devices (utilizing appropriate specialized executable instructions) may be necessary to perform the functionality, for example, due to the volume or complexity of the calculations involved or to provide results substantially in real-time. For example, a video may include many frames, with each frame having millions of pixels, and specifically programmed computer hardware is necessary to process the video data to provide a desired image processing task or application in a commercially reasonable amount of time.

Code modules or any type of data may be stored on any type of non-transitory computer-readable medium, such as physical computer storage including hard drives, solid state memory, random access memory (RAM), read only memory (ROM), optical disc, volatile or non-volatile storage, combinations of the same and/or the like. In some embodiments, the non-transitory computer-readable medium may be part of one or more of the local processing and data module 70, the remote processing module 72, and remote data repository 74. The methods and modules (or data) may also be transmitted as generated data signals (e.g., as part of a carrier wave or other analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). The results of the disclosed processes or process steps may be stored, persistently or otherwise, in any type of non-transitory, tangible computer storage or may be communicated via a computer-readable transmission medium.

Any processes, blocks, states, steps, or functionalities in flow diagrams described herein and/or depicted in the attached figures should be understood as potentially representing code modules, segments, or portions of code which include one or more executable instructions for implementing specific functions (e.g., logical or arithmetical) or steps in the process. The various processes, blocks, states, steps, or functionalities may be combined, rearranged, added to, deleted from, modified, or otherwise changed from the illustrative examples provided herein. In some embodiments, additional or different computing systems or code modules may perform some or all of the functionalities described herein. The methods and processes described herein are also not limited to any particular sequence, and the blocks, steps, or states relating thereto may be performed in other sequences that are appropriate, for example, in serial, in parallel, or in some other manner. Tasks or events may be added to or removed from the disclosed example embodiments. Moreover, the separation of various system components in the embodiments described herein is for illustrative purposes and should not be understood as requiring such separation in all embodiments. It should be understood that the described program components, methods, and systems may generally be integrated together in a single computer product or packaged into multiple computer products.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than restrictive sense.

Indeed, it will be appreciated that the systems and methods of the disclosure each have several innovative aspects, no single one of which is solely responsible or required for the desirable attributes disclosed herein. The various features and processes described above may be used independently of one another, or may be combined in various ways. All possible combinations and subcombinations are intended to fall within the scope of this disclosure.

Certain features that are described in this specification in the context of separate embodiments also may be implemented in combination in a single embodiment. Conversely, various features that are described in the context of a single embodiment also may be implemented in multiple embodiments separately or in any suitable subcombination. Moreover, although features may be described above as acting in certain combinations and even initially exampled as such, one or more features from an exampled combination may in some cases be excised from the combination, and the exampled combination may be directed to a subcombination or variation of a subcombination. No single feature or group of features is necessary or indispensable to each and every embodiment.

It will be appreciated that conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended examples are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted may be incorporated in the example methods and processes that are schematically illustrated. For example, one or more additional operations may be performed before, after, simultaneously, or between any of the illustrated operations. Additionally, the operations may be rearranged or reordered in other embodiments. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products. Additionally, other embodiments are within the scope of the following examples. In some cases, the actions recited in the examples may be performed in a different order and still achieve desirable results.

Accordingly, the disclosure is not intended to be limited to the embodiments or examples shown herein, but are to be accorded the widest scope consistent with this disclosure, the principles and the novel features disclosed herein. For example, although many examples within this disclosure are provided with respect to medical applications in the medical field, certain embodiments described herein may be implemented for a wide variety of other applications and/or in numerous other contexts.

What is claimed is:

1. A head-mounted display system configured to project light to an eye of a user to display augmented reality image content in a vision field of said user, said head-mounted display system comprising:
 a frame configured to be supported on a head of the user;
 a head-mounted display disposed on the frame, said display configured to project light into said user's eye to display augmented reality image content to the user's vision field at different amounts of divergences as if projected from different distances from the user's eye, at least a portion of said display being transparent and disposed at a location in front of the user's eye when the user wears said head-mounted display device such that said transparent portion transmits light from a portion of the environment in front of the user and said head-mounted display to the user's eye to provide a view of said portion of the environment in front of the user and said head-mounted display;
one or more user sensors configured to sense the user;
one or more environmental sensors configured to sense surroundings of the user; and
processing electronics in communication with the display, the one or more user sensors, and the one or more environmental sensors, the processing electronics configured to:
sense a situation involving increased user focus; and
alter user perception of a real or virtual peripheral object within the vision field of the user based at least in part on sensing the increased focus on the peripheral object, wherein sensing the increased user focus on the peripheral object is based at least in part on measurement of accomodation of the user's eye when directed at the peripheral object, and wherein altering user perception comprises moving image content comprising the peripheral object from a peripheral location to a central location.

2. The display system of claim 1, wherein altering user perception further comprises altering at least one of contrast, opacity, color, color saturation, color balance, size, background, brightness, edges, or sharpness of the moved image content comprising the peripheral object.

3. The display system of claim 1, wherein the one or more environmental sensors comprise a depth sensor, a pair of binocular world cameras, a geolocation sensor, a proximity sensor, or a GPS.

4. The display system of claim 1, wherein the one or more user sensors comprise one or more cameras.

5. The display system of claim 1, wherein said situation involving increased user focus comprises driving a motor vehicle.

6. The display system of claim 1, wherein said one or more environmental sensors comprise a sensor configured to detect a radio signal.

7. The display system of claim 1, wherein said one or more environmental sensors comprise a sensor configured to detect a blue tooth signal from an automobile.

8. The display system of claim 5, wherein said processing electronics are configured to alter user perception of said real or virtual object within the vision field of the user based at least in part on one or more data records regarding the user, said one or more data records comprising a driving record of said user.

9. A head-mounted display system configured to project light to an eye of a user to display augmented reality image content, said user's eye having a vision field having a central region and a peripheral region disposed about said central region, said head-mounted display system comprising:
a frame configured to be supported on a head of the user;
a head-mounted display disposed on the frame, said display configured to project light into said user's eye so as to present image content at said central region of said user's vision field, at least a portion of said display being transparent and disposed at a location in front of the user's eye when the user wears said head-mounted display device such that said transparent portion transmits light from a portion of the environment in front of the user and said head-mounted display to the user's eye to provide a view of said portion of the environment in front of the user and said head-mounted display; and
processing electronics in communication with said display to control presentation of image content on said display, the processing electronics configured to:
sense a situation involving increased user focus; and
alter user perception of a real or virtual peripheral object within the vision field of the user based at least in part on sensing the increased focus on the peripheral object, wherein altering user perception comprises presenting image content to said peripheral region of the user's vision field that is enhanced in comparison to image content presented to the central region of the user's vision field.

10. The system of claim 9, further comprising one or more sensors configured to monitor the environment.

11. The system of claim 10, wherein said one or more sensors comprise one or more outward-facing image capture devices configured to image said environment.

12. The system of claim 10, wherein said one or more sensors comprise a distance measuring device.

13. The system of claim 9, further comprising an eye tracking device configured to track position and/or movement of said user's eye.

14. The system of claim 9, wherein the head-mounted display device is configured to process image content presented to at least a portion of said peripheral region of the user's vision field differently in comparison to image content presented to the central region of the user's vision field.

15. The system of claim 14, wherein the head-mounted display device is configured to process image content differently by magnifying image content presented to at least a portion of said peripheral region of the user's vision field in comparison to image content presented to the central region of the user's vision field.

16. The system of claim 14, wherein the head-mounted display device is configured to process image content differently by increasing brightness in image content presented to at least a portion of said peripheral region of the user's vision field in comparison to image content presented to the central region of the user's vision field.

17. The display system of claim 9, wherein the processing electronics is configured to sense a situation involving increased user focus on the peripheral object based at least in part on the measurement of accommodation of the user's eye when directed at the peripheral object.

18. The display system of claim 3, wherein the one or more environmental sensors comprise a depth sensor or a GPS.

19. The display system of claim 3, wherein the one or more environmental sensors comprise a pair of binocular world cameras.

20. The display system of claim 3, wherein the one or more environmental sensors comprise a geolocation sensor or a proximity sensor.

21. A head-mounted display system configured to project light to an eye of a user to display augmented reality image content in a vision field of said user, said head-mounted display system comprising:
a frame configured to be supported on a head of the user;
a head-mounted display disposed on the frame, said display configured to project light into said user's eye to display augmented reality image content to the user's vision field at different amounts of divergences as if projected from different distances from the user's eye, at least a portion of said display being transparent and disposed at a location in front of the user's eye when the user wears said head-mounted display device such that said transparent portion transmits light from a portion of the environment in front of the user and said head-mounted display to the user's eye to provide a view of said portion of the environment in front of the user and said head-mounted display;

one or more user sensors configured to sense the user;

one or more environmental sensors configured to sense surroundings of the user; and processing electronics in communication with the display, the one or more user sensors, and the one or more environmental sensors, the processing electronics configured to:

sense a situation involving increased user focus; and alter user perception of a real or virtual peripheral object within the vision field of the user based at least in part on sensing the increased focus on the peripheral object without reliance on head movement towards the peripheral object, wherein altering user perception comprises moving image content comprising the peripheral object from a peripheral location to a central location.

22. The display system of claim 21, wherein altering user perception further comprises altering at least one of contrast, opacity, color, color saturation, color balance, size, background, brightness, edges, or sharpness of the moved image content comprising the peripheral object.

23. The display system of claim 21, wherein the one or more environmental sensors comprise a depth sensor or a GPS.

24. The display system of claim 21, wherein the one or more environmental sensors comprise a pair of binocular world cameras.

25. The display system of claim 21, wherein the one or more environmental sensors comprise a geolocation sensor or a proximity sensor.

26. The display system of claim 21, wherein the one or more user sensors comprise one or more cameras.

27. The display system of claim 21, wherein said situation involving increased user focus comprises driving a motor vehicle.

28. The display system of claim 21, wherein said one or more environmental sensors comprise a sensor configured to detect a radio signal.

29. The display system of claim 21, wherein said one or more environmental sensors comprise a sensor configured to detect a blue tooth signal from an automobile.

30. The display system of claim 27, wherein said processing electronics are configured to alter user perception of said real or virtual object within the vision field of the user based at least in part on one or more data records regarding the user, said one or more data records comprising a driving record of said user.

31. The display system of claim 9, further comprising one or more sensors, wherein the processing electronics is in communication with the one or more sensors.

* * * * *

EX PARTE REEXAMINATION CERTIFICATE (12444th)
United States Patent
Robaina et al.

(10) Number: US 10,838,210 C1
(45) Certificate Issued: Nov. 21, 2023

(54) IMAGING MODIFICATION, DISPLAY AND VISUALIZATION USING AUGMENTED AND VIRTUAL REALITY EYEWEAR

(71) Applicant: Magic Leap, Inc., Plantation, FL (US)

(72) Inventors: Nastasja U. Robaina, Coconut Grove, FL (US); Nicole Elizabeth Samec, Ft. Lauderdale, FL (US); Christopher M. Harrises, Nashua, NH (US); Rony Abovitz, Hollywood, FL (US); Mark Baerenrodt, Delray Beach, FL (US); Brian Lloyd Schmidt, Bellevue, WA (US)

(73) Assignee: MAGIC LEAP, INC., Plantation, FL (US)

Reexamination Request:
No. 90/019,120, Oct. 11, 2022

Reexamination Certificate for:
Patent No.: 10,838,210
Issued: Nov. 17, 2020
Appl. No.: 15/657,589
Filed: Jul. 24, 2017

Related U.S. Application Data

(60) Provisional application No. 62/366,599, filed on Jul. 25, 2016, provisional application No. 62/396,071, filed on Sep. 16, 2016, provisional application No. 62/440,332, filed on Dec. 29, 2016.

(51) Int. Cl.
*G02B 27/01* (2006.01)
*G06F 3/01* (2006.01)
*A61B 34/00* (2016.01)
*A61B 90/00* (2016.01)

(52) U.S. Cl.
CPC .......... *G02B 27/0172* (2013.01); *A61B 34/25* (2016.02); *A61B 90/36* (2016.02)

(58) Field of Classification Search
CPC .................................................. G02B 27/0172
See application file for complete search history.

(56) References Cited

To view the complete listing of prior art documents cited during the proceeding for Reexamination Control Number 90/019,120, please refer to the USPTO's Patent Electronic System.

*Primary Examiner* — Joseph R Pokrzywa

(57) ABSTRACT

A display system can include a head-mounted display configured to project light to an eye of a user to display augmented reality image content to the user. The display system can include one or more user sensors configured to sense the user and can include one or more environmental sensors configured to sense surroundings of the user. The display system can also include processing electronics in communication with the display, the one or more user sensors, and the one or more environmental sensors. The processing electronics can be configured to sense a situation involving user focus, determine user intent for the situation, and alter user perception of a real or virtual object within the vision field of the user based at least in part on the user intent and/or sensed situation involving user focus. The processing electronics can be configured to at least one of enhance or de-emphasize the user perception of the real or virtual object within the vision field of the user.

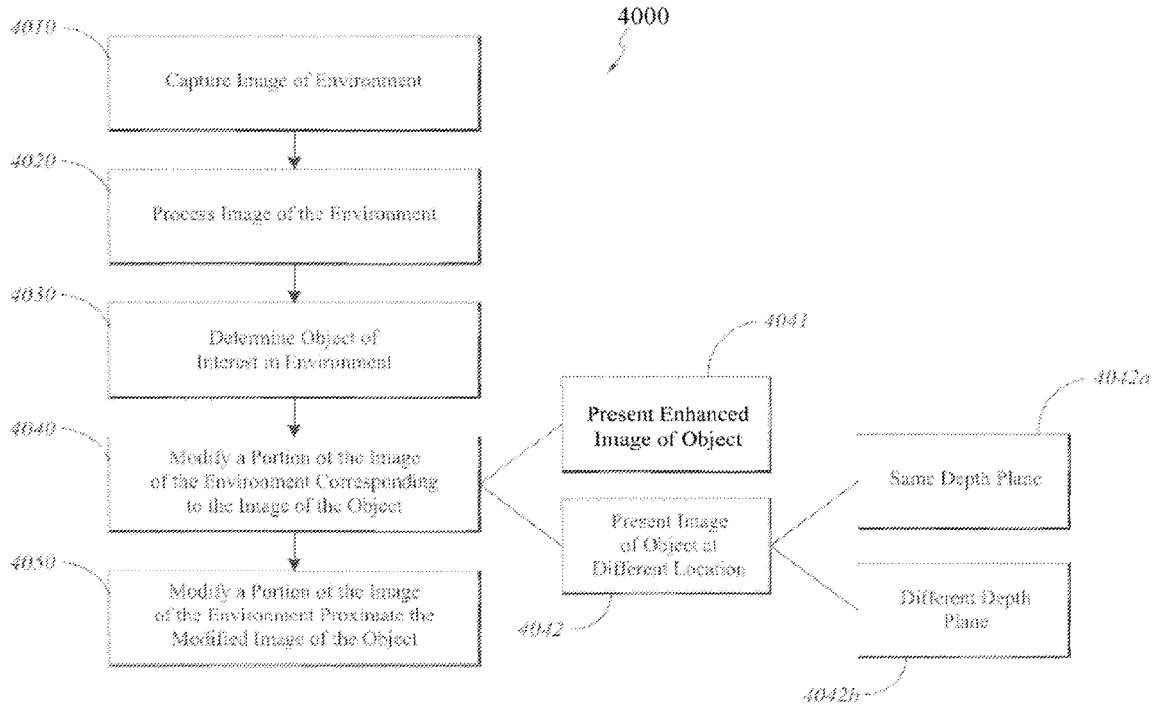

US 10,838,210 C1

EX PARTE
REEXAMINATION CERTIFICATE

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 9-17 and 31 are cancelled.

Claims 1 and 18-21 are determined to be patentable as amended.

Claims 2-8 and 22-30, dependent on an amended claim, are determined to be patentable.

New claims 32-49 are added and determined to be patentable.

1. A head-mounted display system configured to project light to an eye of a user to display augmented reality image content in a vision field of said user, said head-mounted display system comprising:
   a frame configured to be supported on a head of the user;
   a head-mounted display disposed on the frame, said display configured to project light into said user's eye to display augmented reality image content to the user's vision field at different amounts of divergences as if projected from different distances from the user's eye, at least a portion of said display being transparent and disposed at a location in front of the user's eye when the user wears said head-mounted display [device] *system* such that said transparent portion transmits light from a portion of the environment in front of the user and said head-mounted display to the user's eye to provide a view of said portion of the environment in front of the user and said head-mounted display;
   one or more user sensors configured to sense the user;
   one or more environmental sensors configured to sense surroundings of the user; and
   processing electronics in communication with the display, the one or more user sensors, and the one or more environmental sensors, the processing electronics configured to:
   sense a situation involving increased user focus *of a real or virtual object, wherein the real or virtual object is a peripheral object within a peripheral location of a vision field of the user for a particular gaze direction*; and
   alter user perception of [a real or virtual] *the* peripheral object within the vision field of the user *for the particular gaze direction* based at least in part on sensing the increased focus on the peripheral object *in a different gaze direction*,
   wherein sensing the increased user focus on the peripheral object *in the different gaze direction* is based at least in part on
   measurement of accommodation of the user's eye when directed at the peripheral object *in the different gaze direction*, and
   *detecting a minimum frequency of change in gaze direction of the user, and*
   wherein altering user perception comprises:
   moving image content comprising the peripheral object from [a] *the* peripheral location *of the vision field for the particular gaze direction* to a central location *of the vision field for the particular gaze direction; and*
   *wherein, when the peripheral object is a real object, moving the image content comprises moving a virtual copy of the real object to the central location of the vision field for the particular gaze direction.*

18. The display system of claim 3, wherein the one or more environmental sensors [comprise] *is* a depth sensor or a GPS.

19. The display system of claim 3, wherein the one or more environmental sensors [comprise] *is* a pair of binocular world cameras.

20. The display system of claim 3, wherein the one or more environmental sensors [comprise] *is* a geolocation sensor or a proximity sensor.

21. A head-mounted display system configured to project light to an eye of a user to display augmented reality image content in a vision field of said user, said head-mounted display system comprising:
    a frame configured to be supported on a head of the user;
    a head-mounted display disposed on the frame, said display configured to project light into said user's eye to display augmented reality image content to the user's vision field at different amounts of divergences as if projected from different distances from the user's eye, at least a portion of said display being transparent and disposed at a location in front of the user's eye when the user wears said head-mounted display [device] *system* such that said transparent portion transmits light from a portion of the environment in front of the user and said head-mounted display to the user's eye to provide a view of said portion of the environment in front of the user and said head-mounted display;
    one or more user sensors configured to sense the user;
    one or more environmental sensors configured to sense surroundings of the user; and
    processing electronics in communication with the display, the one or more user sensors, and the one or more environmental sensors, the processing electronics configured to:
    sense a situation involving increased user focus *of a real or virtual object, wherein the real or virtual object is a peripheral object within a peripheral location of a vision field of the user for a particular gaze direction*; and
    alter user perception of [a real or virtual] *the* peripheral object within the vision field of the user *for the particular gaze direction* based at least in part on sensing the increased focus on the peripheral object *in a different gaze direction* without reliance on head movement towards the peripheral object,
    *wherein sensing the increased user focus on the peripheral object in the different gaze direction is based at least in part on*
    *measurement of accommodation of the user's eye when directed at the peripheral object in the different gaze direction, and*
    *detecting a minimum frequency of change in gaze direction of the user,*
    wherein altering user perception comprises:
    moving image content comprising the peripheral object from [a] *the* peripheral location *of the vision field for the particular gaze direction* to a central location *of the vision field for the particular gaze direction; and* wherein, when the peripheral object is a real object, moving the image content comprises moving a virtual copy of the real object to the central location of the vision field for the particular gaze direction.

32. The display system of claim 1, wherein sensing the increased user focus on the peripheral object is based on detecting a number of occasions that a user directs the user's head, eyes, or head and eyes toward the different gaze direction.

33. The display system of claim 32, wherein sensing the increased user focus on the peripheral object is based on sensing the user struggling to view the peripheral object.

34. The display system of claim 33, wherein sensing the user struggling to view the peripheral object comprises detecting fluctuations in accommodation of an eye of the user.

35. The display system of claim 34, wherein sensing the user struggling to view the peripheral object comprises detecting fluctuations in vergence of the eye of the user.

36. The display system of claim 1, wherein altering user perception comprises enhancing the image content that is moved to the central location of the vision field for the particular gaze direction.

37. The display system of claim 36, wherein enhancing the image content comprises magnifying the real or virtual object.

38. The display system of claim 36, wherein moving the image content comprising the peripheral object comprises moving the image content to a depth plane in the central location that is closer to the user than a depth plane at which the peripheral object is located in the peripheral location.

39. The display system of claim 36, wherein a degree of enhancement of the image content is based at least in part on one of a distance from the fovea of the user's eye, a minimum distance for two-point distinction, and spatial resolution of an eye of the user.

40. The display system of claim 1, wherein moving the image content comprising the peripheral object from the peripheral location of the vision field for the particular gaze direction to the central location of the vision field for the particular gaze direction comprises moving the image content to a location corresponding to a projected light location of the user's eye that is in a range of 0 to 10 degrees from the center of the fovea of the user's eye.

41. The display system of claim 21, wherein sensing the increased user focus on the peripheral object is based on detecting a number of occasions that a user directs the user's head, eyes, or head and eyes toward the different gaze direction.

42. The display system of claim 41, wherein sensing the increased user focus on the peripheral object is based on sensing the user struggling to view the peripheral object.

43. The display system of claim 42, wherein sensing the user struggling to view the peripheral object comprises detecting fluctuations in accommodation of the user's eye.

44. The display system of claim 43, wherein sensing the user struggling to view the peripheral object comprises detecting fluctuations in vergence of the user's eye.

45. The display system of claim 21, wherein altering user perception comprises presenting an enhanced image of the real or virtual object in the moved image content.

46. The display system of claim 45, wherein presenting the enhanced image comprises magnifying the real or virtual object in the moved image content.

47. The display system of claim 45, wherein moving the image content comprising the peripheral object comprises moving the image content to a depth plane in the central location that is closer to the user than a depth plane at which the peripheral object is located in the peripheral location.

48. The display system of claim 45, wherein a degree of enhancement of the enhanced image of the real or virtual object is based at least in part on one of a distance from the fovea of the user's eye, a minimum distance for two-point distinction, and spatial resolution of the user's eye.

49. The display system of claim 21, wherein moving image content comprising the peripheral object from the peripheral location of the vision field for the particular gaze direction to the central location of the vision field for the particular gaze direction comprises moving the image content to a location corresponding to a projected light location of the user's eye that is in a range of 0 to 10 degrees from the center of the fovea of the user's eye.

* * * * *